US012729200B2

(12) United States Patent
Liang et al.

(10) Patent No.: US 12,729,200 B2
(45) Date of Patent: Sep. 8, 2026

(54) GLP-1R AGONIST AND THERAPEUTIC METHOD THEREOF

(71) Applicant: Ascletis Pharma (China) Co., Limited, Hong Kong (CN)

(72) Inventors: Bin Liang, Hong Kong (CN); Jinzi Jason Wu, Hong Kong (CN); Bailing Yang, Hong Kong (CN)

(73) Assignee: ASCLETIS PHARMA (CHINA) CO., LIMITED, Hong Kong (CN)

( * ) Notice: Subject to any disclaimer, the term of this patent is extended or adjusted under 35 U.S.C. 154(b) by 0 days.

(21) Appl. No.: 19/271,557

(22) Filed: Jul. 16, 2025

(65) Prior Publication Data

US 2025/0346596 A1 Nov. 13, 2025

Related U.S. Application Data

(63) Continuation of application No. 19/051,013, filed on Feb. 11, 2025, which is a continuation of application No. 18/884,965, filed on Sep. 13, 2024, now Pat. No. 12,234,236.

(60) Provisional application No. 63/673,453, filed on Jul. 19, 2024, provisional application No. 63/603,854, filed on Nov. 29, 2023, provisional application No. 63/545,615, filed on Oct. 25, 2023, provisional application No. 63/538,892, filed on Sep. 18, 2023.

(30) Foreign Application Priority Data

| Date | Country | Application |
|---|---|---|
| Sep. 14, 2023 | (CN) | 202311189557.X |
| Oct. 23, 2023 | (CN) | 202311371725.7 |
| Nov. 24, 2023 | (CN) | 202311582240.2 |
| Dec. 8, 2023 | (CN) | 202311686034.6 |
| Jan. 31, 2024 | (CN) | 202410142451.2 |
| Feb. 22, 2024 | (CN) | 202410202078.5 |
| Apr. 2, 2024 | (CN) | 202410398964.X |
| May 11, 2024 | (CN) | 202410584679.7 |
| Jul. 17, 2024 | (CN) | 202410963587.X |
| Sep. 4, 2024 | (CN) | 202411237048.4 |

(51) Int. Cl.
*C07D 471/04* (2006.01)
*A61K 31/437* (2006.01)
*C07D 519/00* (2006.01)

(52) U.S. Cl.
CPC .......... *C07D 471/04* (2013.01); *A61K 31/437* (2013.01); *C07D 519/00* (2013.01)

(58) Field of Classification Search
CPC .................................................... C07D 471/04
USPC .......................................................... 514/300
See application file for complete search history.

(56) References Cited

U.S. PATENT DOCUMENTS

| | | | |
|---|---|---|---|
| 6,482,844 B1 | 11/2002 | He et al. | |
| 9,120,813 B2 | 9/2015 | Mjalli et al. | |
| 9,150,482 B2 | 10/2015 | Wu | |
| 9,198,901 B2 | 12/2015 | Almariego et al. | |
| 10,392,357 B2 | 8/2019 | Chein et al. | |
| 10,858,356 B2 | 12/2020 | Yoshino et al. | |
| 11,584,751 B1 | 2/2023 | Ren | |
| 12,037,339 B2 | 7/2024 | Ren et al. | |
| 12,234,236 B1 | 2/2025 | Liang et al. | |
| 12,291,530 B1 | 5/2025 | Liang et al. | |
| 2011/0064806 A1 | 3/2011 | Polisetti et al. | |
| 2024/0199589 A1 | 6/2024 | Armstrong et al. | |
| 2025/0346596 A1* | 11/2025 | Liang | C07D 519/00 |

FOREIGN PATENT DOCUMENTS

| | | |
|---|---|---|
| CN | 101195612 B | 8/2012 |
| CN | 102378574 B | 11/2013 |
| CN | 104080767 A | 10/2014 |
| CN | 103694195 B | 4/2016 |
| CN | 102946882 B | 5/2016 |
| CN | 106588749 A | 4/2017 |
| CN | 105622687 B | 3/2018 |
| CN | 109867630 A | 6/2019 |
| CN | 112451515 A | 3/2021 |
| CN | 111548311 B | 4/2021 |
| CN | 107074820 B | 5/2021 |
| CN | 113480534 B | 5/2022 |

(Continued)

OTHER PUBLICATIONS

Petition for Post Grant Review (PGR2025-00057) of Claims 1-9, 12-17, and 21-25 of U.S. Pat. No. 12,234,236. p. 1-131, filed Jun. 20, 2025.

(Continued)

*Primary Examiner* — Niloofar Rahmani
(74) *Attorney, Agent, or Firm* — Nevrivy Patent Law Group P.L.L.C.

(57) ABSTRACT

The present disclosure describes GLP-1R modulating compounds that are useful for treating GLP-1R-mediated diseases or conditions, Formula (I)

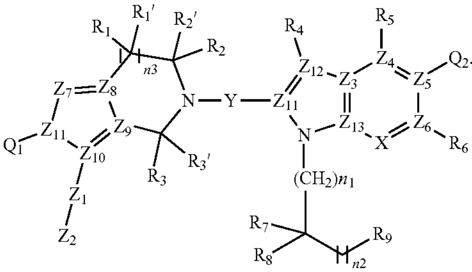

1 Claim, No Drawings

(56) References Cited

FOREIGN PATENT DOCUMENTS

| | | | |
|---|---|---|---|
| CN | 114478497 | B | 5/2022 |
| CN | 114591296 | A | 6/2022 |
| CN | 114634510 | A | 6/2022 |
| CN | 114716423 | A | 7/2022 |
| CN | 114763352 | A | 7/2022 |
| CN | 114790160 | A | 7/2022 |
| CN | 114805336 | A | 7/2022 |
| CN | 114907351 | A | 8/2022 |
| CN | 115279750 | A | 11/2022 |
| CN | 115286550 | A | 11/2022 |
| CN | 115315426 | A | 11/2022 |
| CN | 115697968 | B | 11/2022 |
| CN | 115536638 | A | 12/2022 |
| CN | 115594669 | A | 1/2023 |
| CN | 115667219 | A | 1/2023 |
| CN | 115667268 | B | 1/2023 |
| CN | 115703766 | A | 2/2023 |
| CN | 115703792 | A | 2/2023 |
| CN | 113831337 | B | 3/2023 |
| CN | 115867546 | A | 3/2023 |
| CN | 115872982 | A | 3/2023 |
| CN | 113801136 | B | 4/2023 |
| CN | 116003393 | A | 4/2023 |
| CN | 116102543 | A | 5/2023 |
| CN | 116102555 | A | 5/2023 |
| CN | 116120296 | A | 5/2023 |
| CN | 116217522 | A | 6/2023 |
| CN | 116217558 | A | 6/2023 |
| CN | 116323599 | A | 6/2023 |
| CN | 116354945 | A | 6/2023 |
| CN | 116444355 | A | 7/2023 |
| CN | 112812077 | B | 8/2023 |
| CN | 113816948 | B | 8/2023 |
| CN | 113929698 | B | 8/2023 |
| CN | 116574092 | A | 8/2023 |
| CN | 115667222 | B | 9/2023 |
| CN | 116804013 | A | 9/2023 |
| CN | 202311189557.X | | 9/2023 |
| CN | 116675680 | B | 10/2023 |
| CN | 116903588 | A | 10/2023 |
| CN | 202311371725.7 | | 10/2023 |
| CN | 117003748 | A | 11/2023 |
| CN | 117003749 | A | 11/2023 |
| CN | 117069743 | A | 11/2023 |
| CN | 117100752 | A | 11/2023 |
| CN | 117105932 | A | 11/2023 |
| CN | 202311582240.2 | | 11/2023 |
| CN | 113773310 | B | 12/2023 |
| CN | 117279904 | A | 12/2023 |
| CN | 202311686034.6 | | 12/2023 |
| CN | 117362282 | A | 1/2024 |
| CN | 117377666 | A | 1/2024 |
| CN | 117417329 | A | 1/2024 |
| CN | 117417330 | A | 1/2024 |
| CN | 117447493 | A | 1/2024 |
| CN | 202410142451.2 | | 1/2024 |
| CN | 117500789 | A | 2/2024 |
| CN | 117500808 | A | 2/2024 |
| CN | 117534668 | A | 2/2024 |
| CN | 117586240 | A | 2/2024 |
| CN | 117624145 | A | 3/2024 |
| CN | 117897387 | A | 4/2024 |
| CN | 117964617 | A | 5/2024 |
| CN | 117986264 | A | 5/2024 |
| CN | 118084936 | A | 5/2024 |
| CN | 113493447 | B | 6/2024 |
| CN | 118184637 | A | 6/2024 |
| CN | 118184638 | A | 6/2024 |
| CN | 116003403 | B | 7/2024 |
| CN | 118271299 | A | 7/2024 |
| CN | 118271300 | A | 7/2024 |
| CN | 118344349 | A | 7/2024 |
| CN | 202311372605.9 | | 7/2024 |
| CN | 118420603 | A | 8/2024 |
| CN | 118496200 | A | 8/2024 |
| CN | 2024169773 | A | 8/2024 |
| CN | 119285580 | A | 1/2025 |
| CN | 119306743 | A | 1/2025 |
| CN | 119330949 | A | 1/2025 |
| CN | 119372270 | A | 1/2025 |
| CN | 119431365 | A | 2/2025 |
| CN | 119431369 | A | 2/2025 |
| CN | 119504764 | A | 2/2025 |
| CN | 119528907 | A | 2/2025 |
| CN | 119552158 | A | 3/2025 |
| JP | 7461104 | B2 | 4/2024 |
| KR | 20180101671 | A | 9/2018 |
| TW | I495464 | B | 8/2015 |
| TW | 201613883 | A | 4/2016 |
| TW | I786467 | B | 12/2022 |
| WO | 2000033839 | A1 | 6/2000 |
| WO | 2000042026 | A1 | 7/2000 |
| WO | 0059887 | A1 | 10/2000 |
| WO | 2005056537 | A1 | 6/2005 |
| WO | 2006003096 | A1 | 1/2006 |
| WO | 2009129696 | A1 | 10/2009 |
| WO | 2011094890 | A1 | 8/2011 |
| WO | 2011122815 | A2 | 10/2011 |
| WO | 2012076966 | A1 | 6/2012 |
| WO | 2016094729 | A1 | 6/2016 |
| WO | 2017117556 | A1 | 7/2017 |
| WO | 2017170826 | A1 | 10/2017 |
| WO | 2018056453 | A1 | 3/2018 |
| WO | 2018064476 | A1 | 4/2018 |
| WO | 2018109607 | A1 | 6/2018 |
| WO | 2018200833 | A1 | 11/2018 |
| WO | 2019103060 | A1 | 5/2019 |
| WO | 2019183577 | A1 | 9/2019 |
| WO | 2019239319 | A1 | 12/2019 |
| WO | 2019239371 | A1 | 12/2019 |
| WO | 2020103815 | A1 | 5/2020 |
| WO | 2020110152 | A1 | 6/2020 |
| WO | 2020207474 | A1 | 10/2020 |
| WO | 2020210582 | A1 | 10/2020 |
| WO | 2020234726 | A1 | 11/2020 |
| WO | 2020263695 | A1 | 12/2020 |
| WO | 2021018023 | A1 | 2/2021 |
| WO | 2021044401 | A3 | 4/2021 |
| WO | 2021081207 | A1 | 4/2021 |
| WO | 2021112538 | A1 | 6/2021 |
| WO | 2021116874 | A1 | 6/2021 |
| WO | 2021154796 | A1 | 8/2021 |
| WO | 2021160127 | A1 | 8/2021 |
| WO | 2021187886 | A1 | 9/2021 |
| WO | 2021191812 | A1 | 9/2021 |
| WO | 2021196949 | A1 | 10/2021 |
| WO | 2021197464 | A1 | 10/2021 |
| WO | 2021219019 | A1 | 11/2021 |
| WO | 2021242806 | A1 | 12/2021 |
| WO | 2021244645 | A1 | 12/2021 |
| WO | 2021249492 | A1 | 12/2021 |
| WO | 2021254470 | A1 | 12/2021 |
| WO | 2022007979 | A1 | 1/2022 |
| WO | 2022017338 | A1 | 1/2022 |
| WO | 2022031994 | A1 | 2/2022 |
| WO | 2022040600 | A1 | 2/2022 |
| WO | 2022042691 | A1 | 3/2022 |
| WO | 2022052958 | A1 | 3/2022 |
| WO | 2022061091 | A1 | 3/2022 |
| WO | 2022068772 | A1 | 4/2022 |
| WO | 2022076503 | A1 | 4/2022 |
| WO | 2022078152 | A1 | 4/2022 |
| WO | 2022078352 | A1 | 4/2022 |
| WO | 2022078380 | A1 | 4/2022 |
| WO | 2022078407 | A1 | 4/2022 |
| WO | 2022111624 | A1 | 6/2022 |
| WO | 2022116693 | A1 | 6/2022 |
| WO | 2022127868 | A1 | 6/2022 |
| WO | 2022135572 | A1 | 6/2022 |
| WO | 2022165076 | A1 | 8/2022 |
| WO | 2022184849 | A1 | 9/2022 |
| WO | 2022192428 | A1 | 9/2022 |
| WO | 2022192430 | A1 | 9/2022 |

(56) References Cited

FOREIGN PATENT DOCUMENTS

| | | | |
|---|---|---|---|
| WO | 2022199458 | A1 | 9/2022 |
| WO | 2022199661 | A1 | 9/2022 |
| WO | 2022202864 | A1 | 9/2022 |
| WO | 2022216094 | A1 | 10/2022 |
| WO | 2022219495 | A1 | 10/2022 |
| WO | 2022225914 | A1 | 10/2022 |
| WO | 2022225941 | A1 | 10/2022 |
| WO | 2022228490 | A1 | 11/2022 |
| WO | 2022235717 | A1 | 11/2022 |
| WO | 2022241287 | A2 | 11/2022 |
| WO | 2022246019 | A1 | 11/2022 |
| WO | 2022246230 | A1 | 11/2022 |
| WO | 2022109182 | A9 | 12/2022 |
| WO | 2022241287 | A3 | 12/2022 |
| WO | 2022268152 | A1 | 12/2022 |
| WO | 2022269439 | A1 | 12/2022 |
| WO | 2023001237 | A1 | 1/2023 |
| WO | 2023011395 | A | 1/2023 |
| WO | 2023011539 | A1 | 2/2023 |
| WO | 2023016546 | A1 | 2/2023 |
| WO | 2023025201 | A1 | 3/2023 |
| WO | 2023029380 | A1 | 3/2023 |
| WO | 2023031741 | A1 | 3/2023 |
| WO | 2023049518 | A1 | 3/2023 |
| WO | 2023051490 | A1 | 4/2023 |
| WO | 2023057414 | A1 | 4/2023 |
| WO | 2023057427 | A1 | 4/2023 |
| WO | 2023057429 | A1 | 4/2023 |
| WO | 2023076237 | A1 | 5/2023 |
| WO | 2023098852 | A1 | 6/2023 |
| WO | 2023106310 | A1 | 6/2023 |
| WO | 2023111144 | A1 | 6/2023 |
| WO | 2023111145 | A1 | 6/2023 |
| WO | 2023116879 | A1 | 6/2023 |
| WO | 2023116882 | A1 | 6/2023 |
| WO | 2023124824 | A1 | 7/2023 |
| WO | 2023125896 | A1 | 7/2023 |
| WO | 2023130878 | A1 | 7/2023 |
| WO | 2023138684 | A1 | 7/2023 |
| WO | 2023151574 | A1 | 8/2023 |
| WO | 2023151575 | A1 | 8/2023 |
| WO | 2023152698 | A1 | 8/2023 |
| WO | 2023164050 | A1 | 8/2023 |
| WO | 2023164358 | A1 | 8/2023 |
| WO | 2023169436 | A1 | 9/2023 |
| WO | 2023169456 | A1 | 9/2023 |
| WO | 2023179542 | A1 | 9/2023 |
| WO | 2023182869 | A1 | 9/2023 |
| WO | 2023191408 | A1 | 10/2023 |
| WO | 2023198140 | A1 | 10/2023 |
| WO | 2023220109 | A1 | 11/2023 |
| WO | 2023220112 | A1 | 11/2023 |
| WO | 2024018395 | A1 | 1/2024 |
| WO | 2024026338 | A1 | 2/2024 |
| WO | 2024028795 | A1 | 2/2024 |
| WO | 2024041609 | A1 | 2/2024 |
| WO | 2024046342 | A1 | 3/2024 |
| WO | 2024051700 | A1 | 3/2024 |
| WO | 2024051749 | A1 | 3/2024 |
| WO | 2024063140 | A1 | 3/2024 |
| WO | 2024063143 | A1 | 3/2024 |
| WO | 2024102625 | A1 | 5/2024 |
| WO | 2024107781 | A1 | 5/2024 |
| WO | 2024/129676 | A1 | 6/2024 |
| WO | 2021155841 | A1 | 6/2024 |
| WO | 2022048665 | A1 | 6/2024 |
| WO | 2024125446 | A1 | 6/2024 |
| WO | 2024125602 | A1 | 6/2024 |
| WO | 2024131869 | A1 | 6/2024 |
| WO | 2024137426 | A1 | 6/2024 |
| WO | 2024138048 | A1 | 6/2024 |
| WO | 2024148104 | A1 | 7/2024 |
| WO | 2024149080 | A1 | 7/2024 |
| WO | 2024153041 | A1 | 7/2024 |
| WO | 2024153070 | A1 | 7/2024 |
| WO | 2024160271 | A1 | 8/2024 |
| WO | 2024169952 | A1 | 8/2024 |
| WO | 2025002250 | A1 | 1/2025 |
| WO | 2025002326 | A1 | 1/2025 |
| WO | 2025006921 | A1 | 1/2025 |
| WO | 2025007843 | A1 | 1/2025 |
| WO | 2025021048 | A1 | 1/2025 |
| WO | 2025/026270 | A1 | 2/2025 |
| WO | 2025026436 | A1 | 2/2025 |
| WO | 2025045208 | A1 | 3/2025 |
| WO | 2025057134 | A1 | 3/2025 |
| WO | 2025057134 | A2 | 3/2025 |
| WO | 2025/109387 | A1 | 5/2025 |
| WO | 2025131043 | A1 | 6/2025 |

OTHER PUBLICATIONS

Declaration of Michael C. Pirrung, Ph.D., p. 1-233, Jun. 15, 2025, filed with PGR2025-00057.

Kawai et al., Strucural basis for GLP-1 receptor activation by Ly3502970, an orally active nonpeptide agonist, Proc Natl Acad Sci U S A., (2020), 117:29959-29967.

Patel et al., Conversion of Aryl Azides to Aminopyridines, J Am Chem Soc., (2022), 144:17797-17802.

Talele, The "Cyclopropyl Fragment" is a Versatile Player that Fequently Appears in Preclinical/Clinical Drug Molecules, Journal of Medicinal Chemistry, (2016), 59:8712-8756.

Liu et al., GLP-1R agonists for the treatment of obesity: a patent review (2015-present), Expert Opinion on Therapeutic Patents, (2020), 30:781-794.

Pratt et al., Orforglipron (LY3502970), a novel, oral non-peptide glucagon-like peptide-1 receptor agonist: A Phase 1b, multicentre, blinded, placebo-controlled, randomized, multiple-ascending-dose study in people with type 2 diabetes, Diabetes Obes Metab., (2023), 25:2642-2649.

Frias et al., Efficacy and safety of oral orforglipron in patients with type 2 diabetes: a multicentre, randomised, dose-response, phase 2 study, Lancet, (2023), 402:472-483.

Pennington et al., The Necessary Nitrogen Atom: A Versatile High-Impact Design Element for Multiparameter Optimization, J Med Chem., (2017), 60:3552-3579.

English Translation of Chinese Patent Application No. 202311372605.9.

English Translation of Chinese Patent Application No. 202311371725.7.

English Translation of Chinese Patent Application No. 202311189557.X.

English Translation of Chinese Patent Application No. 202410142451.2.

English Translation of Chinese Patent Application No. 202311582240.2.

English Translation of Chinese Patent Application No. 202311686034.6.

English Translation of Chinese Patent Publication No. CN117069743A.

English Translation of International Publication No. WO 2025/026270.

Analyst and Investor Call to Review Oral GLP-1 Data, The European Association for the Study of Diabetes (EASD) Annual Meeting, Stockholm, Pfizer, (2022), 1-31.

Griffith et al., A Small-Molecule Oral Agonist of the Human Glucagon-like Peptide-1 Receptor, J.Med. Chem., (2022), 65:8208-8226.

Zhao et al., Activation of the GLP-1 receptor by a non-peptidic agonist, Nature, (2020), 577:432-456.

Freeman et al., TTP273, Investigational Oral (Non Peptide) GLP 1R Agonist: Improved Glycemic Control without Nausea and Vomiting in Phase 2, vTv Therapeutics LLC, High Point, NC, USA, p. 1.

Gustavson et al., TTP273, an Orally-Available Glucagon-Like Peptide-1(GLP-1)Agonist, Notably Reduces Glycemia in Subjects with Type 2 Diabetes Mellitus (T2DM), TransTech Pharma, LLC., (2014), 1-16.

Reese David, AMG 133 Program Update, Amgen, (2022). 1-15.

(56) References Cited

OTHER PUBLICATIONS

Saxena et al., Efficacy and Safety of Oral Small Molecule Glucagon-Like Peptide 1 Receptor Agonist Danuglipron for Glycemic Control Among Patients With Type 2 Diabetes A Randomized Clinical Trial, JAMA Network Open, (2023), 6:1-12, e2314493.
Sperry et al., Danuglipron, Drugs of the Future, (2022), 47:407-418.
Pratt et al., Orforglipron (LY3502970), a novel, oral non-peptide glucagon-like peptide-1 receptor agonist: A Phase 1a, blinded, placebo-controlled, randomized, singleand multiple-ascending-dose study in healthy participants, Diabetes Obes Metab, (2023), 25:2634-2641.
Zhang et al., Differential GLP-1R Binding and Activation by Peptide and Non-peptide Agonists, Molecular Cell, (2020), 80:485-500.
Eccogene Announces US INDApproval for GLP-1 Receptor AgonistECC5004, Eccogene, p. 1-2.
Hansen et al., N-terminally and C-terminally truncated forms of glucosedependent insulinotropic polypeptide are high-affinity competitive antagonists of the human GIP receptor, British Journal of Pharmacology, (2016), 173:826-838.
Wharton et al., Daily Oral GLP-1 Receptor Agonist Orforglipron for Adults with Obesity, N Engl J Med, 389:887-888.
Ma et al., Effect of Food Consumption on the Pharmacokinetics, Safety, and Tolerability of Once-Daily Orally Administered Orforglipron (LY3502970), a Non-peptide GLP-1 Receptor Agonist, Diabetes Ther, (2024), 15:819-832.
Stevens et al., GSBR-1290 Phase 1b MAD Results, Structure Therapeutics, (2023), p. 1-24.
Yabe, Daisuke, Twincretin as a potential therapeutic for the management of type 2 diabetes with obesity, J Diabetes Investig, (2019), 10: 902-905.
Burroughs et al., TERN-601 Phase 1 Trial Top-Line Results, Terns Pharmaceuticals, (2024), 1-29.
Clemmensen et al., Emerging hormonal-based combination pharmacotherapies for the treatment of metabolic diseases, Nature Reviews, Endocrinology, 15:91-104.
Stevens et al., GSBR-1290 Obesity Topline Data Presentation, Structure therapeutics, (2024), 1-31.
Zhao et al., Structural insights into multiplexed pharmacological actions of tirzepatide and peptide 20 at the GIP, GLP-1 or glucagon receptors, Nature Communications, (2022), 13:1057, p. 1-16.
Dutta et al., Orforglipron, a novel non-peptide oral daily glucagon-like peptide-1 receptor agonist as an anti-obesity medicine: A systematic review and meta-analysis, Obes Sci Pract., (2024), p. 1-9. e743.
Wu et al., Safety, pharmacokinetics and pharmacodynamics of HRS-7535, a novel oral small molecule glucagon-like peptide-1 receptor agonist, in healthy participants: A phase 1, randomized, double-blind, placebo-controlled, single- and multiple-ascending dose, and food effect trial, Diabetes Obes Metab., (2024), 26:901-910.
Mao et al., Discovery of GSBR-1290, a Highly Potent, Orally Available, Novel Small Molecule GLP-1 Receptor AgonistTing, LinStructure Therapeutics Inc, South San Francisco, CA, United States, (2023), 760-p.
Coll et al., A First-in-human Single Ascending Dose Study of GSBR-1290, a Novel Small Molecule GLP-1 Receptor Agonist, in Healthy Volunteers, A First-in-human Single Ascending Dose Study of GSBR-1290, a Novel Small Molecule GLP-1 Receptor Agonist, in Healthy Volunteers, (2023), 754.
Pending claims in co-pending U.S. Appl. No. 19/271,553, entitled "GLP-1R Agonist and Therapeutic Method Thereof," filed Jul. 16, 2025.
International Search Report and Written Opinion from Appl. No. PCT/IB2024/058943, mailed on May 16, 2025.
International Search Report and Written Opinion from Appl. No. PCT/IB2024/058942, mailed on May 26, 2025.
Pending claims in co-pending U.S. Appl. No. 19/051,016, entitled "GLP-1R Agonist and Therapeutic Method Thereof," filed Feb. 11, 2025.
Pending claims in co-pending U.S. Appl. No. 19/051,013, entitled "GLP-1R Agonist and Therapeutic Method Thereof," filed Feb. 11, 2025.
Pending claims in co-pending U.S. Appl. No. 19/271,548, entitled "GLP-1R Agonist and Therapeutic Method Thereof," filed Jul. 16, 2025.
Pinheiro et al., The Magic Methyl and Its Tricks in Drug Discovery and Development, Pharmaceuticals, (2023), 16:1157, p. 1-22.
Kwak et al., Evaluation of Manassantin A Tetrahydrofuran Core Region Analogues and Cooperative Therapeutic Effects with EGFR Inhibition, J. Med. Chem, (2020), 63:6821-6833.
Ghosh et al., Tetrahydrofuran, tetrahydropyran, triazoles and related heterocyclic derivatives as HIV protease inhibitors, Future Med Chem, (2011), 3:1181-1197.
Compound Summary for CID 9253, Cyclopentane, National Center for Biotechnology Information, PubChem, (2025), p. 1-3.
Compound Summary for CID 8028, Tetrahydrofuran, National Center for Biotechnology Information, PubChem, (2025), p. 1-3.
Wu et al., Poster No. 750-P, ASC30, an Oral GLP-1R Biased Small Molecule Agonist in Participants with Obesity—A First-in-Human Single Ascending Dose Study, (2025).
Ascletis Presented Results from Cohorts 1 and 2 of 28-day Multiple Ascending DoseStudy of Its Oral Small Molecule GLP-1R Agonist ASC30 at the 61st EuropeanAssociation for the Study of Diabetes (EASD) Annual Meeting, Ascletis Pharma Inc. press release (2025).
A Study of Orforglipron (LY3502970) in Adult Participants With Obesity or Overweight With Weight-Related Comorbidities (ATTAIN-1), Lilly Trials, (2018). p. 1-3.
Wharton et al., Daily Oral GLP-1 Receptor Agonist Orforglipron for Adults with Obesity, N Engl J Med, (2023), 389:877-888.
Son et al., Glucagon-Like Peptide-1 Based Therapies: A New Horizon in Obesity Management, Endocrinology and Metabolism, (2024), 39:206-221.
Harmata et al., Bridged bicyclic building block upgrading: Photochemical synthesis of bicyclo[3.1.1]heptan-1-amines, Willard Henry Dow Laboratory, Department of Chemistry, University of Michigan, 930 North University Avenue, Ann Arbor, Michigan 48109, United States.
Clarke et al., A happy medium: the synthesis of medicinally important medium-sized rings via ring expansion, Chem. Sci., (2020), 11:2876-2881.
Poleto et al., Aromatic Rings Commonly Used in Medicinal Chemistry: Force Fields Comparison and Interactions With Water Toward the Design of New Chemical Entities, Frontiers in Pharmacology, (2018), 9:1-20.
Vitaku et al., Analysis of the Structural Diversity, Substitution Patterns, and Frequency of Nitrogen Heterocycles among U.S. FDA Approved Pharmaceuticals, J. Med. Chem, (2014), 57:10257-10274.
Shire et al., Conquering the Synthesis and Functionalization of Bicyclo[1.1.1]pentanes, An Open Access Journal of the American Chemical Society, (2023), 3:1539-1553.
Li et al., Thiadiazole—a Promising Structure in Medicinal Chemistry, ChemMedChem, (2013), 8:27-41.
Boström et al., Oxadiazoles in Medicinal Chemistry, J. Med. Chem., (2012), 55:1817-1830.
Rojas et al., Oxetanes in Drug Discovery Campaigns, J. Med. Chem., (2023), 66:12697-2709.
Huang et al., Applications of oxetanes in drug discovery and medicinal chemistry, European Journal of Medicinal Chemistry, (2023), 261:115802.
Petitioner's Response to Patent Owner Request For Discretionary Denial, PGR2025-00057 (2025), p. 1-29.
Patent Owner's Preliminary Response, PGR2025-00057 (2025), p. 1-49.
Patent Owner's Brief in Support of Discretionary Denial, PGR2025-00057 (2025), p. 1-31.
Certified English Translation of International Publication No. WO 2025/131043 A1 (FP4).

(56) References Cited

OTHER PUBLICATIONS

Notice of Decisions on Institution in PGR2025-00057, mailed Dec. 1, 2025.
Patent Owner's Response in PGR2025-00057, filed Mar. 5, 2026.

* cited by examiner

GLP-1R AGONIST AND THERAPEUTIC METHOD THEREOF

CROSS-REFERENCE TO RELATED APPLICATIONS

The present disclosure claims the benefits of the Chinese patent application No. 202311189557.X entitled "GLP-1R Agonist and Therapeutic Method Thereof" filed Sep. 14, 2023 with the China National Intellectual Property Administration, the U.S. provisional application No. 63/538,892 entitled "GLP-1R Agonist and Therapeutic Method Thereof" filed Sep. 18, 2023 with the U.S. Patent and Trademark Office, the Chinese patent application No. 202311371725.7 entitled "GLP-1R Agonist and Therapeutic Method Thereof" filed Oct. 23, 2023 with the China National Intellectual Property Administration, the U.S. provisional application No. 63/545,615 entitled "GLP-1R Agonist and Therapeutic Method Thereof" filed Oct. 25, 2023 with the U.S. Patent and Trademark Office, the Chinese patent application No. 202311582240.2 entitled "GLP-1R Agonist and Therapeutic Method Thereof" filed Nov. 24, 2023 with the China National Intellectual Property Administration, the U.S. provisional application No. 63/603,854 entitled "GLP-1R Agonist and Therapeutic Method Thereof" filed Nov. 29, 2023 with the U.S. Patent and Trademark Office, the Chinese patent application No. 202311686034.6 entitled "GLP-1R Agonist and Therapeutic Method Thereof" filed Dec. 8, 2023, No. 202410142451.2 entitled "GLP-1R Agonist and Therapeutic Method Thereof" filed Jan. 31, 2024, No. 202410202078.5 entitled "GLP-1R Agonist and Therapeutic Method Thereof" filed Feb. 22, 2024, No. 202410398964.X entitled "GLP-1R Agonist and Therapeutic Method Thereof" filed Apr. 2, 2024, No. 202410584679.7 entitled "GLP-1R Agonist and Therapeutic Method Thereof" filed May 11, 2024, No. 202410963587.X entitled "GLP-1R Agonist and Therapeutic Method Thereof" filed Jul. 17, 2024 with the China National Intellectual Property Administration, the U.S. provisional application No. 63/673,453 entitled "GLP-1R Agonist and Therapeutic Method Thereof" filed Jul. 19, 2024 with the U.S. Patent and Trademark Office, and the Chinese patent application No. 202411237048.4 entitled "GLP-1R Agonist and Therapeutic Method Thereof" filed Sep. 4, 2024 with the China National Intellectual Property Administration, which are incorporated herein by their entireties.

FIELD

The present disclosure generally relates to compounds that bind to and act as agonists or modulators of the glucagon-like peptide-1 receptor (GLP-1R), as well as the use of such compounds for the treatment and/or prevention of GLP-1R-mediated diseases and conditions.

BACKGROUND

Glucagon-like peptide-1 (GLP-1) is a peptide hormone secreted from the enteroendocrine cells in the gut in response to a meal. GLP-1 is believed to play a role in regulation of post-prandial glycemia, via directly augmenting meal-induced insulin secretion from the pancreatic beta-cells, as well as in promoting satiety by delaying the transit of food through the gut. GLP-1 mediates intracellular signaling via the GLP-1 receptor (GLP-1R), which belongs to a family of G-protein coupled receptors that are present on the cell membrane and can result in the accumulation of the secondary messenger cyclic adenosine monophosphate (cAMP) upon activation. Non-alcoholic steatohepatitis (NASH) can be associated with features of metabolic syndrome, including obesity, type 2 diabetes, insulin resistance, and cardiovascular disease.

GLP-1R agonists are currently being investigated in connection with diabetes, obesity, and NASH. GLP-1R agonists include peptides, such as exenatide, liraglutide, and dulaglutide, that have been approved for the management of type 2 diabetes. Such peptides are predominantly administered by subcutaneous injection. Oral GLP-1 agonists are also under investigation for treatment of type 2 diabetes. Some GLP-1R agonists, such as liraglutide, dulaglutide, and exenatide, are resistant to rapid degradation by dipeptidyl peptidase 4, resulting in longer half-lives than endogenous GLP-1.

There remains a need for compounds, such as agonists of GLP-1R, with desirable therapeutic properties, metabolic properties, and/or easy administration in the treatment of GLP-1R-mediated diseases and conditions.

SUMMARY

One aspect of the present disclosure provides a compound of Formula (I), a stereoisomer, a pharmaceutically acceptable salt, or a deuterated compound thereof:

Formula (I)

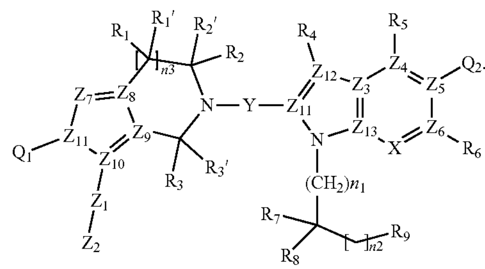

wherein:

X is selected from the group consisting of N and —$CR^a$; wherein $R^a$ is selected from the group consisting of hydrogen, halogen, and $C_{1-6}$ alkyl;

wherein Y is —C(═O)—;

wherein each of $Z_3$, $Z_4$, $Z_5$, $Z_6$, $Z_7$, $Z_8$, $Z_9$, $Z_{10}$, $Z_{11}$, $Z_{12}$ and $Z_{13}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and —$NR^{Qa}R^{Qb}$, or wherein two $C_{1-6}$ alkyl groups optionally together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein each of $R_1$, $R_2$, $R_3$, $R_1'$, $R_2'$ and $R_3'$ is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl; or wherein $R_2$ and $R_3$ together with the carbon atom to which they are attached form 4- to 8-membered heterocycloalkyl;

each of $R_4$, $R_5$ and $R_6$ is independently selected from the group consisting of hydrogen, halogen and $C_{1-6}$ alkyl;

each of $R_7$ and $R_8$ is independently selected from the group consisting of hydrogen and $C_{1-6}$ alkyl, wherein $C_{1-6}$ alkyl is optionally substituted with one or more substituents independently selected from the group consisting of halogen and $C_{3-15}$ cycloalkyl;

or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl, wherein $C_{1-6}$ alkyl is optionally substituted by one or more substituents independently selected from the group consisting of halogen, hydroxyl, —$NR^{7a}R^{7b}$, $C_{1-6}$ alkoxy and 3- to 12-membered heterocyclic, and $R^{7a}$ and $R^{7b}$ are independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ carbocyclic ring;

n1 is 0, 1, 2 or 3;

n2 is 0, 1, 2, 3, 4 or 5;

n3 is 0 or 1;

$R_9$ is selected from the group consisting of:

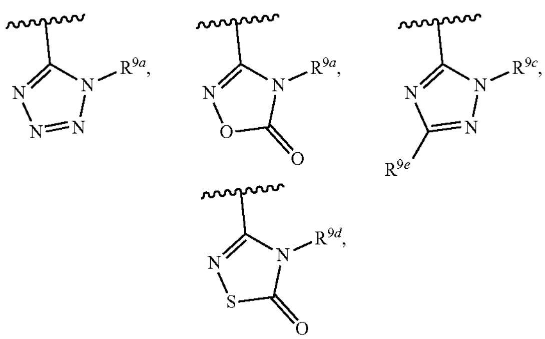

—$CO_2R^{9f}$ and —C(═O)—$NR^{9g}R^{9h}$; and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy;

$R^{9e}$ is selected from the group consisting of hydrogen and $C_{1-6}$ alkyl optionally substituted by one or more halogen;

$R^{9f}$ is selected from the group consisting of hydrogen and $C_{1-6}$ alkyl;

$R^{9h}$ is selected from the group consisting of hydrogen, $C_{1-6}$ alkyl, ($C_{1-6}$ alkyl) carbonyl, cyano and —$S(═O)_{n9}$—$R^{9i}$; n9 is 0, 1 or 2;

$R^{9i}$ is $C_{1-6}$ alkyl;

$Z_1$ is selected from the group consisting of:

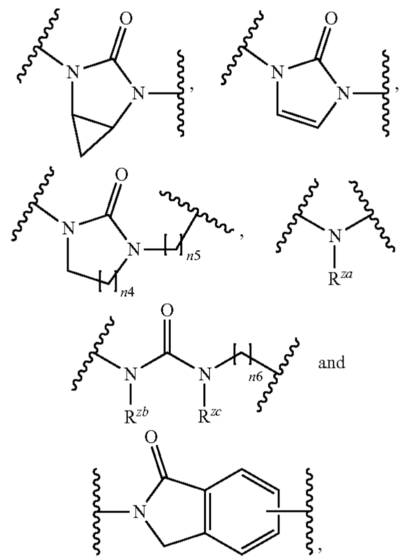

wherein $R^{za}$ is selected from the group consisting of hydrogen, $C_{1-6}$ alkyl and ($C_{1-6}$ alkyl) carbonyl, and each of $R^{zb}$ and $R^{zc}$ is independently selected from the group consisting of hydrogen and $C_{1-6}$ alkyl;

n4 is 1, 2 or 3;

each of n5 and n6 is independently an integer selected from 0 to 10;

$Z_2$ is 5- to 10-membered heteroaryl, and $Z_2$ is substituted with one halogen and one of $C_3$-$C_{15}$ cycloalkyl and $C_1$-$C_6$ alkyl-$C_3$-$C_{15}$ cycloalkyl; wherein the cycloalkyl or alkyl is optionally substituted with one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted with halogen.

Another aspect of the present disclosure provides a compound of Formula (III), a stereoisomer, a pharmaceutically acceptable salt, or a deuterated compound thereof:

Formula (III)

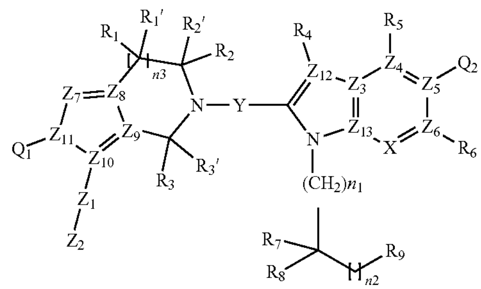

wherein:

X is —$CR^a$; $R^a$ is H;

Y is —C(═O)—;

$Z_3$, $Z_4$, $Z_5$, $Z_6$, $Z_8$, $Z_9$, $Z_{10}$, $Z_{12}$ and $Z_{13}$ are C;

$Z_7$ and $Z_{11}$ are N;

$Q_1$ is $C_{6-10}$ aryl, wherein $C_{6-10}$ aryl is optionally substituted with one to five substituents independently selected from the group consisting of halogen and $C_{1-6}$ alkyl;

$Q_2$ is 3- to 12-membered heterocyclic; wherein 3- to 12-membered heterocyclic is optionally substituted with 1-3 substituents independently selected from the group consisting of halogen and $C_{1-6}$ alkyl, or wherein two $C_{1-6}$ alkyl groups optionally together with the carbon atoms to which they are attached form $C_{3-8}$ carbocyclic ring;

wherein each of $R_1$, $R_2$, $R_1'$, and $R_2'$ is independently selected from the group consisting of hydrogen and $C_{1-6}$ alkyl;

$R_3$ and $R_3'$ are independently selected from the group consisting of hydrogen and $C_{1-6}$ alkyl;

$R_4$, $R_5$ and $R_6$ are H;

each of $R_7$ and $R_8$ is independently selected from the group consisting of hydrogen and $C_{1-6}$ alkyl; or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl;

$n_1$ is 0 or 1;

n2 is 0 or 1;

n3 is 1;

$R_9$ is

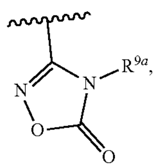

and $R^{9a}$ is H;

$Z_1$ is

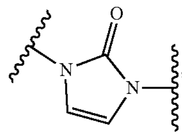

$Z_2$ is 5- to 10-membered heteroaryl, and $Z_2$ is substituted with one halogen and one of $C_3$-$C_{15}$ cycloalkyl and $C_1$-$C_6$ alkyl-$C_3$-$C_{15}$ cycloalkyl; wherein the cycloalkyl or alkyl is optionally substituted with one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted with halogen.

Still another aspect of the present disclosure provides a compound of Formula (IV), a stereoisomer, a pharmaceutically acceptable salt, or a deuterated compound thereof:

Formula (IV)

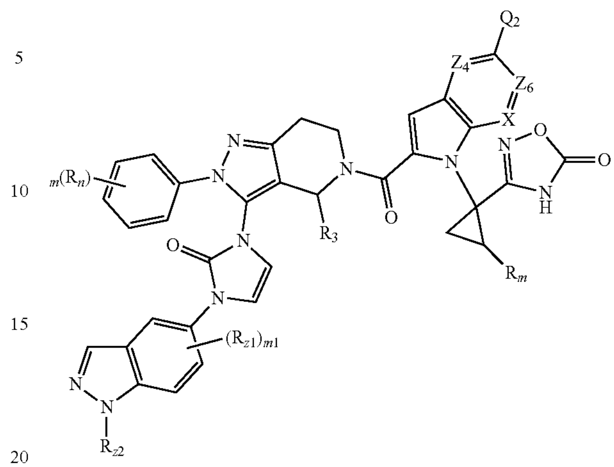

wherein:

each of X, $Z_4$ and $Z_6$ is independently selected from the group consisting of N and CH;

$R_{z1}$ is selected from the group consisting of halogen, $C_{1-3}$ alkyl, and $C_{3-8}$ cycloalkyl;

$R_{z2}$ is selected from the group consisting of $C_{3-8}$ cycloalkyl and $C_{1-6}$ alkyl-$C_{3-8}$ cycloalkyl; and $R_{z2}$ is optionally substituted with substituents independently selected from the group consisting of halogen, —OH, $C_{1-6}$ alkyl, and $C_{1-6}$ alkoxy;

m1 is 0, 1, 2 or 3.

Yet still another aspect of the present disclosure provides a compound of Formula (V), a stereoisomer, a pharmaceutically acceptable salt, or a deuterated compound thereof:

Formula (V)

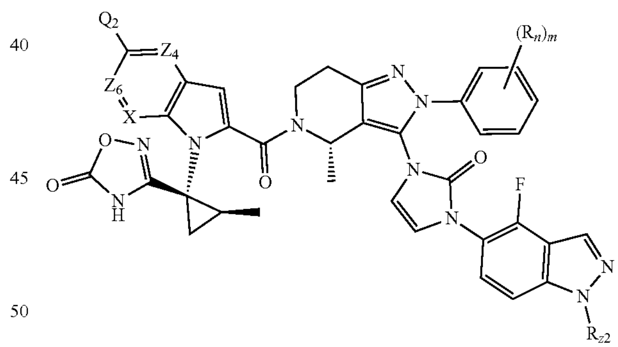

wherein:

each of X, $Z_4$ and $Z_6$ is independently selected from the group consisting of N and CH;

$Q_2$ is selected from the group consisting of

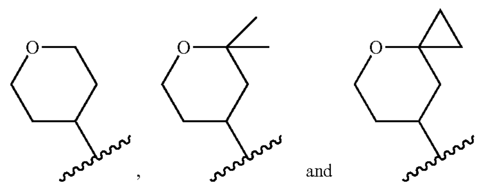

, and ;

$R_n$ is selected from the group consisting of halogen, $C_{1-6}$ alkyl, $C_{1-6}$ haloalkyl and $C_{1-6}$ alkoxy;

m is 0, 1, 2 or 3;

$R_{z2}$ is selected from the group consisting of $C_{3-8}$ cycloalkyl and $C_{1-6}$ alkyl-$C_{3-8}$ cycloalkyl; and $R_{z2}$ is optionally substituted with substituents independently selected from the group consisting of halogen, hydroxyl, $C_{1-6}$ alkyl and $C_{1-6}$ alkoxy.

Yet still another aspect of the present disclosure provides a compound of Formula (VIII), a stereoisomer, a pharmaceutically acceptable salt, or a deuterated compound thereof:

Formula (VIII)

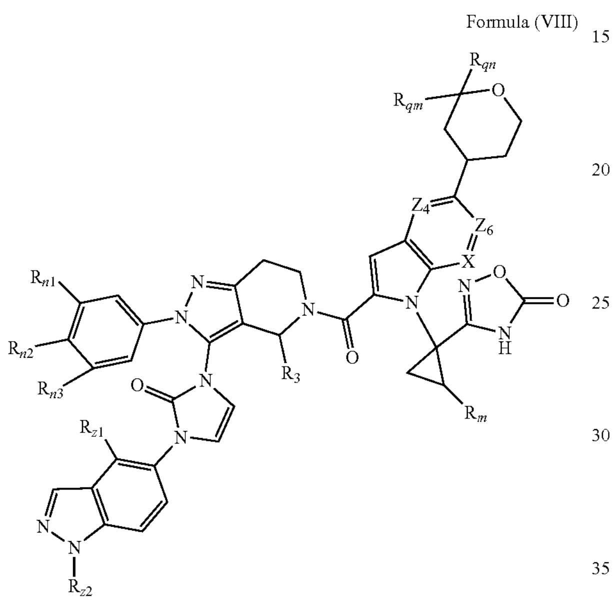

wherein:

each of X, $Z_4$ and $Z_6$ is independently selected from the group consisting of N and CH;

$R_m$ is selected from the group consisting of H, $C_{1-6}$ alkyl, $C_{1-6}$ haloalkyl, $C_{1-6}$ alkoxy and $C_{1-6}$ haloalkoxy;

$R_{n1}$ and $R_{n3}$ are each independently selected from the group consisting of hydrogen, halogen, $C_{1-6}$ alkyl, $C_{1-6}$ haloalkyl, $C_{1-6}$ alkoxy, and $C_{1-6}$ haloalkoxy; $R_{n2}$ is selected from halogen;

$R_3$ is selected from the group consisting of hydrogen, halogen, $C_{1-6}$ alkyl, $C_{1-6}$ haloalkyl, $C_{1-6}$ alkoxy and $C_{1-6}$ haloalkoxy;

$R_{z1}$ is selected from the group consisting of hydrogen, halogen, $C_{1-3}$ alkyl and $C_{3-8}$ cycloalkyl;

$R_{z2}$ Selected from the group consisting of

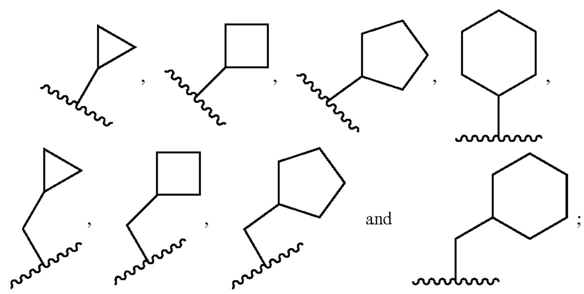

$R_{qm}$ and $R_{qn}$ are each independently selected from the group consisting of H, methyl, and ethyl, or $R_{qm}$ and $R_{qn}$ together with the carbon atom to which they are attached to form a $C_{3-6}$ cycloalkyl.

Yet still another aspect of the present disclosure provides a compound of Formula (IX), a stereoisomer, a pharmaceutically acceptable salt, or a deuterated compound thereof:

Formula (IX)

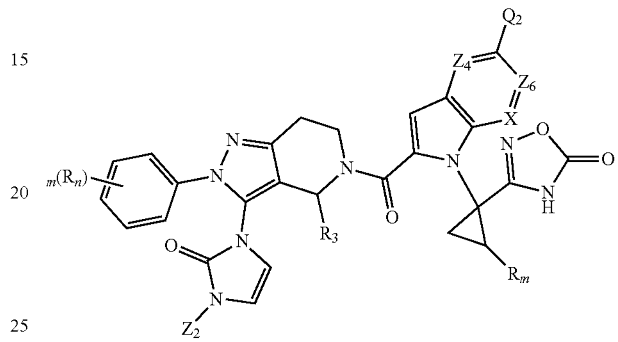

wherein:

each of X, $Z_4$ and $Z_6$ is independently selected from the group consisting of N and CH;

$Z_2$ is selected from the group consisting of

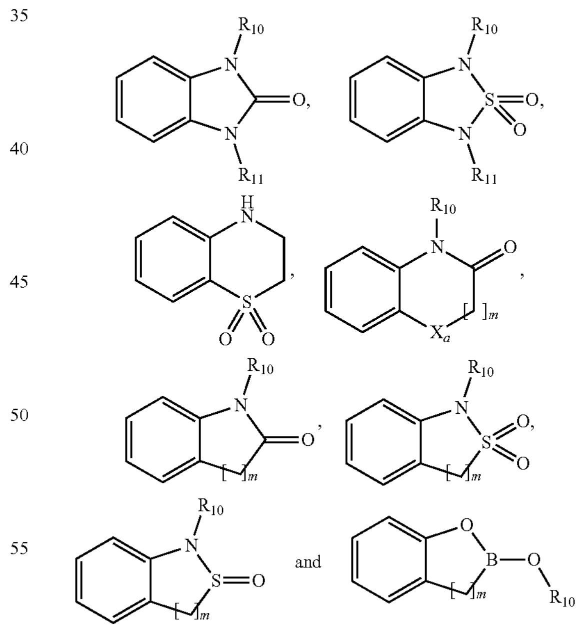

$R_n$ is selected from the group consisting of halogen, $C_{1-6}$ alkyl, $C_{1-6}$ haloalkyl and $C_{1-6}$ alkoxy;

m is 0, 1, 2 or 3.

Yet still another aspect of the present disclosure provides a compound of Formula (X), a stereoisomer, a pharmaceutically acceptable salt, or a deuterated compound thereof:

Formula (X)

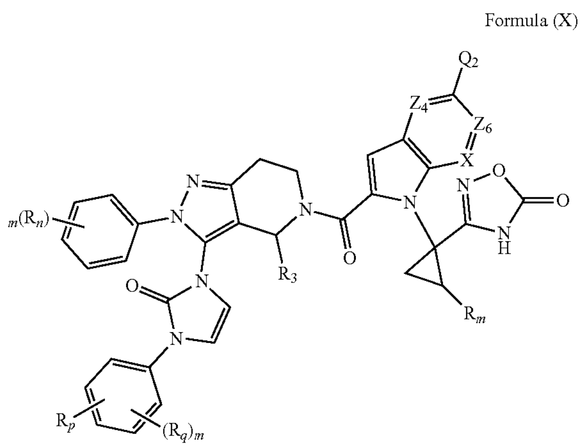

wherein:

each of X, $Z_4$ and $Z_6$ is independently selected from the group consisting of N and CH;

m is 0, 1, 2 or 3;

$R_p$ is selected from the group consisting of $—CH_2—P(=O)R^{zm}R^{zn}$ and $—P(=O)OR^{zm}OR^{zn}$;

$R_q$ is selected from the group consisting of halogen, $—NH—C_{1-6}$ alkyl, $—C_{1-6}$ alkyl, $—O—C_{1-6}$ alkyl, 3- to 12-membered heterocyclic, $—C_3-C_{15}$ cycloalkyl and $C_1-C_6$ alkyl-$C_3-C_{15}$ cycloalkyl;

wherein each of $R^{zm}$ and $R^{zn}$ is independently selected from the group consisting of hydrogen, $C_{1-6}$ alkyl and $C_{6-10}$ aryl; or $R^{zm}$ and $R^{zn}$ together with the phosphorous atom to which they are attached form 5- to 8-membered heterocycloalkyl, wherein the heterocycloalkyl is optionally substituted with 1-3 $C_{1-6}$ alkyl.

Yet still another aspect of the present disclosure provides a compound of Formula (XI), a stereoisomer, a pharmaceutically acceptable salt, or a deuterated compound thereof:

Formula (XI)

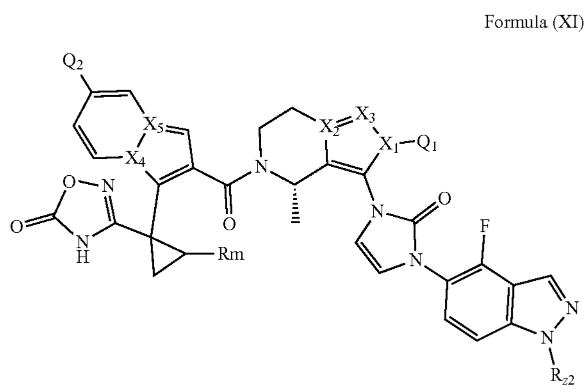

wherein:

$Q_1$ is $C_{6-10}$ aryl, and the $C_{6-10}$ aryl is optionally substituted with one to five substituents selected from the group consisting of halogen, $C_{1-6}$ alkyl, $C_{1-6}$ haloalkyl and $C_{1-6}$ alkoxy;

$Q_2$ is selected from the group consisting of 3- to 12-membered heterocyclic, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, and $C_{1-6}$ alkoxy, wherein two $C_{1-6}$ alkyl groups optionally together with the carbon atoms to which they are attached form a $C_{3-8}$ carbocyclic ring;

$X_1$, $X_2$, and $X_3$ are independently selected from the group consisting of N and C;

$X_4$, and $X_5$ are independently selected from the group consisting of N and C;

$R_m$ is selected from the group consisting of H, $C_{1-6}$ alkyl, $C_{1-6}$ haloalkyl, $C_{1-6}$ alkoxy and $C_{1-6}$ haloalkoxy;

$R_{z2}$ is selected from the group consisting of $C_{3-8}$ cycloalkyl and $C_{1-6}$ alkyl-$C_{3-8}$ cycloalkyl.

Yet still another aspect of the present disclosure provides a compound, a stereoisomer, a pharmaceutically acceptable salt, or a deuterated compound thereof, selected from the group consisting of:

3

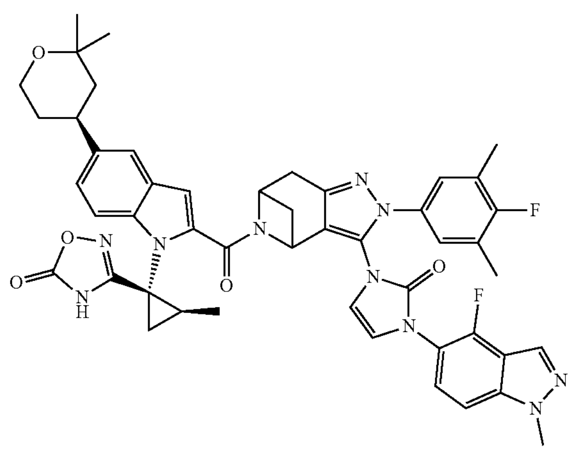

4

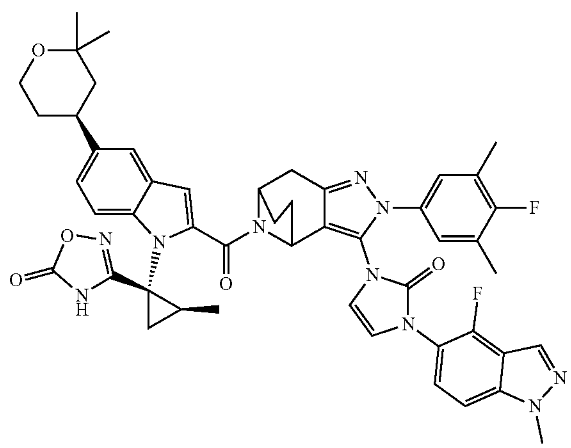

-continued
5
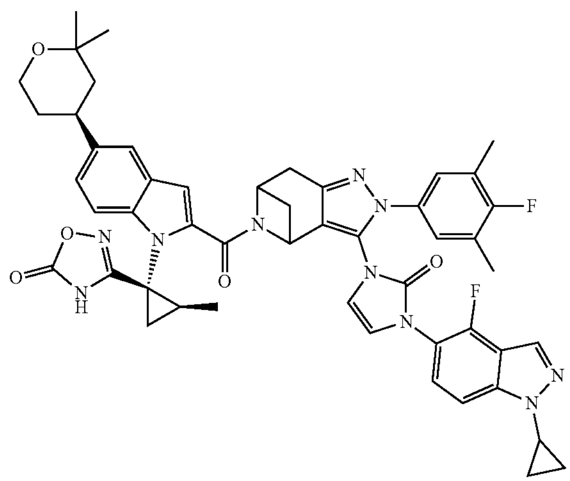
6
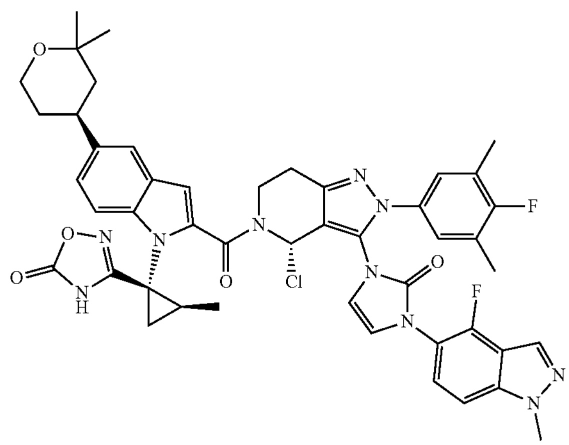
7
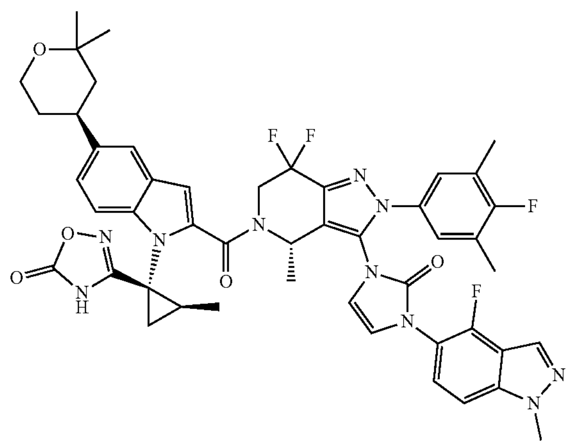
-continued
8
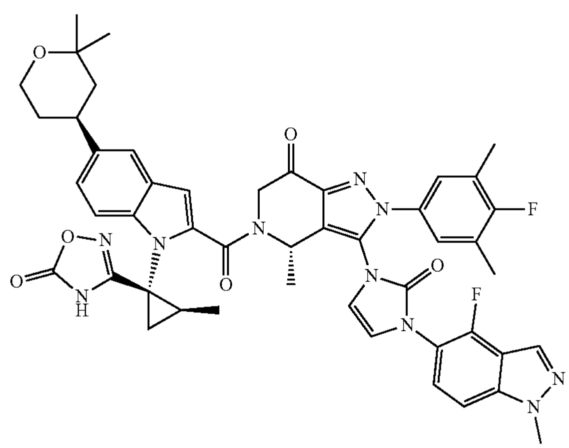
9
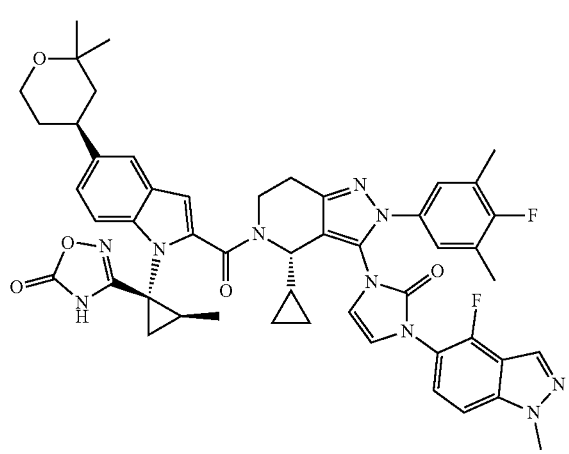
10
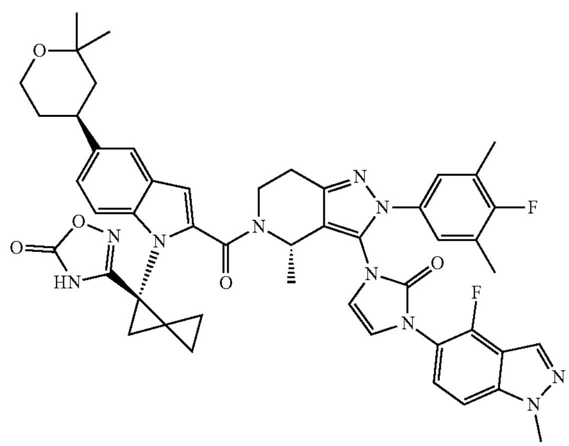

-continued
11
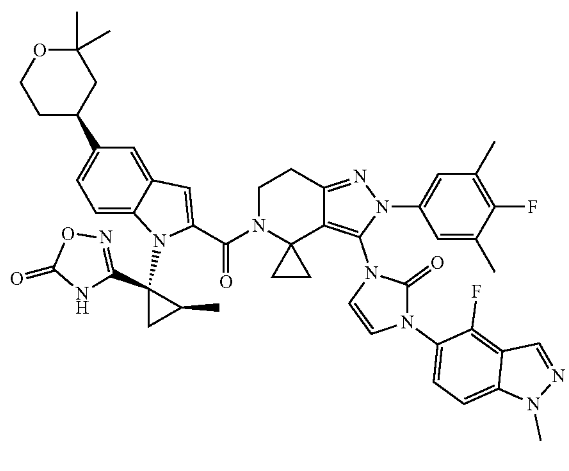
12
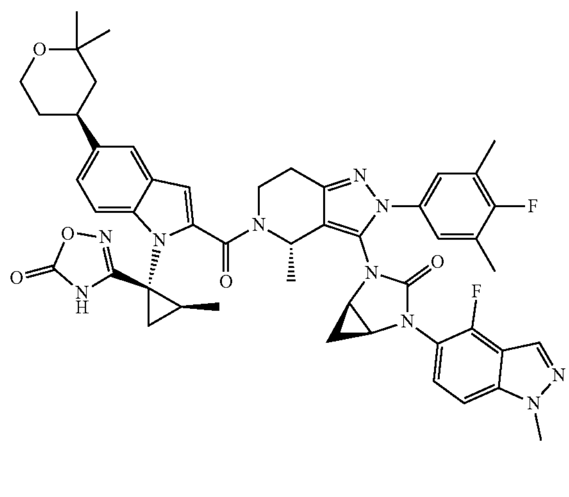
14
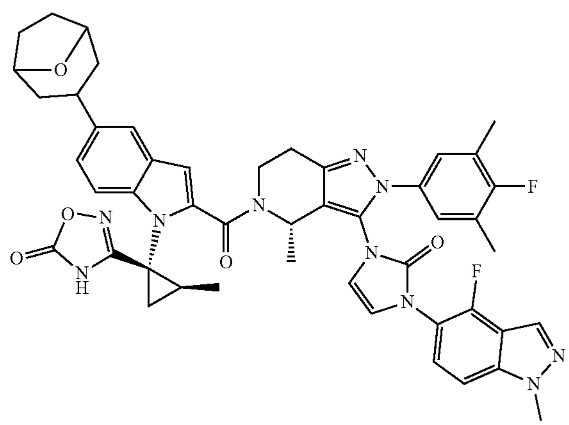
-continued
15
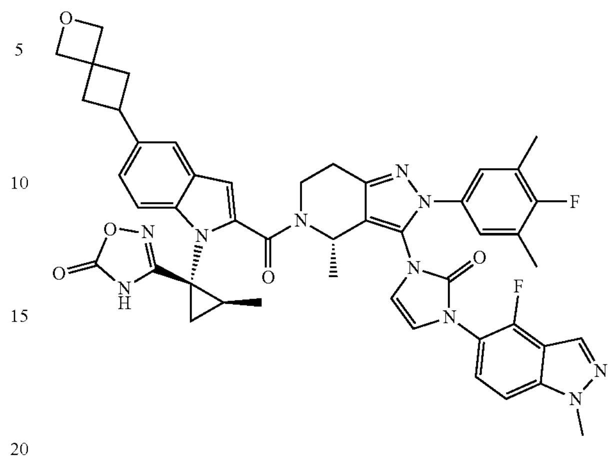
16
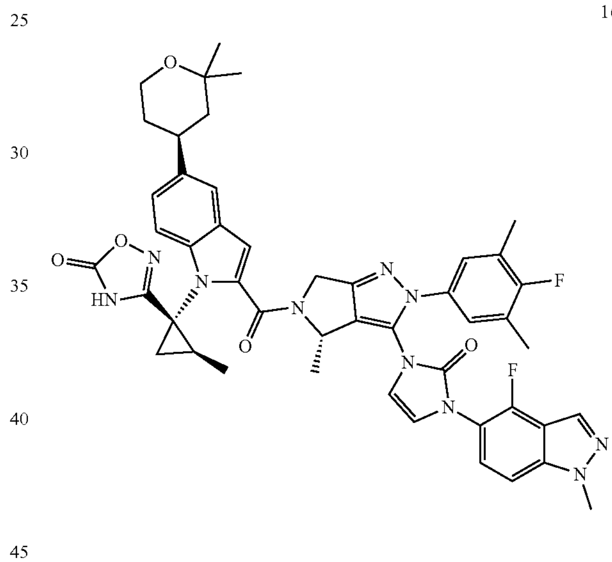
17
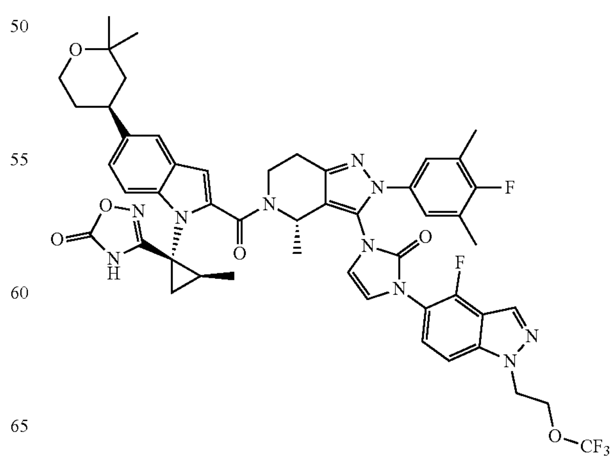

-continued
22
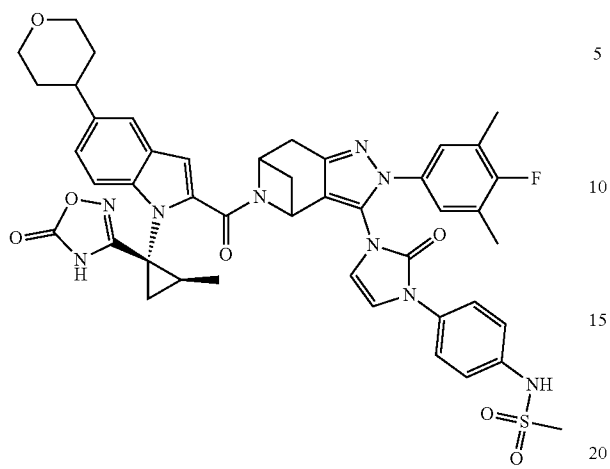
25
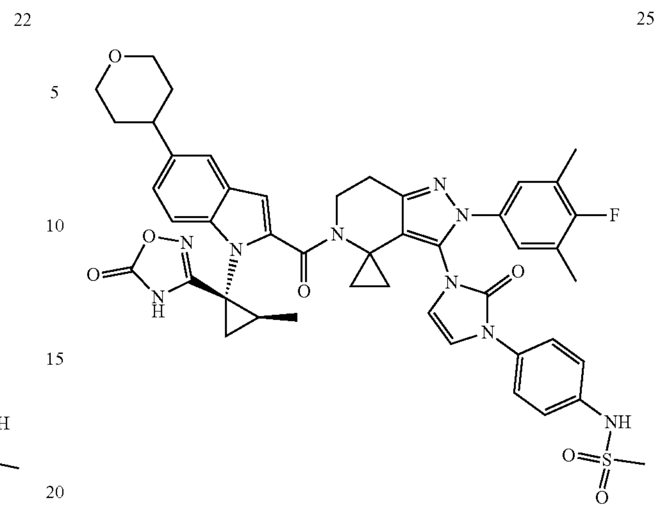
23
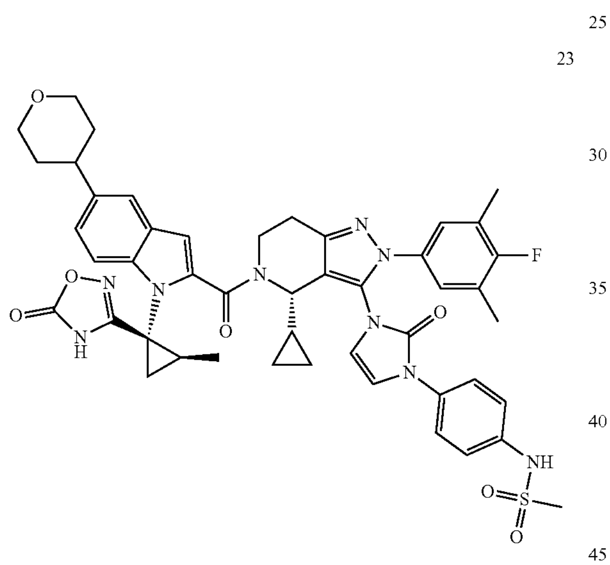
26
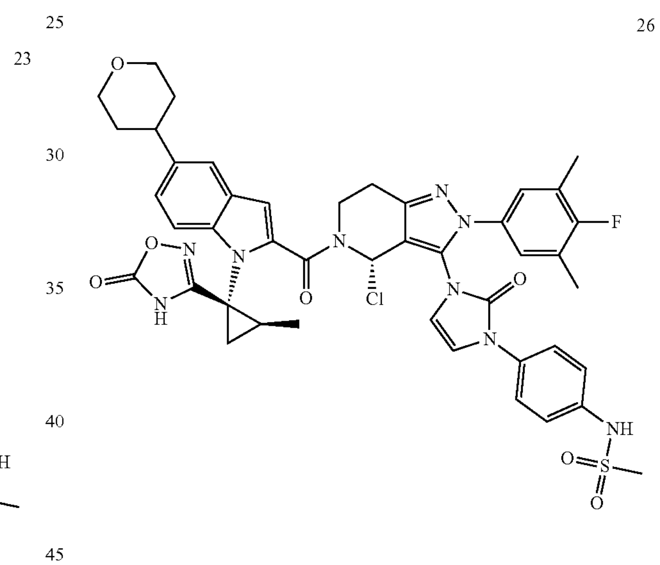
24
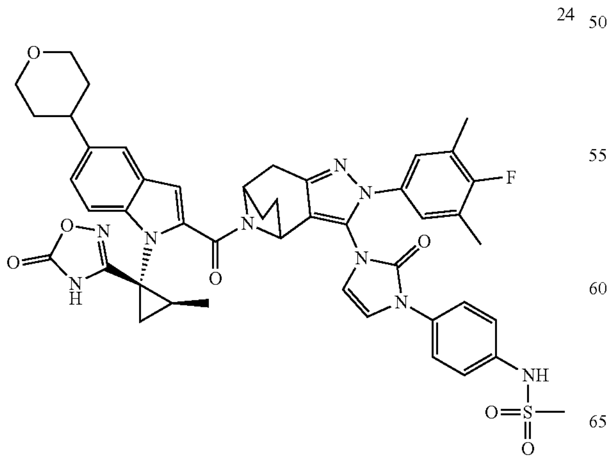
27
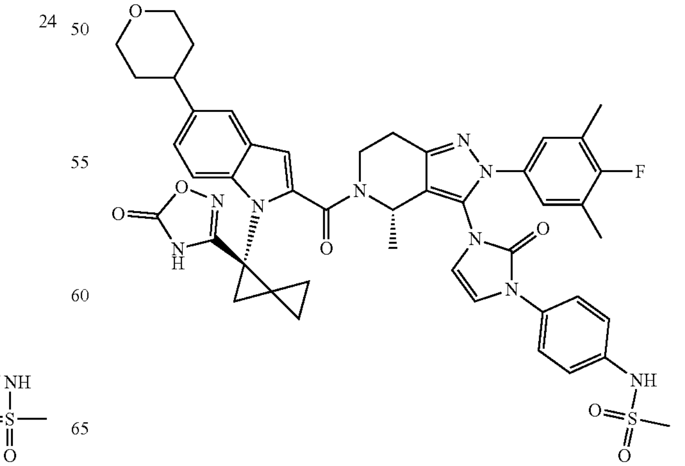

-continued
28
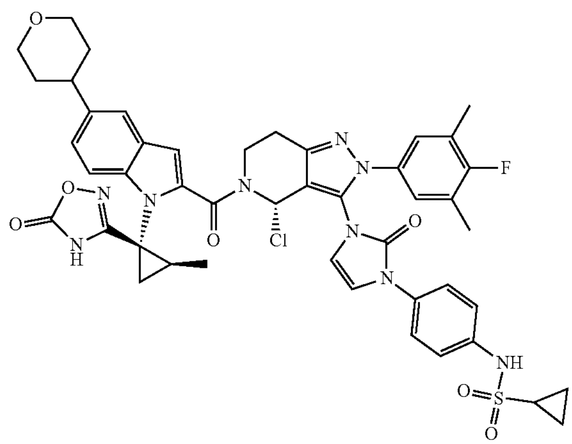
31
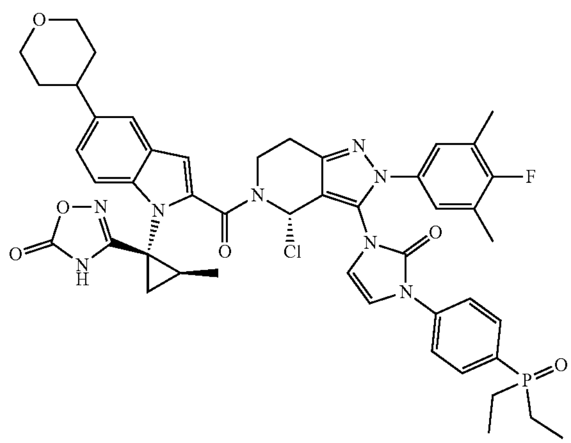
32
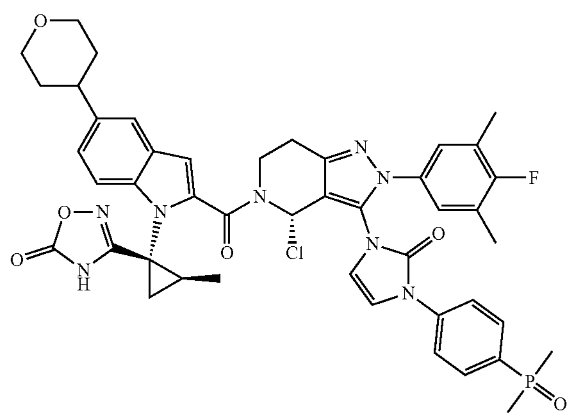
-continued
49
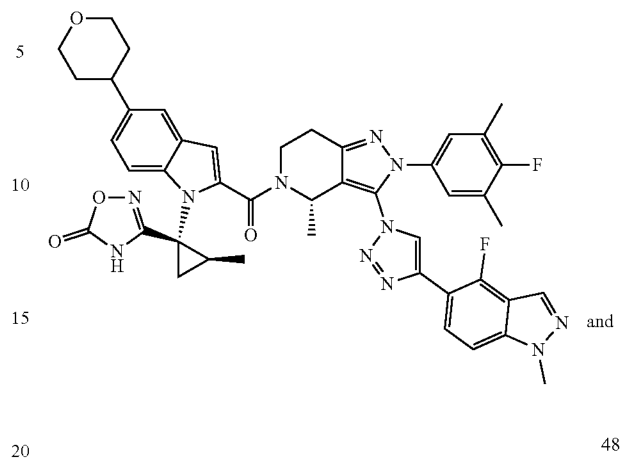
and
48
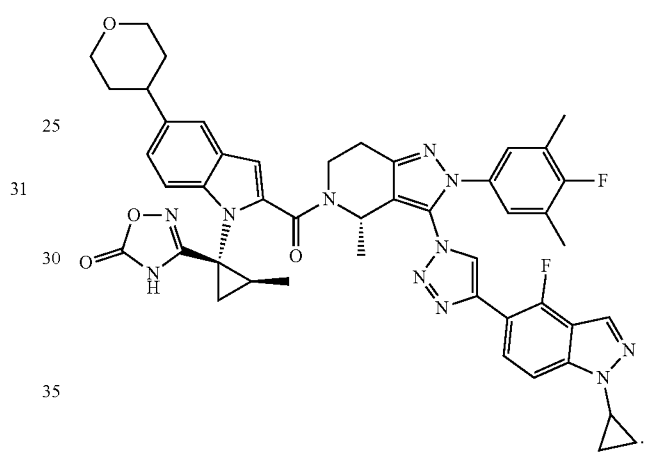
Yet still another aspect of the present disclosure provides a compound or a pharmaceutically acceptable salt thereof, wherein the compound is selected from the group consisting of:
1
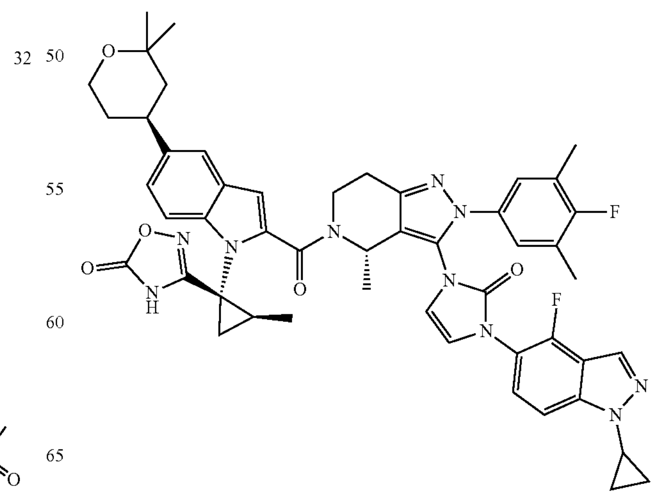

-continued
13
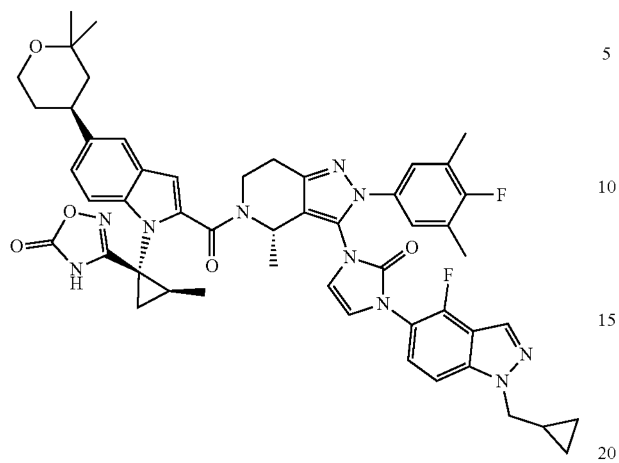
18
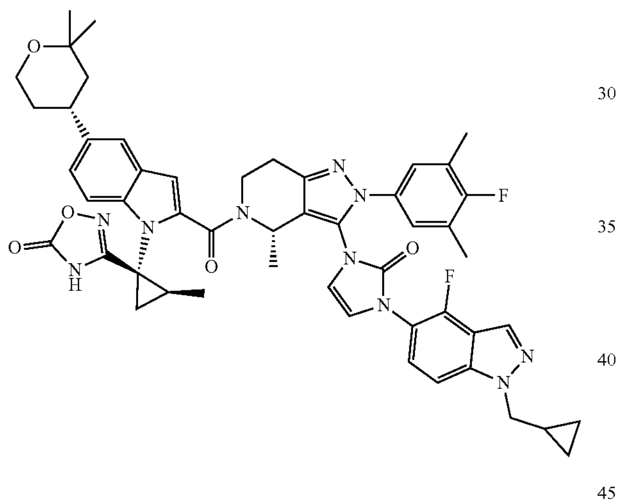
19
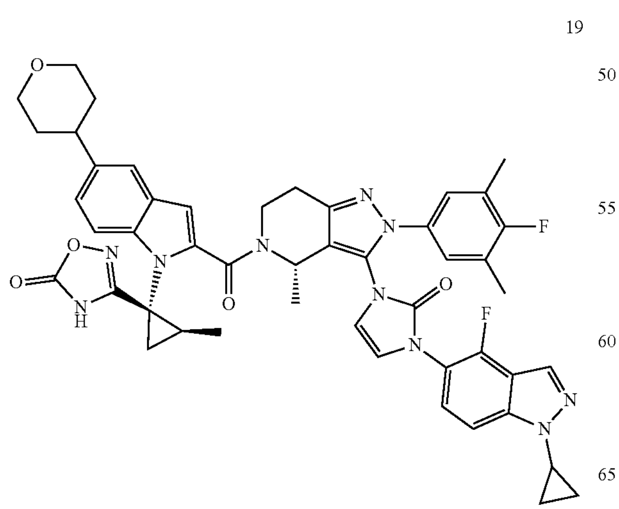
-continued
20
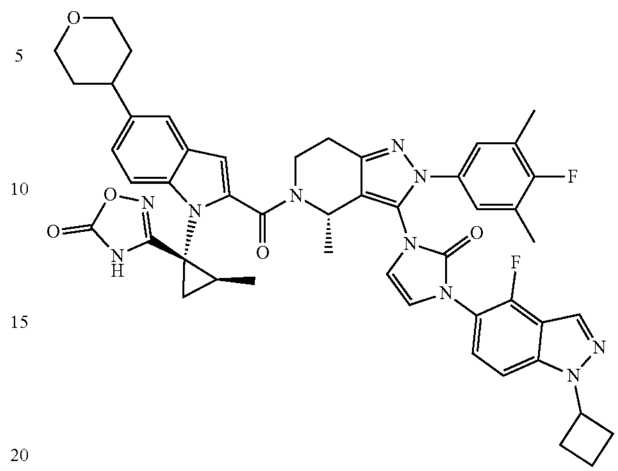
21
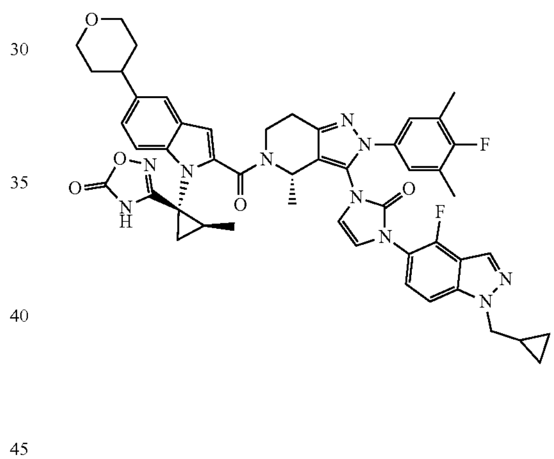
and
65
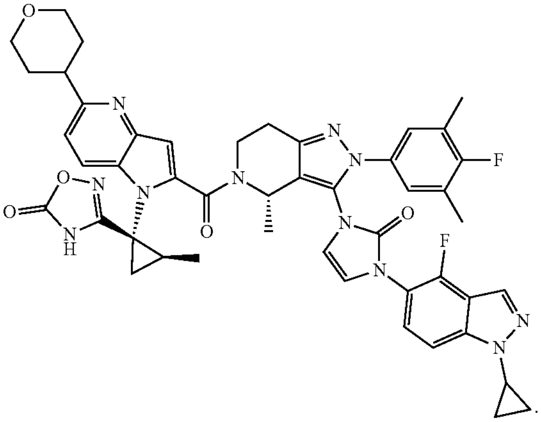
.
Yet still another aspect of the present disclosure provides a compound, selected from the group consisting of:

-continued
1
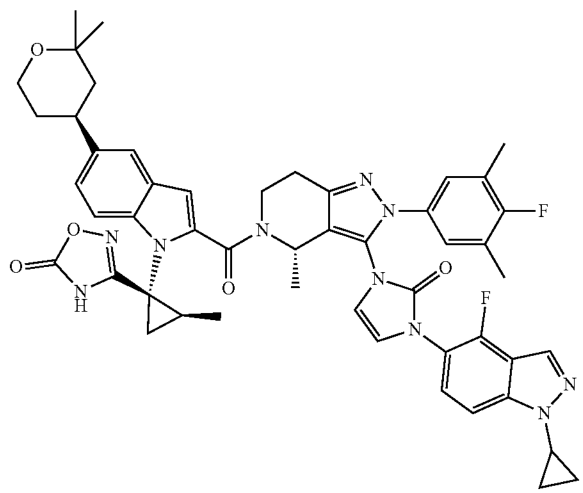
19
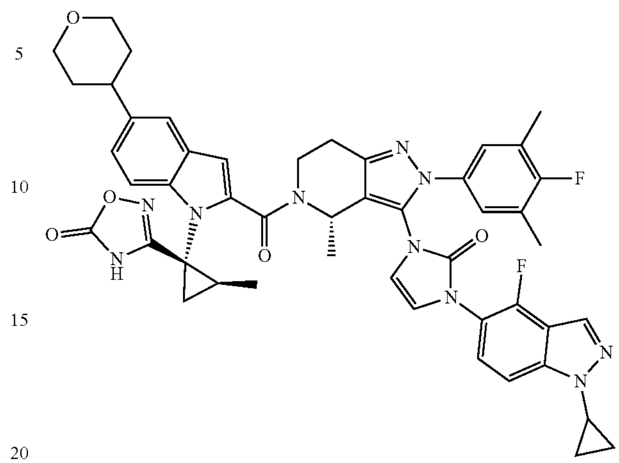
13
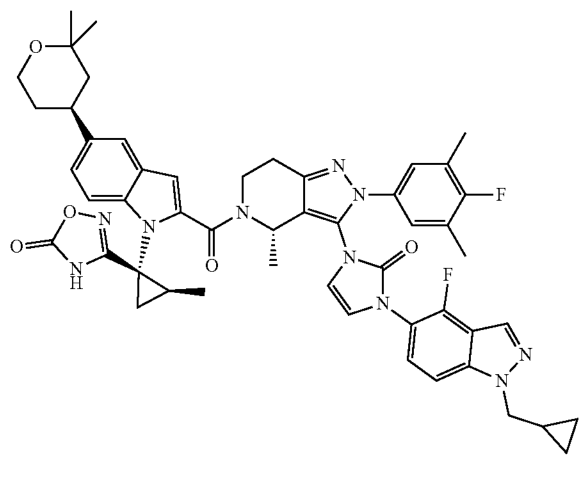
20
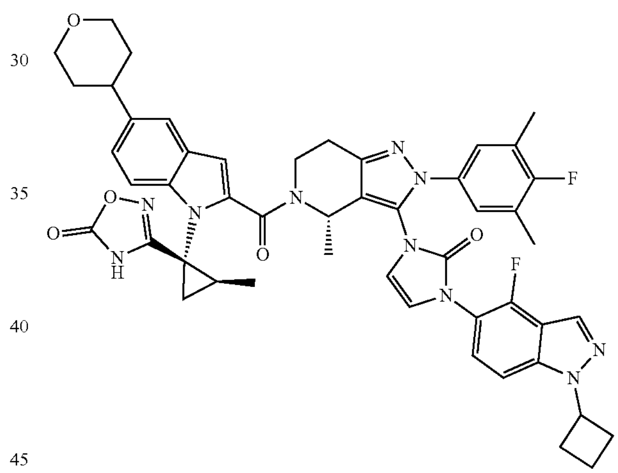
18
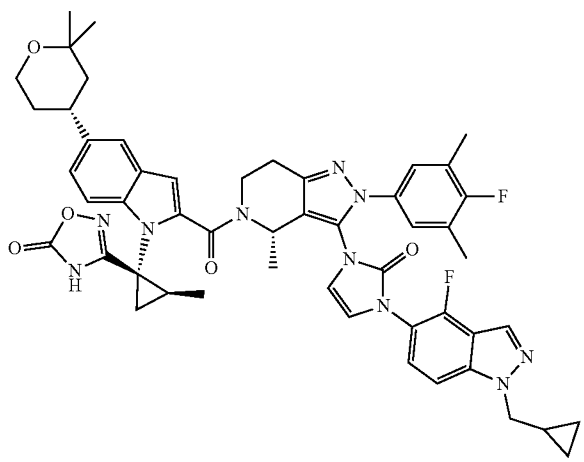
21
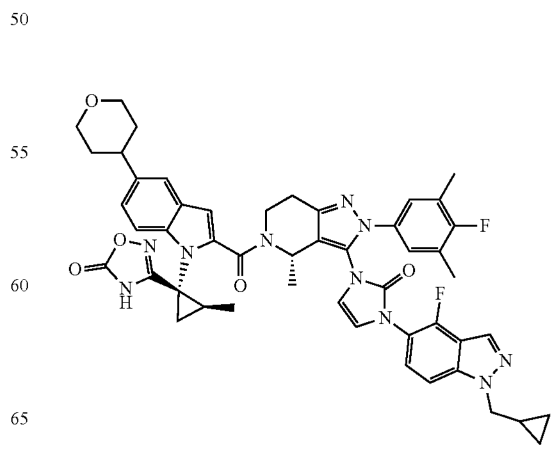
and -continued

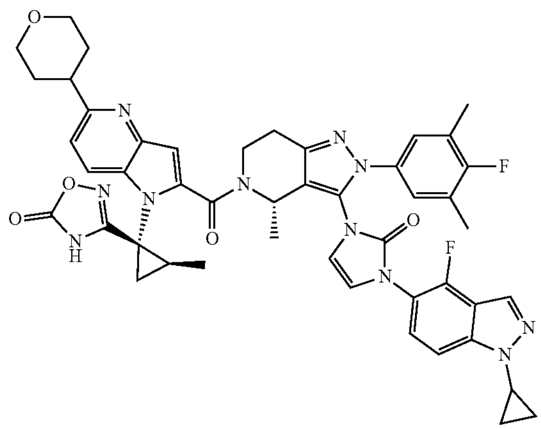

Yet still another aspect of the present disclosure provides the composition comprising the compound, the stereoisomer, the pharmaceutically acceptable salt, or the deuterated compound thereof of the present disclosure, and a pharmaceutically acceptable excipient.

Yet still another aspect of the present disclosure provides a method for treating GLP-1R mediated diseases or conditions, comprising administering to a subject in need thereof a therapeutically effective amount of the compound, the stereoisomer, the pharmaceutically acceptable salt, or the deuterated compound thereof, or a pharmaceutical composition of the present disclosure.

DETAILED DESCRIPTION

In the following description, certain specific details are included to provide a comprehensive understanding of the various disclosed embodiments. However, those skilled in the art will recognize that embodiments may be achieved without the use of one or more of these specific details and with the use of other methods, components, materials, etc.

Unless otherwise required in this disclosure, throughout the specification and subsequent claims, the words "including" and "comprising" are to be interpreted in an open-ended, inclusive sense, i.e., "including, without limitation".

As used in this disclosure and the appended claims, singular referents without indication of quantity include plural referents unless the context clearly indicates otherwise.

Throughout this specification, references to "an embodiment" or "embodiments" or "in another embodiment" or "in some embodiments" means to include in at least one embodiment a specific reference element, structure or feature related to that embodiment as described in that embodiment. Accordingly, the phrases "in an embodiment" or "in an embodiment" or "in another embodiment" or "in some embodiments" appearing at various places throughout the specification are intended to mean that at least one embodiment includes a specific reference element or feature related to that embodiment as described therein. "in some embodiments" need not all refer to the same embodiment. In addition, specific elements, structures, or features may be combined in one or more embodiments in any suitable manner.

It should be understood that the singular form of the article "one" (corresponding to the English words "a", "an", and "the") is used in the specification of the present disclosure and the appended claims. "The" is used in the claims in the singular form to include objects in the plural unless the context explicitly states otherwise. Thus, for example, reference to an extended-release tablet comprising "pharmaceutically acceptable excipients" includes one pharmaceutically acceptable excipient or two or more pharmaceutically acceptable excipients.

It should be understood that the singular form of the article "a" (corresponding to the English "a", "an", and "the") used in this disclosure and the accompanying claims includes plural objects unless otherwise explicitly stated in the text. Therefore, for example, a sustained-release tablet containing "pharmaceutically acceptable excipients" includes one pharmaceutically acceptable excipient or two or more pharmaceutically acceptable excipients.

Definition

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or "$C_u$-$C_v$" indicates that the following group has from u to v carbon atoms, where u and v are integers. For example, "$C_{1-6}$ alkyl" or "$C_1$-$C_6$ alkyl" indicates that the alkyl group has from 1 to 6 carbon atoms. "$C_3$-$C_{10}$ cycloalkyl" describes a cycloalkyl group having a total of 3 to 10 carbon atoms.

The terms "and/or" are used in this disclosure to denote "and" or "or" unless otherwise indicated.

"Substituted" as used herein refers to wherein one or more hydrogen atoms of the group are independently replaced by one or more substituents (e.g., 1, 2, 3, or 4 or more) as indicated. The substituent is selected from the following substituents, but are not limited to: alkyl, cycloalkyl, aryl, heteroaryl, heteroaryl, hydroxy, protected hydroxy, alkoxy, aryloxy, mercapto, alkylthio, arylsulfanyl, cyano, halogenated, carbonyl, thiocarbonyl, O-carbamoyl, N-carbamoyl O-thiocarbamoyl, N-thiocarbamoyl, C-acylamino, N-acylamino, S-sulfinylamino, N-sulfinylamino, C-carboxylic, protected C-carboxylic, O-carboxylic, isocyanatocarbonyl, cyanothiocyanatocarbonyl, isothiocyanatocarbonyl, nitro, methyldimethylsilanyl, trihalomethanesulfonyl, —NR' R" (R' and R" are alkyl groups as defined in this disclosure) or a protected amino group.

"Alkyl" is a monovalent or divalent linear or branched saturated hydrocarbon radical. For example, an alkyl group can have 1 to 10 carbon atoms (i.e., $C_{1-10}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-Propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2, 3-dimethyl-2-butyl (—$C(CH_3)_2CH(CH_3)_2$), 3, 3-dimethyl-2-butyl (—$CH(CH_3)C(CH_3)_3$, and octyl (—$(CH_2)_7CH_3$). Alkyl groups can be unsubstituted or substituted.

The alkyl group may be optionally substituted, i.e., substituted or unsubstituted. When substituted, the substituent group is individually and independently selected from one or more of the following: cycloalkyl, aryl, heteroaryl, heteroaryl, hydroxy, alkoxy, aryloxy, thiol, alkylthio, arylthio, cyano, halo, carbonyl, thiocarbonyl, O-carbamoyl, N-carbamoyl, O-thiocarbamoyl, N-thiocarbamoyl, C-acylamino. N-acyl amino, S-sulfinylamino, N-sulfinylamino, C-carboxyl, O-carboxyl, isocyanato, cyanothio, isothiocyanato, nitro, methylsilyl, trihalomethanesulfonyl, —NR'R" (R' and R" are alkyl groups as defined in the present disclosure) or amino groups including mono- and di-substituted amino groups, and protected derivatives thereof.

In some embodiments, exemplary examples of alkyl groups that can be used in the present disclosure include, but are not limited to, methyl, ethyl, propyl, isopropyl, butyl, isobutyl, tert-butyl, pentyl, and hexyl. Whenever a substituent is described as being "optionally substituted", the substituent may be substituted with one of the above substituents.

"Alkoxy" refers to the group —O-alkyl, where alkyl is as defined above. For example, $C_{1-4}$ alkoxy refers to an —O-alkyl group having 1 to 4 carbons. Alkoxy groups can be unsubstituted or substituted.

"Alkoxyalkyl" is an alkoxy group attached to an alkyl as defined above, such that the alkyl is divalent. For example, $C_{2-6}$ alkoxyalkyl includes —$CH_2$—OMe, —$CH_2$—O-iPr, —$CH_2$—$CH_2$—OMe, —$CH_2$—$CH_2$—O—$CH_2$—$CH_3$, and —$CH_2$—$CH_2$—O-tBu. Alkoxyalkyl groups can be unsubstituted or substituted.

"Alkenyl" is a monovalent or divalent linear or branched hydrocarbon radical with at least one carbon-carbon double bond. For example, an alkenyl group can have 2 to 8 carbon atoms (i.e., $C_{2-8}$ alkenyl) or 2 to 6 carbon atoms (i.e., $C_{2-6}$ alkenyl) or 2 to 4 carbon atoms (i.e., $C_{2-4}$ alkenyl). Examples of alkenyl groups include, but are not limited to, ethenyl (—$CH{=}CH_2$), allyl (—$CH_2CH{=}CH_2$), and —$CH_2$—$CH{=}CH$—$CH_3$. Alkenyl groups can be unsubstituted or substituted.

"Alkynyl" is a monovalent or divalent linear or branched hydrocarbon radical with at least one carbon-carbon triple bond. For example, an alkynyl group can have 2 to 8 carbon atoms (i.e., $C_{2-8}$ alkynyl) or 2 to 6 carbon atoms (i.e., $C_{2-6}$ alkynyl) or 2 to 4 carbon atoms (i.e., $C_{2-4}$ alkynyl). Examples of alkynyl groups include, but are not limited to, acetylenyl (—$C{\equiv}CH$), propargyl (—$CH_2C{\equiv}CH$), and —$CH_2$—$C{\equiv}C$—$CH_3$. Alkynyl groups can be unsubstituted or substituted.

"Oxo" as used herein refers to =O.

"Halogen" or "halo" refers to fluoro (—F), chloro (—Cl), bromo (—Br) and iodo (—I).

"Haloalkyl" is an alkyl as defined herein, wherein one or more hydrogen atoms of the alkyl are independently replaced by a halogen, which may be the same or different, such that the alkyl is divalent. The alkyl group and the halogen can be any of those described above. In some embodiments, the haloalkyl defines the number of carbon atoms in the alkyl portion, e.g., $C_{1-4}$ haloalkyl includes $CF_3$, $CH_2F$, $CHF_2$, $CH_2CF_3$, $CH_2CH_2CF_3$, $CCl_2CH_2CH_2CH_3$, and $C(CH_3)_2(CF_2H)$. Haloalkyl groups can be unsubstituted or substituted.

"Haloalkoxy" is an alkoxy as defined herein, wherein one or more hydrogen atoms of the alkyl in the alkyloxy are independently replaced by a halogen, which may be the same or different, such that the alkyl is divalent. The alkoxy group and the halogen can be any of those described above. In some embodiments, the haloalkoxy defines the number of carbon atoms in the alkyl portion, e.g., $C_{1-4}$ haloalkoxy includes $OCF_3$, $OCH_2F$, $OCH_2CF_3$, $OCH_2CH_2CF_3$, $OCCl_2CH_2CH_2CH_3$, and $OC(CH_3)_2(CF_2H)$. Haloalkoxy groups can be unsubstituted or substituted.

"Cycloalkyl" is a monovalent or divalent single all carbon ring or a multiple condensed all carbon ring system wherein the ring in each instance is a non-aromatic saturated or unsaturated ring. For example, in some embodiments, a cycloalkyl group has 3 to 12 carbon atoms, 3 to 10 carbon atoms, 3 to 8 carbon atoms, 3 to 6 carbon atoms, 3 to 5 carbon atoms, or 3 to 4 carbon atoms. Exemplary single ring cycloalkyl groups include cyclopropyl, cyclobutyl, cyclopentyl, cyclohexyl, cyclohexenyl, cycloheptyl, cycloheptenyl, and cyclooctyl. Cycloalkyl also includes multiple condensed ring systems (e.g., ring systems comprising 2 rings) having about 7 to 12 carbon atoms. The rings of the multiple condensed ring system can be connected to each other via fused, spiro, or bridged bonds when allowed by valency requirements. Exemplary multiple ring cycloalkyl groups include octahydropentalene, bicyclo[2. 2. 1]heptane, bicyclo[2. 2. 2]octane, bicyclo[2. 2. 2]oct-2-ene, and spiro[2. 5]octane. Cycloalkyl groups can be unsubstituted or substituted.

The term "cycloalkyl" is intended to include a cycloalkyl group as defined above optionally substituted by one or more groups selected from the following substituents: cycloalkyl, aryl, heteroaryl, heteroaliphatic, hydroxy, alkoxy, aryloxy, mercapto, alkylthio, arylthio, cyano, halo, carbonyl, thio carbonyl, isocyanate, cyanothionyl, isothiocyanate, nitro, —NR'R" (R' and R" are alkyl groups as defined in the present disclosure) or amino groups including mono- and di-substituted amino groups, and protected derivatives thereof.

In some embodiments, "$C_{3-6}$ cycloalkyl" refers to a cycloalkyl group as defined above having three to six carbon atoms. $C_{3-6}$ cycloalkyl groups may be optionally substituted as defined above for cycloalkyl.

In some embodiments, "$C_{3-8}$ cycloalkyl" refers to a cycloalkyl group having from three to eight carbon atoms as defined above. $C_{3-8}$ cycloalkyl groups may be optionally substituted as defined above for cycloalkyl.

In some embodiments, the term "$C_{3-15}$ cycloalkyl" refers to a cycloalkyl group as defined above having from three to twelve carbon atoms. $C_{3-15}$ cycloalkyl groups may be optionally substituted as defined above for cycloalkyl.

"Aryl" as used herein refers to a monovalent or divalent single all carbon aromatic ring or a multiple condensed all carbon ring system wherein the ring is aromatic. For example, in some embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which multiple rings are aromatic. The rings of the multiple condensed ring system can be connected to each other via fused bonds when allowed by valency requirements. It is also understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl. Non-limiting examples of aryl groups include, but are not limited to, phenyl, naphthyl, anthracenyl, and the like. Aryl groups can be unsubstituted or substituted.

"Heterocyclyl" or "heterocycle" or "heterocycloalkyl" or "heterocyclic" or "heterocyclic ring" as used herein refers to a single saturated or partially unsaturated non-aromatic ring or a non-aromatic multiple ring system that has at least one heteroatom in the ring (i.e., at least one annular (i.e., ring-shaped) heteroatom selected from oxygen, nitrogen, and sulfur). Unless otherwise specified, a heterocyclyl group has from 3 to about 20 annular atoms, for example from 3 to 12 annular atoms, for example from 4 to 12 annular atoms, 4 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane(epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3. 3]heptan-6-yl, 6-oxa-1-azaspiro[3. 3]heptan-1-yl, 2-thia-6-azaspiro[3. 3]heptan-6-yl, 2, 6-diazaspiro[3. 3]heptan-2-yl, 2-azabicyclo[3. 1. 0]hexan-2-yl, 3-azabicyclo[3. 1. 0]hexanyl, 2-azabicyclo[2. 1. 1]hexanyl, 2-azabicyclo[2. 2. 1]heptan-2-yl, 4-azaspiro[2. 4]heptanyl, 5-azaspiro[2. 4]heptanyl, and the like. Heterocyclyl groups can be unsubstituted or substituted.

"5-10 membered heteroaryl" refers to an aromatic ring that has at least one atom other than carbon in the ring, wherein the atom is selected from the group consisting of oxygen, nitrogen and sulfur; "5-10 membered heteroaryl" also includes multiple condensed ring systems that have at least one such aromatic ring, which multiple condensed ring systems are further described below. Thus, "5-10 membered heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary 5-10 membered heteroaryl ring systems include but are not limited to pyridyl, pyrimidinyl, oxazolyl or furyl. "5-10 membered heteroaryl" also includes multiple condensed ring systems (e.g., ring systems comprising 2, 3 or 4 rings) wherein a 5-10 membered heteroaryl group, as defined above, is condensed with one or more rings selected from 5-10 membered heteroaryls (to form for example 1, 8-naphthyridinyl) and aryls (to form, for example, benzimidazolyl or indazolyl) to form the multiple condensed ring system. Thus, a 5-10 membered heteroaryl (a single aromatic ring or multiple condensed ring system) can have about 1-20 carbon atoms and about 1-6 heteroatoms within the 5-10 membered heteroaryl ring. For example, tetrazolyl has 1 carbon atom and 4 nitrogen heteroatoms within the ring. The rings of the multiple condensed ring system can be connected to each other via fused bonds when allowed by valency requirements. It is to be understood that the individual rings of the multiple condensed ring system may be connected in any order relative to one another. It is to be understood that the point of attachment for a 5-10 membered heteroaryl or 5-10 membered heteroaryl multiple condensed ring system can be at any suitable atom of the 5-10 membered heteroaryl or 5-10 membered heteroaryl multiple condensed ring system including a carbon atom and a heteroatom (e.g., a nitrogen). It also to be understood that when a reference is made to a certain atom-range membered (e.g., a 5-10 membered heteroaryl), the atom range is for the total ring atoms of the 5-10 membered heteroaryl and includes carbon atoms and heteroatoms. It is also to be understood that the rings of the multiple condensed ring system may include an aryl ring fused to a heterocyclic ring with saturated or partially unsaturated bonds (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. For example, a 5-10 membered heteroaryl includes thiazolyl and a 5-10 membered heteroaryl includes quinolinyl. Exemplary 5-10 membered heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, benzofuranyl, benzimidazolyl, thianaphthenyl, pyrrolo[2, 3-b]pyridinyl, quinazolinyl-4(3H)-one, triazolyl, and tetrazolyl. 5-10 membered heteroaryl groups can be unsubstituted or substituted.

The term "5-10 membered heteroaryl" is intended to include an aromatic ring group as defined above optionally substituted by one or more groups selected from the following substituents: cycloalkyl, aryl, heteroaryl, heteroaliphatic, hydroxy, alkoxy, aryloxy, mercapto, alkylthio, arylthio, cyano, halo, carbonyl, thio carbonyl, isocyanate, cyanothionyl, isothiocyanate, nitro, —NR'R" (R' and R" are alkyl groups as defined in the present disclosure) or amino groups including mono- and di-substituted amino groups, and protected derivatives thereof.

"($C_{1-6}$ alkyl)carbonyl" means the group: ($C_{1-6}$ alkyl)-C(O)— group, wherein alkyl is defined as mentioned above. The carbonyl refers to the C(O)— group, which is a carbon atom double-bonded to an oxygen atom. Examples include methyl carbonyl (acetyl), ethyl carbonyl (propionyl), n-propyl carbonyl, isopropyl carbonyl, n-butyl carbonyl, isobutyl carbonyl, sec-butyl carbonyl, tert-butyl carbonyl, 1-methylpropyl carbonyl, n-amyl carbonyl, isoamyl carbonyl, 2-methylbutyl carbonyl, 1,1-dimethylpropyl carbonyl, 1-ethylpropyl carbonyl, n-hexyl carbonyl, 4-methylpentyl carbonyl, and 2-ethylbutyl carbonyl. Carbonyl ethylpentane, 4-methylpentylcarbonyl, and 2-ethylbutylcarbonyl.

A "compound of the present disclosure" includes compound disclosed herein, for example a compound of the present disclosure includes compound of Formula (I), (II), (III), (IV), (V), (VI), (VII), (VIII), (IX), (X), (XI), (Ia), (Ib), (Ic), (Id), (Ie), (If), and (Ig), but also includes the compound of the examples.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Therapeutically effective amount" or "effective amount" as used herein refers to an amount that is effective to elicit the desired biological or medical response, including the amount of a compound that, when administered to a subject for treating a disease, is sufficient to affect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the subject.

Provided are also pharmaceutically acceptable salts, hydrates, solvates, tautomeric forms, polymorphs, and prodrugs of the compounds described herein.

"Pharmaceutically acceptable" refers to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1, 6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21st Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $N(C_1\text{-}C_4\ alkyl)_4^+$. Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, tautomer, diastereomers, and other stereoisomeric forms that may be defined, in terms of absolute stereochemistry, as (R)- or (S)- or, as (D)- or (L)- for amino acids, as well as deuterated analogs thereof. The chemical formula shown in the present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. In some embodiments, the present disclosure includes tautomers of said compounds.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Prodrug" as used herein refers to a derivative of a drug that upon administration to the human body is converted to the parent drug according to some chemical or enzymatic pathway. In some embodiments, a prodrug is a biologically inactive derivative of a drug that upon administration to the human body is converted to the biologically active parent drug according to some chemical or enzymatic pathway.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival. "At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

Compound

One aspect of the present disclosure provides a compound of Formula (I), a stereoisomer, a pharmaceutically acceptable salt, or a deuterated compound thereof:

Formula (I)

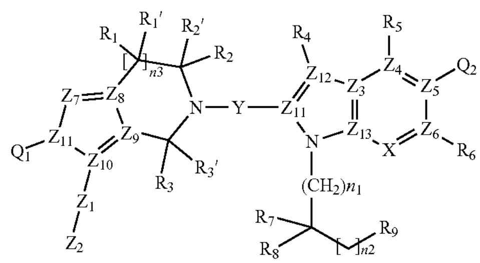

wherein:

X is selected from the group consisting of N and —$CR^a$; wherein $R^a$ is selected from the group consisting of hydrogen, halogen, and $C_{1-6}$ alkyl;

wherein Y is —C(═O)—;

wherein each of $Z_3$, $Z_4$, $Z_5$, $Z_6$, $Z_7$, $Z_8$, $Z_9$, $Z_{10}$, $Z_{11}$, $Z_{12}$ and $Z_{13}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and —$NR^{Qa}R^{Qb}$, or wherein two $C_{1-6}$ alkyl groups optionally together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein each of $R_1$, $R_2$, $R_3$, $R_1'$, $R_2'$ and $R_3'$ is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl; or wherein $R_2$ and $R_3$ together with the carbon atom to which they are attached form 4- to 8-membered heterocycloalkyl;

each of $R_4$, $R_5$ and $R_6$ is independently selected from the group consisting of hydrogen, halogen and $C_{1-6}$ alkyl;

each of $R_7$ and $R_8$ is independently selected from the group consisting of hydrogen and $C_{1-6}$ alkyl, wherein $C_{1-6}$ alkyl is optionally substituted with one or more substituents independently selected from the group consisting of halogen and $C_{3-15}$ cycloalkyl;

or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl, wherein $C_{1-6}$ alkyl is optionally substituted by one or more substituents independently selected from the group consisting of halogen, hydroxyl, —$NR^{7a}R^{7b}$, $C_{1-6}$ alkoxy and 3- to 12-membered heterocyclic, and $R^{7a}$ and $R^{7b}$ are independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ carbocyclic ring;

n1 is 0, 1, 2 or 3;

n2 is 0, 1, 2, 3, 4 or 5;

n3 is 0 or 1;

$R_9$ is selected from the group consisting of:

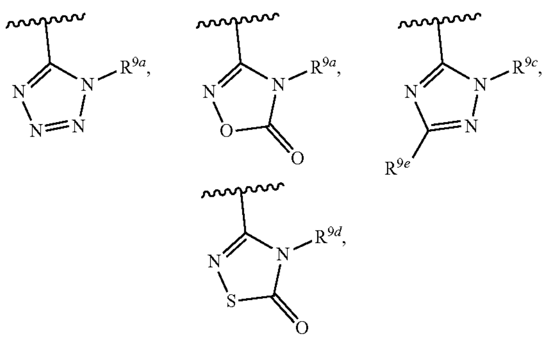

—$CO_2R^{9f}$ and —C(═O)—$NR^{9g}R^{9h}$; and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy;

$R^{9e}$ is selected from the group consisting of hydrogen and $C_{1-6}$ alkyl optionally substituted by one or more halogen;

$R^{9f}$ is selected from the group consisting of hydrogen and $C_{1-6}$ alkyl;

$R^{9h}$ is selected from the group consisting of hydrogen, $C_{1-6}$ alkyl, ($C_{1-6}$ alkyl) carbonyl, cyano and —S(═O)$_{n9}$—$R^{9i}$; n9 is 0, 1 or 2;

$R^{9i}$ is $C_{1-6}$ alkyl;

$Z_1$ is selected from the group consisting of:

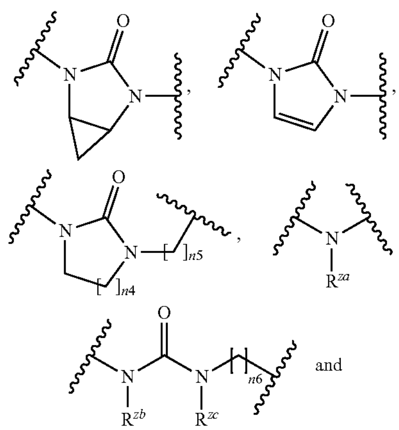

and

-continued

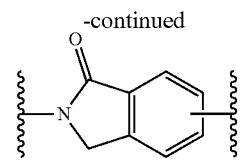

wherein $R^{za}$ is selected from the group consisting of hydrogen, $C_{1-6}$ alkyl and ($C_{1-6}$ alkyl) carbonyl, and each of $R^{zb}$ and $R^{zc}$ is independently selected from the group consisting of hydrogen and $C_{1-6}$ alkyl;

n4 is 1, 2 or 3;

each of n5 and n6 is independently an integer selected from 0 to 10;

$Z_2$ is 5- to 10-membered heteroaryl; and $Z_2$ is substituted with one halogen and one of $C_3$-$C_{15}$ cycloalkyl and $C_1$-$C_6$ alkyl-$C_3$-$C_{15}$ cycloalkyl; wherein the cycloalkyl or alkyl is optionally substituted by one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted with halogen.

In some embodiments, in the compound of Formula (I), the stereoisomer, the pharmaceutically acceptable salt, or the deuterated compound thereof, $Z_2$ is indazolyl.

In some embodiments, in the compound of Formula (I), the stereoisomer, the pharmaceutically acceptable salt, or the deuterated compound thereof, the indazolyl is substituted with one halogen and one of $C_3$-$C_{15}$ cycloalkyl and $C_1$-$C_6$ alkyl-$C_3$-$C_{15}$ cycloalkyl.

In some embodiments, in the compound of Formula (I), the stereoisomer, the pharmaceutically acceptable salt, or the deuterated compound thereof, $Q_1$ is $C_{6-10}$ aryl, and the $C_{6-10}$ aryl is optionally substituted with one to five substituents selected from the group consisting of halogen, $C_{1-6}$ alkyl, $C_{1-6}$ haloalkyl, and $C_{1-6}$ alkoxy.

In some embodiments, in the compound of Formula (I), the stereoisomer, the pharmaceutically acceptable salt, or the deuterated compound thereof, the compound is selected from the group consisting of:

1

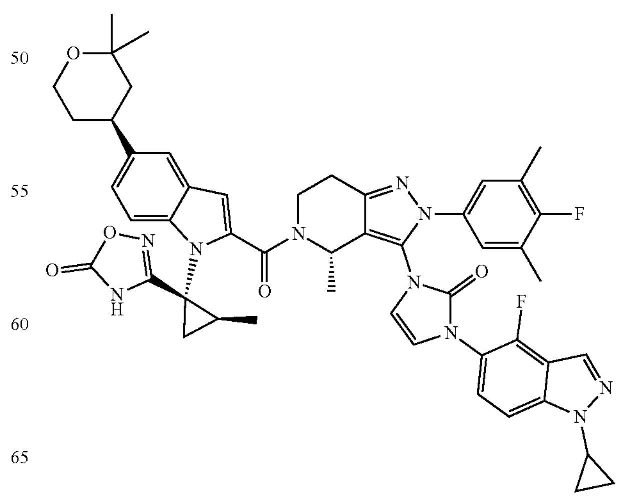

-continued

2

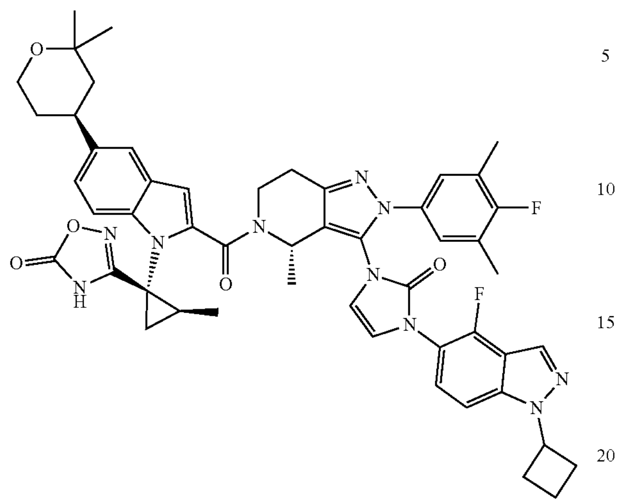

5

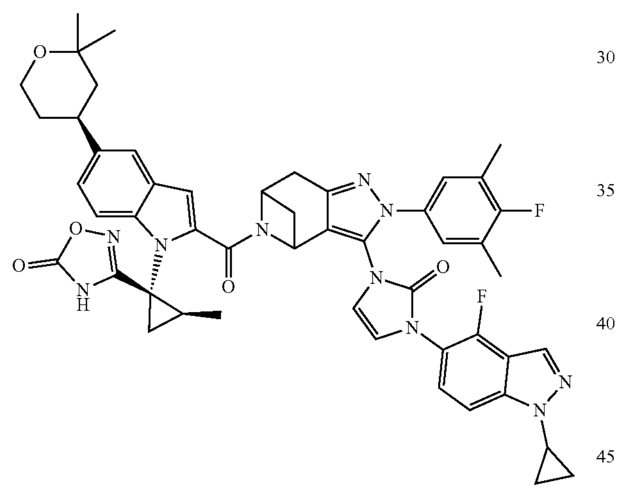

13

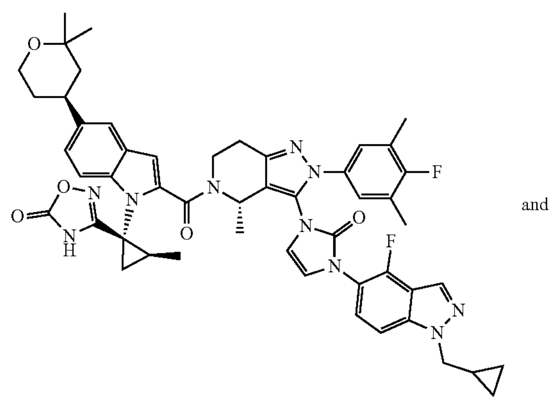

and

-continued

18

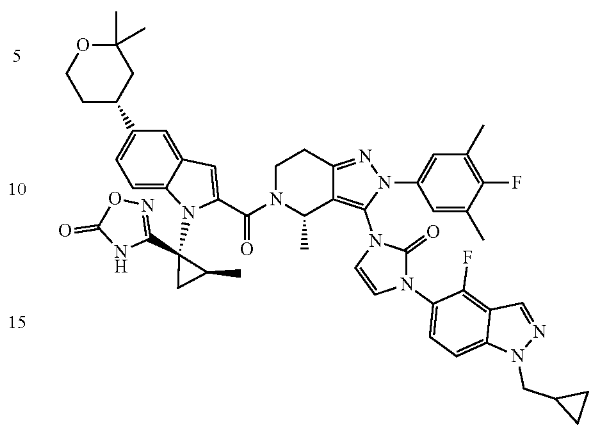

In some embodiments, in the compound of Formula (I), the stereoisomer, the pharmaceutically acceptable salt, or the deuterated compound thereof, the compound has a structure of Formula (II):

Formula (II)

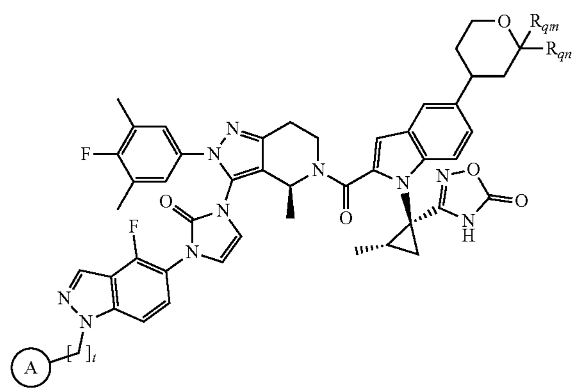

wherein:

ring A is selected from the group consisting of cyclopropyl, cyclobutyl, and cyclopentyl;

t is 0 or 1; and $R_{qm}$ and $R_{qn}$ are each independently selected from the group consisting of hydrogen and $C_{1-6}$ alkyl.

In some embodiments, in the compound of Formula (I), the stereoisomer, the pharmaceutically acceptable salt, or the deuterated compound thereof, the compound is selected from the group consisting of:

-continued
19
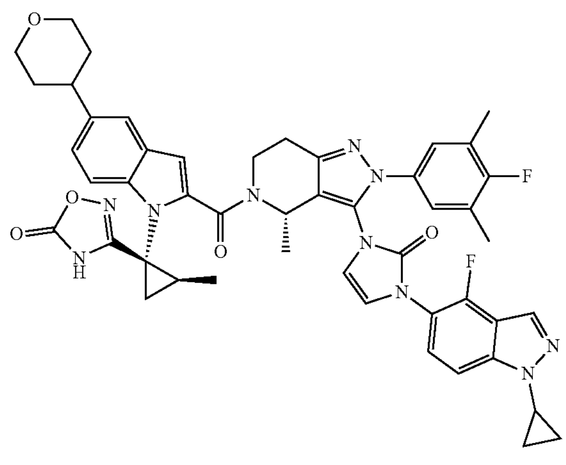
75
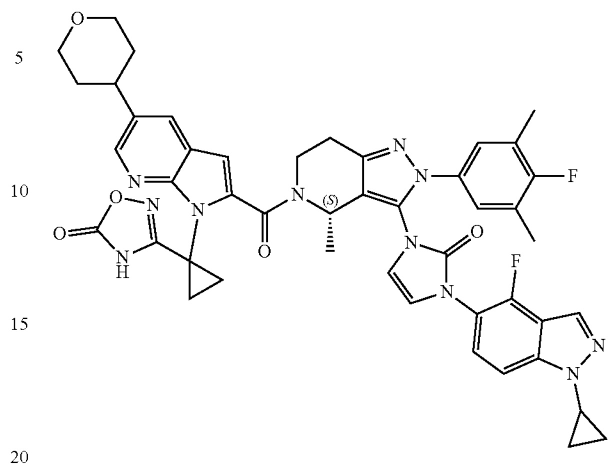
20
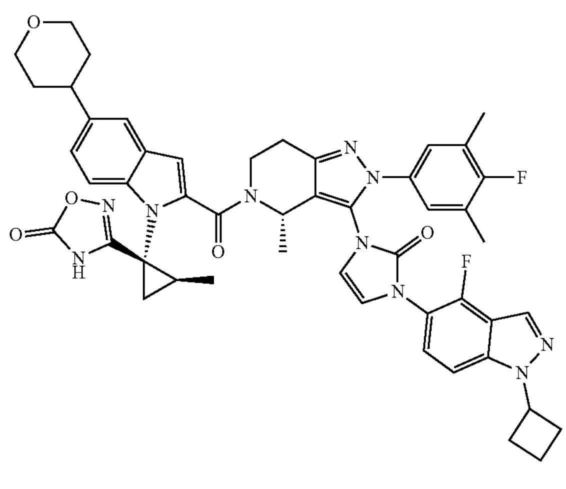
65
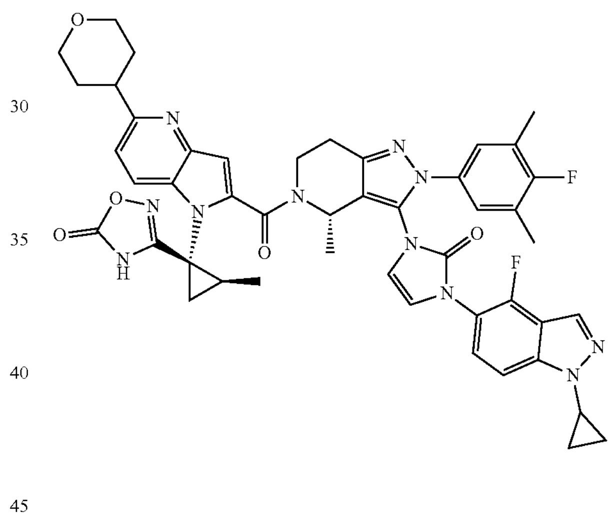
21
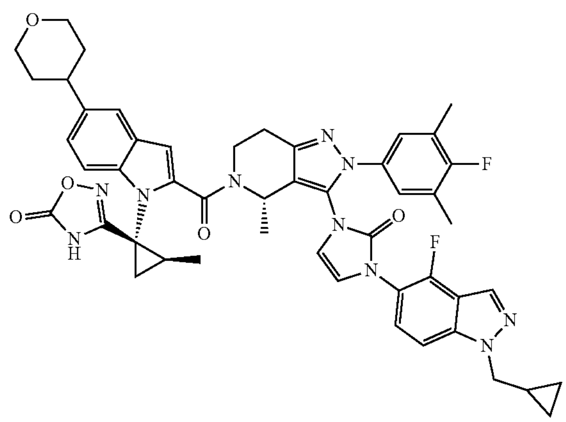
66
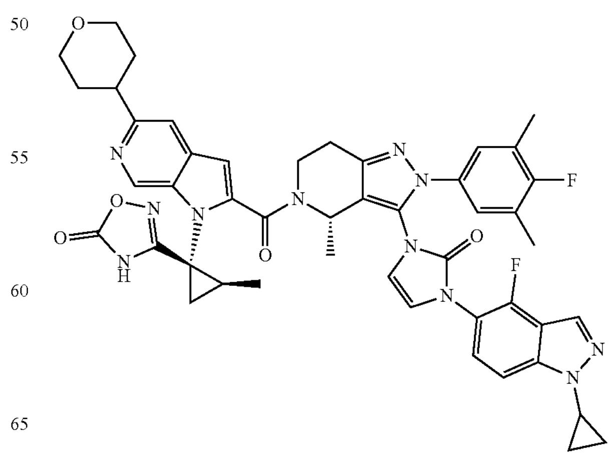

-continued

67

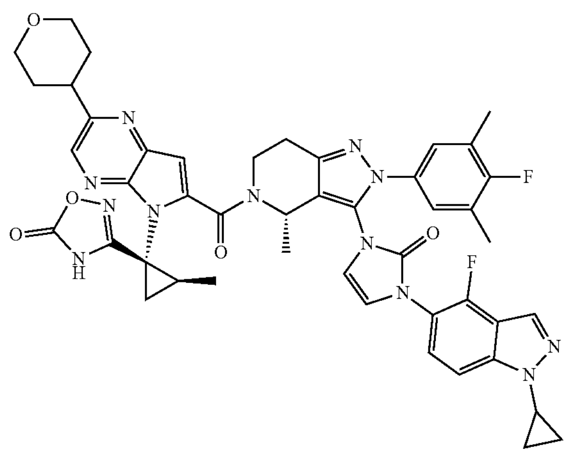

68

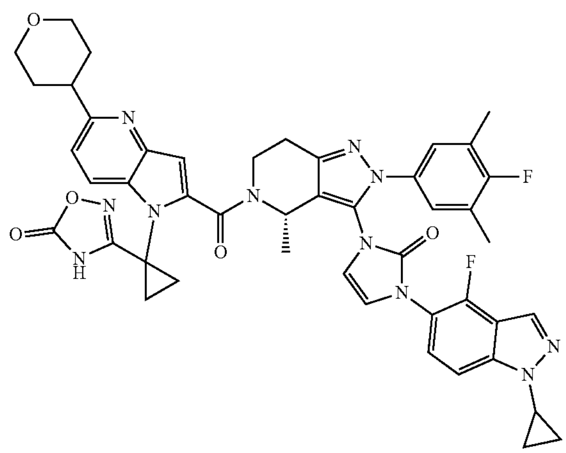

69

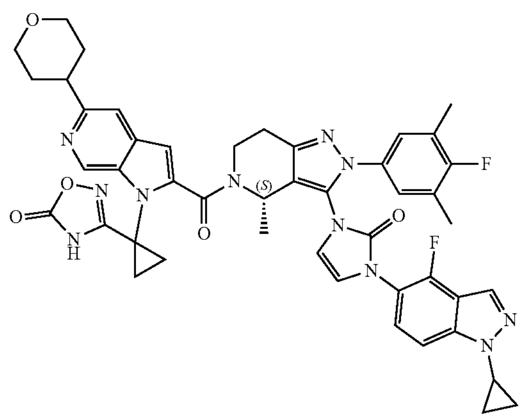

-continued

70

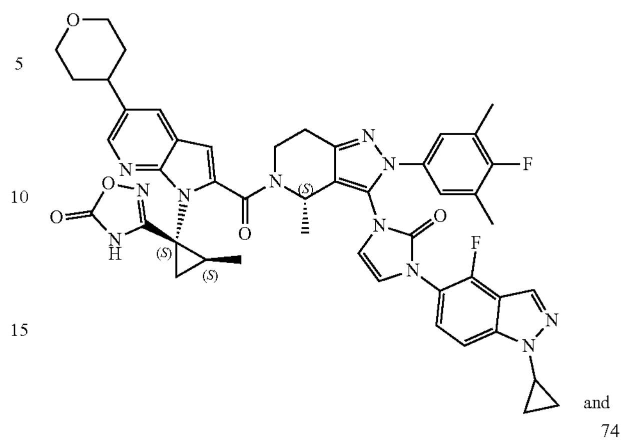

and

74

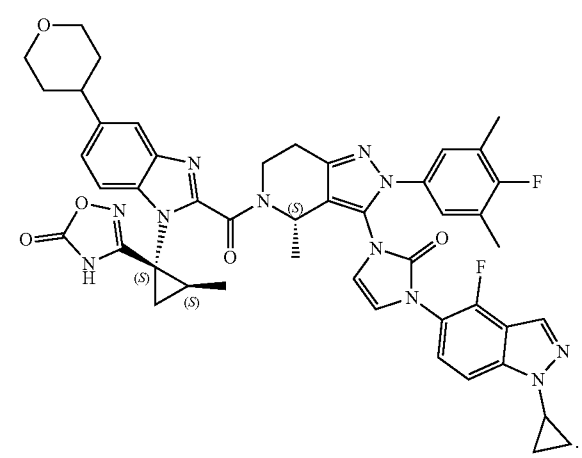

Another aspect of the present disclosure provides a compound of Formula (111), a stereoisomer, a pharmaceutically acceptable salt, or a deuterated compound thereof:

Formula (III)

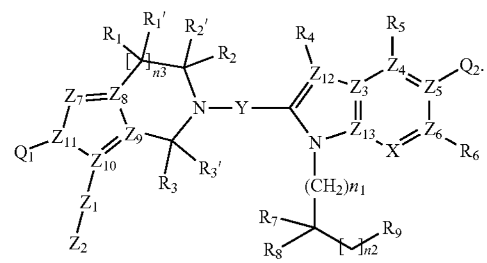

wherein:

X is —$CR^a$; $R^a$ is H;

Y is —C(═O)—;

$Z_3$, $Z_4$, $Z_5$, $Z_6$, $Z_8$, $Z_9$, $Z_{10}$, $Z_{12}$ and $Z_{13}$ are C;

$Z_7$ and $Z_{11}$ are N;

$Q_1$ is $C_{6-10}$ aryl, wherein $C_{6-10}$ aryl is optionally substituted with one to five substituents independently selected from the group consisting of halogen and $C_{1-6}$ alkyl;

$Q_2$ is 3- to 12-membered heterocyclic; wherein 3- to 12-membered heterocyclic is optionally substituted with 1-3 substituents independently selected from the group consisting of halogen and $C_{1-6}$ alkyl, or wherein two $C_{1-6}$ alkyl groups optionally together with the carbon atoms to which they are attached form $C_{3-8}$ carbocyclic ring;

wherein each of $R_1$, $R_2$, $R_1'$, and $R_2'$ is independently selected from the group consisting of hydrogen and $C_{1-6}$ alkyl;

$R_3$ and $R_3'$ are independently selected from the group consisting of hydrogen and $C_{1-6}$ alkyl;

$R_4$, $R_5$ and $R_6$ are H:

each of $R_7$ and $R_8$ is independently selected from the group consisting of hydrogen and $C_{1-6}$ alkyl; or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl;

$n_1$ is 0 or 1;

n2 is 0 or 1;

n3 is 1;

$R_9$ is

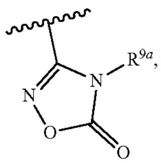

and $R^{9a}$ is H;

$Z_1$ is

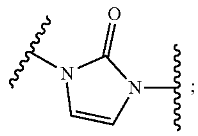 [SMILES: *n1ccn(*)c1=O ; ";"]

$Z_2$ is 5- to 10-membered heteroaryl, and $Z_2$ is substituted with one halogen and one of $C_3$-$C_{15}$ cycloalkyl and $C_1$-$C_6$ alkyl-$C_3$-$C_{15}$ cycloalkyl; wherein the cycloalkyl or alkyl is optionally substituted with one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted with halogen.

In some embodiments, in the compound of Formula (III), the stereoisomer, the pharmaceutically acceptable salt, or the deuterated compound thereof, $Q_1$ is

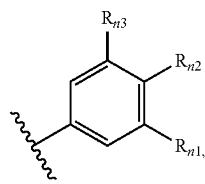

and $R_{n1}$ and $R_{n3}$ are each independently selected from the group consisting of H, methyl, and ethyl; $R_{n2}$ is halogen.

In some embodiments, in the compound of Formula (III), the stereoisomer, the pharmaceutically acceptable salt, or the deuterated compound thereof, $Q_2$ is

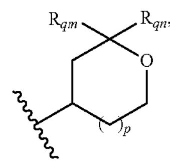

wherein $R_{qm}$ and $R_{qn}$ are each independently selected from the group consisting of H, methyl, and ethyl; or $R_{qm}$ and $R_{qn}$ together with the carbon atom to which they are attached to form $C_{3-6}$ cycloalkyl; p is 0, 1, or 2.

In some embodiments, in the compound of Formula (III), the stereoisomer, the pharmaceutically acceptable salt, or the deuterated compound thereof, $Z_2$ is

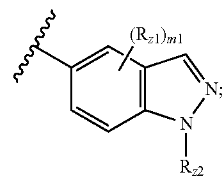

wherein $R_{z1}$ is halogen, m1 is 1;

$R_{z2}$ is selected from the group consisting of $C_{3-8}$ cycloalkyl and $C_{1-6}$ alkyl-$C_{3-8}$ cycloalkyl; and $R_{z2}$ is optionally substituted with one or more substituents selected from the group consisting of halogen, $C_{1-6}$ alkyl, and $C_{1-6}$ alkoxy.

In some embodiments, in the compound of Formula (III), or the stereoisomer, the pharmaceutically acceptable salt, or the deuterated compound thereof, $Z_2$ is

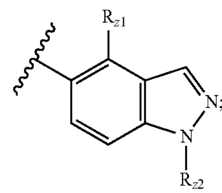

$R_{z1}$ is selected from the group consisting of F, Cl, and Br, $R_{z2}$ is selected from the group consisting of

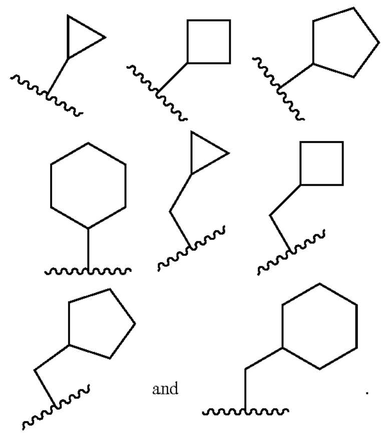

and .

In some embodiments, in the compound of Formula (III), the stereoisomer, the pharmaceutically acceptable salt, or the deuterated compound thereof, $Z_2$ is selected from the group consisting of

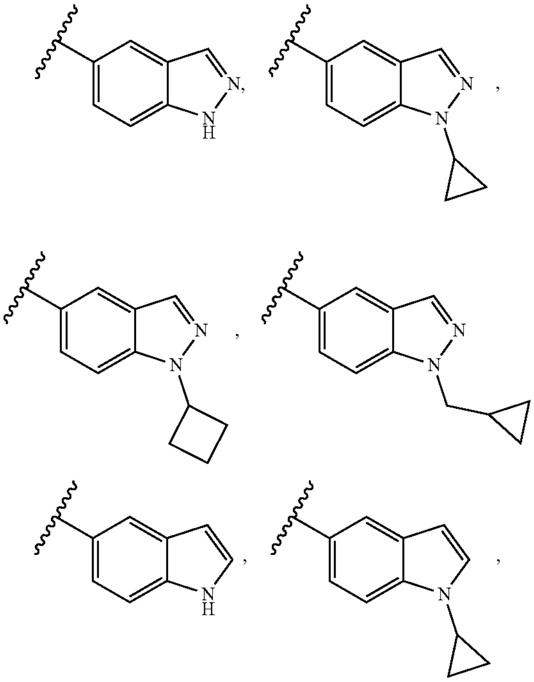

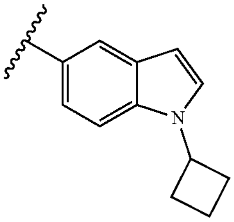

and

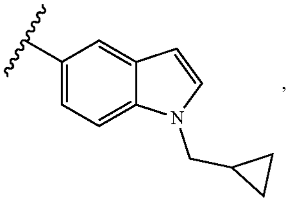

and $Z_2$ is substituted with one halogen.

In some embodiments, in the compound of Formula (III), the stereoisomer, the pharmaceutically acceptable salt, or the deuterated compound thereof, $Z_2$ is selected from the group consisting of

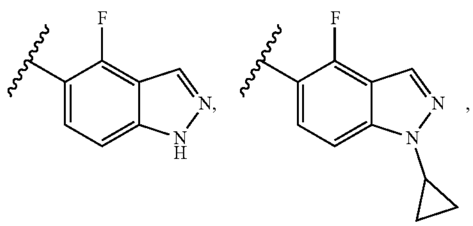

-continued

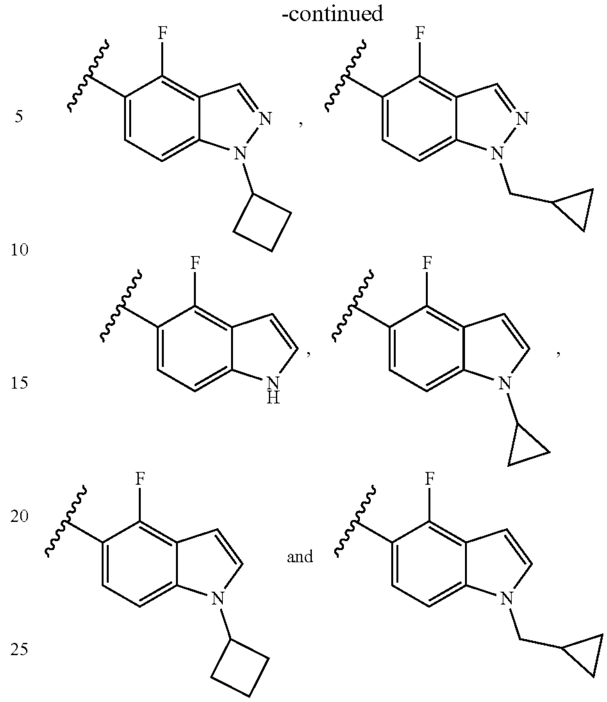

Still another aspect of the present disclosure provides a compound of Formula (IV), a stereoisomer, a pharmaceutically acceptable salt, or a deuterated compound thereof:

Formula (IV)

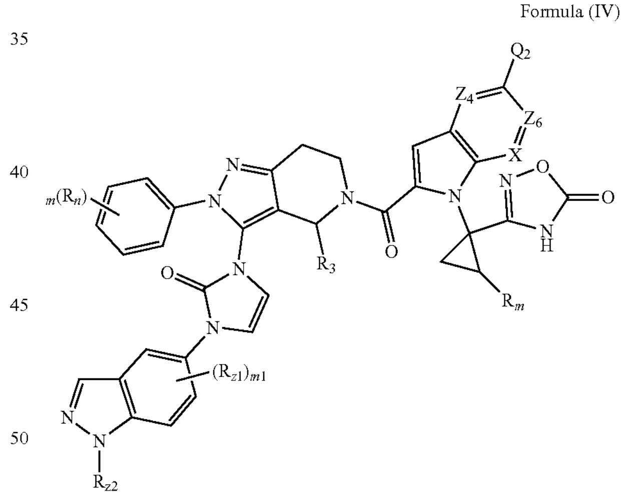

wherein:

each of X, $Z_4$ and $Z_6$ is independently selected from the group consisting of N and CH;

$R_{z1}$ is selected from the group consisting of halogen, $C_{1-3}$ alkyl, and $C_{3-8}$ cycloalkyl;

$R_{z2}$ is selected from the group consisting of $C_{3-8}$ cycloalkyl and $C_{1-6}$ alkyl-$C_{3-8}$ cycloalkyl; and $R_{z2}$ is optionally substituted with substituents independently selected from the group consisting of halogen, —OH, $C_{1-6}$ alkyl, and $C_{1-6}$ alkoxy;

m1 is 0, 1, 2 or 3.

In some embodiments, in the compound of Formula (IV), the stereoisomer, the pharmaceutically acceptable salt, or the deuterated compound thereof, $R_m$ is selected from the group consisting of H, $C_{1-6}$ alkyl, $C_{1-6}$ haloalkyl, and $C_{1-6}$ alkoxy;

$R_n$ is selected from the group consisting of halogen, $C_{1-6}$ alkyl, $C_{1-6}$ haloalkyl, and $C_{1-6}$ alkoxy;

m is 0, 1, 2, or 3;

$R_3$ is selected from the group consisting of H, halogen, $C_{1-6}$ alkyl, $C_{1-6}$ alkoxy and $C_{1-6}$ haloalkoxy.

In some embodiments, in the compound of Formula (IV), the stereoisomer, the pharmaceutically acceptable salt, or the deuterated compound thereof:

$R_{z1}$ is selected from the group consisting of F, Cl, Br, methyl, ethyl, n-Propyl, isopropyl and cyclopropyl;

m is 0, 1, 2 or 3;

$R_{z2}$ is selected from the group consisting of

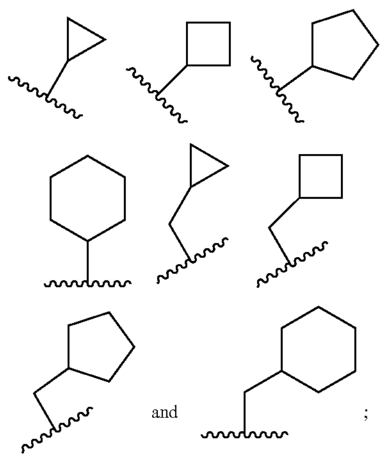

and ;

$R_m$ is independently selected from the group consisting of halogen, —$CH_3$, —$CH_2CH_3$ and —$OCH_3$;

$R_n$ is selected from the group consisting of methyl, ethyl, F, and Cl;

$R_3$ is methyl.

In some embodiments, in the compound of Formula (IV), the stereoisomer, the pharmaceutically acceptable salt, or the deuterated compound thereof:

$Q_2$ is

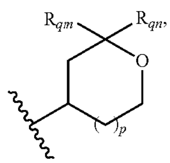

wherein $R_{qm}$ and $R_{qn}$ are each independently selected from the group consisting of H, methyl, and ethyl; or $R_{qm}$ and $R_{qn}$ together with the carbon atom to which they are attached form $C_{3-6}$ Cycloalkyl; p is 0, 1, or 2.

In some embodiments, in the compound of Formula (IV), the stereoisomer, the pharmaceutically acceptable salt, or the deuterated compound thereof, $Q_2$ is selected from the group consisting of

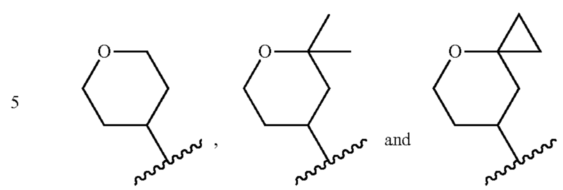

, and .

Yet still another aspect of the present disclosure provides a compound of Formula (V), a stereoisomer, a pharmaceutically acceptable salt, or a deuterated compound thereof:

Formula (V)

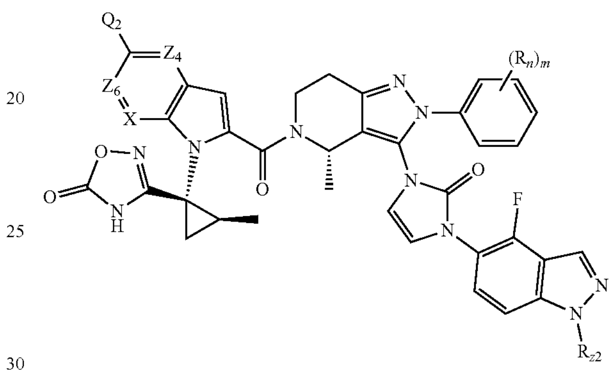

wherein:

each of X, $Z_4$ and $Z_6$ is independently selected from the group consisting of N and CH;

$Q_2$ is selected from the group consisting of

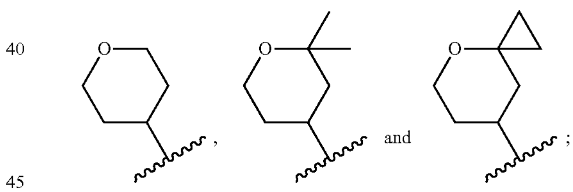

, and ;

$R_n$ is selected from the group consisting of halogen, $C_{1-6}$ alkyl, $C_{1-6}$ haloalkyl and $C_{1-6}$ alkoxy;

m is 0, 1, 2 or 3;

$R_{z2}$ is selected from the group consisting of $C_{3-8}$ cycloalkyl and $C_{1-6}$ alkyl-$C_{3-8}$ cycloalkyl; and $R_{z2}$ is optionally substituted with substituents independently selected from the group consisting of halogen, hydroxyl, $C_{1-6}$ alkyl and $C_{1-6}$ alkoxy.

In some embodiments, in the compound of Formula (V), the stereoisomer, the pharmaceutically acceptable salt, or the deuterated compound thereof, $R_{z2}$ is selected from the group consisting of

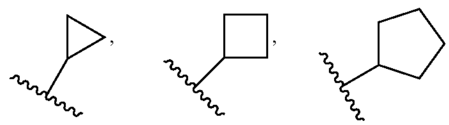

, , ,

-continued

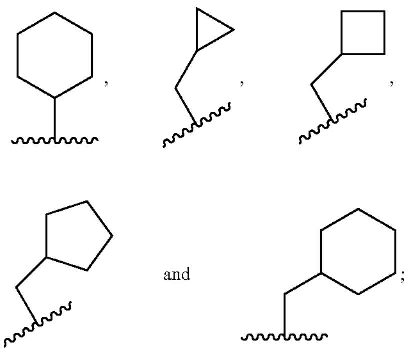

$R_u$ is selected from the group consisting of methyl, ethyl, F, and Cl.

In some embodiments, in the compound of Formula (V), the stereoisomer, the pharmaceutically acceptable salt, or the deuterated compound thereof, the compound has a structure of Formula (VI), Formula (VI)

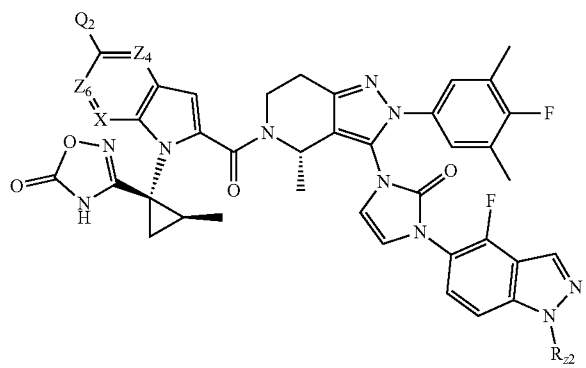

wherein:

each of X, $Z_4$ and $Z_6$ is independently selected from the group consisting of N and CH;

$R_{z2}$ is selected from the group consisting of $C_{3-8}$ cycloalkyl and $C_{1-6}$ alkyl-$C_{3-8}$ cycloalkyl; and $R_{z2}$ is optionally substituted with substituents independently selected from the group consisting of halogen, hydroxyl, $C_{1-6}$ alkyl and $C_{1-6}$ alkoxy;

$Q_2$ is selected from the group consisting of

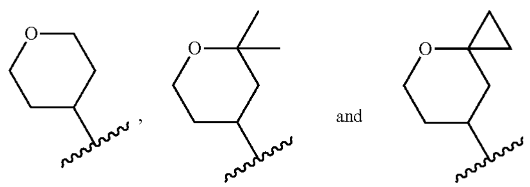

In some embodiments, in the compound of Formula (VI), the stereoisomer, the pharmaceutically acceptable salt, or the deuterated compound thereof, $R_{z2}$ is selected from the group consisting of

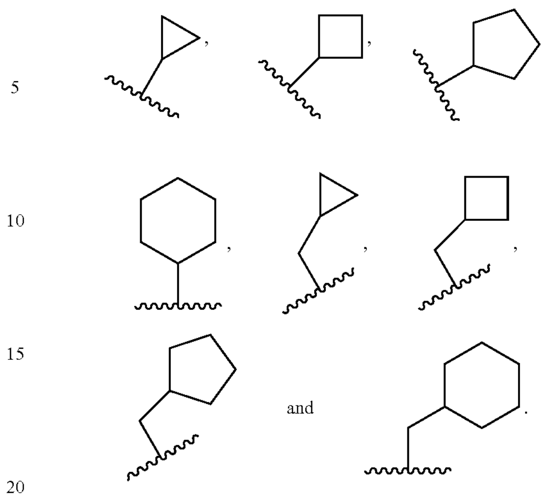

In some embodiments, in the compound of Formula (VII), the stereoisomer, the pharmaceutically acceptable salt, or the deuterated compound thereof, the compound has a structure of Formula (VII), Formula (VII)

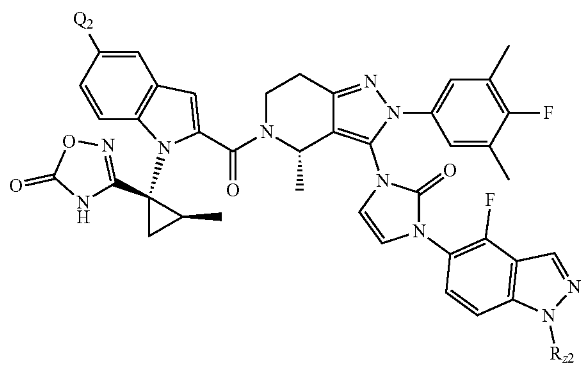

wherein:

$R_{z2}$ is selected from the group consisting of $C_{3-8}$ cycloalkyl and $C_{1-6}$ alkyl-$C_{3-8}$ cycloalkyl; and $R_{z2}$ is optionally substituted with substituents independently selected from the group consisting of halogen, hydroxyl, $C_{1-6}$ alkyl and $C_{1-6}$ alkoxy;

$Q_2$ is selected from the group consisting of

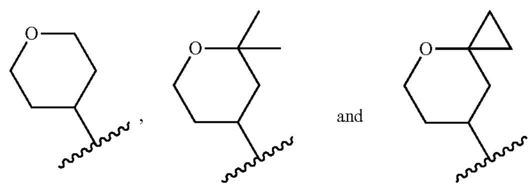

In some embodiments, in the compound of Formula (VII), the stereoisomer, the pharmaceutically acceptable salt, or the deuterated compound thereof, $Q_2$ is selected from the group consisting of

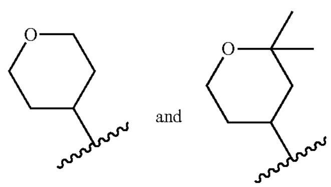

and .

In some embodiments, in the compound of Formula (VII), the stereoisomer, the pharmaceutically acceptable salt, or the deuterated compound thereof, $R_{z2}$ is selected from the group consisting of

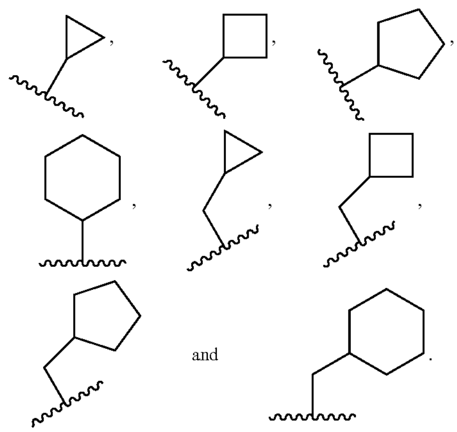

, , , , , , and .

Yet still another aspect of the present disclosure provides a compound of Formula (VIII), a stereoisomer, a pharmaceutically acceptable salt, or a deuterated compound thereof:

Formula (VIII)

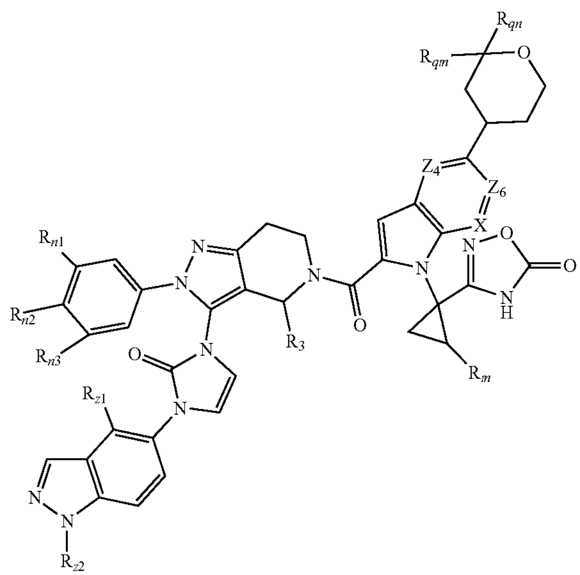

wherein:

each of X, $Z_4$ and $Z_6$ is independently selected from the group consisting of N and CH;

$R_m$ is selected from the group consisting of H, $C_{1-6}$ alkyl, $C_{1-6}$ haloalkyl, $C_{1-6}$ alkoxy and $C_{1-6}$ haloalkoxy;

$R_{n1}$, and $R_{n3}$ are each independently selected from the group consisting of hydrogen, halogen, $C_{1-6}$ alkyl, $C_{1-6}$ haloalkyl, $C_{1-6}$ alkoxy, and $C_{1-6}$ haloalkoxy; $R_{n2}$ is halogen;

$R_3$ is selected from the group consisting of hydrogen, halogen, $C_{1-6}$ alkyl, $C_{1-6}$ haloalkyl, $C_{1-6}$ alkoxy and $C_{1-6}$ haloalkoxy;

$R_{z1}$ is selected from the group consisting of hydrogen, halogen, $C_{1-3}$ alkyl and $C_{3-8}$ cycloalkyl;

$R_{z2}$ Selected from the group consisting of

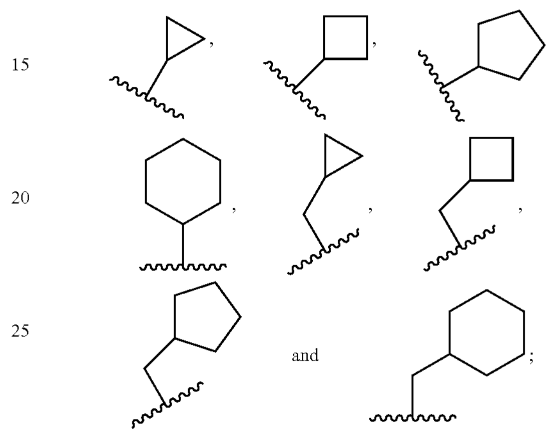

, , , , , , and ;

$R_{qm}$ and $R_{qn}$ are each independently selected from the group consisting of H, methyl, and ethyl, or $R_{qm}$ and $R_{qn}$ together with the carbon atom to which they are attached to form a $C_{3-6}$ cycloalkyl.

In some embodiments, in the compound of Formula (VIII), the stereoisomer, the pharmaceutically acceptable salt, or the deuterated compound thereof, $R_m$ is independently selected from the group consisting of halogen. $-CH_3$, $-CH_2CH_3$ and $-OCH_3$;

$R_{n1}$ and $R_{n3}$ are each independently selected from the group consisting of hydrogen, methyl, and ethyl;

$R_{n2}$ is F;

$R_3$ is methyl;

$R_{z1}$ is selected from the group consisting of hydrogen, F, Cl, methyl, ethyl, n-propyl, isopropyl, and cyclopropyl.

Yet still another aspect of the present disclosure provides a compound of Formula (IX), a stereoisomer, a pharmaceutically acceptable salt, or a deuterated compound thereof:

Formula (IX)

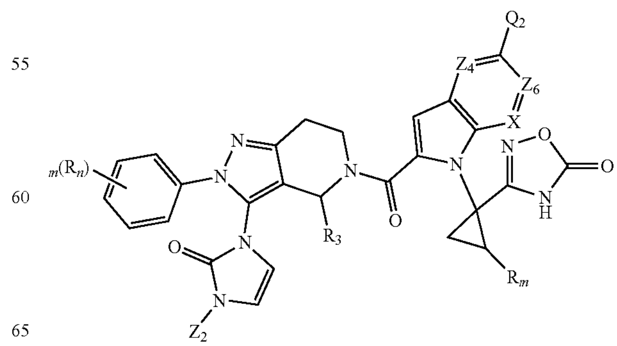

wherein:

each of X, $Z_4$ and $Z_6$ is independently selected from the group consisting of N and CH;

$Z_2$ is selected from the group consisting of

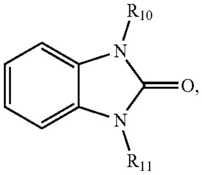
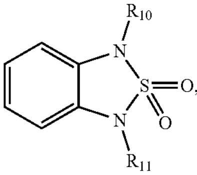
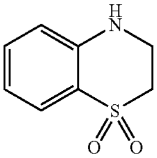
,
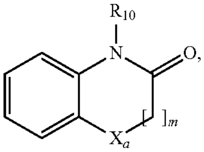
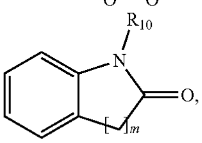
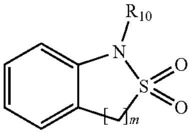
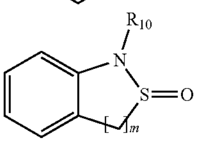
and
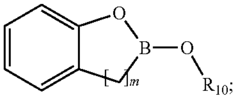

$R_n$ is selected from the group consisting of halogen, $C_{1-6}$ alkyl, $C_{1-6}$ haloalkyl and $C_{1-6}$ alkoxy.

m is 0, 1, 2 or 3.

In some embodiments, in the compound of Formula (IX), the stereoisomer, the pharmaceutically acceptable salt, or the deuterated compound thereof, $R_m$ is selected from the group consisting of H, $C_{1-6}$ alkyl, $C_{1-6}$ haloalkyl, and $C_{1-6}$ alkoxy;

$R_3$ is selected from the group consisting of H, halogen, $C_{1-6}$ alkyl, $C_{1-6}$ alkoxy and $C_{1-6}$ haloalkoxy;

$R_{10}$ and $R_{11}$ is independently selected from the group consisting of H, F, Cl, methyl, ethyl, n-propyl, isopropyl, and cyclopropyl.

In some embodiments, in the compound of Formula (IX), the stereoisomer, the pharmaceutically acceptable salt, or the deuterated compound thereof, $R_m$ is independently selected from the group consisting of halogen, $—CH_3$, $—CH_2CH_3$ and $—OCH_3$;

$R_n$ is independently selected from the group consisting of $—CH_3$, $—CH_2CH_3$, F, and Cl;

$R_3$ is $—CH_3$.

In some embodiments, in the compound of Formula (IX), the stereoisomer, the pharmaceutically acceptable salt, or the deuterated compound thereof, $Z_2$ is selected from the group consisting of

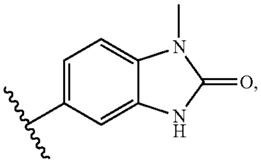
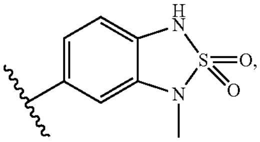

-continued

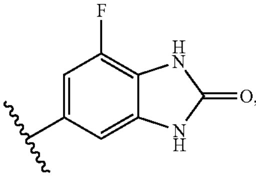
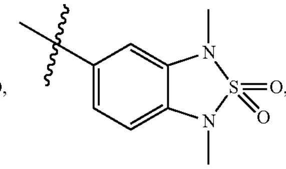
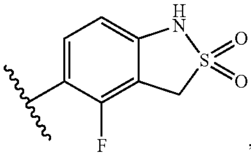
,
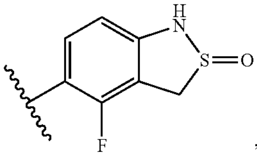
,
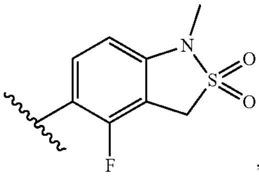
,
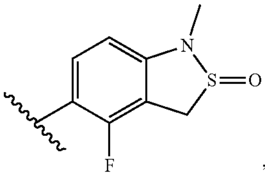
,
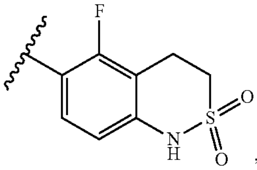
,
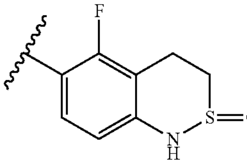
,
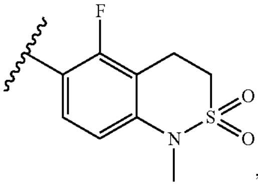
,
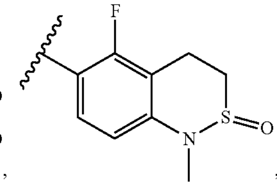
,
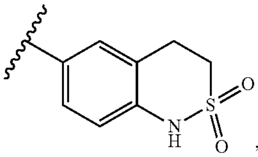
,
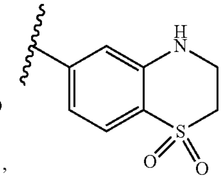
,
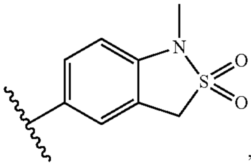
,
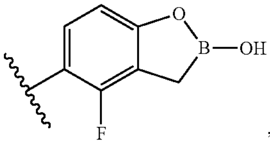
,
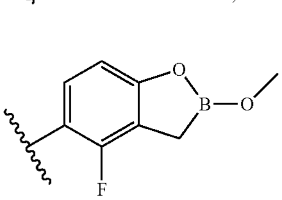
,
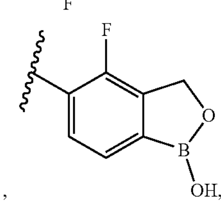
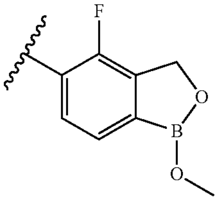
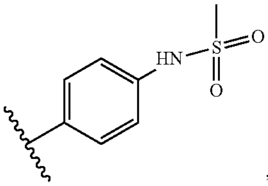
, -continued

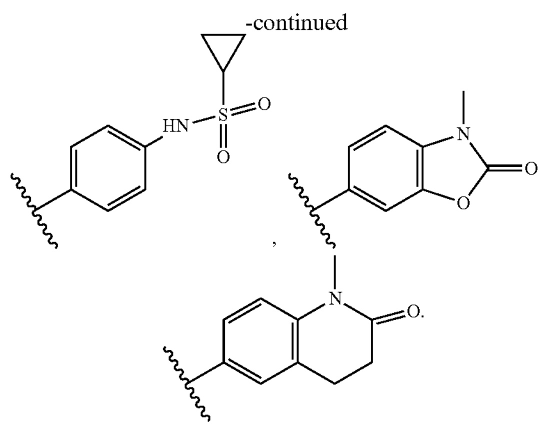

, and .

In some embodiments, in the compound of Formula (IX), the stereoisomer, the pharmaceutically acceptable salt, or the deuterated compound thereof, $Q_2$ is

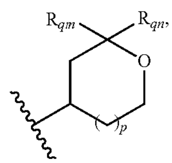

wherein $R_{qm}$ and $R_{qn}$ are each independently selected from the group consisting of H, methyl, and ethyl; or $R_{qm}$ and $R_{qn}$ together with the carbon atom to which they are attached to form a $C_{3-6}$ Cycloalkyl; p is 0, 1, or 2.

In some embodiments, in the compound of Formula (IX), the stereoisomer, the pharmaceutically acceptable salt, or the deuterated compound thereof, $Q_2$ is selected from the group consisting of

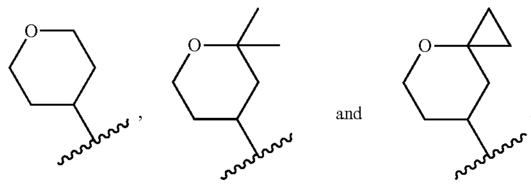

, and .

In some embodiments, in the compound, the stereoisomer, the pharmaceutically acceptable salt, or the deuterated compound thereof of the present disclosure, the compound is selected from the group consisting of:

29

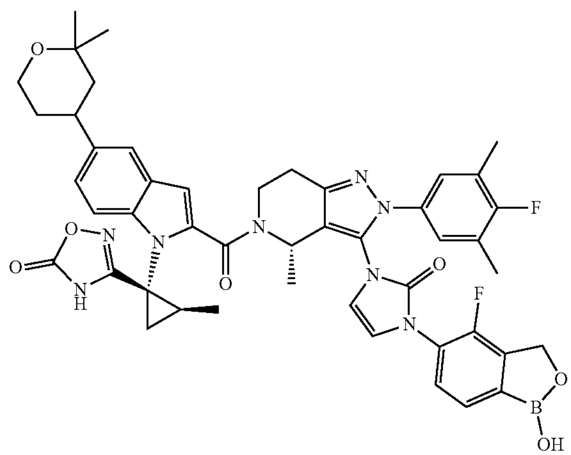

-continued

30

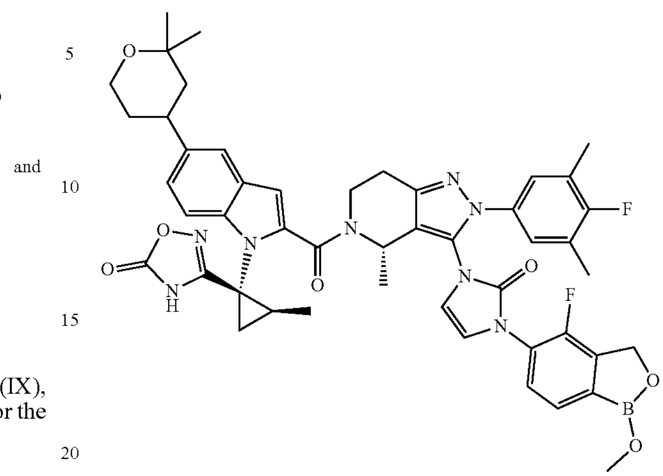

34

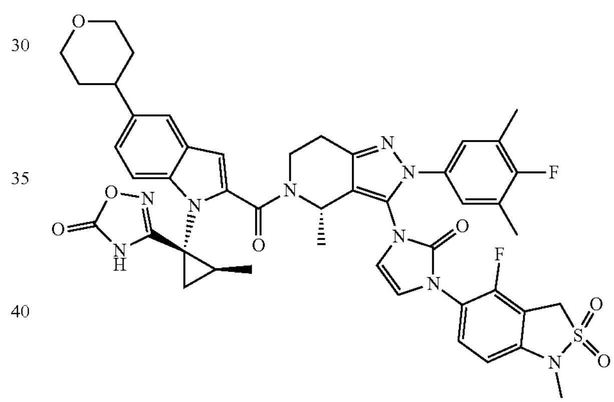

35

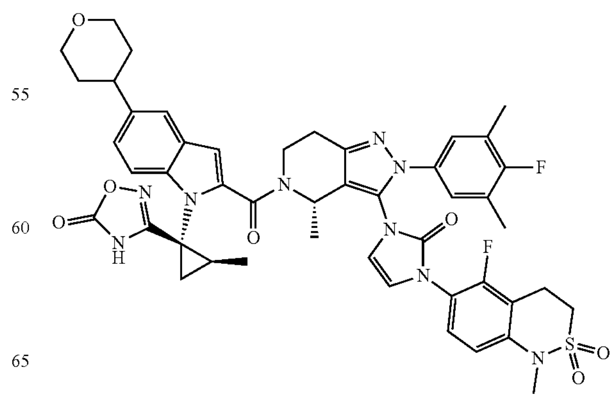

-continued
36
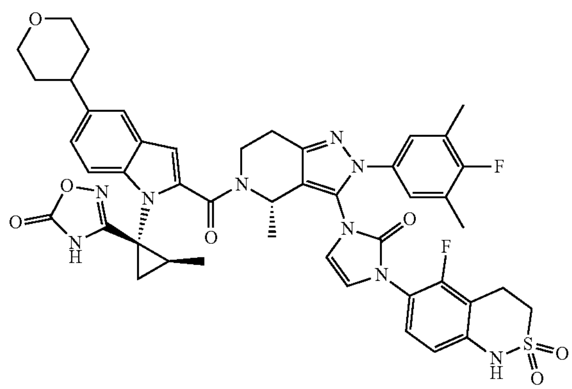
37
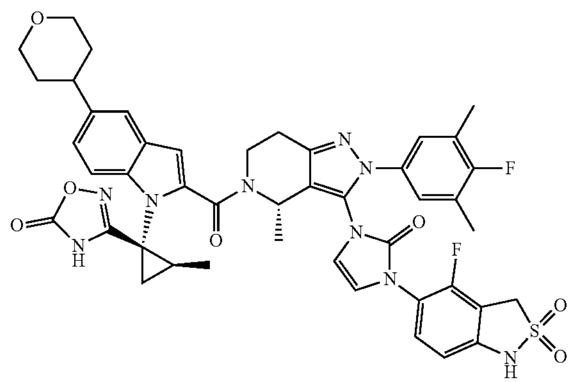
38
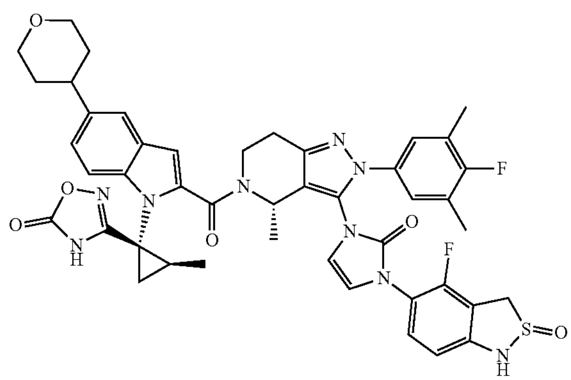
39
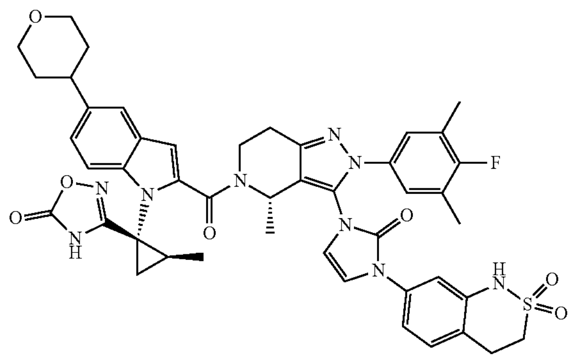
-continued
55
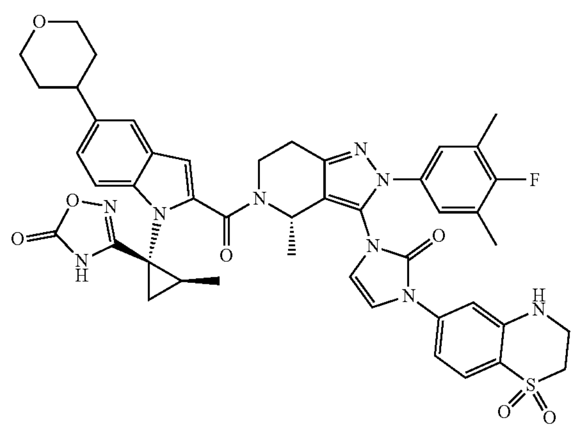
76
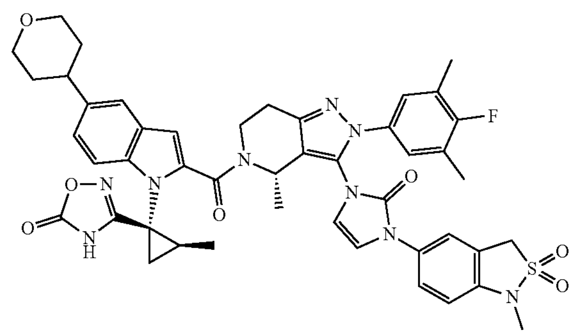
58
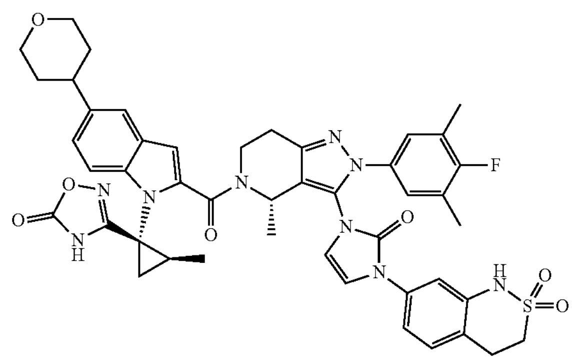
77
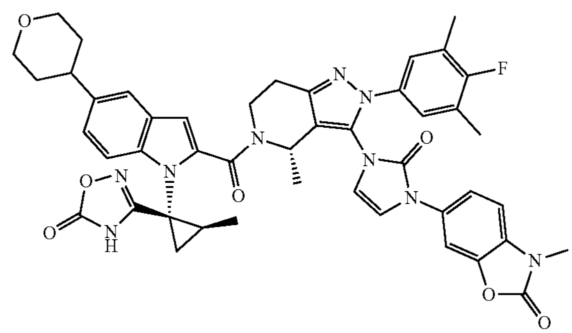

-continued

78

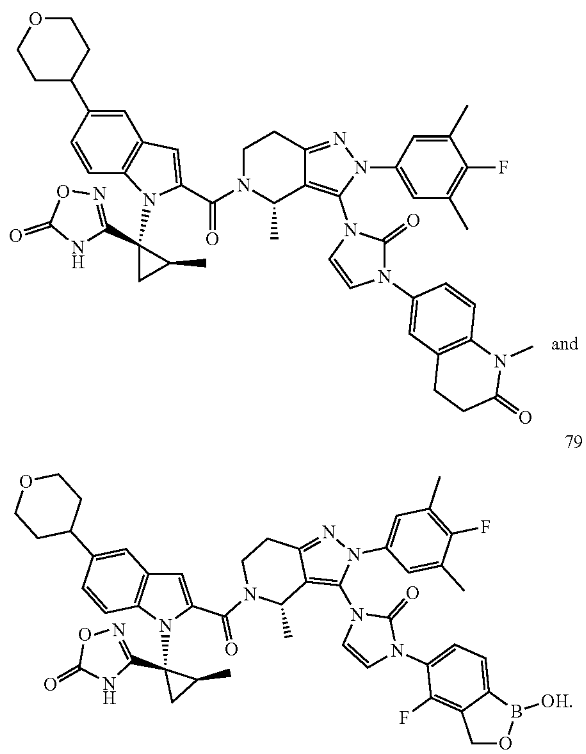

and

79

Yet still another aspect of the present disclosure provides a compound of Formula (X), a stereoisomer, a pharmaceutically acceptable salt, or a deuterated compound thereof:

Formula (X)

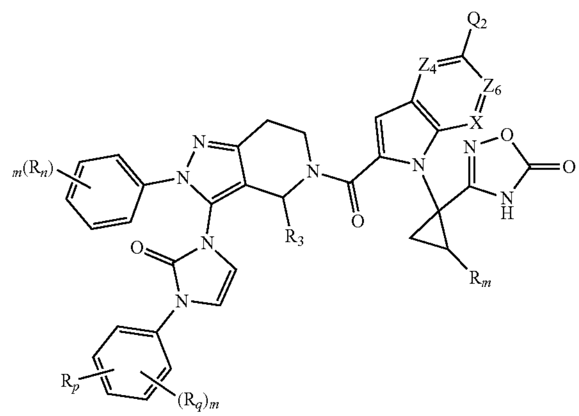

wherein:

each of X, $Z_4$ and $Z_6$ is independently selected from the group consisting of N and CH;

m is 0, 1, 2 or 3;

$R_p$ is selected from the group consisting of $-CH_2-P(=O)R^{zm}R^{zn}$ and $-P(=O)OR^{zm}OR^{zn}$;

$R_q$ is selected from the group consisting of halogen, $-NH-C_{1-6}$ alkyl, $-C_{1-6}$ alkyl, $-O-C_{1-6}$ alkyl, 3- to 12-membered heterocyclic, $-C_3$-$C_{15}$ cycloalkyl and $C_1$-$C_6$ alkyl-$C_3$-$C_{15}$ cycloalkyl;

wherein each of $R^{zm}$ and $R^{zn}$ is independently selected from the group consisting of hydrogen, $C_{1-6}$ alkyl and $C_{6-10}$ aryl; or $R^{zm}$ and $R^{zn}$ together with the phosphorous atom to which they are attached form 5- to 8-membered heterocycloalkyl, wherein the heterocycloalkyl is optionally substituted with 1-3 $C_{1-6}$ alkyl.

In some embodiments, in the compound of Formula (X), the stereoisomer, the pharmaceutically acceptable salt, or the deuterated compound thereof, $R_p$ is selected from the group consisting of

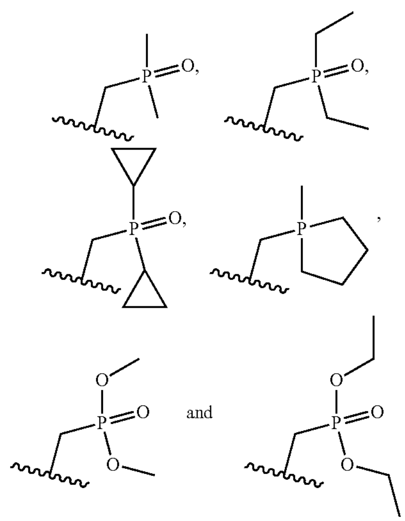

$R_m$ is selected from the group consisting of H, $C_{1-6}$ alkyl, $C_{1-6}$ haloalkyl, and $C_{1-6}$ alkoxy;

$R_n$ is selected from the group consisting of halogen, $C_{1-6}$ alkyl, $C_{1-6}$ haloalkyl, and $C_{1-6}$ alkoxy;

m is 0, 1, 2, and 3;

$R_3$ is selected from the group consisting of H, halogen, $C_{1-6}$ alkyl, $C_{1-6}$ alkoxy and $C_{1-6}$ haloalkoxy.

In some embodiments, in the compound of Formula (X), the stereoisomer, the pharmaceutically acceptable salt, or the deuterated compound thereof, $R_m$ is selected from the group consisting of H, methyl, ethyl, and methoxy; $R_n$ is selected from the group consisting of methyl, ethyl, F and Cl, $R_3$ is methyl.

In some embodiments, in the compound of Formula (X), the stereoisomer, the pharmaceutically acceptable salt, or the deuterated compound thereof, $Q_2$ is

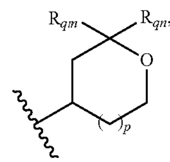

wherein $R_{qm}$ and $R_{qn}$ are each independently selected from the group consisting of H, methyl, and ethyl; or $R_{qm}$ and $R_{qn}$ together with the carbon atom to which they are attached to form $C_{3-6}$ Cycloalkyl; p is 0, 1, or 2.

In some embodiments, in the compound of Formula (X), the stereoisomer, the pharmaceutically acceptable salt, or the deuterated compound thereof, $Q_2$ is selected from the group consisting of

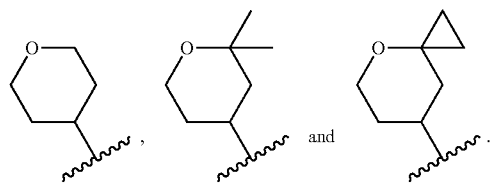

, and .

In some embodiments, in the compound of Formula (X), the stereoisomer, the pharmaceutically acceptable salt, or the deuterated compound thereof, the compound is selected from the group consisting of:

80

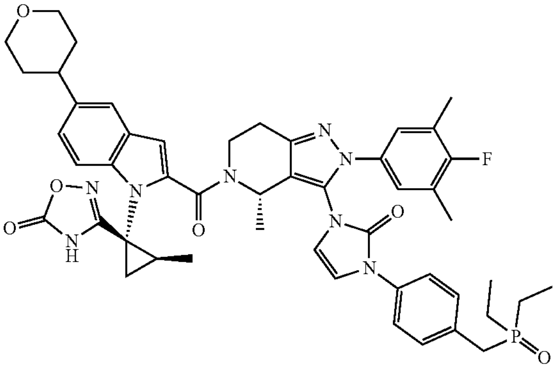

81

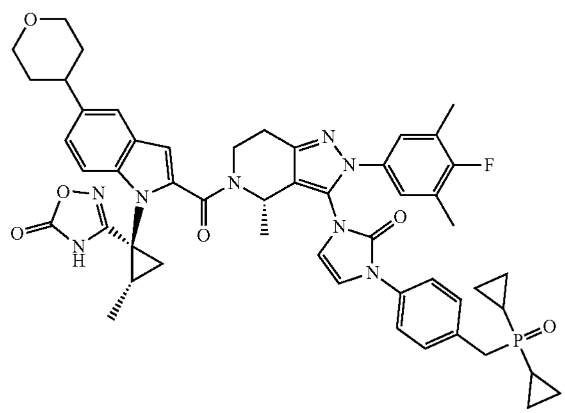

82

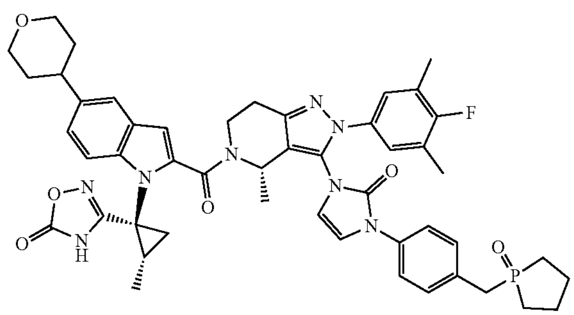

-continued

84

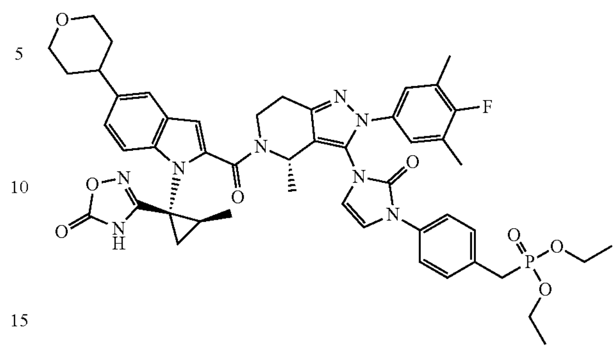

50

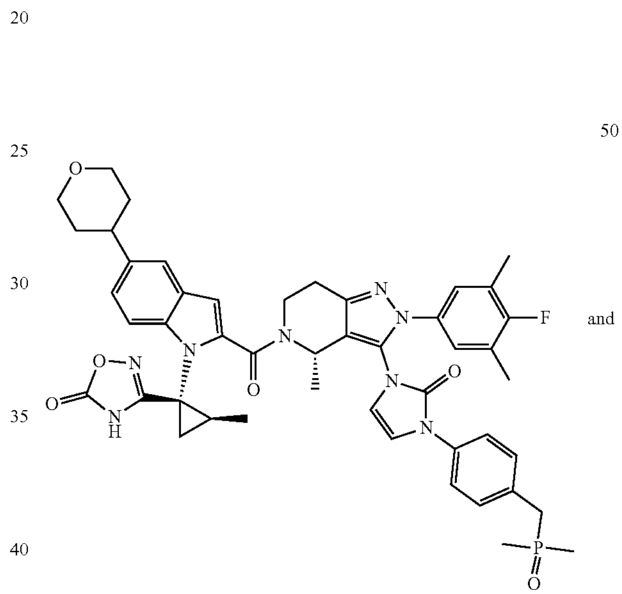

and

53

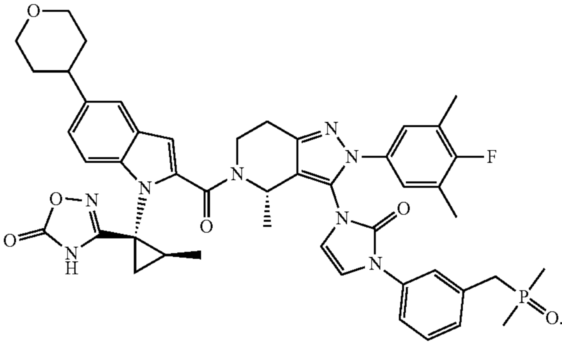

.

Yet still another aspect of the present disclosure provides a compound of Formula (XI), a stereoisomer, a pharmaceutically acceptable salt, or a deuterated compound thereof:

Formula (XI)

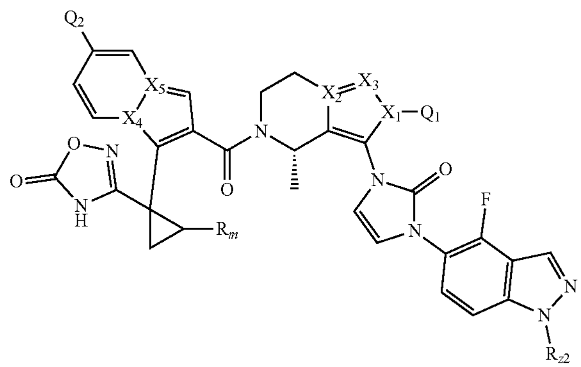

wherein $Q_1$ is $C_{6-10}$ aryl, and the $C_{6-10}$ aryl is optionally substituted with one to five substituents selected from the group consisting of halogen, $C_{1-6}$ alkyl, $C_{1-6}$ haloalkyl and $C_{1-6}$ alkoxy;

$Q_2$ is selected from the group consisting of 3- to 12-membered heterocyclic, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, and $C_{1-6}$ alkoxy, wherein two $C_{1-6}$ alkyl groups optionally together with the carbon atoms to which they are attached form a $C_{3-8}$ carbocyclic ring;

$X_1$, $X_2$, and $X_3$ are independently selected from the group consisting of N and C;

$X_4$, and $X_5$ are independently selected from the group consisting of N and C;

$R_m$ is selected from the group consisting of H, $C_{1-6}$ alkyl, $C_{1-6}$ haloalkyl, $C_{1-6}$ alkoxy and $C_{1-6}$ haloalkoxy;

$R_{z2}$ is selected from the group consisting of $C_{3-8}$ cycloalkyl and $C_{1-6}$ alkyl-$C_{3-8}$ cycloalkyl.

In some embodiments, in the compound of Formula (XI), the stereoisomer, the pharmaceutically acceptable salt, or the deuterated compound thereof, $Q_1$ is

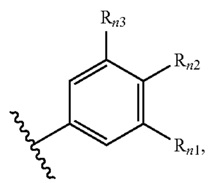

and $R_{n1}$ and $R_{n3}$ are each independently selected from the group consisting of H, methyl, and ethyl; $R_{n2}$ is halogen;

$Q_2$ is selected from the group consisting of

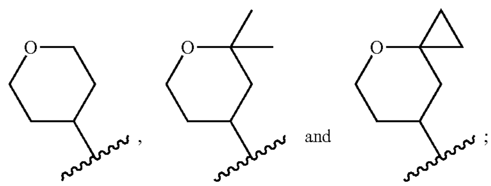

, and ;

$R_{z2}$ is selected from the group consisting of

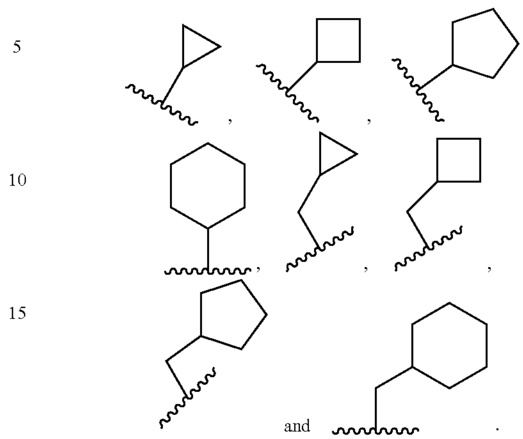

, , , , , , and .

In some embodiments, in the compound, the stereoisomer, the pharmaceutically acceptable salt, or the deuterated compound thereof of the present disclosure, the compound is selected from the group consisting of:

42

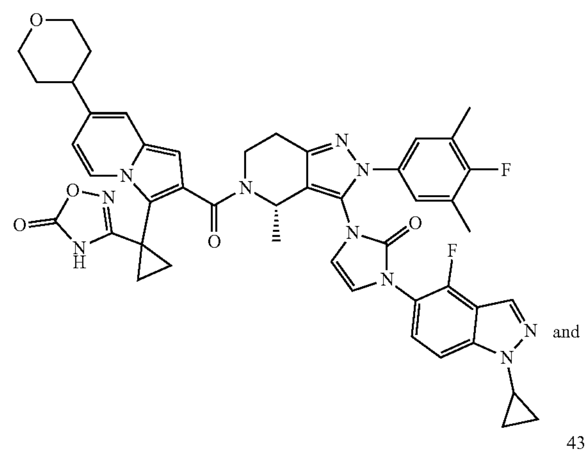

and

43

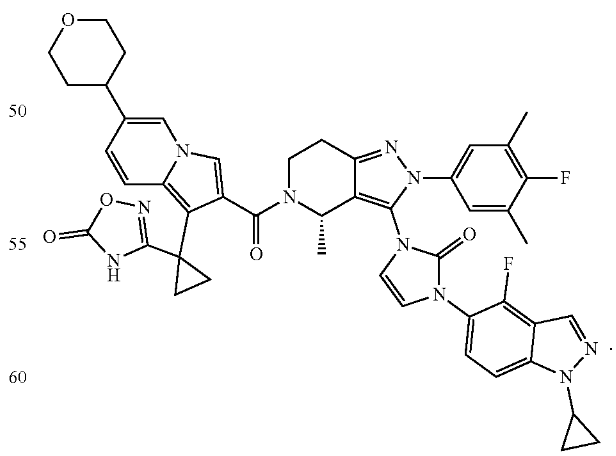

.

Yet still another aspect of the present disclosure provides a compound of Formula (Ia), a stereoisomer, a pharmaceutically acceptable salt, or a deuterated compound thereof:

Formula (Ia)

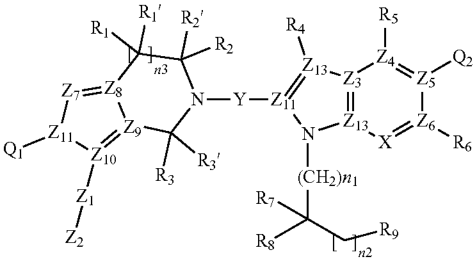

wherein X is selected from the group consisting of N and $—CR^a$; wherein $R^a$ is selected from the group consisting of hydrogen, halogen, and $C_{1-6}$ alkyl;

wherein Y is —C(═O)—;

wherein each of $Z_3$, $Z_4$, $Z_5$, $Z_6$, $Z_7$, $Z_8$, $Z_9$, $Z_{10}$, $Z_{11}$, $Z_{12}$ and $Z_{13}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic, bridged ring, spiro ring, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and $—NR^{Qa}R^{Qb}$, wherein two $C_{1-6}$ alkyl groups optionally together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein each of $R_1$, $R_2$, $R_3$, $R_1'$, $R_2'$ and $R_3'$ is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl;

wherein $R_2$ and $R_3$ together with the carbon atom to which they are attached form 4- to 8-membered heterocycloalkyl;

wherein $R_1$ and $R_1'$ optionally together with the carbon atom to which they are attached form $C_3$-$C_8$ cycloalkyl, and $R_2$ and $R_2'$ optionally together with the carbon atom to which they are attached form $C_3$-$C_8$ cycloalkyl; and $R_3$ and $R_3'$ optionally together with the carbon atom to which they are attached form $C_3$-$C_8$ cycloalkyl;

each of $R_4$, $R_5$ and $R_6$ is independently selected from the group consisting of hydrogen, halogen and $C_{1-6}$ alkyl;

each of $R_7$ and $R_8$ is independently selected from the group consisting of hydrogen and $C_{1-6}$ alkyl, wherein $C_{1-6}$ alkyl is optionally substituted with one or more substituents independently selected from the group consisting of halogen and $C_{3-15}$ cycloalkyl;

or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl, wherein each $C_{1-6}$ alkyl is optionally substituted by one or more substituents independently selected from the group consisting of halogen, hydroxyl, $—NR^{7a}R^{7b}$, $C_{1-6}$ alkoxy and 3- to 12-membered heterocyclic, and $R^{7a}$ and $R^{7b}$ are independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ carbocyclic ring;

$n_1$ is 0, 1, 2 or 3;

n2 is 0, 1, 2, 3, 4 or 5;

n3 is 0 or 1;

$R_9$ is selected from the group consisting of:

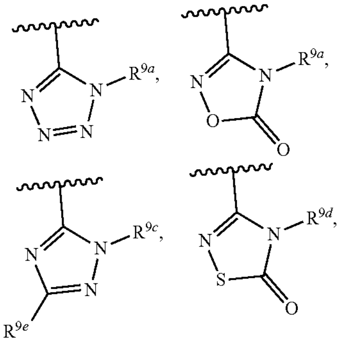

$—CO_2R^{9f}$ and $—C(═O)—NR^{9g}R^{9h}$;

and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy:

$R^{9e}$ is selected from the group consisting of hydrogen and $C_{1-6}$ alkyl optionally substituted by one or more halogen atoms;

$R^{9f}$ is selected from the group consisting of hydrogen and $C_{1-6}$ alkyl;

$R^{9h}$ is selected from the group consisting of hydrogen, $C_{1-6}$ alkyl, ($C_{1-6}$ alkyl) carbonyl, cyano and $—S(═O)_{n9}—R^{9i}$; n9 is 0, 1 or 2;

$R^{9i}$ is $C_{1-6}$ alkyl;

$Z_1$ is selected from the group consisting of:

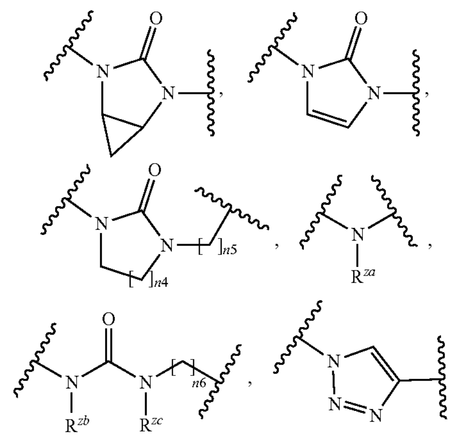

-continued

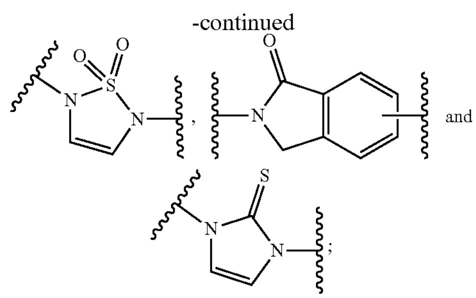

and

;

wherein $R^{za}$ is selected from the group consisting of hydrogen, $C_{1-6}$ alkyl and ($C_{1-6}$ alkyl) carbonyl, and each of $R^{zb}$ and $R^{zc}$ is independently selected from the group consisting of hydrogen and $C_{1-6}$ alkyl;

n4 is 1, 2 or 3; each of n5 and n6 is independently an integer selected from 0 to 10;

$Z_2$ is selected from the group consisting of $C_{1-6}$ alkyl, $C_{3-15}$ cycloalkyl, 3- to 12-membered heterocyclic, $C_{6-10}$ aryl, 5- to 10-membered heteroaryl,

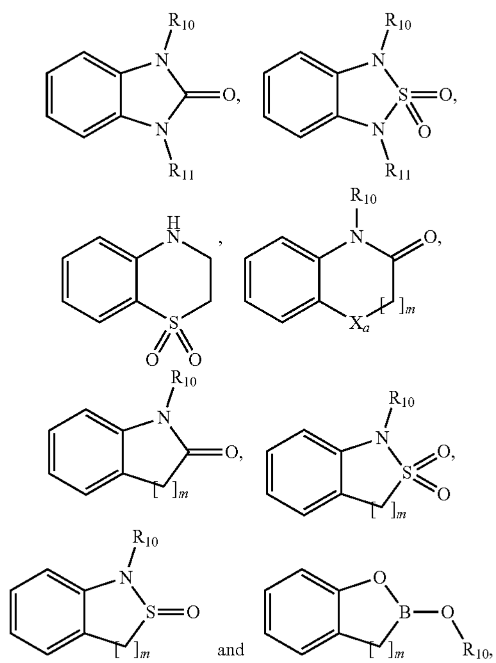

wherein $Z_2$ is independently optionally substituted with one to five G;

m is 1, 2, or 3;

each of $R_{10}$ and $R_{11}$ is independently selected from the group consisting of hydrogen, $C_{1-6}$ alkyl, ($C_{1-6}$ alkyl) aryl, $C_{1-6}$ haloalkyl, $C_{3-15}$ cycloalkyl and $C_{1-6}$ alkyl-$C_{3-15}$ cycloalkyl, wherein G is selected from the group consisting of:

a. Oxo;

b. Halogen;

c. Cyano;

d. —$NR^{zd}R^{ze}$; wherein $R^{zd}$ and $R^{ze}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

e. —C(═O)—$NR^{zf}R^{zg}$; wherein $R^{zf}$ and $R^{zg}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

f. —$S(═O)_{n7}$—$R^{zh}$; wherein n7 is 0, 1 or 2; $R^{zh}$ is selected from the group consisting of hydrogen and $C_{1-6}$ alkyl;

g. $C_{1-6}$ alkyl; wherein $C_{1-6}$ alkyl is optionally substituted with one or more substituents independently selected from the group consisting of halogen, hydroxyl, —$NR^{zi}R^{zj}$, $C_{1-6}$ alkoxy, $C_{1-6}$ haloalkoxy and 3- to 12-membered heterocyclic; wherein each of $R^{zi}$ and $R^{zj}$ is independently selected from the group consisting of hydrogen and $C_{1-6}$ alkyl, wherein the 3- to 12-membered heterocyclic groups are optionally substituted with one or more substituents selected from the group consisting of cyano, $C_{1-6}$ alkyl and 3- to 12-membered heterocyclic;

h. $C_{1-6}$ alkoxy; wherein $C_{1-6}$ alkoxy is optionally substituted by one or more substituents of hydroxyl, halogen and $C_{1-6}$ alkoxy;

i. 3- to 12-membered heterocyclic; wherein 3- to 12-membered heterocyclic is optionally substituted by one or more substituents independently selected from the group consisting of $C_{1-6}$ alkyl and ($C_{1-6}$ alkyl) carbonyl;

j. $C_{6-10}$ aryl; wherein $C_{6-10}$ aryl is optionally substituted by one or more ($C_{1-6}$ alkyl) carbonyl;

k. 5- to 10-membered heteroaryl; wherein the 5- to 10-membered heteroaryl is optionally substituted with one or more substituents independently selected from the group consisting of $C_{1-6}$ alkyl, $C_{1-6}$ alkoxy, —$NR^{zk}R^{zl}$, and 3- to 12-membered heterocyclic; wherein $R^{zk}$ and $R^{zl}$ are independently selected from the group consisting of hydrogen, $C_{1-6}$ alkyl, and ($C_{1-6}$ alkyl) carbonyl and wherein the 3- to 12-membered heterocyclic is optionally substituted with one or more substituents independently selected from the group consisting of $C_{1-6}$ alkyl, and ($C_{1-6}$ alkyl)carbonyl;

l. $C_3$-$C_{15}$ cycloalkyl or $C_1$-$C_6$ alkyl-$C_3$-$C_{15}$ cycloalkyl; wherein cycloalkyl or alkyl is optionally substituted by one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted by halogen; and m. —P(═O)$R^{zm}R^{zn}$, —$(CH_2)_{n8}$—P(═O)$R^{zm}R^{zn}$, —$NR^{zm}$S(═O)$R^{zn}$ and —$NR^{zm}S(═O)_2R^{zn}$, wherein each $R^{zm}$ and $R^{zn}$ is independently selected from the group consisting of hydrogen, $C_{1-6}$ alkyl and $C_{6-10}$ aryl; n8 is 1 or 2; wherein $C_{1-6}$ alkyl is substituted by one to six substituents selected from the group consisting of $C_{1-6}$ alkoxy, $C_{3-6}$ cycloalkyl and halogen, and $C_{3-6}$ cycloalkyl is optionally substituted by one to three substituents selected from the group consisting of $C_{1-3}$ alkyl and halogen; wherein the $C_{6-10}$ aryl is optionally substituted by one to three substituents selected from the group consisting of $C_{1-3}$ alkyl; or $R^{zm}$ and $R^{zn}$ together with the phosphorous atom to which they are attached form a ring with 5 to 8 ring atoms, wherein 0 to 2 of the ring atoms other than phosphorus are heteroatoms each independently selected from: O, S, and N, wherein the ring is optionally substituted with from 1-3 independently selected $C_{1-6}$ alky.

Yet still another aspect of present disclosure provides a compound of Formula (Ib), a stereoisomer, a pharmaceutically acceptable salt, or a deuterated compound thereof:

Formula (Ib)

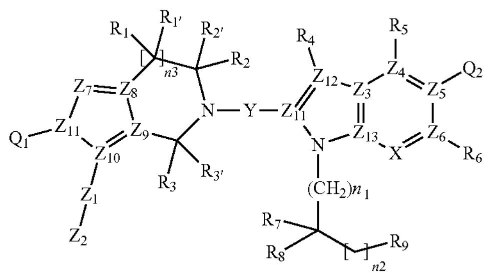

wherein X is selected from the group consisting of N and —$CR^a$; wherein $R^a$ is selected from the group consisting of hydrogen, halogen, and $C_{1-6}$ alkyl;

wherein Y is —C(═O)—;

wherein each of $Z_3$, $Z_4$, $Z_5$, $Z_6$, $Z_7$, $Z_8$, $Z_9$, $Z_{10}$, $Z_{11}$, $Z_{12}$ and $Z_{13}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic, bridged ring, spiro ring, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and —$NR^{Qa}R^{Qb}$, wherein two $C_{1-6}$ alkyl groups optionally together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein each of $R_1$, $R_2$, $R_3$, $R_1$', $R_2$' and $R_3$' is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl;

wherein $R_2$ and $R_3$ together with the carbon atom to which they are attached form 4- to 8-membered heterocycloalkyl;

wherein $R_1$ and $R_1$' optionally together with the carbon atom to which they are attached form $C_3$-$C_8$ cycloalkyl, and $R_2$ and $R_2$' optionally together with the carbon atom to which they are attached form $C_3$-$C_8$ cycloalkyl; and $R_3$ and $R_3$' optionally together with the carbon atom to which they are attached form $C_3$-$C_8$ cycloalkyl;

each of $R_4$, $R_5$ and $R_6$ is independently selected from the group consisting of hydrogen, halogen and $C_{1-6}$ alkyl;

each of $R_7$ and $R_8$ is independently selected from the group consisting of hydrogen and $C_{1-6}$ alkyl, wherein $C_{1-6}$ alkyl is optionally substituted with one or more substituents independently selected from the group consisting of halogen and $C_{3-15}$ cycloalkyl:

or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl, wherein $C_{1-6}$ alkyl is optionally substituted by one or more substituents independently selected from the group consisting of halogen, hydroxyl, —$NR^{7a}R^{7b}$, $C_{1-6}$ alkoxy and 3- to 12-membered heterocyclic, and $R^{7a}$ and $R^{7b}$ are independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ is carbocyclic ring;

$n_1$ is 0, 1, 2 or 3;

n2 is 0, 1, 2, 3, 4 or 5;

n3 is 0 or 1:

$R_9$ is selected from the group consisting of:

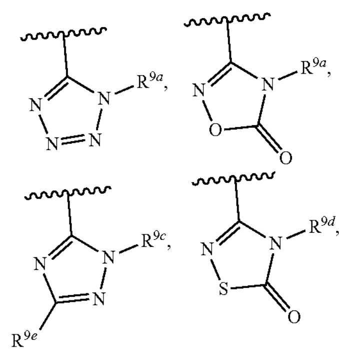

—$CO_2R^{9f}$ and —C(═O)—$NR^{9g}R^{9h}$; and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy;

$R^{9c}$ is selected from the group consisting of hydrogen and $C_{1-6}$ alkyl optionally substituted by one or more halogen atoms;

$R^{9f}$ is selected from the group consisting of hydrogen and $C_{1-4}$ alkyl;

$R^{9h}$ is selected from the group consisting of hydrogen, $C_{1-6}$ alkyl, ($C_{1-6}$ alkyl) carbonyl, cyano and —$S(═O)_{n9}$—$R^{9i}$; n9 is 0, 1 or 2;

$R^{9i}$ is $C_{1-6}$ alkyl;

$Z_1$ is selected from the group consisting of:

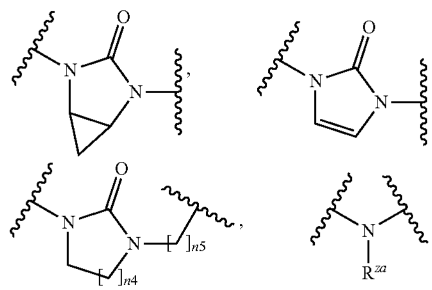

-continued

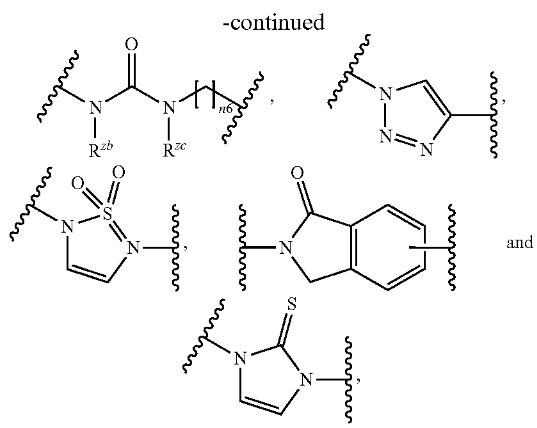

and wherein $R^{za}$ is selected from the group consisting of hydrogen, $C_{1-6}$ alkyl and ($C_{1-6}$ alkyl) carbonyl, and each of $R^{zb}$ and $R^{zc}$ is independently selected from the group consisting of hydrogen and $C_{1-6}$ alkyl;

n4 is 1, 2 or 3; each of n5 and n6 is independently an integer selected from 0 to 10;

$Z_2$ is selected from the group consisting of $C_{1-6}$ alkyl, $C_{3-15}$ cycloalkyl, 3- to 12-membered heterocyclic, $C_{6-10}$ aryl, 5- to 10-membered heteroaryl,

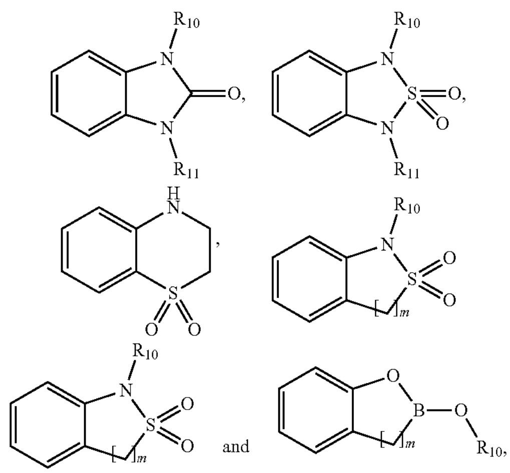

wherein $Z_2$ is independently optionally substituted with one to five G;

m is 1, 2, or 3;

each of $R_{10}$ and $R_{11}$ is independently selected from the group consisting of hydrogen, $C_{1-6}$ alkyl, ($C_{1-6}$ alkyl) aryl, $C_{1-6}$ haloalkyl, $C_{3-15}$ cycloalkyl and $C_{1-6}$ alkyl-$C_{3-15}$ cycloalkyl.

wherein G is selected from the group consisting of:

a. Oxo;

b. Halogen;

c. Cyano;

d. —$NR^{zd}R^{ze}$; wherein $R^{zd}$ and $R^{ze}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

e. —C(═O)—$NR^{zf}R^{zg}$; wherein $R^{zf}$ and $R^{zg}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

f. —$S(═O)_{n7}$—$R^{zh}$; wherein n7 is 0, 1 or 2; $R^{zh}$ is selected from the group consisting of hydrogen and $C_{1-6}$ alkyl;

g. $C_{1-6}$ alkyl; wherein $C_{1-6}$ alkyl is optionally substituted with one or more substituents independently selected from the group consisting of halogen, hydroxyl, —$NR^{zi}R^{zj}$, $C_{1-6}$ alkoxy, $C_{1-6}$ haloalkoxy and 3- to 12-membered heterocyclic; wherein each of $R^{zi}$ and $R^{zj}$ is independently selected from the group consisting of hydrogen and $C_{1-6}$ alkyl, wherein the 3- to 12-membered heterocyclic groups are optionally substituted with one or more substituents selected from the group consisting of cyano, $C_{1-6}$ alkyl and 3- to 12-membered heterocyclic:

h. $C_{1-6}$ alkoxy; wherein $C_{1-6}$ alkoxy is optionally substituted by one or more substituents of hydroxyl, halogen and $C_{1-6}$ alkoxy;

i. 3- to 12-membered heterocyclic; wherein 3- to 12-membered heterocyclic is optionally substituted by one or more substituents independently selected from the group consisting of $C_{1-6}$ alkyl and ($C_{1-6}$ alkyl) carbonyl;

j. $C_{6-10}$ aryl; wherein $C_{6-10}$ aryl is optionally substituted by one or more ($C_{1-6}$ alkyl) carbonyl;

k. 5- to 10-membered heteroaryl; wherein the 5- to 10-membered heteroaryl is optionally substituted with one or more substituents independently selected from the group consisting of $C_{1-6}$ alkyl, $C_{1-6}$ alkoxy, —$NR^{zk}R^{zl}$, and 3- to 12-membered heterocyclic; wherein $R^{zk}$ and $R^{zl}$ are independently selected from the group consisting of hydrogen, $C_{1-6}$ alkyl, and ($C_{1-6}$ alkyl) carbonyl and wherein the 3- to 12-membered heterocyclic is optionally substituted with one or more substituents independently selected from the group consisting of $C_{1-6}$ alkyl, and ($C_{1-6}$ alkyl)carbonyl;

l. $C_3$-$C_{15}$ cycloalkyl or $C_1$-$C_6$ alkyl-$C_3$-$C_{15}$ cycloalkyl; wherein cycloalkyl or alkyl is optionally substituted by one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted by halogen; and m. —P(═O)$R^{zm}R^{zn}$, —$(CH2)_{n8}$—P(═O)$R^{zm}R^{zn}$, —$NR^{zm}$S(═O)$R^{zn}$ and —$NR^{zm}S(═O)_2R^{zn}$, wherein each $R^{zm}$ and $R^{zn}$ is independently selected from the group consisting of hydrogen, $C_{1-6}$ alkyl and $C_{6-10}$ aryl; n8 is 1 or 2; wherein $C_{1-6}$ alkyl is substituted by one to six substituents selected from the group consisting of $C_{1-6}$ alkoxy, $C_{3-6}$ cycloalkyl and halogen, and $C_{3-6}$ cycloalkyl is optionally substituted by one to three substituents selected from the group consisting of $C_{1-3}$ alkyl and halogen; wherein the $C_{6-10}$ aryl is optionally substituted by one to three substituents selected from the group consisting of $C_{1-3}$ alkyl; or $R^{zm}$ and $R^{zn}$ together with the phosphorous atom to which they are attached form a ring with 5 to 8 ring atoms, wherein 0 to 2 of the ring atoms other than phosphorus are heteroatoms each independently selected from: O, S, and N, wherein the ring is optionally substituted with from 1-3 independently selected $C_{1-6}$ alky.

Yet still another aspect of the present disclosure provides a compound of Formula (Ic), a stereoisomer, a pharmaceutically acceptable salt, or a deuterated compound thereof:

Formula (Ic)

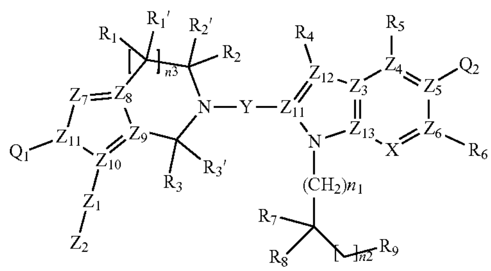

wherein X is selected from the group consisting of N and —$CR^a$; wherein $R^a$ is selected from the group consisting of hydrogen, halogen, and $C_{1-6}$ alkyl;

wherein Y is —C(═O)—;

wherein each of $Z_3$, $Z_4$, $Z_5$, $Z_6$, $Z_7$, $Z_8$, $Z_9$, $Z_{10}$, $Z_{11}$, $Z_{12}$ and $Z_{13}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic, bridged ring, spiro ring, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and —$NR^{Qa}R^{Qb}$, wherein two $C_{1-6}$ alkyl groups optionally together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein each of $R_1$, $R_2$, $R_3$, $R_1'$, $R_2'$ and $R_3'$ is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl;

wherein $R_2$ and $R_3$ together with the carbon atom to which they are attached form 4- to 8-membered heterocycloalkyl;

wherein $R_1$ and $R_1'$ optionally together with the carbon atom to which they are attached form $C_3$-$C_8$ cycloalkyl, and $R_2$ and $R_2'$ optionally together with the carbon atom to which they are attached form $C_3$-$C_8$ cycloalkyl; and $R_3$ and $R_3'$ optionally together with the carbon atom to which they are attached form $C_3$-$C_8$ cycloalkyl;

each of $R_4$, $R_5$ and $R_6$ is independently selected from the group consisting of hydrogen, halogen and $C_{1-6}$ alkyl;

each of $R_7$ and $R_8$ is independently selected from the group consisting of hydrogen and $C_{1-6}$ alkyl, wherein $C_{1-6}$ alkyl is optionally substituted with one or more substituents independently selected from the group consisting of halogen and $C_{3-15}$ cycloalkyl;

or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl, wherein each $C_{1-6}$ alkyl is optionally substituted by one or more substituents independently selected from the group consisting of halogen, hydroxyl, —$NR^{7a}R^{7b}$, $C_{1-6}$ alkoxy and 3- to 12-membered heterocyclic, and $R^{7a}$ and $R^{7b}$ are independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ carbocyclic ring;

$n_1$ is 0, 1, 2 or 3;

n2 is 0, 1, 2, 3, 4 or 5;

n3 is 0 or 1;

$R_9$ is selected from the group consisting of:

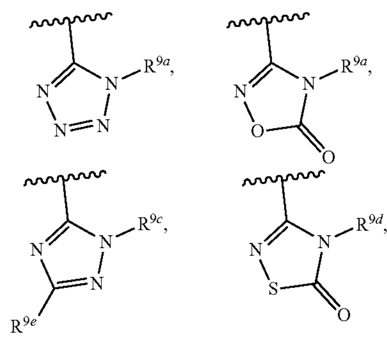

—$CO_2R^{9f}$ and —C(═O)—$NR^{9g}R^{9h}$; and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy:

$R^{9e}$ is selected from the group consisting of hydrogen and $C_{1-6}$ alkyl optionally substituted by one or more halogen atoms;

$R^{9f}$ is selected from the group consisting of hydrogen and $C_{1-6}$ alkyl;

$R^{9h}$ is selected from the group consisting of hydrogen, $C_{1-6}$ alkyl, ($C_{1-6}$ alkyl) carbonyl, cyano and —$S(═O)_{n9}$—$R^{9i}$; n9 is 0, 1 or 2;

$R^{9i}$ is $C_{1-6}$ alkyl;

$Z_1$ is selected from the group consisting of:

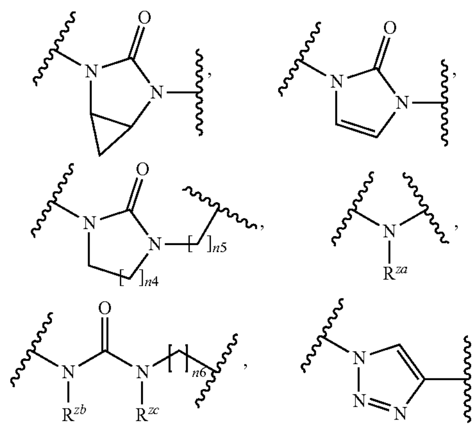

-continued

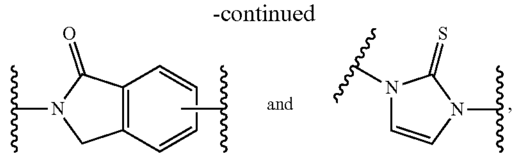

wherein $R^{za}$ is selected from the group consisting of hydrogen, $C_{1-6}$ alkyl and ($C_{1-6}$ alkyl) carbonyl, and each of $R^{zb}$ and $R^{zc}$ is independently selected from the group consisting of hydrogen and $C_{1-6}$ alkyl;

n4 is 1, 2 or 3;

each of n5 and n6 is independently an integer selected from 0 to 10;

$Z_2$ is selected from the group consisting of $C_{1-6}$ alkyl, $C_{3-15}$ cycloalkyl, 3- to 12-membered heterocyclic, $C_{6-10}$ aryl, 5- to 10-membered heteroaryl,

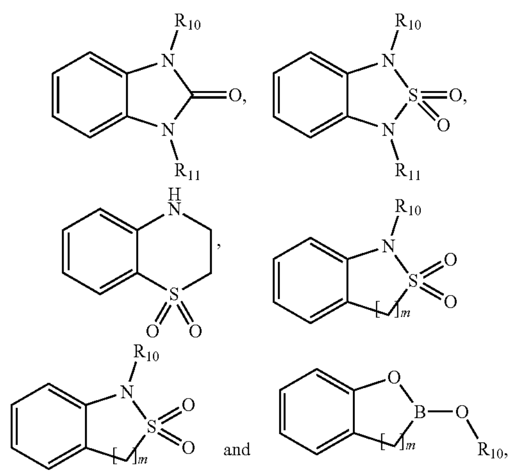

wherein $Z_2$ is independently optionally substituted with one to five G;

m is 1, 2, or 3;

each of $R_{10}$ and $R_{11}$ is independently selected from the group consisting of hydrogen, $C_{1-6}$ alkyl, ($C_{1-6}$ alkyl) aryl, $C_{1-6}$ haloalkyl, $C_{3-15}$ cycloalkyl and $C_{1-6}$ alkyl-$C_{3-15}$ cycloalkyl;

wherein G is selected from the group consisting of:

a. Oxo;

b. Halogen;

c. Cyano;

d. —$NR^{zd}R^{ze}$; wherein $R^{zd}$ and $R^{ze}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

e. —C(═O)—$NR^{zf}R^{zg}$; wherein $R^{zf}$ and $R^{zg}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

f. —S(═O)$_{n7}$—$R^{zh}$; wherein n7 is 0, 1 or 2; $R^{zh}$ is selected from the group consisting of hydrogen and $C_{1-6}$ alkyl;

g. $C_{1-6}$ alkyl; wherein $C_{1-6}$ alkyl is optionally substituted with one or more substituents independently selected from the group consisting of halogen, hydroxyl, —$NR^{zi}R^{zj}$, $C_{1-6}$ alkoxy, $C_{1-6}$ haloalkoxy and 3- to 12-membered heterocyclic; wherein each of $R^{zi}$ and $R^{zj}$ is independently selected from the group consisting of hydrogen and $C_{1-6}$ alkyl, wherein the 3- to 12-membered heterocyclic groups are optionally substituted with one or more substituents selected from the group consisting of cyano. $C_{1-6}$ alkyl and 3- to 12-membered heterocyclic:

h. $C_{1-6}$ alkoxy; wherein $C_{1-6}$ alkoxy is optionally substituted by one or more substituents of hydroxyl, halogen and $C_{1-6}$ alkoxy;

i. 3- to 12-membered heterocyclic; wherein 3- to 12-membered heterocyclic is optionally substituted by one or more substituents independently selected from the group consisting of $C_{1-6}$ alkyl and ($C_{1-6}$ alkyl) carbonyl;

j. $C_{6-10}$ aryl; wherein $C_{6-10}$ aryl is optionally substituted by one or more ($C_{1-6}$ alkyl) carbonyl;

k. 5- to 10-membered heteroaryl; wherein the 5- to 10-membered heteroaryl is optionally substituted with one or more substituents independently selected from the group consisting of $C_{1-6}$ alkyl, $C_{1-6}$ alkoxy, —$NR^{zk}R^{zl}$, and 3- to 12-membered heterocyclic; wherein $R^{zk}$ and $R^{zl}$ are independently selected from the group consisting of hydrogen, $C_{1-6}$ alkyl, and ($C_{1-6}$ alkyl) carbonyl and wherein the 3- to 12-membered heterocyclic is optionally substituted with one or more substituents independently selected from the group consisting of $C_{1-6}$ alkyl, and ($C_{1-6}$ alkyl)carbonyl;

l. $C_3$-$C_{15}$ cycloalkyl or $C_1$-$C_6$ alkyl-$C_3$-$C_{15}$ cycloalkyl; wherein cycloalkyl or alkyl is optionally substituted by one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted by halogen; and m. —P(═O)$R^{zm}R^{zn}$, —(CH2)$_{n8}$—P(═O)$R^{zm}R^{zn}$, —$NR^{zm}$S(═O)$R^{zn}$ and —$NR^{zm}$S(═O)$_2R^{zm}$, wherein each $R^{zm}$ and $R^{zn}$ is independently selected from the group consisting of hydrogen, $C_{1-6}$ alkyl and $C_{6-10}$ aryl; n8 is 1 or 2; Wherein $C_{1-6}$ alkyl is substituted by one to six substituents selected from the group consisting of $C_{1-6}$ alkoxy, $C_{3-6}$ cycloalkyl and halogen, and $C_{3-6}$ cycloalkyl is optionally substituted by one to three substituents selected from the group consisting of $C_{1-3}$ alkyl and halogen; wherein the $C_{6-10}$ aryl is optionally substituted by one to three substituents selected from the group consisting of $C_{1-3}$ alkyl; or $R^{zm}$ and $R^{zn}$ together with the phosphorous atom to which they are attached form a ring with 5 to 8 ring atoms, wherein 0 to 2 of the ring atoms other than phosphorus are heteroatoms each independently selected from: O, S, and N, wherein the ring is optionally substituted with from 1-3 independently selected $C_{1-6}$ alky.

Yet still another aspect of the present disclosure provides a compound of Formula (Id), a stereoisomer, a pharmaceutically acceptable salt, or a deuterated compound thereof:

Formula (Id)

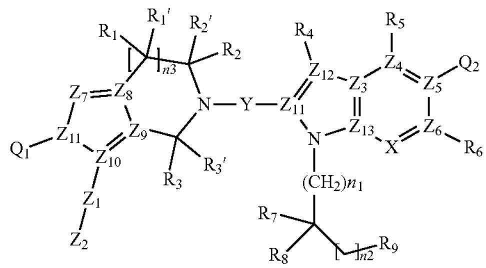

wherein X is selected from the group consisting of N and —$CR^a$; wherein $R^a$ is selected from the group consisting of hydrogen, halogen, and $C_{1-6}$ alkyl;

wherein Y is —C(═O)—;

wherein each of $Z_3$, $Z_4$, $Z_5$, $Z_6$, $Z_7$, $Z_8$, $Z_9$, $Z_{10}$, $Z_{11}$, $Z_{12}$ and $Z_{13}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic, bridged ring, spiro ring, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and —$NR^{Qa}R^{Qb}$, wherein two $C_{1-6}$ alkyl groups optionally together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein each of $R_1$, $R_2$, $R_3$, $R_1$', $R_2$' and $R_3$' is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl;

wherein $R_2$ and $R_3$ together with the carbon atom to which they are attached form 4- to 8-membered heterocycloalkyl;

wherein $R_1$ and $R_1$' optionally together with the carbon atom to which they are attached form $C_3$-$C_8$ cycloalkyl, and $R_2$ and $R_2$' optionally together with the carbon atom to which they are attached form $C_3$-$C_8$ cycloalkyl; and $R_3$ and $R_3$' optionally together with the carbon atom to which they are attached form $C_3$-$C_8$ cycloalkyl;

each of $R_4$, $R_5$ and $R_6$ is independently selected from the group consisting of hydrogen, halogen and $C_{1-6}$ alkyl;

each of $R_7$ and $R_8$ is independently selected from the group consisting of hydrogen and $C_{1-6}$ alkyl, wherein $C_{1-6}$ alkyl is optionally substituted with one or more substituents independently selected from the group consisting of halogen and $C_{3-15}$ cycloalkyl;

or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl, wherein each $C_{1-6}$ alkyl is optionally substituted by one or more substituents independently selected from the group consisting of halogen, hydroxyl, —$NR^{7a}R^{7b}$, $C_{1-6}$ alkoxy and 3- to 12-membered heterocyclic, and $R^{7a}$ and $R^{7b}$ are independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ carbocyclic ring;

$n_1$ is 0, 1, 2 or 3;

n2 is 0, 1, 2, 3, 4 or 5;

n3 is 0 or 1;

$R_9$ is selected from the group consisting of:

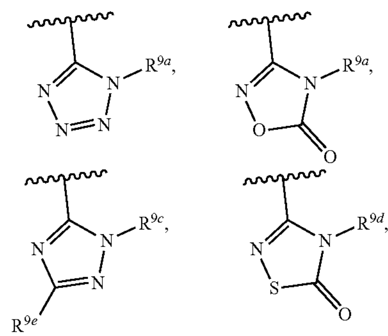

—$CO_2R^{9f}$ and —C(═O)—$NR^{9g}R^{9h}$; and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy;

$R^{9e}$ is selected from the group consisting of hydrogen and $C_{1-6}$ alkyl optionally substituted by one or more halogen atoms;

$R^{9f}$ is selected from the group consisting of hydrogen and $C_{1-6}$ alkyl;

$R^{9h}$ is selected from the group consisting of hydrogen, $C_{1-6}$ alkyl, ($C_{1-6}$ alkyl) carbonyl, cyano and —$S(═O)_{n9}$—$R^{9i}$; n9 is 0, 1 or 2;

$R^{9i}$ is $C_{1-6}$ alkyl;

$Z_1$ is selected from the group consisting of:

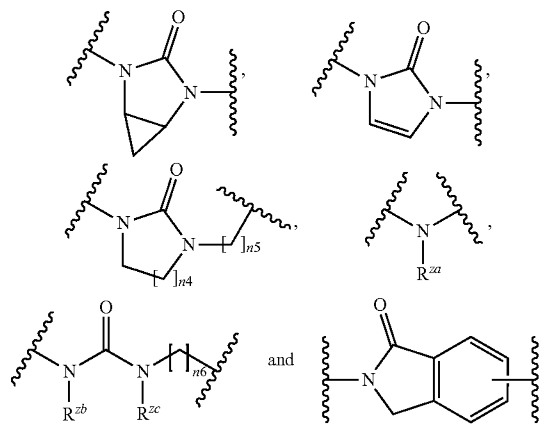

wherein $R^{za}$ is selected from the group consisting of hydrogen, $C_{1-6}$ alkyl and ($C_{1-6}$ alkyl) carbonyl, and each of $R^{zb}$ and $R^{zc}$ is independently selected from the group consisting of hydrogen and $C_{1-6}$ alkyl;

n4 is 1, 2 or 3;

each of n5 and n6 is independently an integer selected from 0 to 10;

$Z_2$ is selected from the group consisting of $C_{1-6}$ alkyl, $C_{3-15}$ cycloalkyl, 3- to 12-membered heterocyclic, $C_{6-10}$ aryl, 5- to 10-membered heteroaryl:

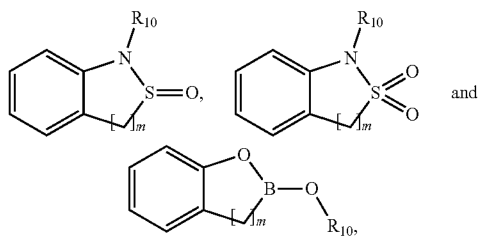

and wherein $Z_2$ is independently optionally substituted with one to five G;

m is 1, 2, or 3;

$R_{10}$ is independently selected from the group consisting of hydrogen, $C_{1-6}$ alkyl, ($C_{1-6}$ alkyl) aryl, $C_{1-6}$ haloalkyl, $C_{3-15}$ is cycloalkyl and $C_{1-6}$ alkyl-$C_{3-15}$ cycloalkyl.

wherein G is selected from the group consisting of:

a. Oxo;

b. Halogen;

c. Cyano;

d. —$NR^{zd}R^{ze}$; wherein $R^{zd}$ and $R^{ze}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

e. —C(═O)—$NR^{zf}R^{zg}$; wherein $R^{zf}$ and $R^{zg}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

f. —$S(═O)_{n7}$—$R^{zh}$; wherein n7 is 0, 1 or 2; $R^{zh}$ is selected from the group consisting of hydrogen and $C_{1-6}$ alkyl;

g. $C_{1-6}$ alkyl; wherein $C_{1-6}$ alkyl is optionally substituted with one or more substituents independently selected from the group consisting of halogen, hydroxyl, —$NR^{zi}R^{zj}$, $C_{1-6}$ alkoxy, $C_{1-6}$ haloalkoxy and 3- to 12-membered heterocyclic; wherein each of $R^{zi}$ and $R^{zj}$ is independently selected from the group consisting of hydrogen and $C_{1-6}$ alkyl, wherein the 3- to 12-membered heterocyclic groups are optionally substituted with one or more substituents selected from the group consisting of cyano, $C_{1-6}$ alkyl and 3- to 12-membered heterocyclic;

h. $C_{1-6}$ alkoxy; wherein $C_{1-6}$ alkoxy is optionally substituted by one or more substituents of hydroxyl, halogen and $C_{1-6}$ alkoxy;

i. 3- to 12-membered heterocyclic; wherein 3- to 12-membered heterocyclic is optionally substituted by one or more substituents independently selected from the group consisting of $C_{1-6}$ alkyl and ($C_{1-6}$ alkyl) carbonyl;

j. $C_{6-10}$ aryl; wherein $C_{6-10}$ aryl is optionally substituted by one or more ($C_{1-6}$ alkyl) carbonyl;

k. 5- to 10-membered heteroaryl; wherein the 5- to 10-membered heteroaryl is optionally substituted with one or more substituents independently selected from the group consisting of $C_{1-6}$ alkyl, $C_{1-6}$ alkoxy, —$NR^{zk}R^{zl}$, and 3- to 12-membered heterocyclic; wherein $R^{zk}$ and $R^{zl}$ are independently selected from the group consisting of hydrogen, $C_{1-6}$ alkyl, and ($C_{1-6}$ alkyl)carbonyl and wherein the 3- to 12-membered heterocyclic is optionally substituted with one or more substituents independently selected from the group consisting of $C_{1-6}$ alkyl, and ($C_{1-6}$ alkyl)carbonyl;

l. $C_3$-$C_{15}$ cycloalkyl or $C_1$-$C_6$ alkyl-$C_3$-$C_{15}$ cycloalkyl; wherein cycloalkyl or alkyl is optionally substituted by one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted by halogen; and m. —P(═O)$R^{zm}R^{zn}$, —$(CH2)_{n8}$—P(═O)$R^{zm}R^{zn}$, —$NR^{zm}S(═O)R^{zn}$ and —$NR^{zm}S(═O)_2R^{zn}$, wherein each $R^{zm}$ and $R^{zn}$ is independently selected from the group consisting of hydrogen, $C_{1-6}$ alkyl and $C_{6-10}$ aryl; n8 is 1 or 2; wherein $C_{1-6}$ alkyl is substituted by one to six substituents selected from the group consisting of $C_{1-6}$ alkoxy, $C_{3-6}$ cycloalkyl and halogen, and $C_{3-6}$ cycloalkyl is optionally substituted by one to three substituents selected from the group consisting of $C_{1-3}$ alkyl and halogen; wherein the $C_{6-10}$ aryl is optionally substituted by one to three substituents selected from the group consisting of $C_{1-3}$ alkyl; or $R^{zm}$ and $R^{zn}$ together with the phosphorous atom to which they are attached form a ring with 5 to 8 ring atoms, wherein 0 to 2 of the ring atoms other than phosphorus are heteroatoms each independently selected from: O, S, and N, wherein the ring is optionally substituted with from 1-3 independently selected $C_{1-6}$ alky.

Yet still another aspect of the present disclosure provides a compound of Formula (Ie), a stereoisomer, a pharmaceutically acceptable salt, or a deuterated compound thereof:

Formula (Ie)

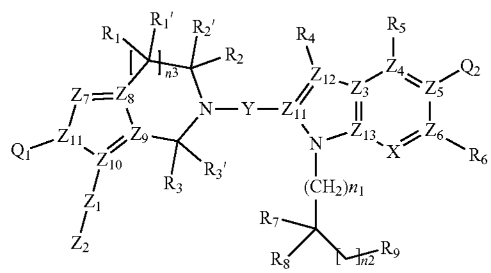

wherein X is selected from the group consisting of N and —$CR^a$; wherein $R^a$ is selected from the group consisting of hydrogen, halogen, and $C_{1-6}$ alkyl;

wherein Y is —C(═O)—;

wherein each of $Z_3$, $Z_4$, $Z_5$, $Z_6$, $Z_7$, $Z_8$, $Z_9$, $Z_{10}$, $Z_{11}$, $Z_{12}$ and $Z_{13}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic, bridged ring, spiro ring, and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and —$NR^{Qa}R^{Qb}$, wherein two $C_{1-6}$ alkyl groups optionally together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein each of $R_1$, $R_2$, $R_3$, $R_1'$, $R_2'$ and $R_3'$ is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl;

wherein $R_2$ and $R_3$ together with the carbon atom to which they are attached form 4- to 8-membered heterocycloalkyl;

wherein $R_1$ and $R_1'$ optionally together with the carbon atom to which they are attached form $C_3$-$C_8$ cycloalkyl, and $R_2$ and $R_2'$ optionally together with the carbon atom to which they are attached form $C_3$-$C_8$ cycloalkyl; and $R_3$ and $R_3'$ optionally together with the carbon atom to which they are attached form $C_3$-$C_8$ cycloalkyl;

each of $R_4$, $R_5$ and $R_6$ is independently selected from the group consisting of hydrogen, halogen and $C_{1-6}$ alkyl;

each of $R_7$ and $R_8$ is independently selected from the group consisting of hydrogen and $C_{1-6}$ alkyl, wherein $C_{1-6}$ alkyl is optionally substituted with one or more substituents independently selected from the group consisting of halogen and $C_{3-15}$ cycloalkyl;

or $R_7$ and $R_8$ together with the carbon atom to which they are attached form $C_{3-15}$ carbocyclic ring, wherein the $C_{3-15}$ carbocyclic ring is optionally substituted by one to three $C_{1-6}$ alkyl, wherein each $C_{1-6}$ alkyl is optionally substituted by one or more substituents independently selected from the group consisting of halogen, hydroxyl, —$NR^{7a}R^{7b}$, $C_{1-6}$ alkoxy and 3- to 12-membered heterocyclic, and $R^{7a}$ and $R^{7b}$ are independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ carbocyclic ring;

$n_1$ is 0, 1, 2 or 3;

n2 is 0, 1, 2, 3, 4 or 5;

n3 is 0 or 1:

$R_9$ is selected from the group consisting of:

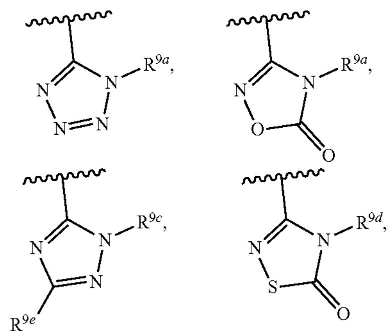

—$CO_2R^{9f}$ and —C(═O)—$NR^{9g}R^{9h}$; and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy;

$R^{9e}$ is selected from the group consisting of hydrogen and $C_{1-6}$ alkyl optionally substituted by one or more halogen atoms;

$R^{9f}$ is selected from the group consisting of hydrogen and $C_{1-6}$ alkyl;

$R^{9h}$ is selected from the group consisting of hydrogen, $C_{1-6}$ alkyl, ($C_{1-6}$ alkyl) carbonyl, cyano and —S(═O)$_{n9}$—$R^{9i}$; n9 is 0, 1 or 2;

$R^{9i}$ is $C_{1-6}$ alkyl;

$Z_1$ is selected from the group consisting of:

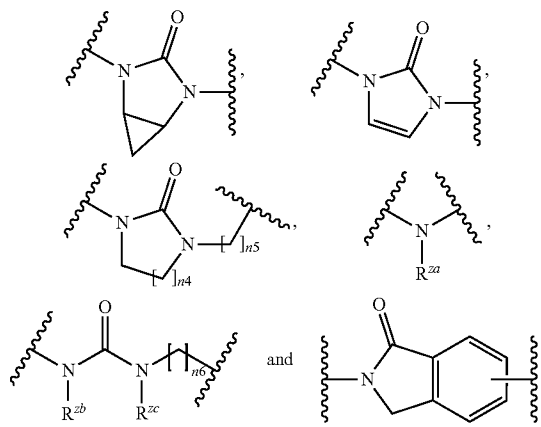

and wherein $R^{za}$ is selected from the group consisting of hydrogen, $C_{1-6}$ alkyl and ($C_{1-6}$ alkyl) carbonyl, and each of $R^{zb}$ and $R^{zc}$ is independently selected from the group consisting of hydrogen and $C_{1-6}$ alkyl;

n4 is 1, 2 or 3;

each of n5 and n6 is independently an integer selected from 0 to 10;

$Z_2$ is selected from the group consisting of $C_{1-6}$ alkyl, $C_{3-15}$ cycloalkyl, 3- to 12-membered heterocyclic, $C_{6-10}$ aryl, and 5- to 10-membered heteroaryl;

wherein $C_{3-15}$ cycloalkyl and 3- to 12-membered heterocyclic is independently optionally substituted with one to five G;

wherein G is selected from the group consisting of:

a. Oxo:

b. Halogen;

c. Cyano;

d. —$NR^{zd}R^{ze}$; wherein $R^{zd}$ and $R^{ze}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

e. —C(═O)—$NR^{zf}R^{zg}$; wherein $R^{zf}$ and $R^{zg}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

f. —S(=O)$_{n7}$—$R^{zh}$; wherein n7 is 0, 1 or 2; $R^{zh}$ is selected from the group consisting of hydrogen and $C_{1-6}$ alkyl;

g. $C_{1-6}$ alkyl; wherein $C_{1-6}$ alkyl is optionally substituted with one or more substituents independently selected from the group consisting of halogen, hydroxyl, —$NR^{zi}R^{zj}$, $C_{1-6}$ alkoxy, $C_{1-6}$ haloalkoxy and 3- to 12-membered heterocyclic; wherein each of $R^{zi}$ and $R^{zj}$ is independently selected from the group consisting of hydrogen and $C_{1-6}$ alkyl, wherein the 3- to 12-membered heterocyclic groups are optionally substituted with one or more substituents selected from the group consisting of cyano, $C_{1-6}$ alkyl and 3- to 12-membered heterocyclic;

h. $C_{1-6}$ alkoxy; wherein $C_{1-6}$ alkoxy is optionally substituted by one or more substituents of hydroxyl, halogen and $C_{1-6}$ alkoxy;

i. 3- to 12-membered heterocyclic; wherein 3- to 12-membered heterocyclic is optionally substituted by one or more substituents independently selected from the group consisting of $C_{1-6}$ alkyl and ($C_{1-6}$ alkyl) carbonyl;

j. $C_{6-10}$ aryl; wherein $C_{6-10}$ aryl is optionally substituted by one or more ($C_{1-6}$ alkyl) carbonyl;

k. 5- to 10-membered heteroaryl; wherein the 5- to 10-membered heteroaryl is optionally substituted with one or more substituents independently selected from the group consisting of $C_{1-6}$ alkyl, $C_{1-6}$ alkoxy, —$NR^{zk}R^{zl}$, and 3- to 12-membered heterocyclic; wherein $R^{zk}$ and $R^{zl}$ are independently selected from the group consisting of hydrogen, $C_{1-6}$ alkyl, and ($C_{1-6}$ alkyl)carbonyl and wherein the 3- to 12-membered heterocyclic is optionally substituted with one or more substituents independently selected from the group consisting of $C_{1-6}$ alkyl, and ($C_{1-6}$ alkyl)carbonyl; and l. $C_3$-$C_{15}$ cycloalkyl or $C_1$-$C_6$ alkyl-$C_3$-$C_{15}$ cycloalkyl; wherein cycloalkyl or alkyl is optionally substituted by one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted by halogen.

In some embodiments, in the compound of any one of Formula (Ia), (Ib), (Ic), (Id) or (Ie), the stereoisomer, the pharmaceutically acceptable salt, or the deuterated compound thereof, the compound has a Formula (If):

Formula (If)

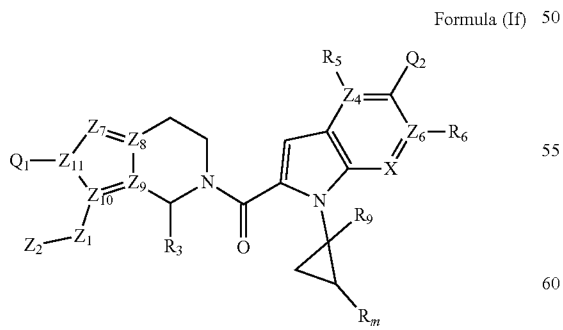

wherein:

wherein X is selected from the group consisting of N and —$CR^a$; wherein $R^a$ is selected from the group consisting of hydrogen, halogen and $C_{1-6}$ alkyl;

wherein each of $Z_4$, $Z_6$, $Z_7$, $Z_8$, $Z_9$, $Z_{10}$ and $Z_{11}$ is independently selected from the group consisting of N and C;

wherein $Q_1$ is selected from the group consisting of $C_{6-10}$ aryl and 5- to 10-membered heteroaryl, wherein $C_{6-10}$ aryl or 5- to 10-membered heteroaryl is optionally substituted by one to five substituents independently selected from the group consisting of halogen, $C_{1-6}$ alkyl, $C_{1-6}$ haloalkyl and $C_{1-6}$ alkoxy;

wherein $Q_2$ is selected from the group consisting of 3- to 12-membered heterocyclic, bridged ring, spiro ring and 5- to 10-membered heteroaryl, wherein 3- to 12-membered heterocyclic, and 5- to 10-membered heteroaryl are optionally substituted by 1-3 substituents independently selected from the group consisting of halogen, $C_{1-6}$ alkyl, $C_{1-6}$ haloalkyl, $C_{1-6}$ alkoxy, and —$NR^{Qa}R^{Qb}$, wherein two $C_{1-6}$ alkyl groups together with the carbon atoms to which they are attached form $C_{3-8}$ carbocyclic ring; wherein $R^{Qa}$ and $R^{Qb}$ are independently selected from the group consisting of hydrogen, $C_{1-6}$ alkyl, $C_{1-6}$ haloalkyl and ($C_{1-6}$ alkyl) carbonyl;

wherein $R_3$ is independently selected from the group consisting of hydrogen, halogen, $C_{1-6}$ alkyl, $C_{1-6}$ alkoxy, $C_{1-6}$ haloalkoxy, cycloalkyl and heterocycloalkyl; wherein $C_{1-6}$ alkyl, cycloalkyl or heterocycloalkyl is optionally substituted by one or more substituents independently selected from the group consisting of halogen, $C_{1-6}$ alkoxy and hydroxyl;

each of $R_5$ and $R_6$ is independently selected from the group consisting of hydrogen, halogen and $C_{1-6}$ alkyl;

$R_m$ is $C_{1-6}$ alkyl; wherein $C_{1-6}$ alkyl is optionally substituted with one or more substituents independently selected from the group consisting of halogen, hydroxyl, —$NR^{7a}R^{7b}$, $C_{1-6}$ alkoxy and 3- to 12-membered heterocyclic, wherein $R^{7a}$ and $R^{7b}$ is independently selected from the group consisting of hydrogen, $C_{1-6}$ alkyl and ($C_{1-6}$ alkyl) carbonyl; and any two $C_{1-6}$ alkyl optionally together with the carbon atom to which they are attached form $C_{3-15}$ carbocyclic ring;

$R_9$ is selected from the group consisting of:

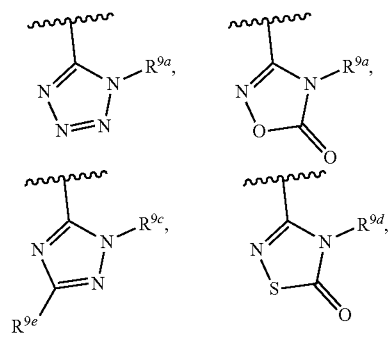

$CO_2R^{9f}$ and —C(=O)—$NR^{9g}R^{9h}$; and each of $R^{9a}$, $R^{9b}$, $R^{9c}$, $R^{9d}$ and $R^{9g}$ is independently selected from the group consisting of hydrogen, $C_{1-6}$ alkyl and ($C_{1-6}$ alkyl) carbonyl, wherein $C_{1-6}$ alkyl is optionally substituted with one or more substituents independently selected from the group consisting of halogen and $C_{1-6}$ alkoxy;

$R^{9e}$ is selected from the group consisting of hydrogen and $C_{1-6}$ alkyl optionally substituted by one or more halogen atoms;

$R^{9f}$ is selected from the group consisting of hydrogen and $C_{1-6}$ alkyl;

$R^{9h}$ is selected from the group consisting of hydrogen, $C_{1-6}$ alkyl, ($C_{1-6}$ alkyl) carbonyl, cyano and —S(═O)$_{n9}$—$R^{9i}$; n9 is 0, 1 or 2;

$R^{9i}$ is $C_{1-6}$ alkyl;

$Z_1$ is selected from the group consisting of:

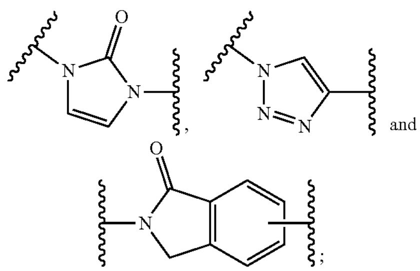

$Z_2$ is selected from the group consisting of $C_{1-6}$ alkyl, $C_{3-15}$ cycloalkyl, 3- to 12-membered heterocyclic, $C_{6-10}$ aryl, 5- to 10-membered heteroaryl,

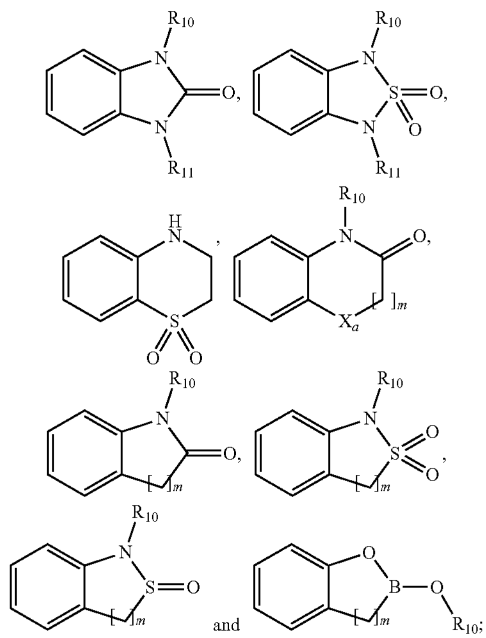

wherein $Z_2$ is independently optionally substituted with one to five G;

m is 1, 2 or 3;

each of $R_{10}$ and $R_{11}$ is independently selected from the group consisting of hydrogen, $C_{1-6}$ alkyl, ($C_{1-6}$ alkyl)-aryl, $C_{1-6}$ haloalkyl, $C_{3-15}$ cycloalkyl and $C_{1-6}$ alkyl-$C_{3-15}$ cycloalkyl;

$X_a$ is $CH_2$ or O;

wherein G is selected from the group consisting of:

a. Oxo:

b. Halogen;

c. Cyano;

d. —$NR^{zd}R^{ze}$; wherein $R^{zd}$ and $R^{ze}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

e. —C(═O)—$NR^{zf}R^{zg}$; wherein $R^{zf}$ and $R^{zg}$ are independently selected from the group consisting of hydrogen, $C_{1-6}$ alkyl and ($C_{1-6}$ alkyl) carbonyl; wherein $C_{1-6}$ alkyl is optionally substituted by one or more substituents independently selected from the group consisting of hydroxyl, halogen and $C_{1-6}$ alkoxy;

f. —S(═O)$_{n7}$—$R^{zh}$; wherein n7 is 0, 1 or 2; $R^{zh}$ is selected from the group consisting of hydrogen and $C_{1-6}$ alkyl;

g. $C_{1-6}$ alkyl; wherein $C_{1-6}$ alkyl is optionally substituted with one or more substituents independently selected from the group consisting of halogen, hydroxyl, —$NR^{zi}R^{zj}$, $C_{1-6}$ alkoxy, $C_{1-6}$ haloalkoxy and 3- to 12-membered heterocyclic group; wherein each of $R^{zi}$ and $R^{zj}$ is independently selected from the group consisting of hydrogen and $C_{1-6}$ alkyl, wherein the 3- to 12-membered heterocyclic groups are optionally substituted with one or more substituents selected from the group consisting of cyano, $C_{1-6}$ alkyl and 3- to 12-membered heterocyclic;

h. $C_{1-6}$ alkoxy; wherein $C_{1-6}$ alkoxy is optionally substituted by one or more substituents of hydroxyl, halogen and $C_{1-6}$ alkoxy;

i. 3- to 12-membered heterocyclic; wherein 3- to 12-membered heterocyclic is optionally substituted by one or more substituents independently selected from the group consisting of $C_{1-6}$ alkyl and ($C_{1-6}$ alkyl) carbonyl;

j. $C_{6-10}$ aryl; wherein $C_{6-10}$ aryl is optionally substituted by one or more ($C_{1-6}$ alkyl) carbonyl;

k. 5- to 10-membered heteroaryl; wherein the 5- to 10-membered heteroaryl is optionally substituted with one or more substituents independently selected from the group consisting of $C_{1-6}$ alkyl, $C_{1-6}$ alkoxy, —$NR^{zk}R^{zl}$, and 3- to 12-membered heterocyclic; wherein $R^{zk}$ and $R^{zl}$ are independently selected from the group consisting of hydrogen, $C_{1-6}$ alkyl, and ($C_{1-6}$ alkyl)carbonyl and wherein the 3- to 12-membered heterocyclic is optionally substituted with one or more substituents independently selected from the group consisting of $C_{1-6}$ alkyl, and ($C_{1-6}$ alkyl)carbonyl;

l. $C_3$-$C_{15}$ cycloalkyl or $C_1$-$C_6$ alkyl-$C_3$-$C_{15}$ cycloalkyl; wherein cycloalkyl or alkyl is optionally substituted by one or more substituents independently selected from the group consisting of halogen, oxo, $C_{1-6}$ alkyl, $C_{1-6}$ alkoxy and ($C_{1-6}$ alkyl) carbonyl, wherein each of alkyl and alkoxy is optionally substituted by halogen; and m. —P(═O)$R^{zm}R^{zn}$, —(CH2)$_{n8}$—P(═O)$R^{zm}R^{zn}$, —$NR^{zm}$S(═O)$R^{zn}$ and —$NR^{zm}$S(═O)$_2R^{zn}$, wherein each $R^{zm}$ and $R^{zn}$ is independently selected from the group consisting of hydrogen, $C_{1-6}$ alkyl and $C_{6-10}$ aryl; n8 is 1 or 2; wherein $C_{1-6}$ alkyl is substituted by one to six substituents selected from the group consisting of $C_{1-6}$ alkoxy, $C_{3-6}$ cycloalkyl and halogen, and $C_{3-6}$ cycloalkyl is optionally substituted by one to three substituents selected from the group consisting of $C_{1-3}$ alkyl and halogen; wherein the $C_{6-10}$ aryl is optionally substituted by one to three substituents selected from the group consisting of $C_{1-3}$ alkyl; Or $R^{zm}$ and $R^{zn}$ optionally together with the phosphorous atom to which they are attached form a ring with 5 to 8 ring atoms, wherein 0 to 2 of the ring atoms other than phosphorus are heteroatoms each independently selected from: O, S, and N, wherein the ring is optionally substituted with from 1-3 independently selected $C_{1-6}$ alky.

In some embodiments, in the compound of any one of Formula (Ia), (Ib), (Ic), (Id) or (Ie), the stereoisomer, the pharmaceutically acceptable salt, or the deuterated compound thereof, the compound has a Formula (Ig), Formula (Ig)

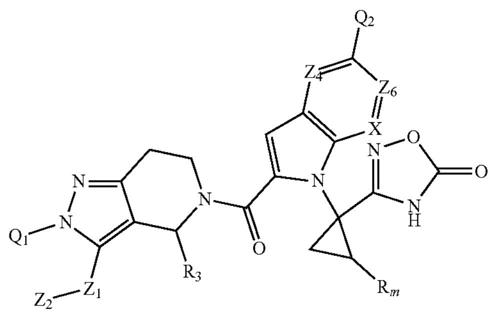

wherein each of X, $Z_4$ and $Z_6$ is independently selected from the group consisting of N and CH;

$R_3$ is independently selected from the group consisting of hydrogen, halogen, $C_{1-6}$ alkyl; wherein $C_{1-6}$ alkyl is optionally substituted with one or more halogens;

$R_m$ is $C_{1-6}$ alkyl; wherein $C_{1-6}$ alkyl is optionally substituted with one or more halogens;

$Z_1$ is selected from the group consisting of:

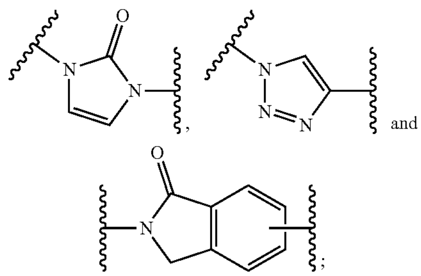

$Z_2$ is selected from the group consisting of $C_{6-10}$ aryl, 5- to 10-membered heteroaryl,

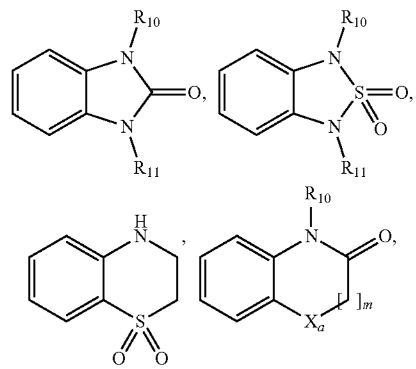

-continued

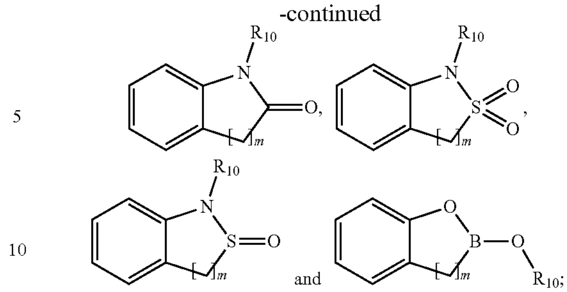

In some embodiments, in the compound of any one of Formula (Ia), (Ib), (Ic), (Id), (Ie), (If), or (Ig), the stereoisomer, the pharmaceutically acceptable salt, or the deuterated compound thereof, $Z_2$ is selected from

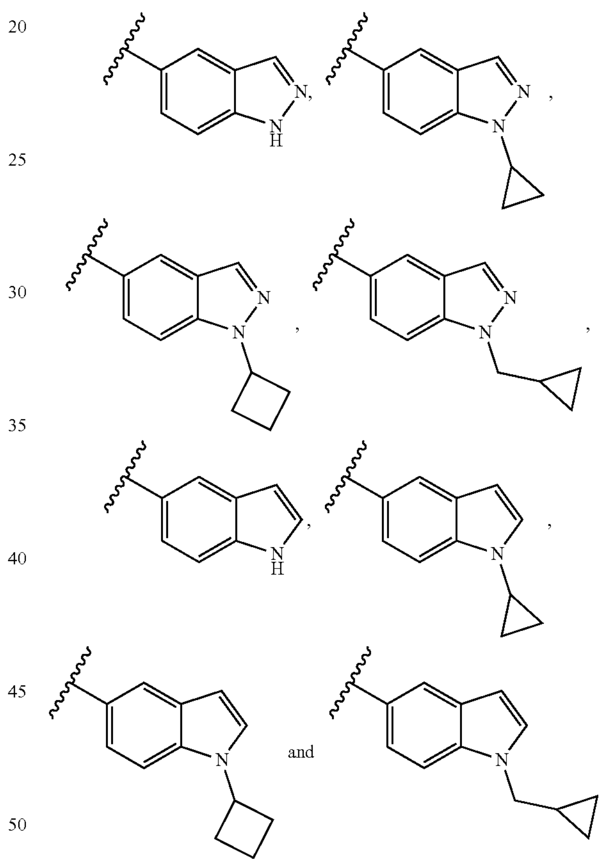

and $Z_2$ is substituted by one to five substituents selected from the group consisting of halogen, $C_{1-6}$ alky and $C_{1-6}$ alkoxy.

In some embodiments, in the compound of any one of Formula (Ia), (Ib), (Ic), (Id), (Ie), (If), or (Ig), the stereoisomer, the pharmaceutically acceptable salt, or the deuterated compound thereof, Q1 is $C_{6-10}$ aryl.

In some embodiments, in the compound of any one of Formula (Ia), (Ib), (Ic), (Id), (Ie), (If), or (Ig), the stereoisomer, the pharmaceutically acceptable salt, or the deuterated compound thereof, $Q_1$ is $C_{6-10}$ aryl, and the $C_{6-10}$ aryl is optionally substituted with one to five substituents selected from the group consisting of halogen, $C_{1-6}$ alkyl, $C_{1-6}$ haloalkyl and $C_{1-6}$ alkoxy.

In some embodiments, in the compound of any one of formula (Ia), (Ib), (Ic), (Id), (Ie), (If), or (Ig), the stereoisomer, the pharmaceutically acceptable salt, or the deuterated compound thereof. $R_3$ is selected from the group consisting of H, halo, and $C_{1-6}$ alkyl.

In some embodiments, in the compound of any one of Formula (If) or Formula (Ig), the stereoisomer, the pharmaceutically acceptable salt, or the deuterated compound thereof, $R_m$ is $C_{1-6}$ alkyl, and the $C_{1-6}$ alkyl is optionally substituted with one or more halogens.

In some embodiments, in the compound of any one of Formula (Ia), (Ib), (Ic), (Id), (Ie), (If), or (Ig), the stereoisomer, the pharmaceutically acceptable salt, or the deuterated compound thereof, $R_9$ is

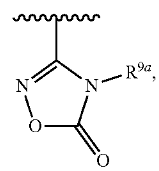

$R^{9a}$ is selected from the group consisting of hydrogen, $C_{1-6}$ alkyl and ($C_{1-6}$ alkyl) carbonyl.

In some embodiments, in the compound, the stereoisomer, the pharmaceutically acceptable salt, or the deuterated compound thereof of the present disclosure, the compound is selected from the group consisting of:

3

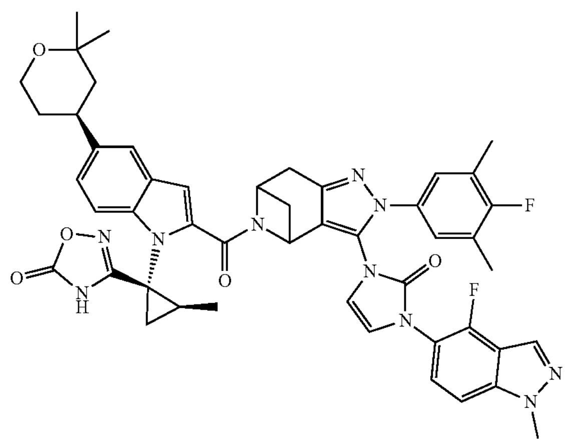

4

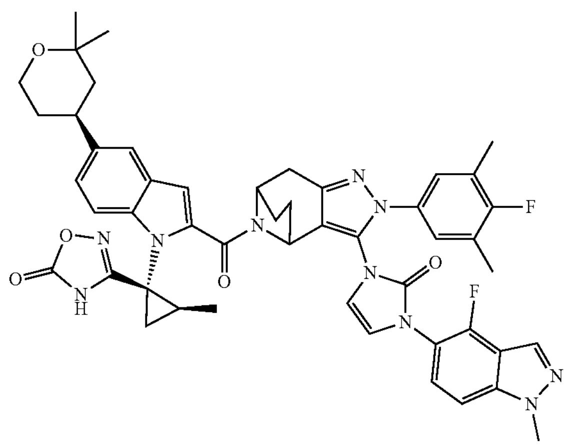

5

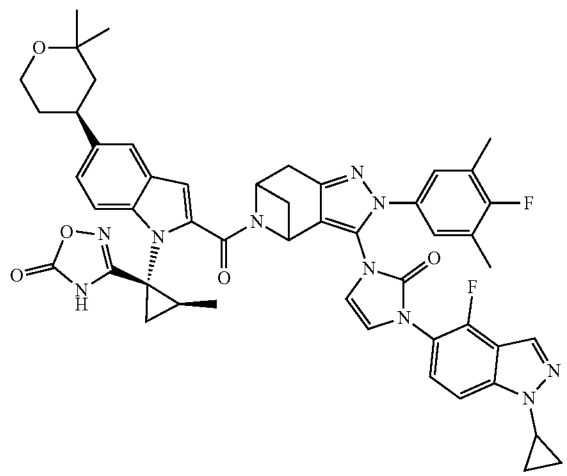

6

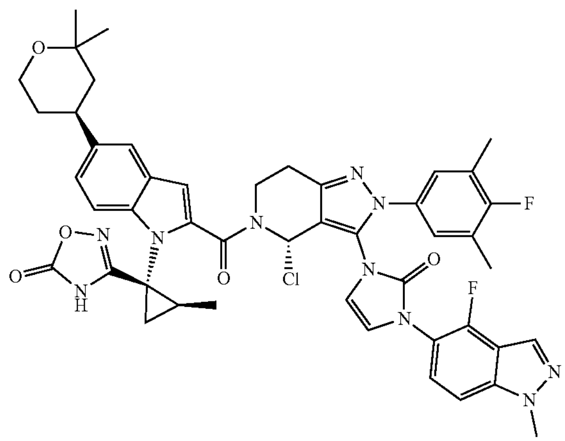

-continued
7
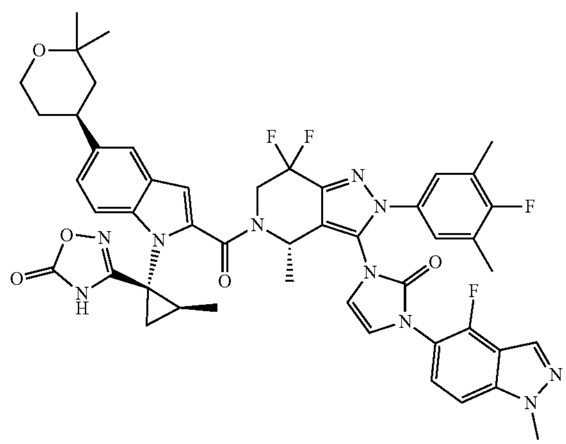
8
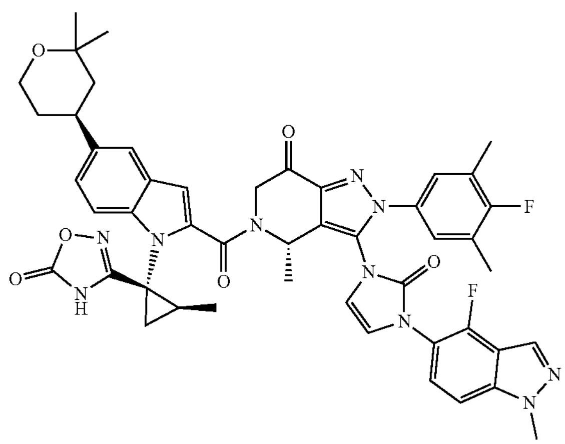
9
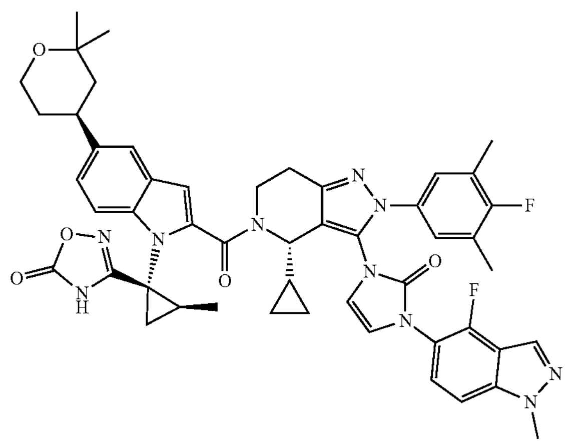
10
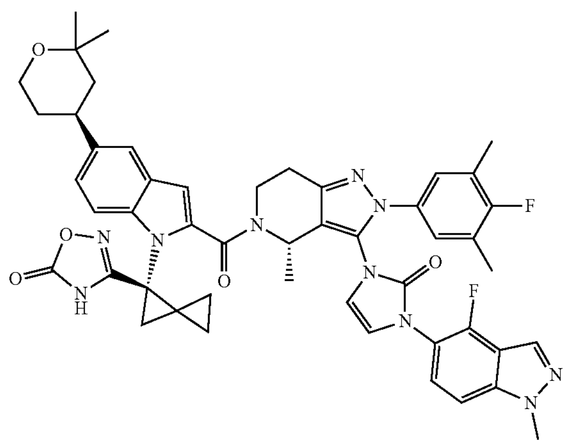
11
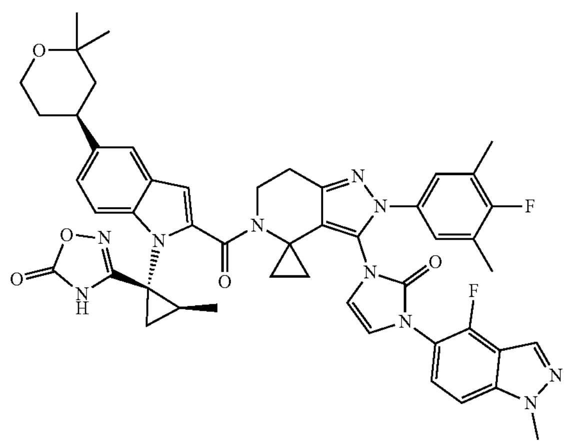
12
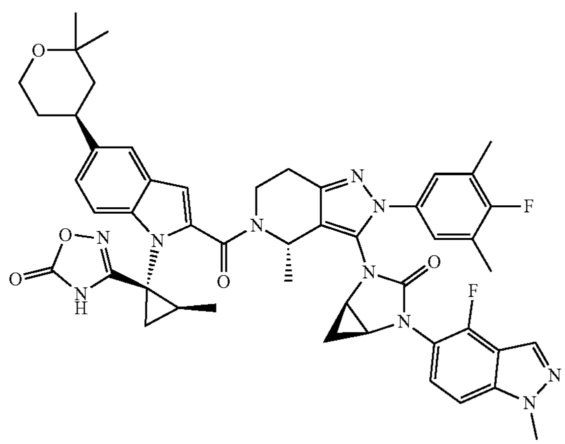

-continued
14
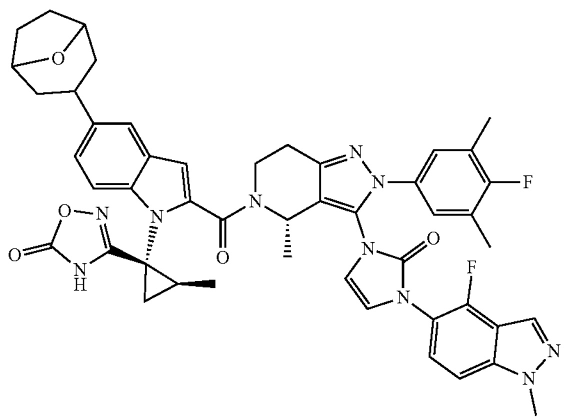
15
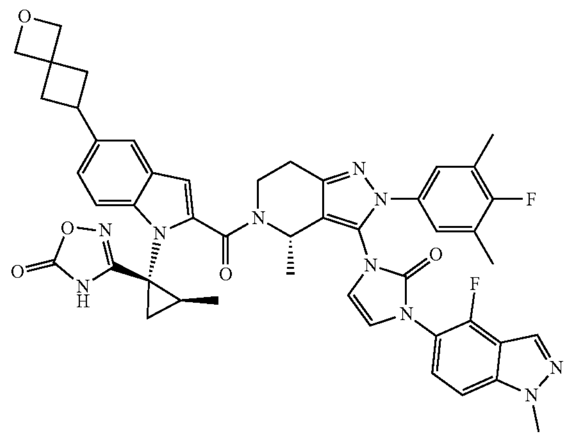
16
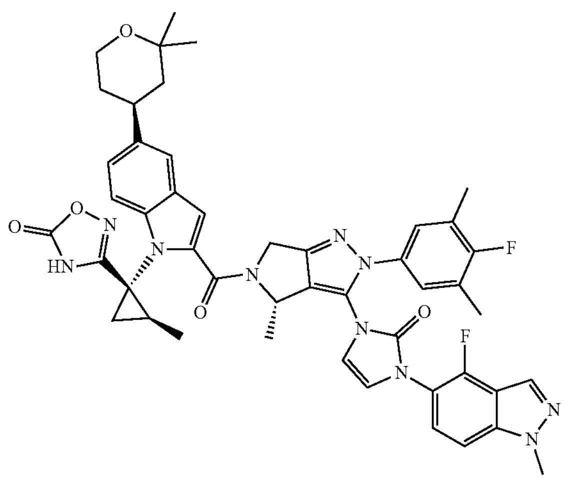
17
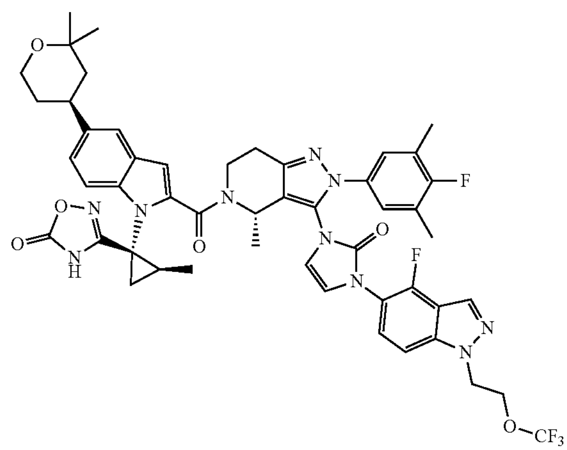
22
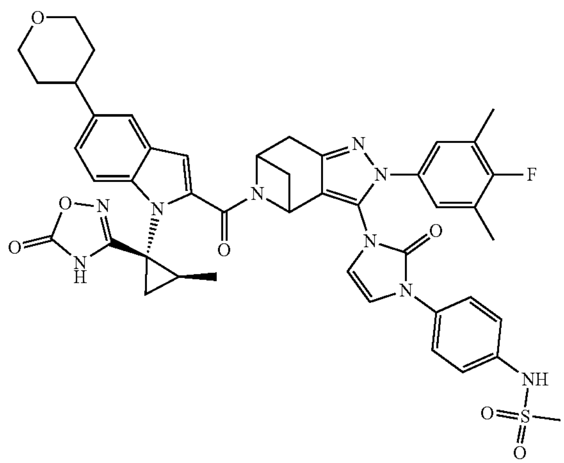
23
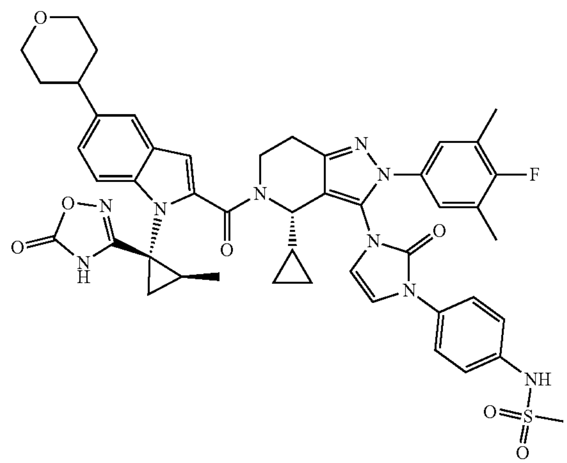

-continued
24
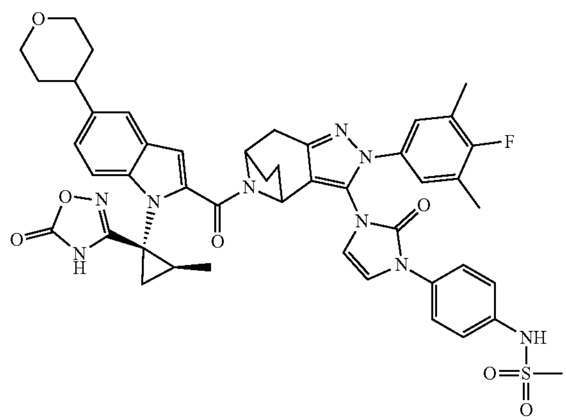
25
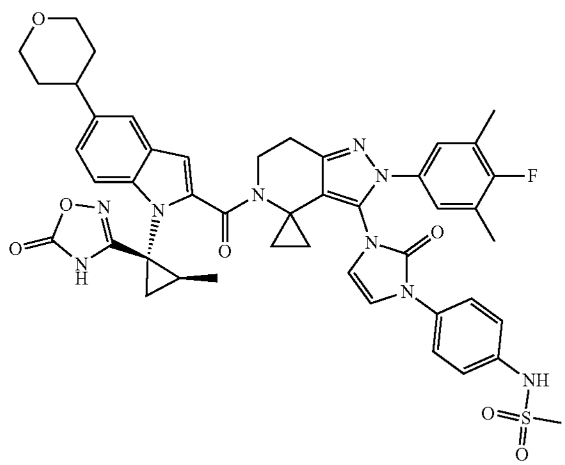
26
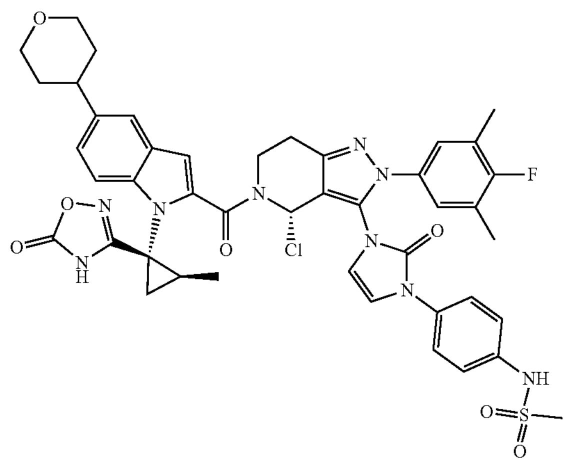
27
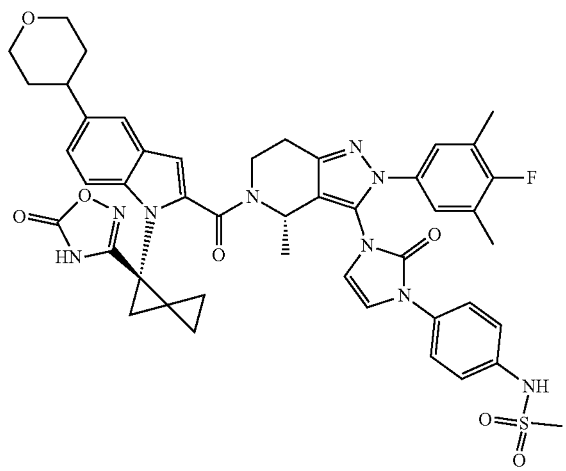
28
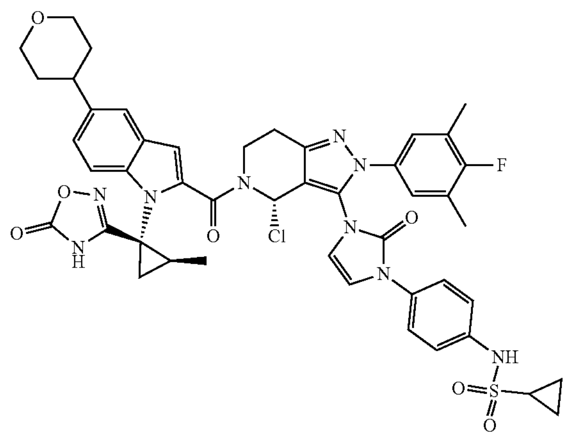
31
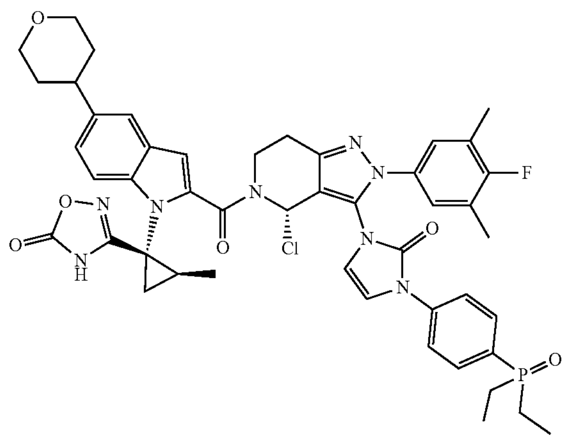

-continued
32
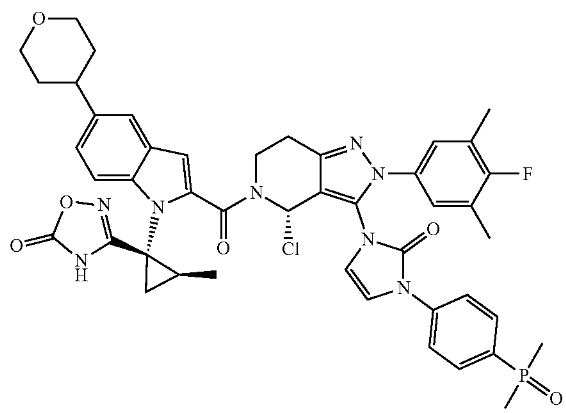
49
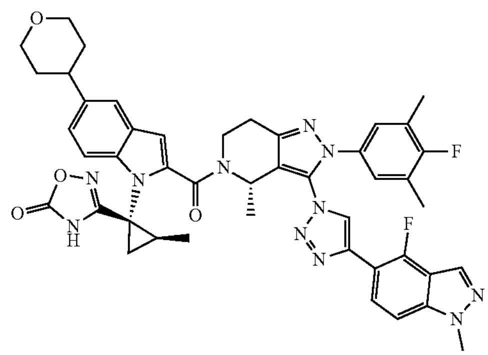
and
48
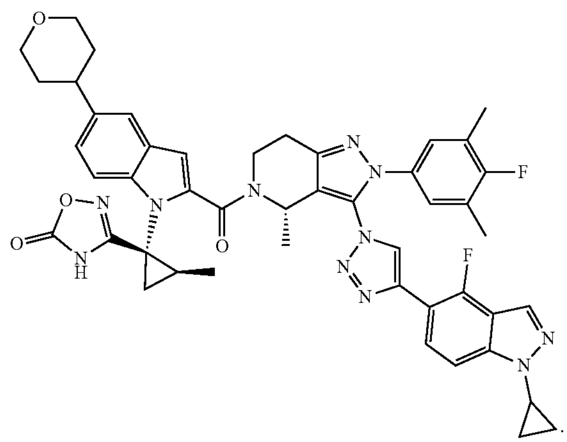

In some embodiments, the pharmaceutically acceptable salt of the present disclosure, is selected from a sodium salt, a calcium salt, a potassium salt, a magnesium salt and a lithium salt.
In some embodiments, the compound of the present disclosure is selected from the group consisting of
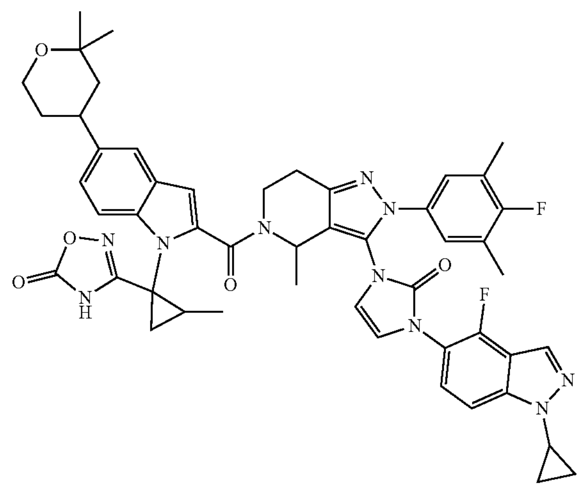
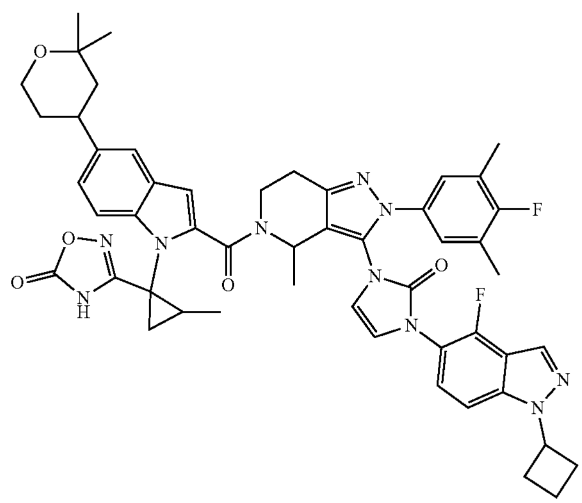
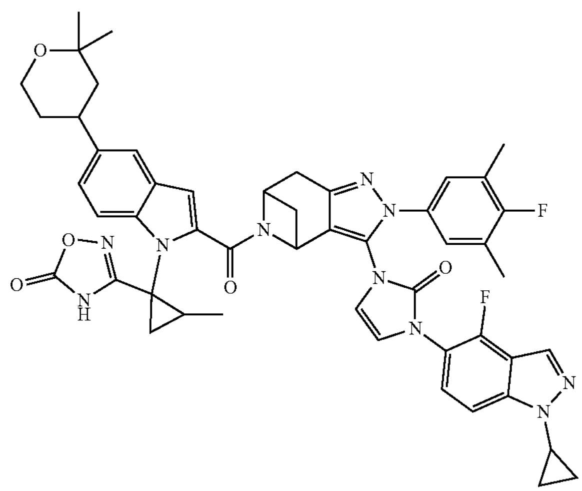
-continued
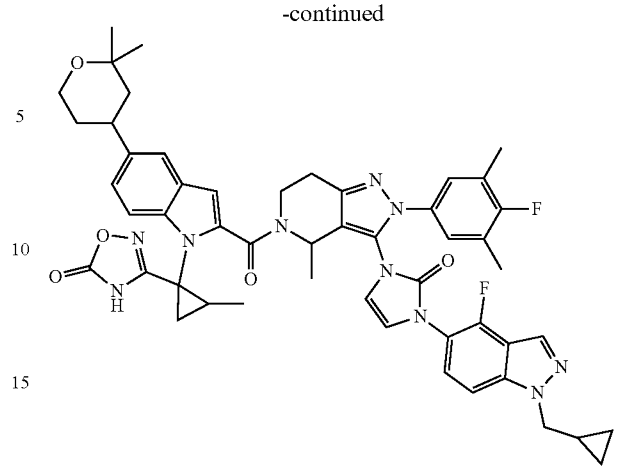
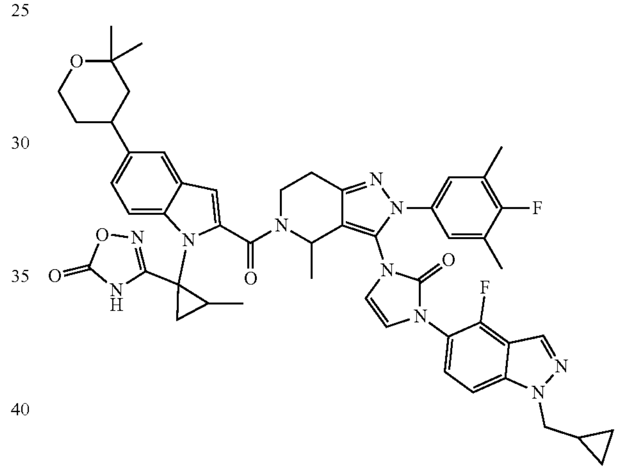
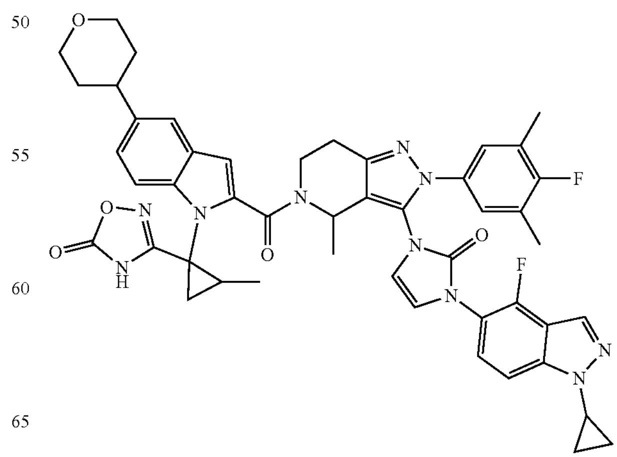

-continued
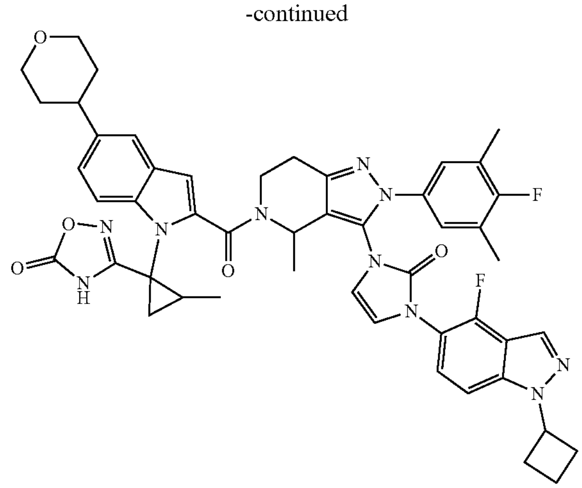
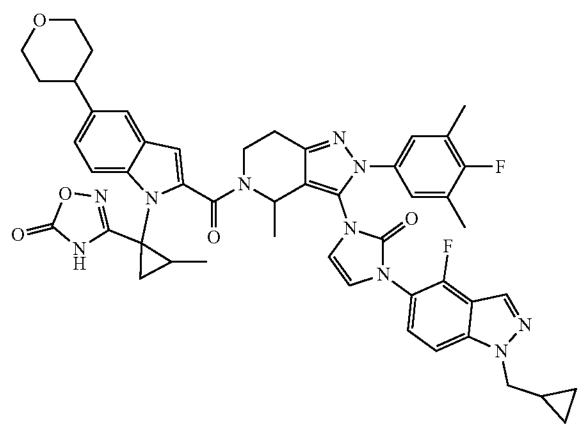
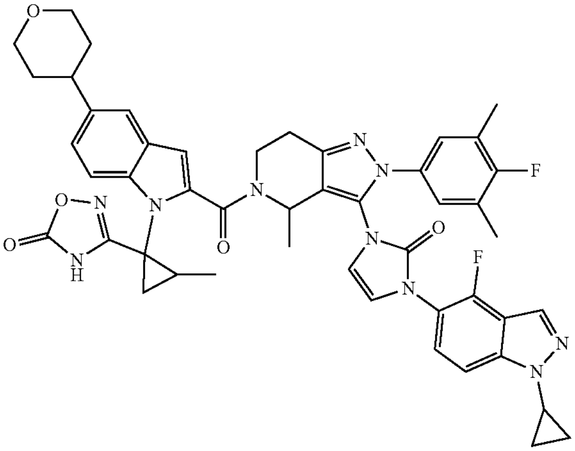
-continued
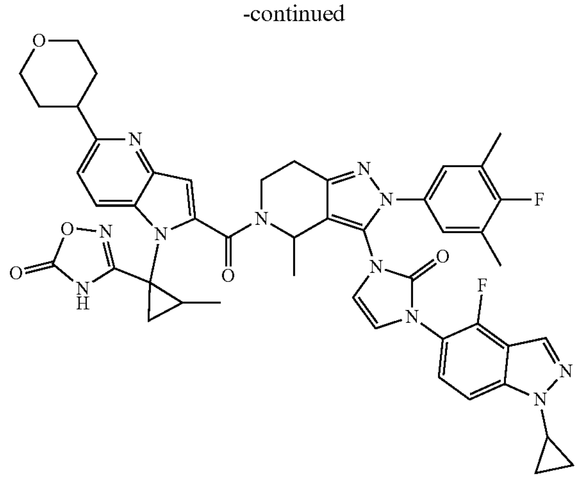
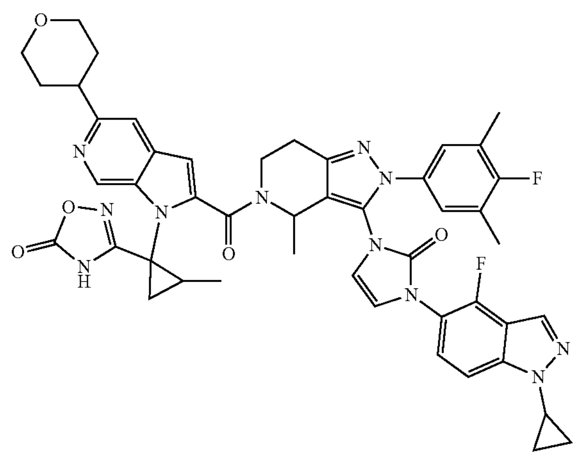
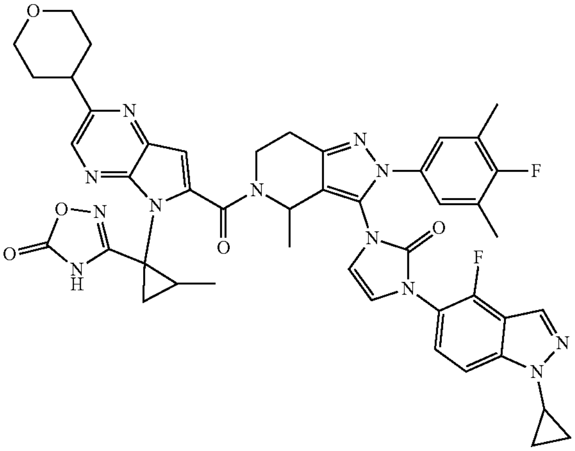

-continued
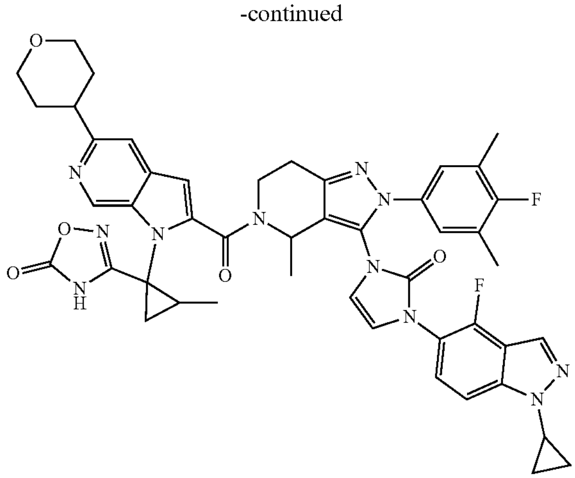
-continued
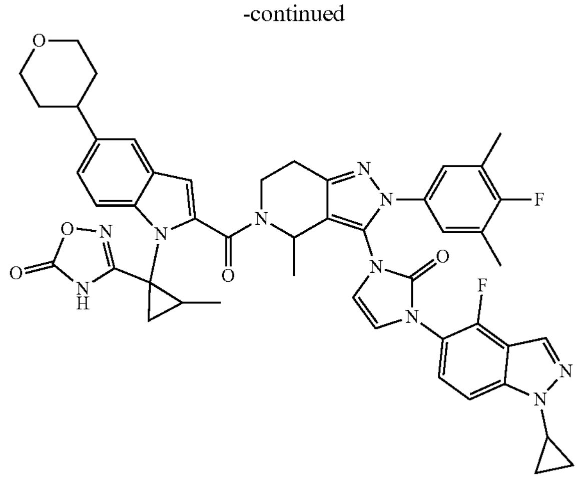
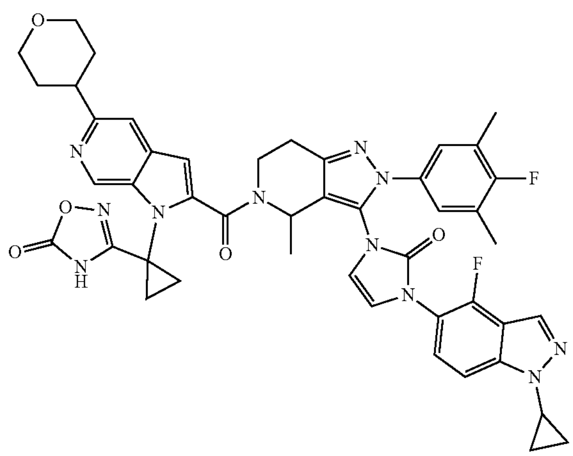
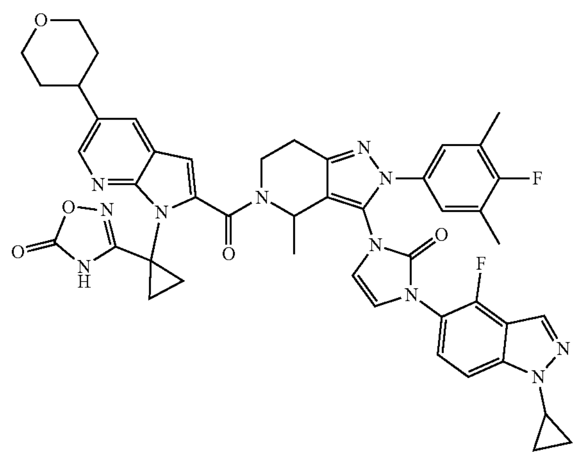
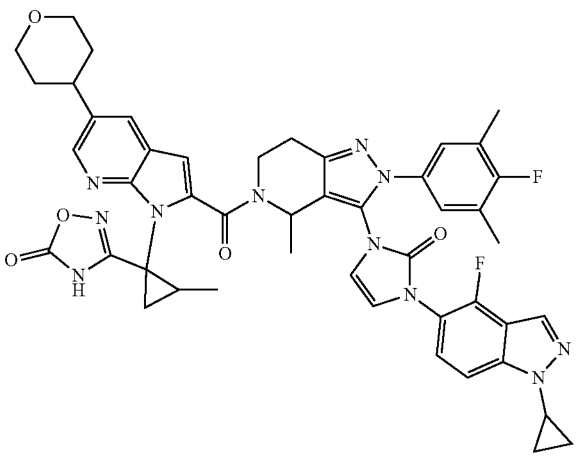
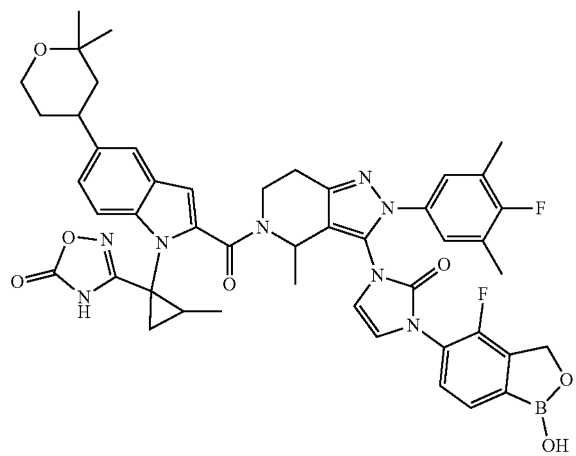

-continued
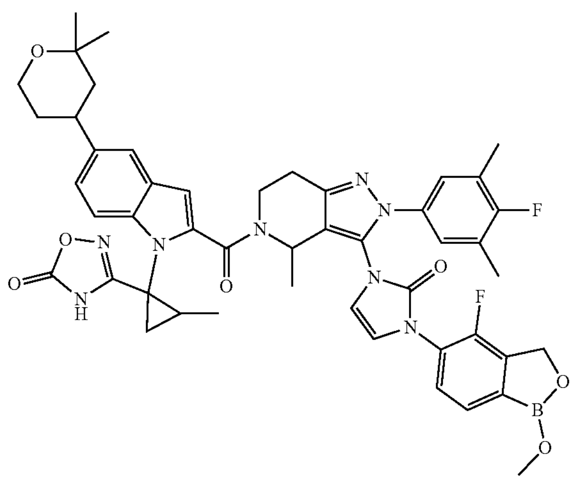
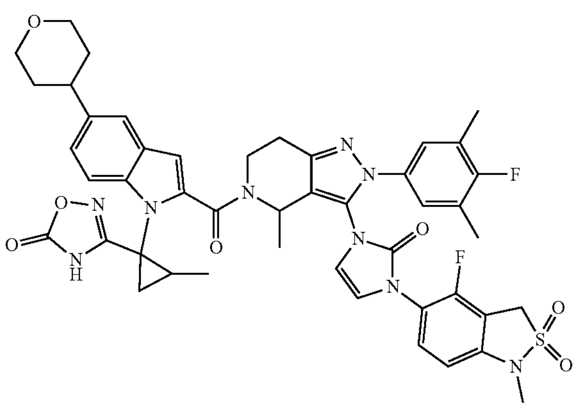
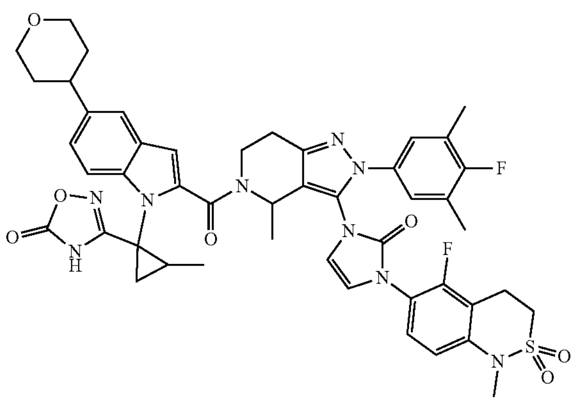
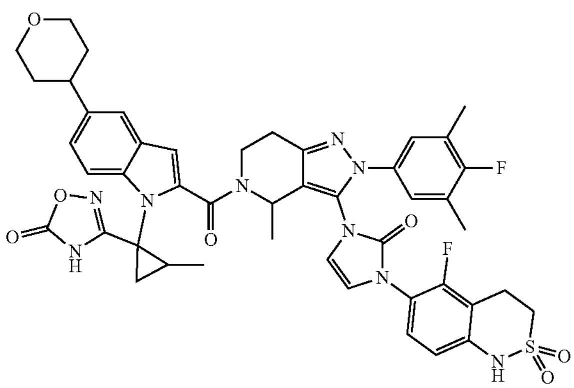
-continued
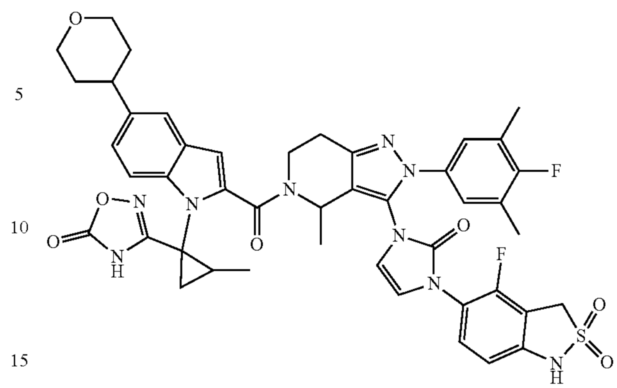
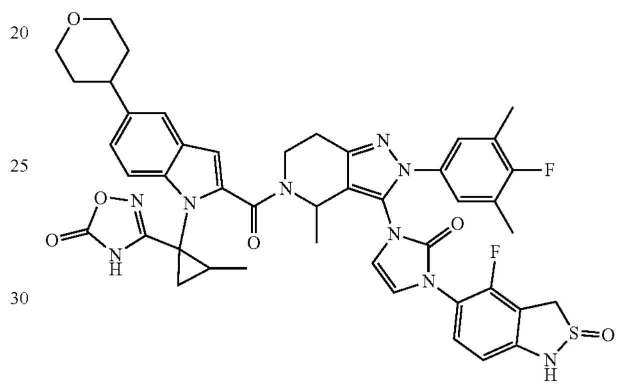
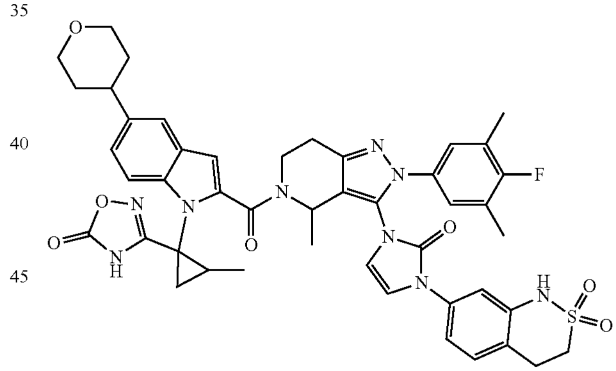
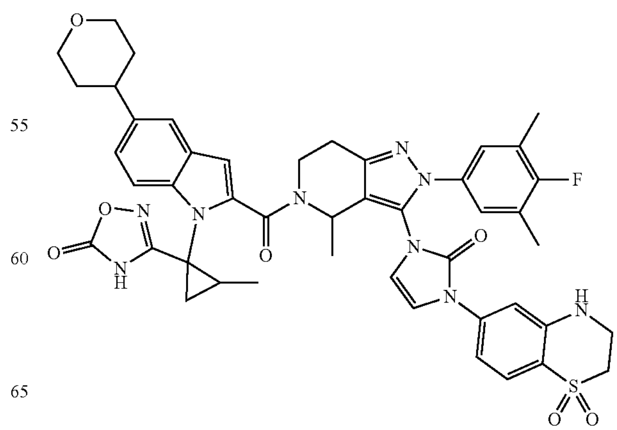

-continued
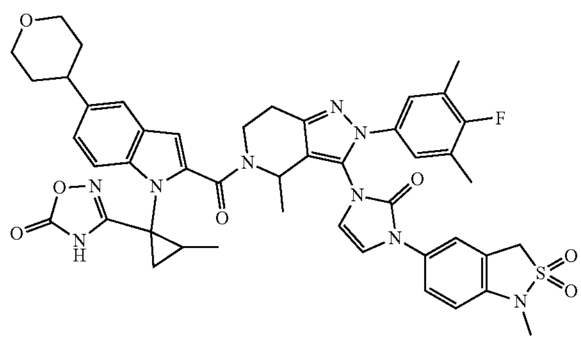
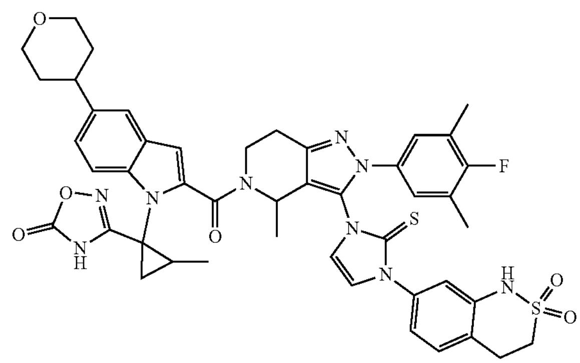
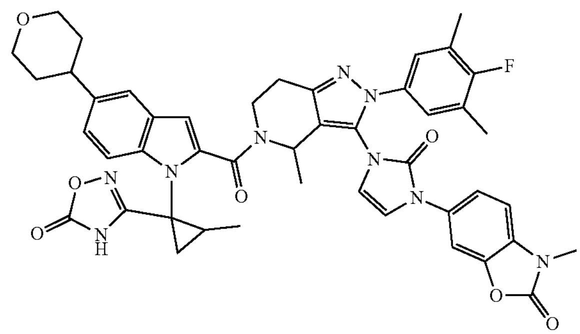
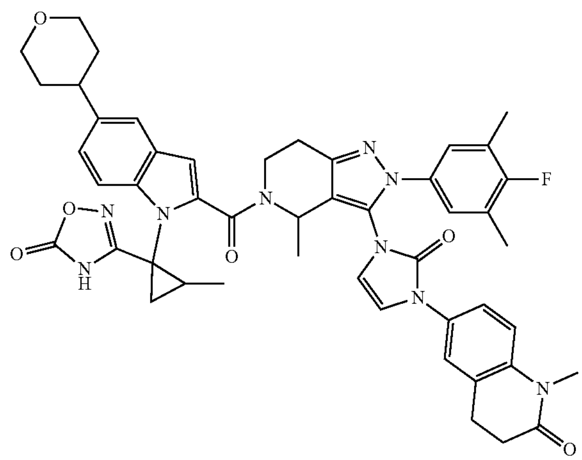
-continued
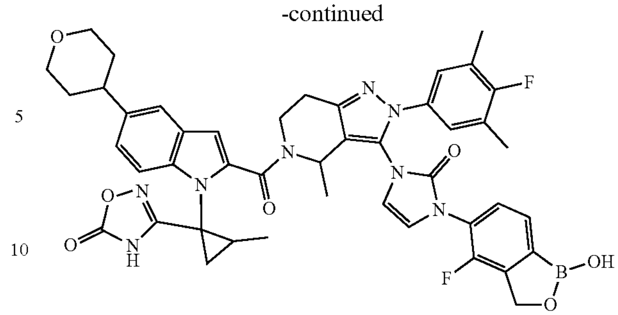
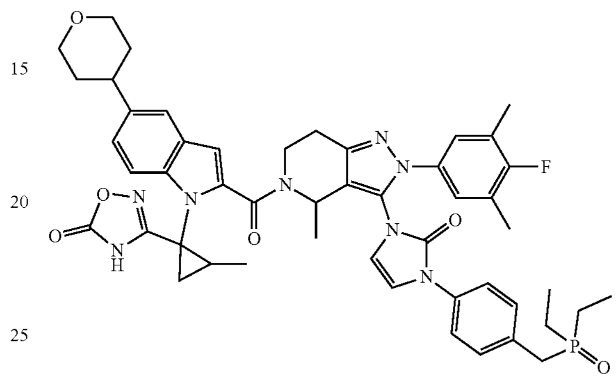
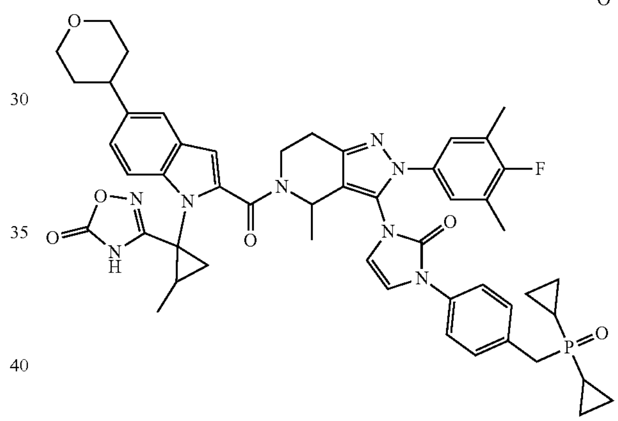
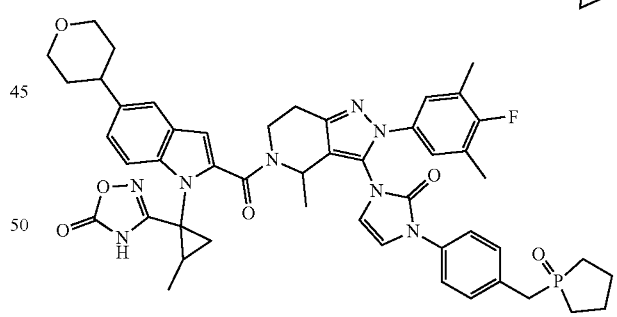
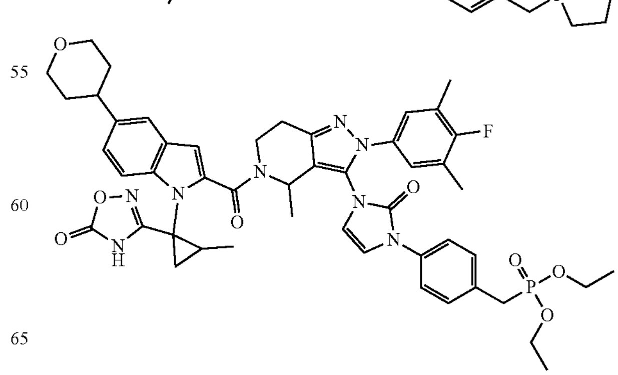

-continued
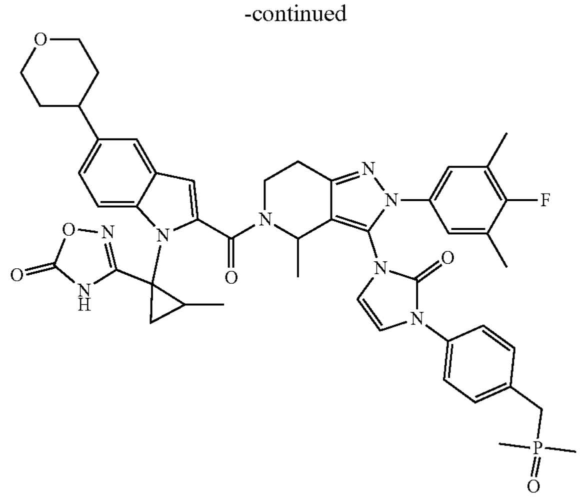
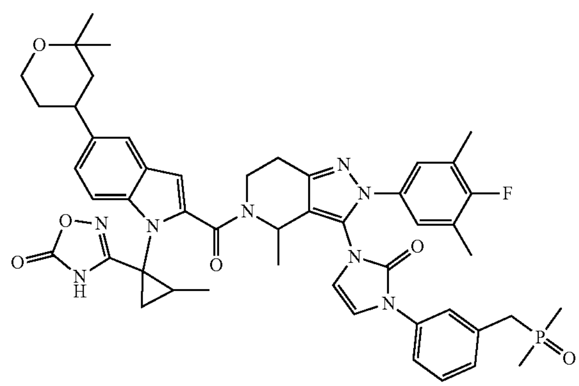
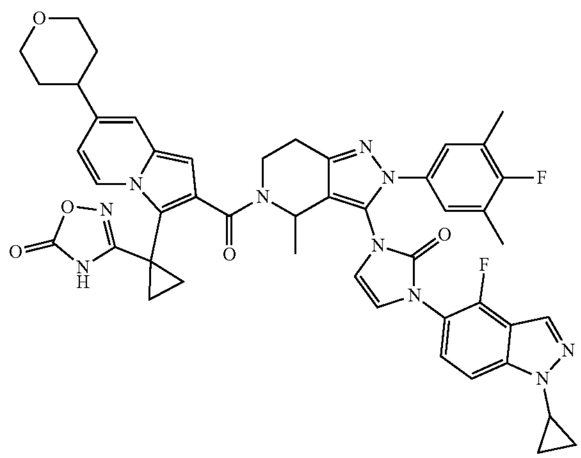
-continued
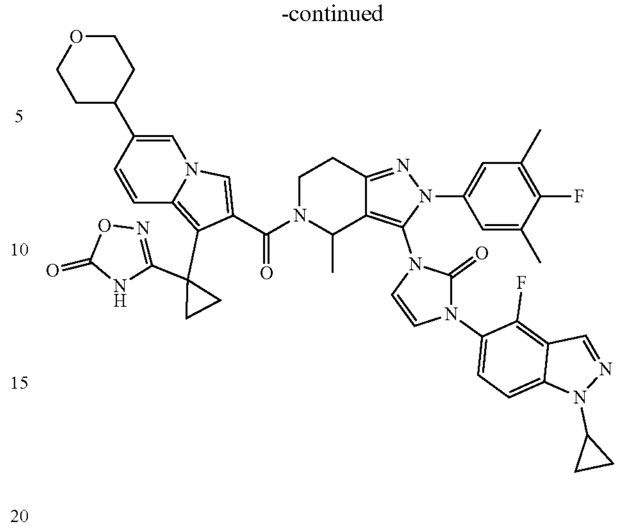
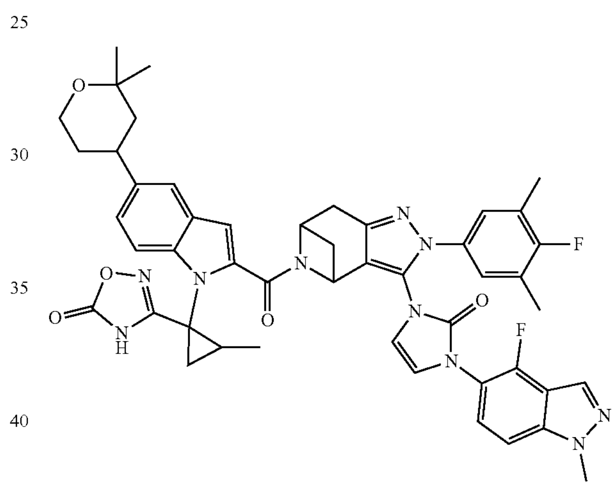
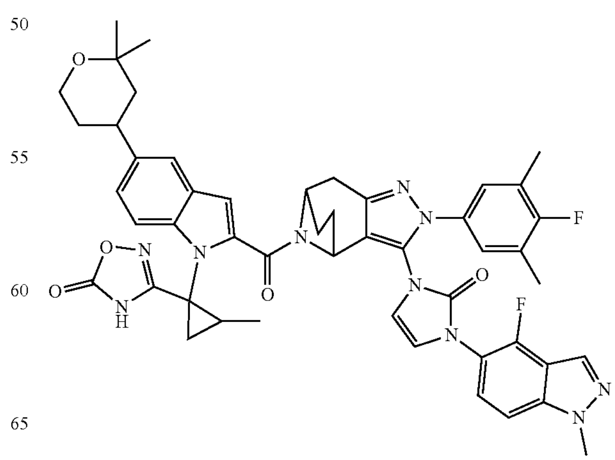

-continued
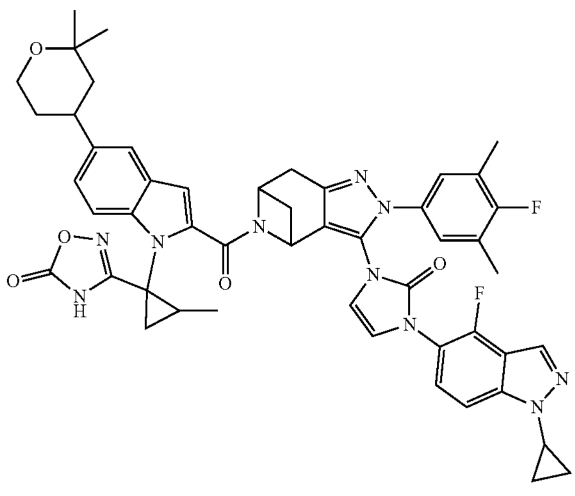
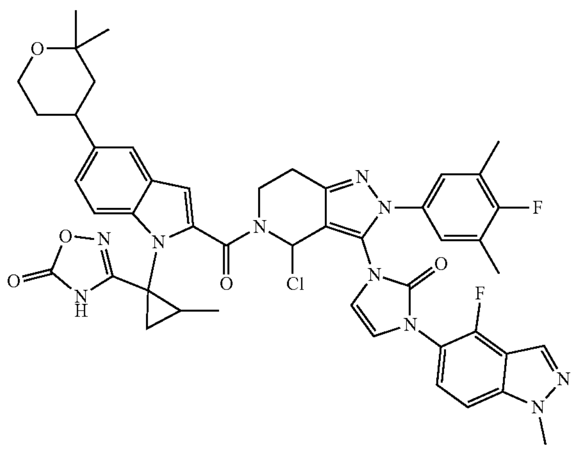
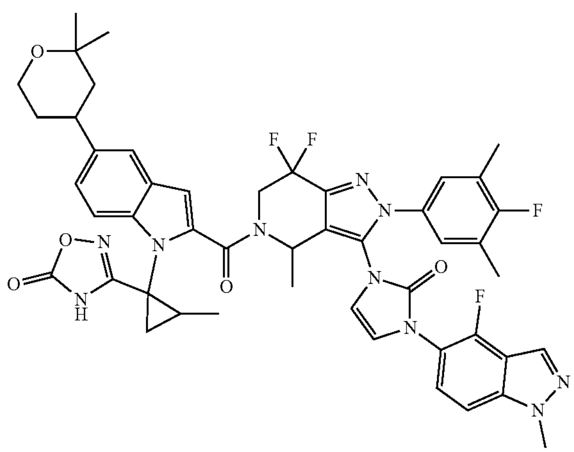
-continued
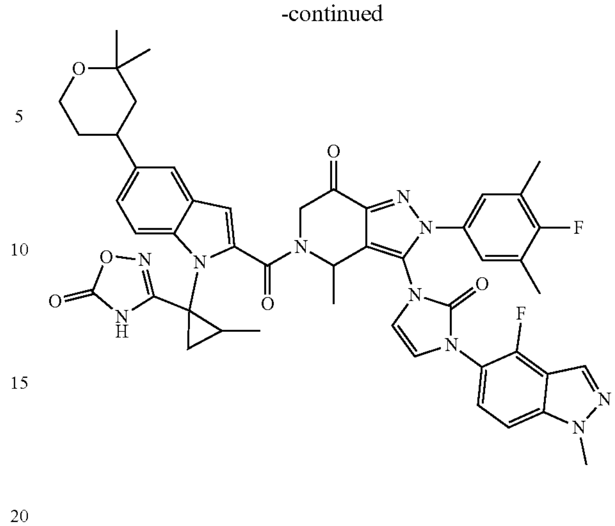
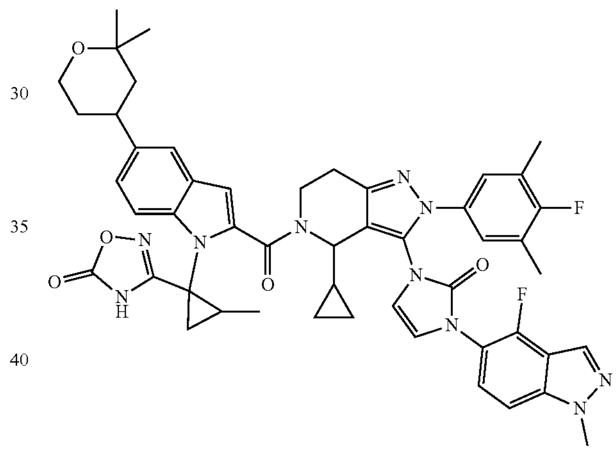
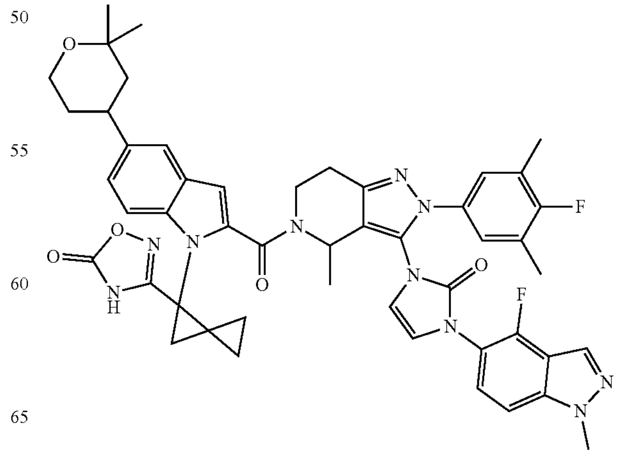

-continued
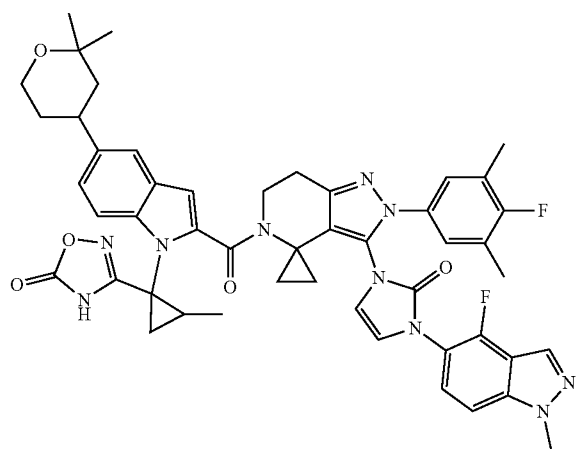
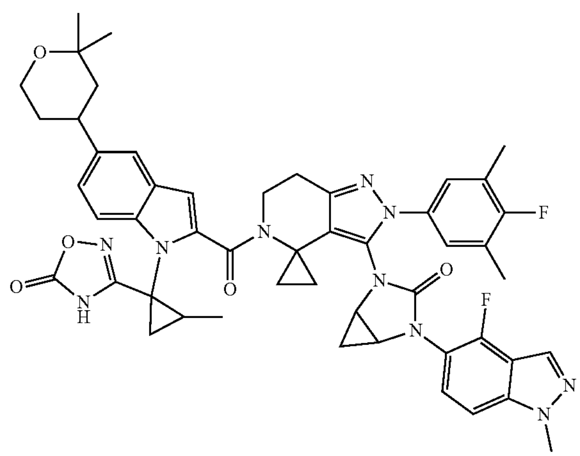
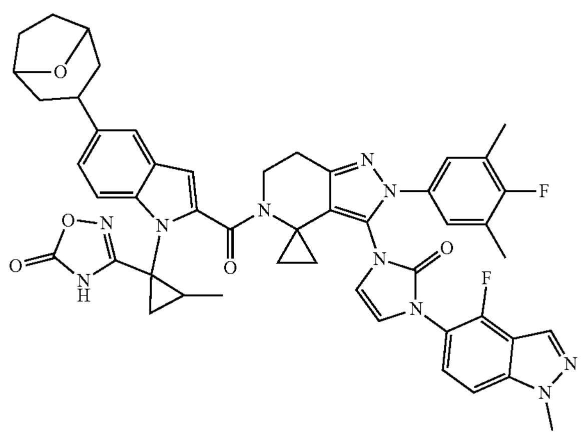
-continued
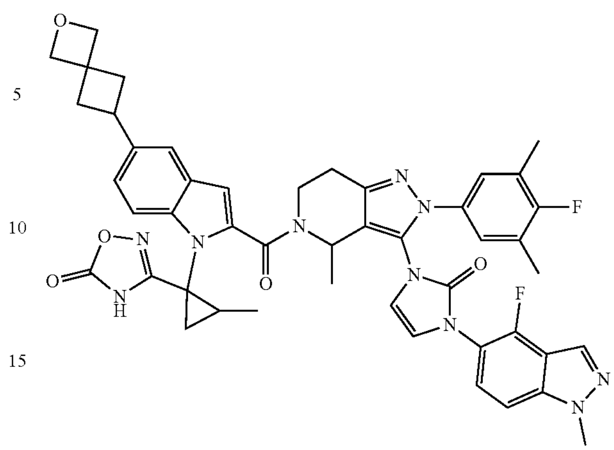
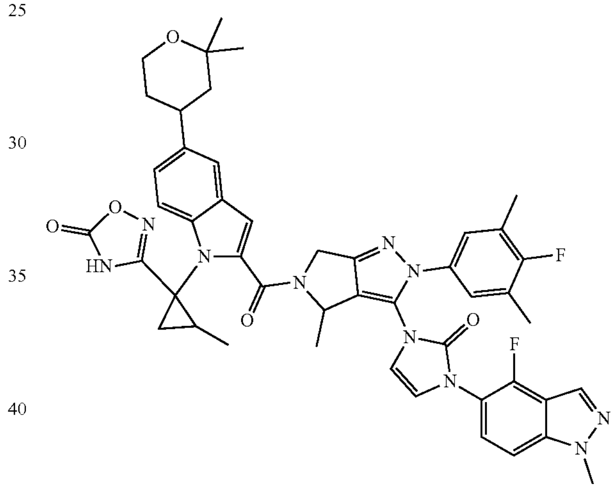
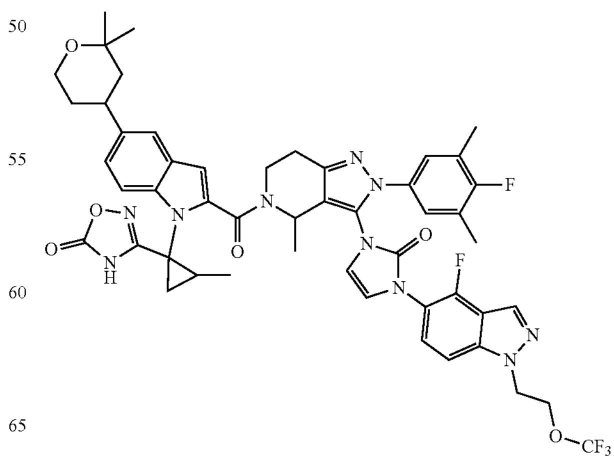

-continued
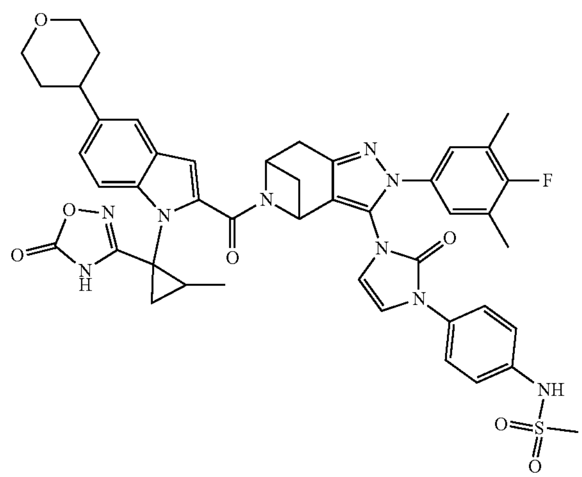 [SMILES: Cc1cc(-n2nc3c(c2-n2ccn(-c4ccc(NS(C)(=O)=O)cc4)c2=O)C2(CC2)N(C(=O)c2cc4cc(C5CCOCC5)ccc4n2C2(c4noc(=O)[nH]4)CC2C)CC3)cc(C)c1F]
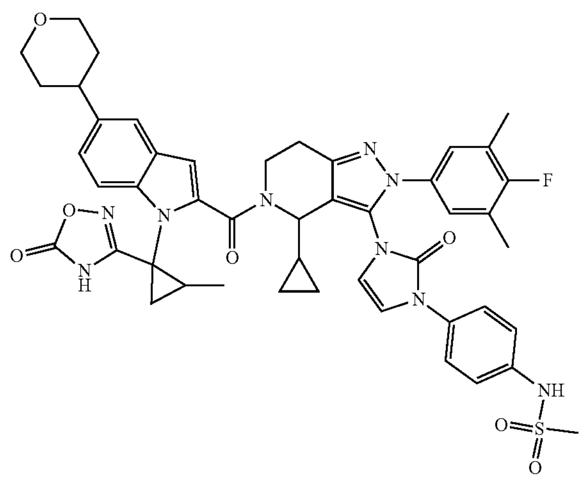
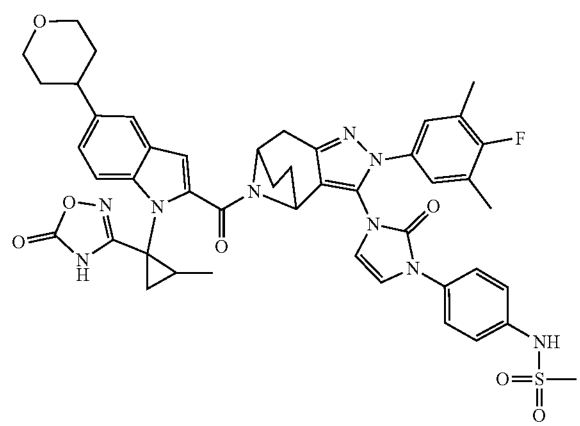
-continued
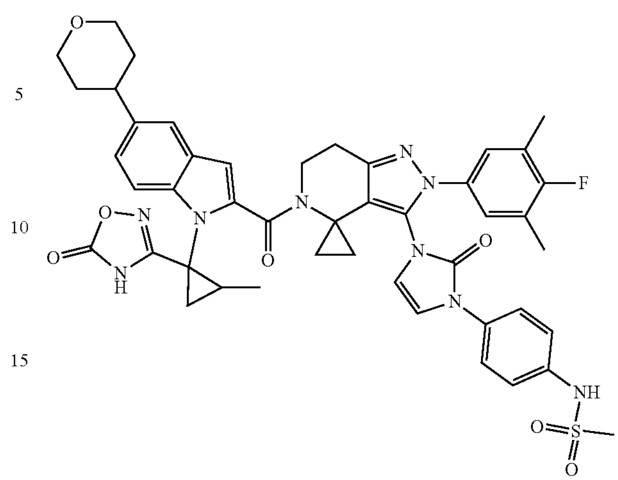
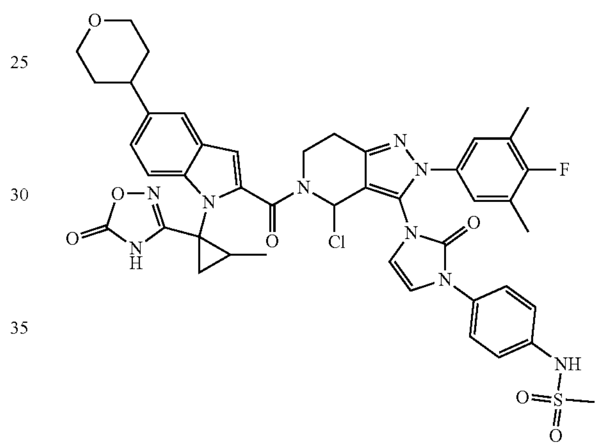
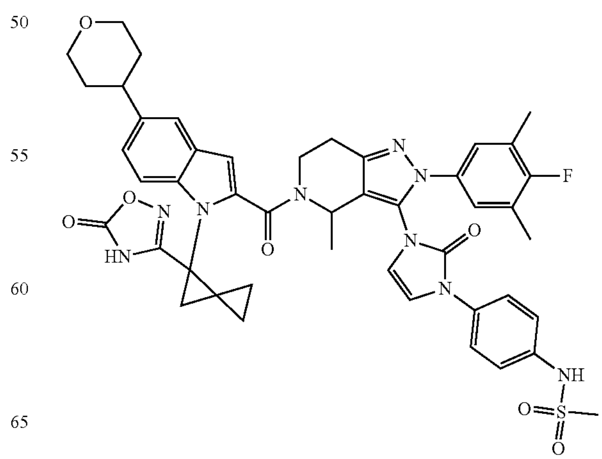

-continued
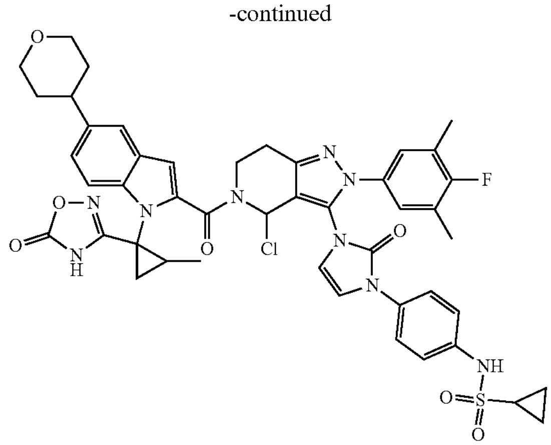
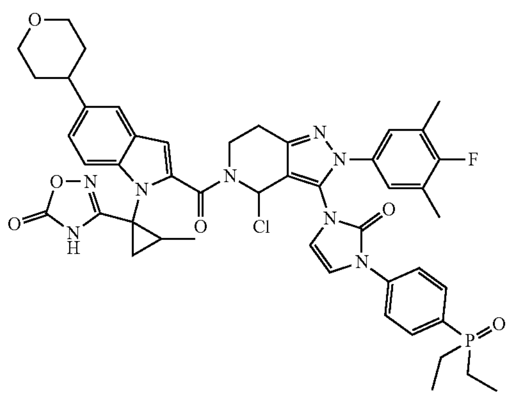
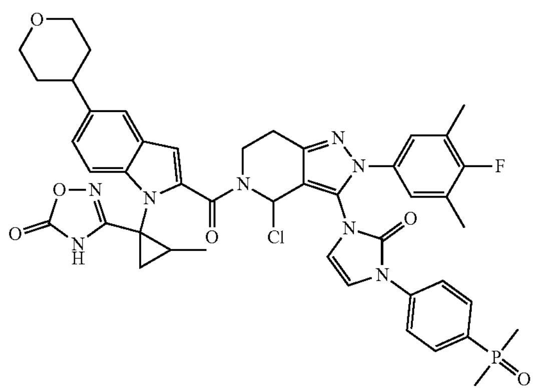
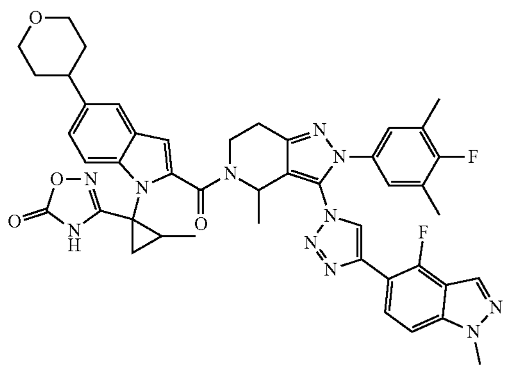
and
-continued
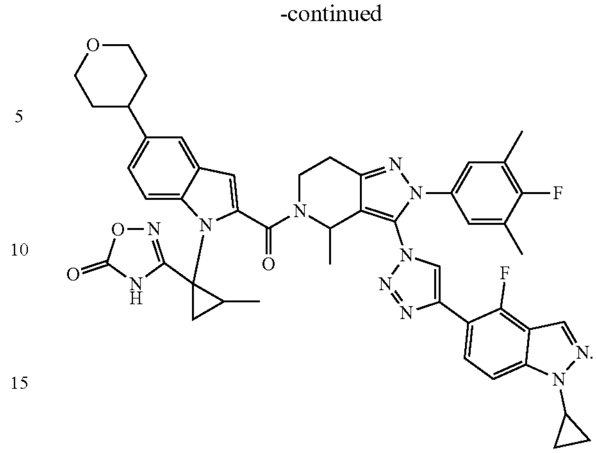
Yet still another aspect of the present disclosure provides a compound or a pharmaceutically acceptable salt thereof, wherein the compound is selected from the group consisting of:
1
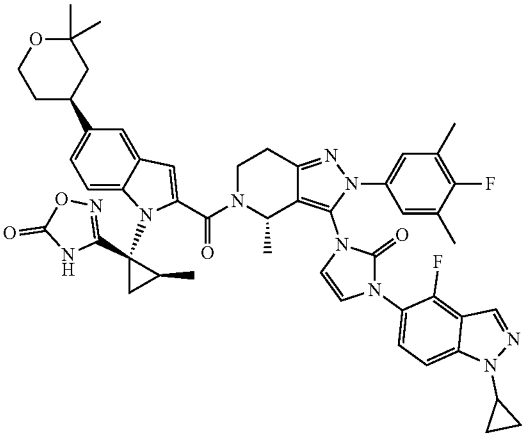
13
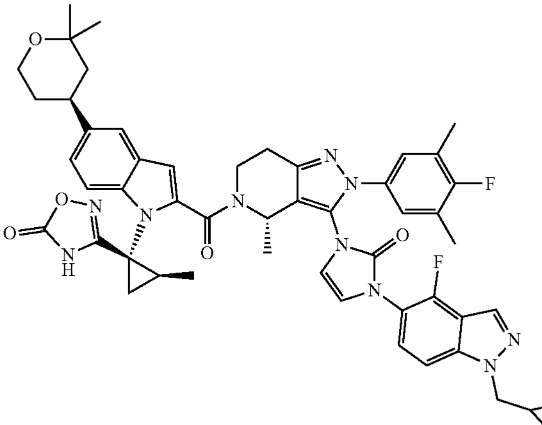

-continued
18
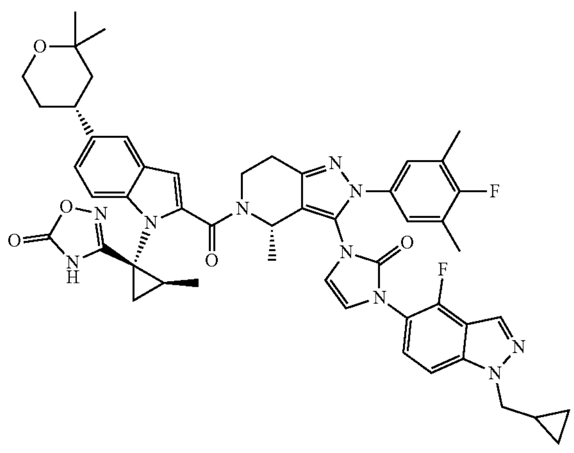
19
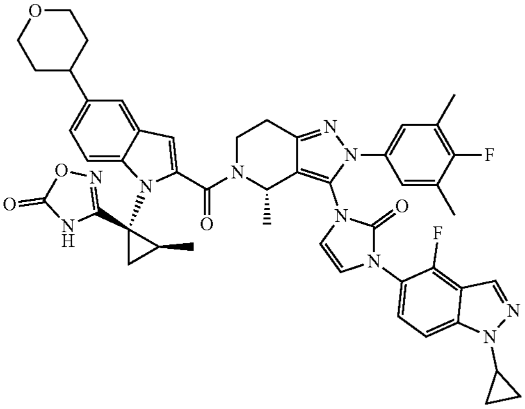
20
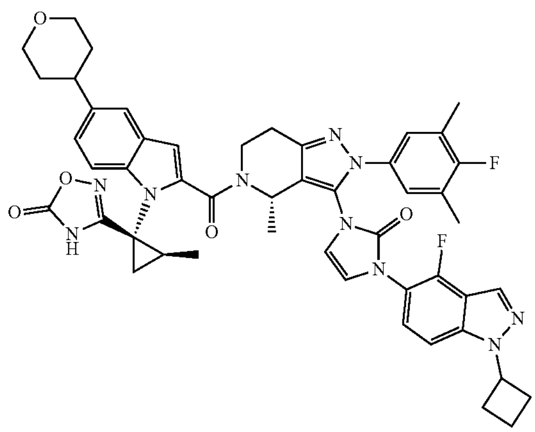
-continued
21
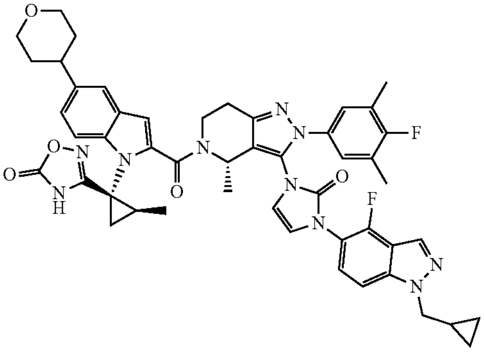
and
65
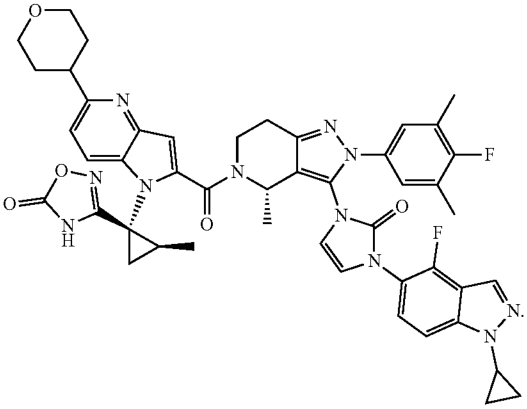
Yet still another aspect of the present disclosure provides a compound, selected from the group consisting of:
1
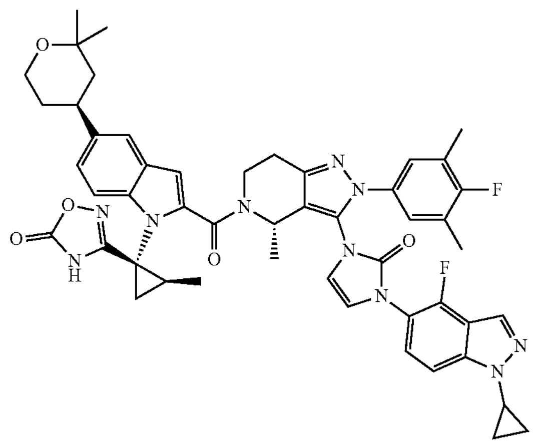

-continued
13
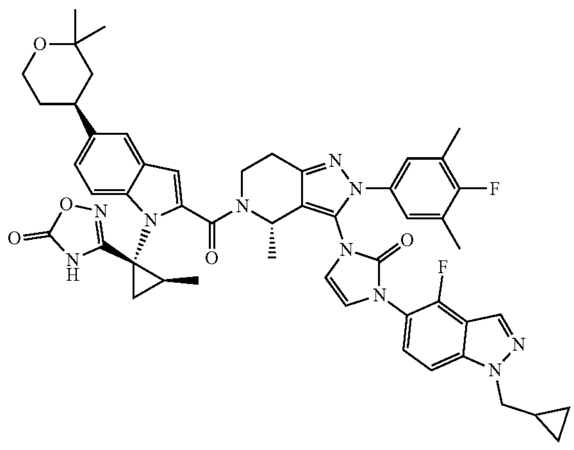
18
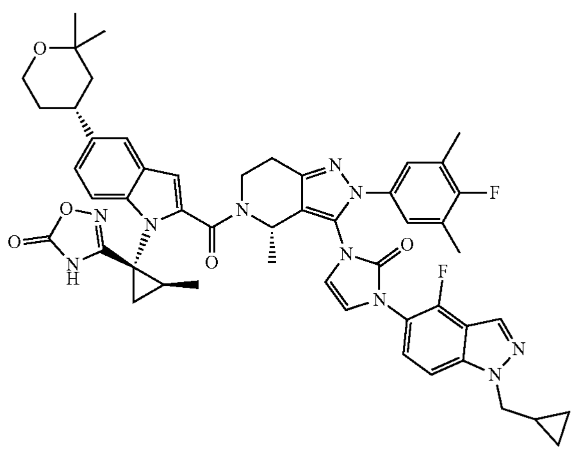
19
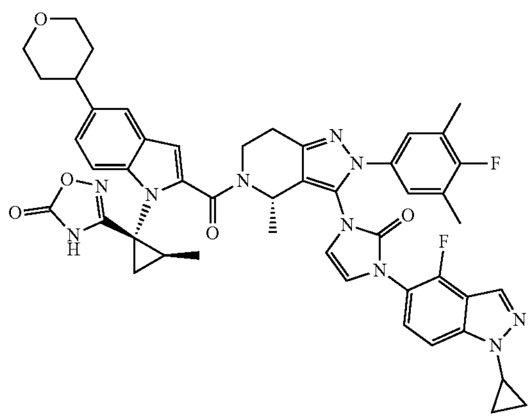
-continued
20
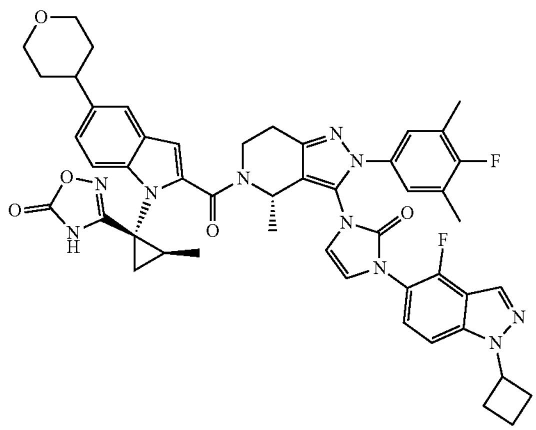
21
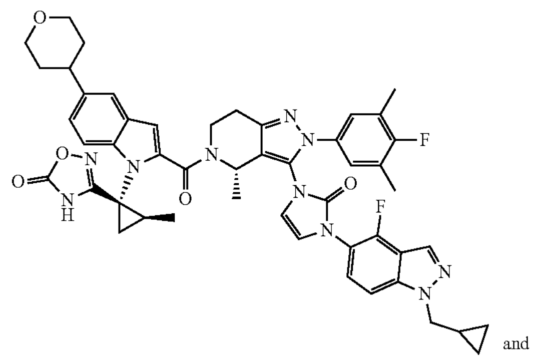
and
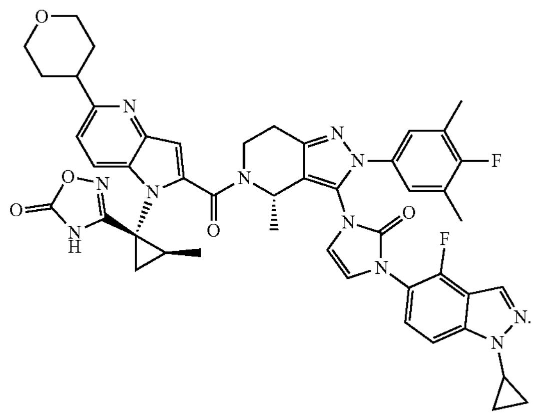
.
In some embodiments, the pharmaceutically acceptable salt of the compound of the present disclosure is selected from the group consisting of:

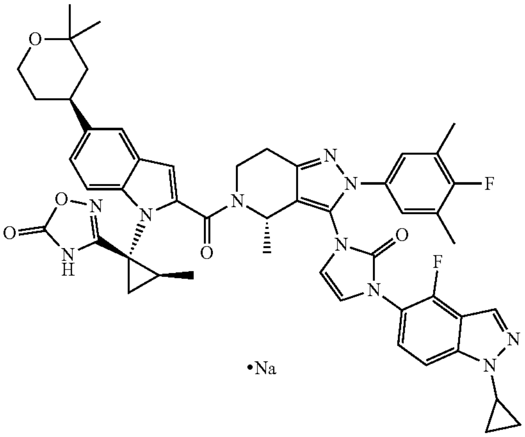
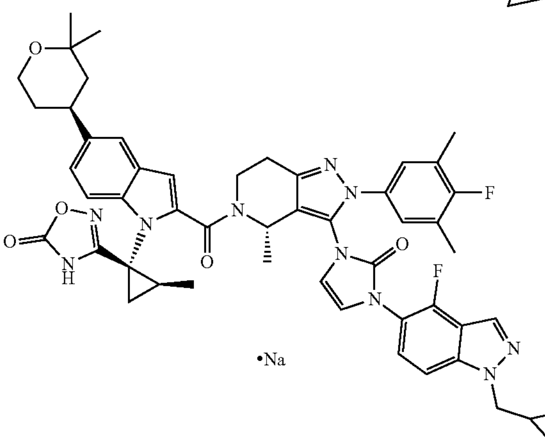
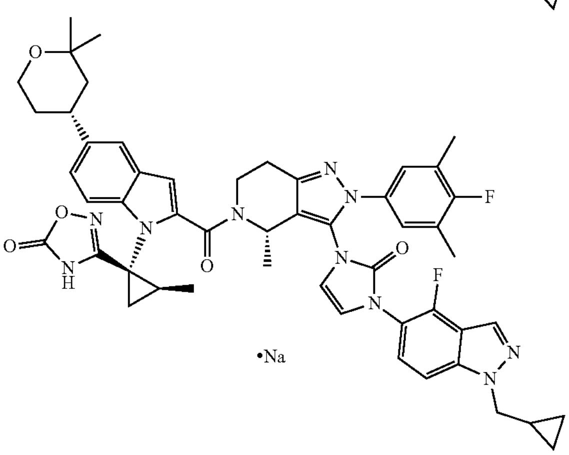
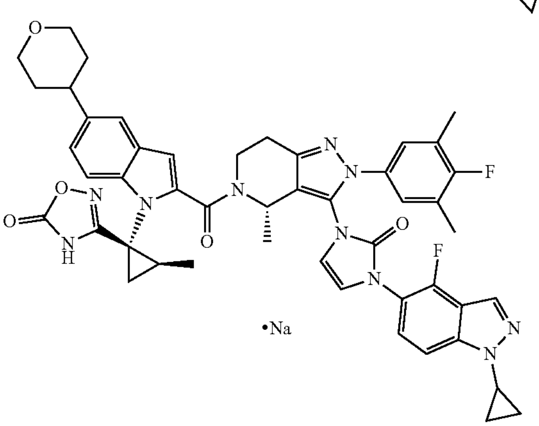
-continued
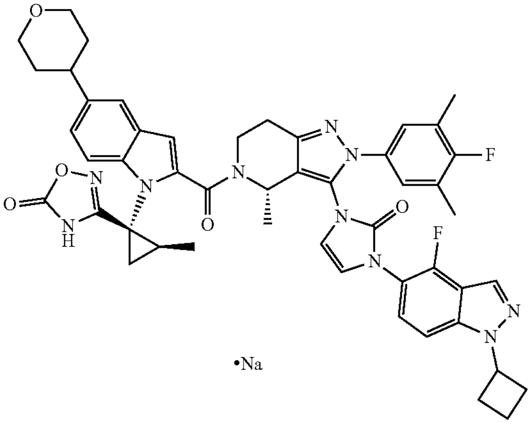
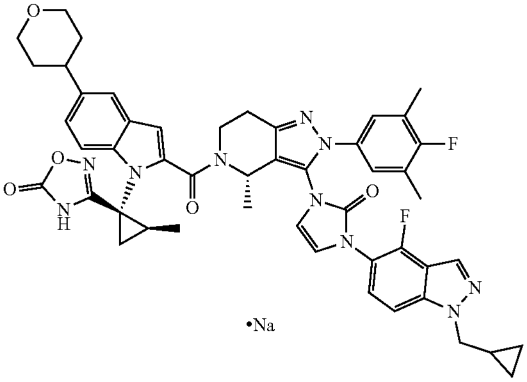
and
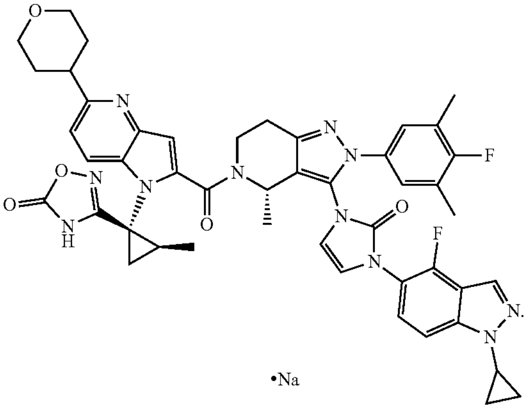
In some embodiments, the pharmaceutically acceptable salt of the compound of the present disclosure is selected from the group consisting of:

-continued
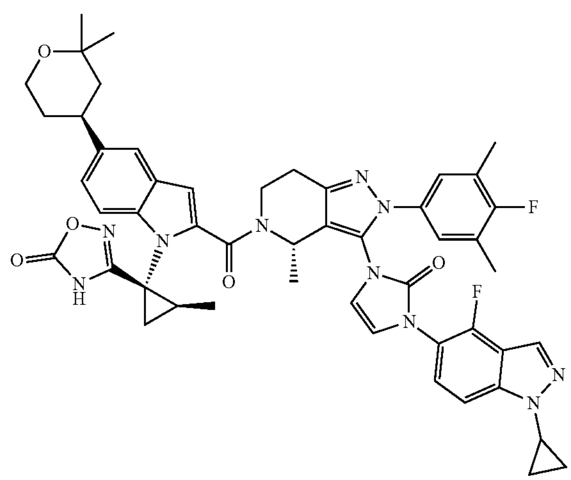
*1/2 Ca
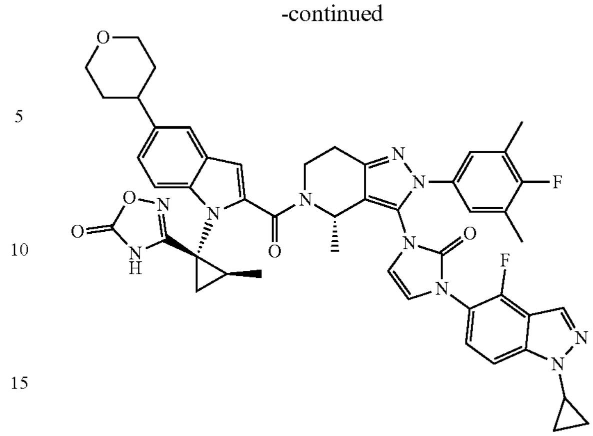
*1/2 Ca
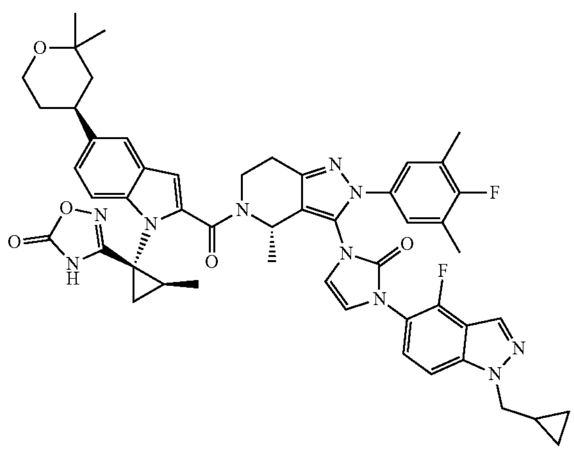
*1/2 Ca
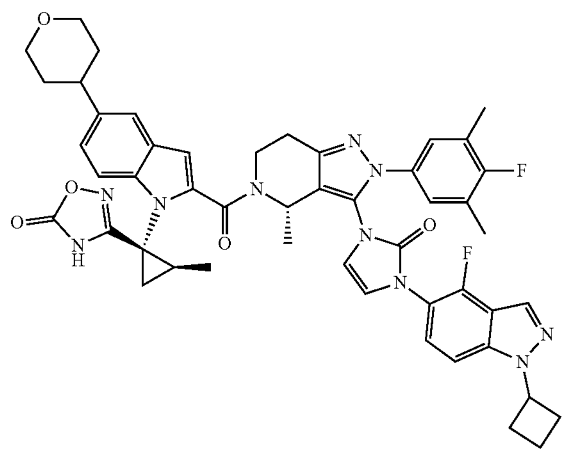
*1/2 Ca
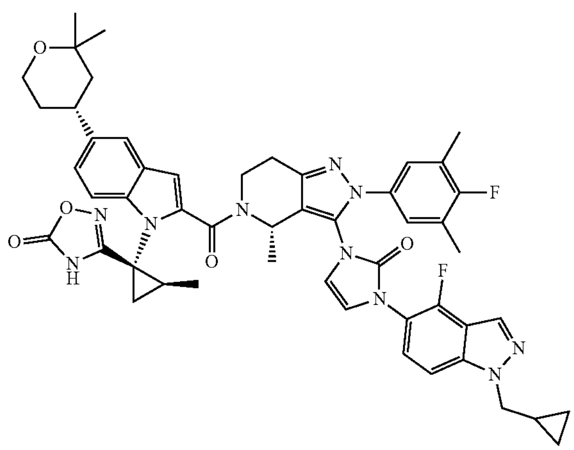
*1/2 Ca
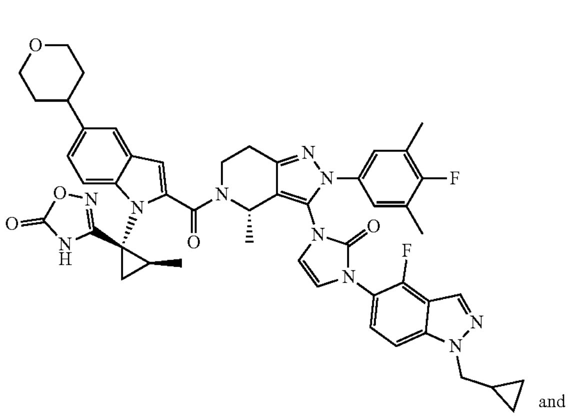
and
*1/2 Ca -continued
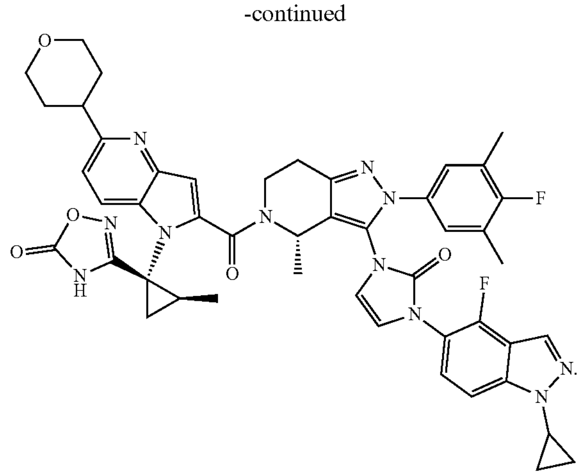
*1/2 Ca
In certain embodiments, in the compound or the pharmaceutically acceptable salt thereof of the present disclosure, the compound is selected from the group consisting of:
1
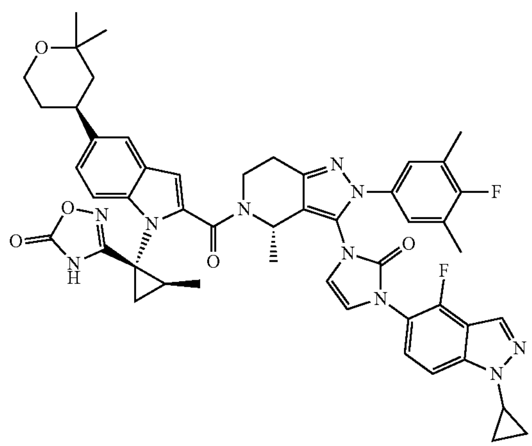
13
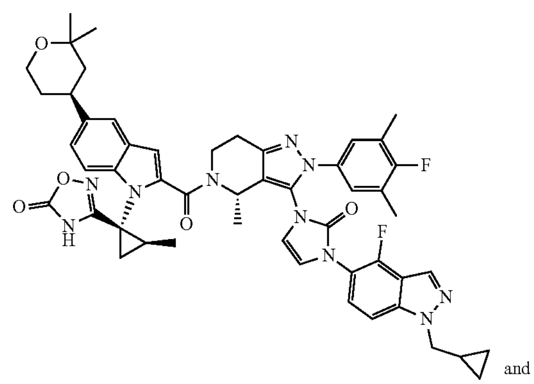
and
-continued
18
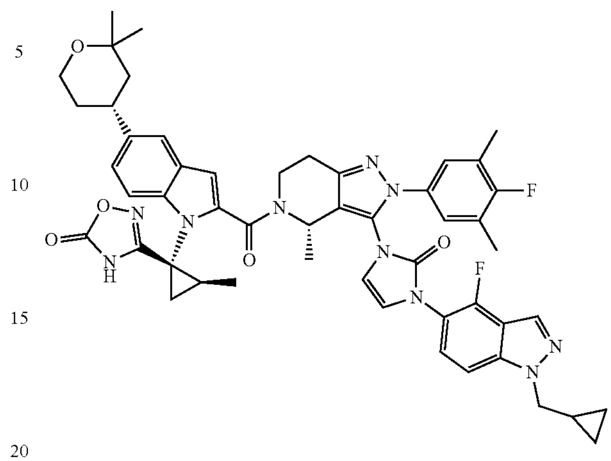
In some embodiments, the compound of the present disclosure is selected from the group consisting of:
19
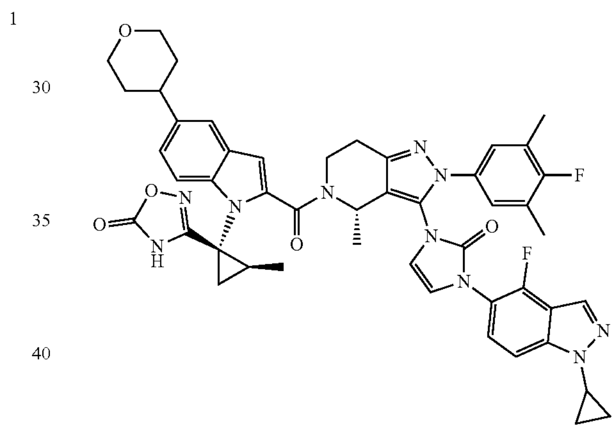
20
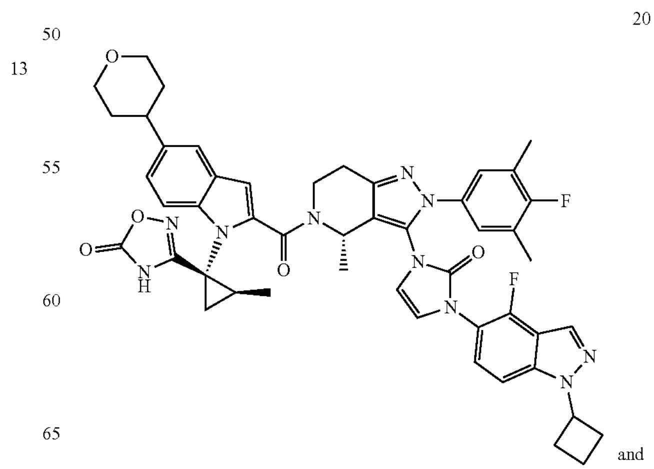
and -continued

21

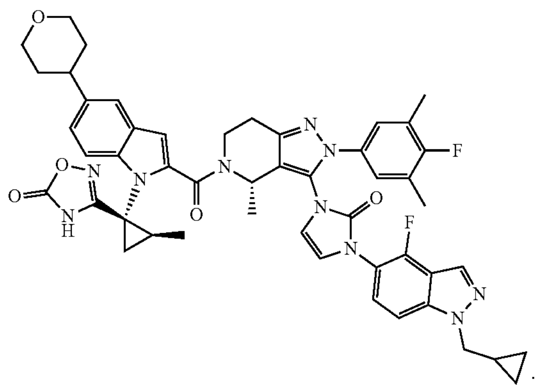

In some embodiments, the compound of the present disclosure is

1

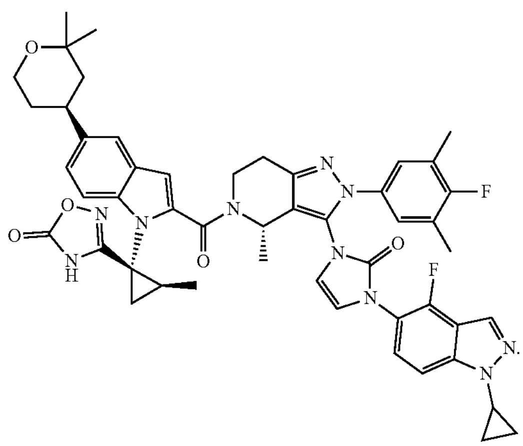

In some embodiments, the pharmaceutically acceptable salt of the compound of the present disclosure is

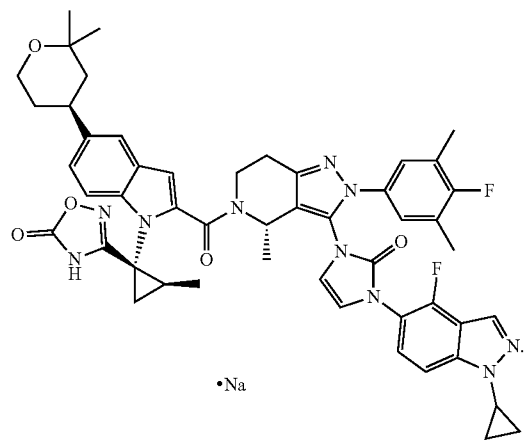

In some embodiments, the pharmaceutically acceptable salt of the compound of the present disclosure is

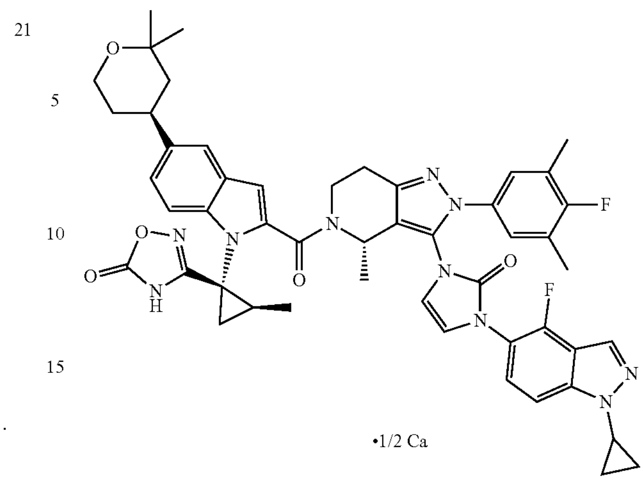

In some embodiments, the compound of the present disclosure is

13

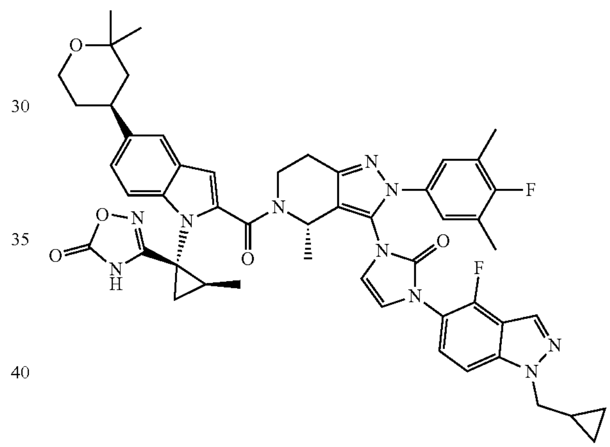

In some embodiments, the compound of the present disclosure is

18

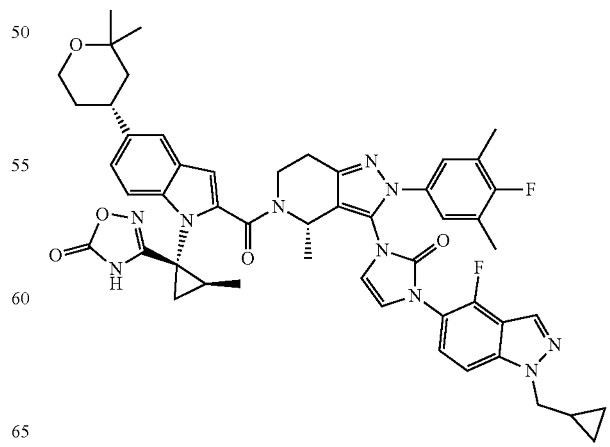

In some embodiments, the compound of the present disclosure is

19

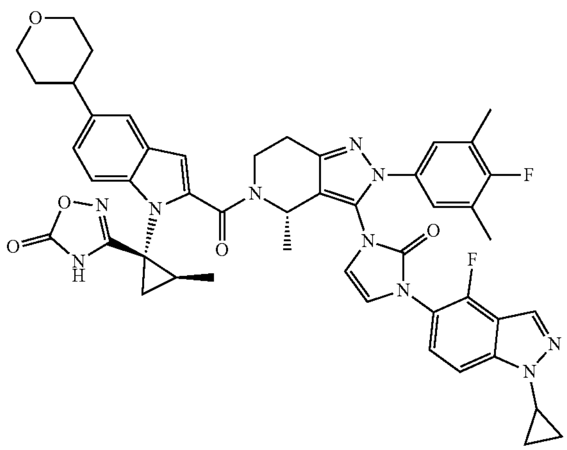

In some embodiments, the pharmaceutically acceptable salt of the compound of the present disclosure is

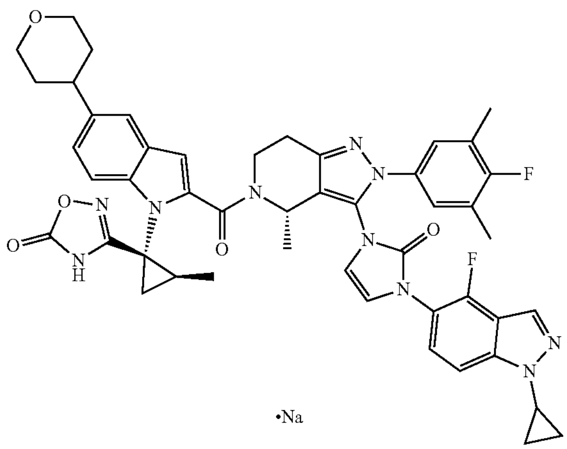

In some embodiments, the pharmaceutically acceptable salt of the compound of the present disclosure is

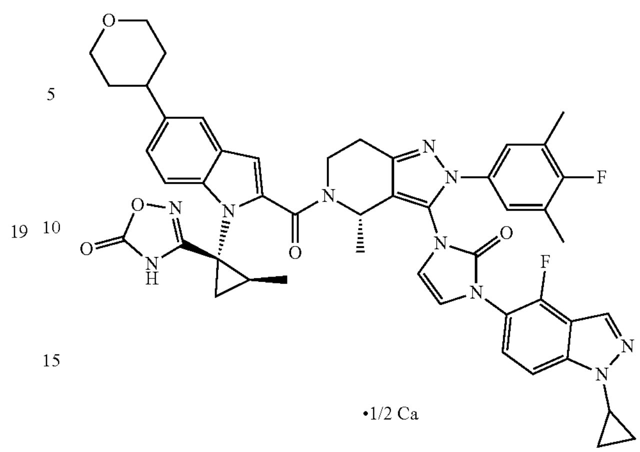

In some embodiments, the compound of the present disclosure is

20

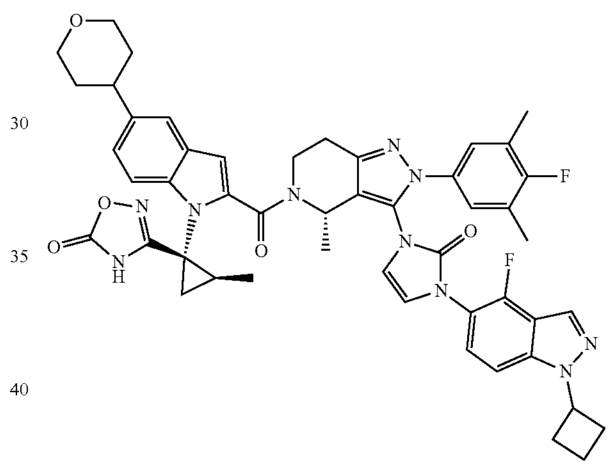

In some embodiments, the pharmaceutically acceptable salt of the compound of the present disclosure is

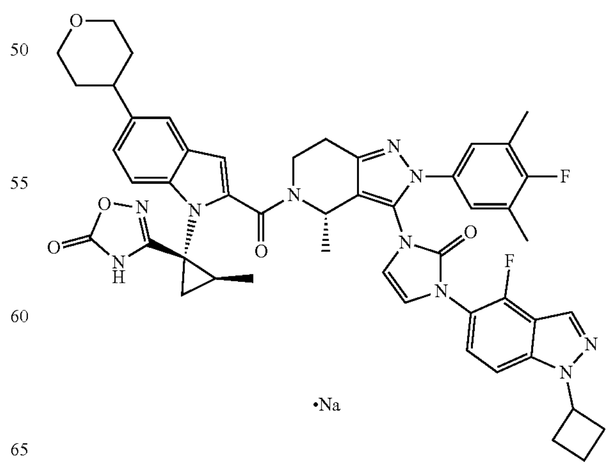

In some embodiments, the pharmaceutically acceptable salt of the compound of the present disclosure is

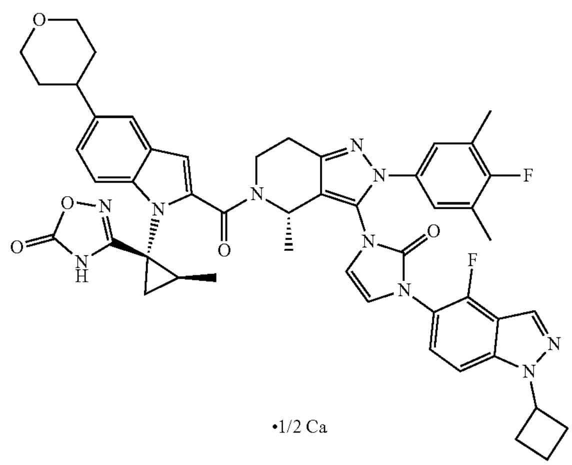 [SMILES: Cc1cc(-n2nc3c(c2-n2ccn(-c4ccc5c(cnn5C5CCC5)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F ; "·1/2 Ca"]

In some embodiments, the compound of the present disclosure is

21

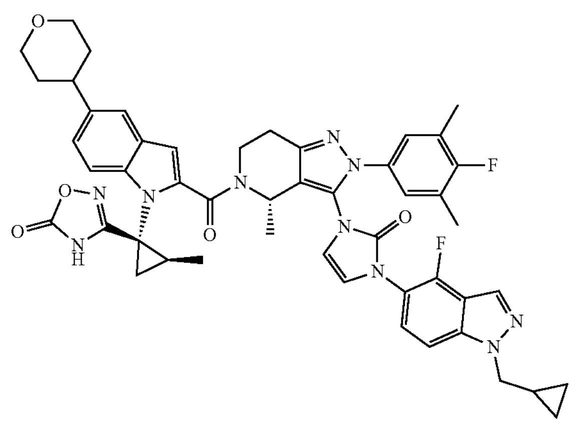

In some embodiments, the pharmaceutically acceptable salt of the compound of the present disclosure is

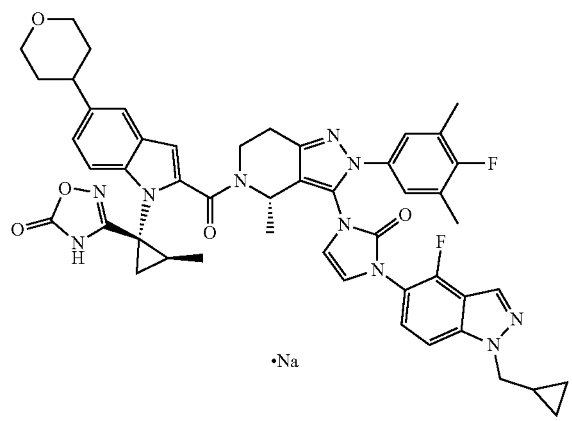

In some embodiments, the pharmaceutically acceptable salt of the compound of the present disclosure is

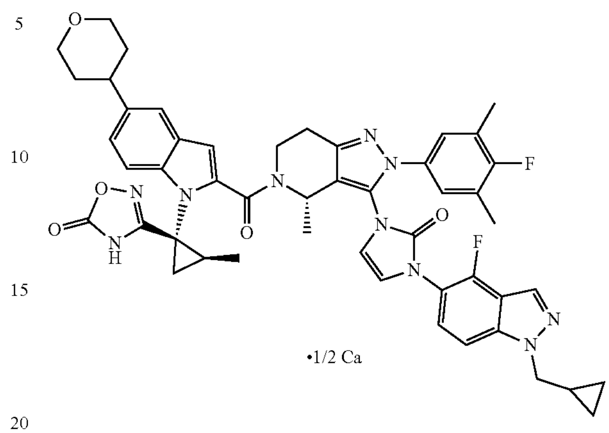

In some embodiments, the compound of the resent disclosure is

65

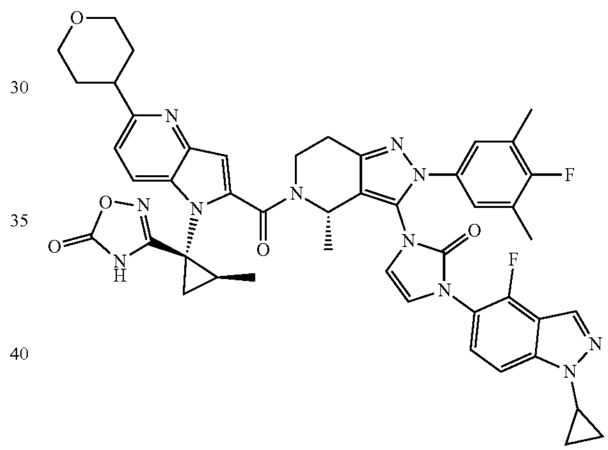

In some embodiments, the pharmaceutically acceptable salt of the compound of the present disclosure is

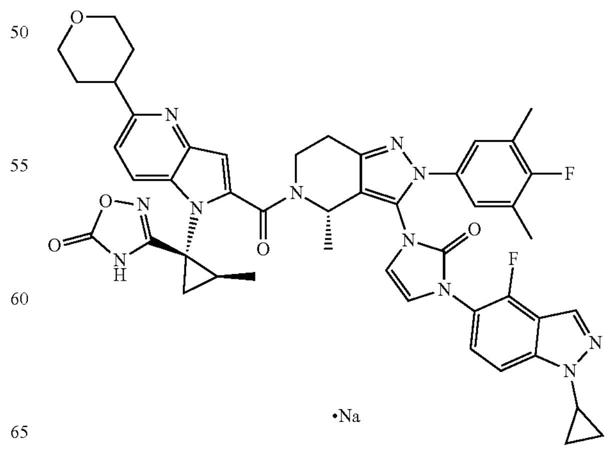

In some embodiments, the pharmaceutically acceptable salt of the compound of the present disclosure is

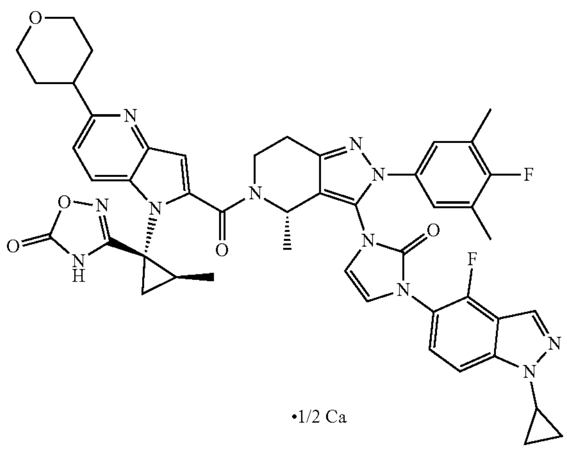

Pharmaceutical Composition

Another aspect of the present disclosure provides a pharmaceutical composition that comprise the compound, the stereoisomer, the pharmaceutically acceptable salt, or the deuterated compound thereof of the present disclosure, and a pharmaceutically acceptable excipient.

In some embodiments, the pharmaceutical composition comprising the compound, the stereoisomer, the pharmaceutically acceptable salt, or the deuterated compound thereof of the present disclosure may be prepared with one or more pharmaceutically acceptable excipients, the excipients may be selected in accordance with conventional practice. Tablets may contain excipients, including flow aids, fillers, binders, and the like. Aqueous compositions may be prepared in a sterile form and may generally be isotonic when intended to be delivered by means other than oral administration.

In some embodiments, the compositions may comprise excipients, such as those set forth in Rowe et al, Handbook of Pharmaceutical Excipients, 6th edition, American Pharmacists Association, 2009. Excipients may include ascorbic acid and other antioxidants, chelating agents such as ethylenediaminetetraacetic acid, carbohydrates such as dextrin, hydroxyalkylcellulose, hydroxyalkylmethylcellulose, stearic acid, and the like. In some embodiments, the compositions are provided in solid dosage forms, including solid oral dosage forms.

The pharmaceutical composition may be prepared by any of the methods well known in the art of pharmacy, including oral administration. Such methods include the step of bringing into association the active ingredient (e.g., a compound of the present disclosure or a pharmaceutical salt thereof) with one or more pharmaceutically acceptable excipients. In some embodiments, the pharmaceutical compositions are prepared by uniformly and intimately bringing into association the active ingredient with liquid excipients or finely divided solid excipients or both, and then, if desired, shaping the product. Techniques and formulations generally are found in Remington: The Science and Practice of Pharmacy, 21st Edition, Lippincott Williams and Wilkins, Philadelphia, Pa., 2006.

In some embodiments, the pharmaceutical compositions of the present disclosure are presented in unit dosage form, including but not limited to capsules, sachets, or tablets, each containing a predetermined amount of the active ingredient. In one embodiment, the pharmaceutical composition is a tablet.

The pharmaceutical composition disclosed herein comprises one or more of the compound, the stereoisomer, the pharmaceutically acceptable salt, or the deuterated compound thereof of the present disclosure, as well as pharmaceutically acceptable excipients and, optionally, other therapeutic agents. The pharmaceutical compositions containing the active ingredient may be in any form suitable for the intended method of administration. When intended for oral use, for example, tablets, lozenges, ingots, aqueous or oil suspensions, dispersible powders or granules, emulsions, hard or soft capsules, syrups, or elixirs may be prepared. Compositions for oral use may be prepared according to any method known in the art for the manufacture of pharmaceutical compositions, and such compositions may contain one or more excipients, including sweeteners, flavoring agents, coloring agents, and preservatives, to provide palatable formulations. Tablets containing the active ingredient with a non-toxic pharmaceutically acceptable excipient are acceptable and said excipient is suitable for the production of tablets. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredients that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5% to about 95% of the total compositions (weight: weight).

In some embodiments, the pharmaceutical composition of the present disclosure does not contain an agent that affects the rate at which the active ingredient is metabolized. Thus, it is understood that pharmaceutical compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture, and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the above-described pharmaceutical compositions are for use in humans or animals.

The present disclosure also includes compound of the present disclosure which are administered as a single active ingredient of a pharmaceutically acceptable composition that may be prepared by conventional methods known in the art, for example, by combining the active ingredient to a pharmaceutically acceptable, therapeutically inert organic and/or inorganic carrier or excipient, or by mixing therewith.

In one aspect, provided herein are uses of the compound of the present disclosure as a second or other active ingredient, said second or other active ingredient being synergistic with other active ingredients in known drugs, or the compound of the present disclosure being administered with such drugs.

The compound of the present disclosure may also be used in the form of a prodrug or other suitably modified form that releases the active ingredient in vivo.

Method of Treatment

Another aspect of the present disclosure provides a method for treating a GLP-1R-mediated disease or condition, comprising administering to a subject in need thereof a therapeutically effective amount of the compound, the stereoisomer, the pharmaceutically acceptable salt, or the deuterated compound thereof of the present disclosure, or a pharmaceutical composition of the present disclosure.

In some embodiments, the GLP-1R-mediated disease or condition is selected from the group consisting of T1D (type 1 diabetes), T2DM (type 2 diabetes mellitus), pre-diabetes, idiopathic T1D (idiopathic type 1 diabetes). LADA (latent autoimmune diabetes in adults), EOD (early onset diabetes), YOAD (young onset adult diabetes), MODY (maturity onset diabetes of the young), malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, sleep apnea, obesity, overweight, eating disorders, weight gain from use of other agents, excessive sugar craving, dyslipidemia, hyperinsulinemia, NAFLD (non-alcoholic fatty liver disease), NASH, fibrosis, cirrhosis, hepatocellular carcinoma, cardiovascular disease, atherosclerosis, coronary artery disease, peripheral vascular disease, hypertension, endothelial dysfunction, impaired vascular compliance, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, parkinson's disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, alzheimer's disease, schizophrenia, impaired cognition, inflammatory bowel disease, short bowel syndrome, crohn's disease, colitis, irritable bowel syndrome, polycystic ovary syndrome and substance addiction.

In some embodiments, the GLP-1R-mediated disease or condition is selected from the group consisting of weight management, chronic weight management, chronic kidney disease, atherosclerotic cardiovascular disease, heart failure; heart failure with reduced ejection fraction; heart failure with preserved ejection fraction; diabetes prevention, and obstructive sleep apnea.

The compound of the present disclosure (also referred to herein as the active ingredients) or the pharmaceutical composition of the present disclosure can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compound disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of the compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Kits that comprise the compound e, the stereoisomers, the pharmaceutically acceptable salts, or the deuterated compound thereof, are also included in the present disclosure In some embodiments, a kit further includes a label and/or instructions for the use of the compound in the treatment of the indications, such as the diseases or conditions described herein. In one embodiment, the kit comprises a compound of the present disclosure, or pharmaceutically acceptable salt thereof, in combination with one or more (e.g., one, two, three, four, one or two, or one to three, or one to four) additional therapeutic agents.

EXAMPLES

Example 1 Synthesis

The compounds of the disclosure may be prepared using methods disclosed herein and routine modifications thereof which will be apparent given the disclosure herein and methods well known in the art. Conventional and well-known synthetic methods may be used in addition to the teachings herein.

The synthesis of typical compounds of Formula I, or a pharmaceutically acceptable salt thereof, e.g., compounds having structures described by one or more of Formula I, or other formulas or compounds disclosed herein, may be accomplished as described in the following examples.

General Syntheses

Typical embodiments of compounds in accordance with the present disclosure may be synthesized using the general reaction schemes and/or examples described below. It will be apparent, given the description herein that the general schemes may be altered by substituting the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds that are embodiments of the present disclosure, inspection of the structure of the compound to be synthesized will provide the identity of each substituent group, the identity of the final product will generally render apparent the identity of the necessary starting materials by a simple process of inspection, given the examples herein. Group labels (e.g., R1, R2) used in the reaction schemes herein are for illustrative purposes only and unless otherwise specified, do not necessarily match by name or function the labels used elsewhere to describe compounds of Formula (I), (II), (III), (IV), (V), (VI), (VII), (VIII), (IX), (X), (XI), (Ia), (Ib), (Ic), (Id), (Ie), (If), and (Ig), or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of the present disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5, and Supplemental (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), N, N-dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the prevue of one skilled in the art.

Intermediate Preparation:

Preparation of Intermediate A

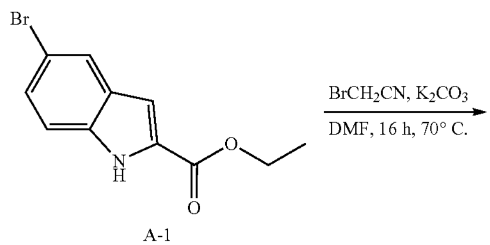

A-1

-continued

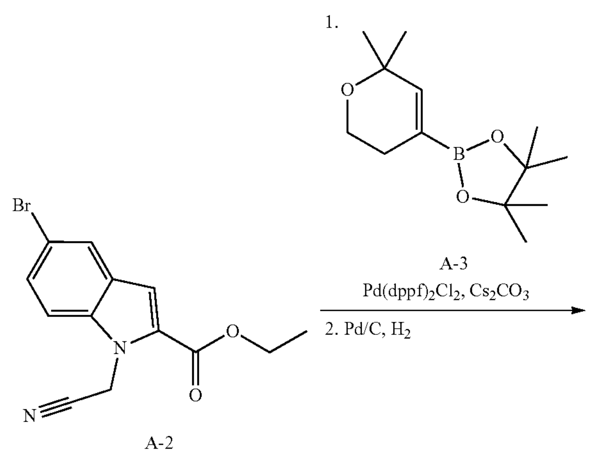

A-2

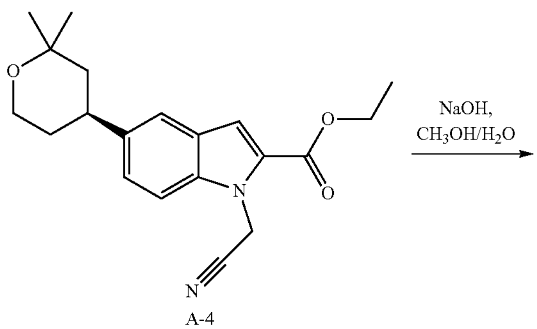

A-4

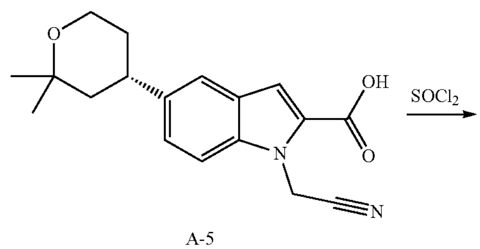

A-5

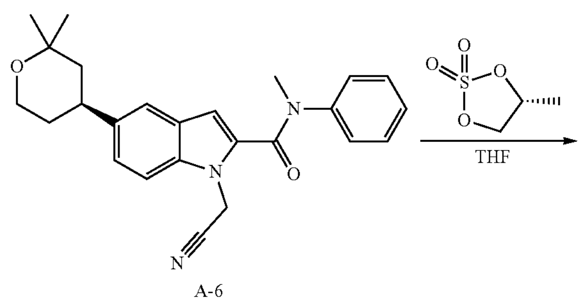

A-6

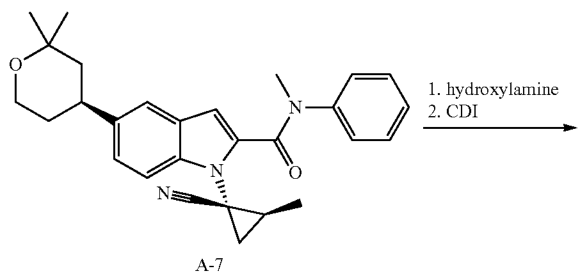

A-7

-continued

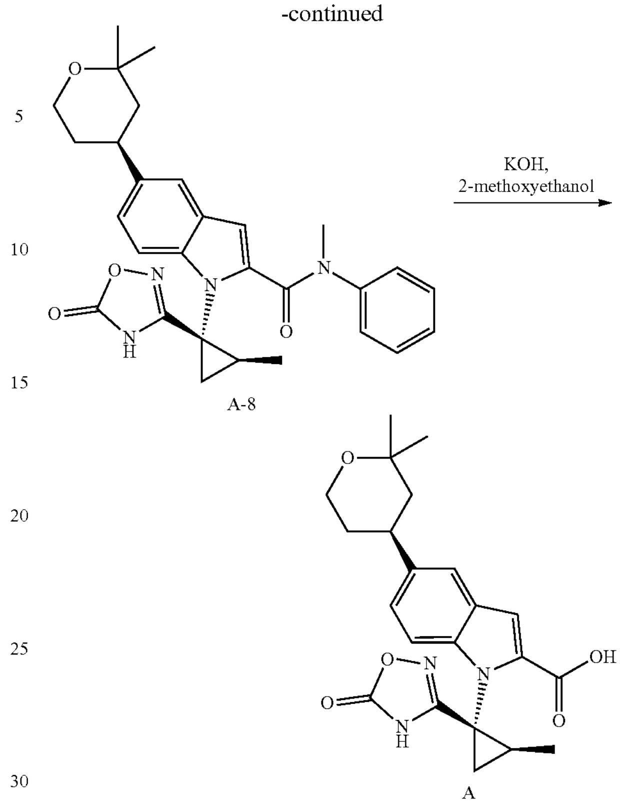

A-8

A

To a solution of A-1 (5 g, 18.65 mmol), potassium carbonate (5.16 g, 37.3 mmol) and sodium iodide (0.28 g, 1.86 mmol) in DMF (30 mL), was added dropwise bromo-acetonitrile (3.36 g, 28.0 mmol). The mixture was heated to 70° C. and stirred for 16 hours. Then the mixture was cooled down to room temperature. Water (60 mL) was added into the mixture to get a suspension. The suspension was filtered to obtain a brown solid, 4 g, with a yield of 49.0%.

A suspension of A-2 (2.0 g, 6.51 mmol), A-3 (1.71 g, 7.16 mmol), cesium carbonate (3.18 g, 9.77 mmol) and $Pd(dppf)_2Cl_2$ (0.5 g, 0.6 mmol) in dioxane (20 mL) was heated to 100° C. under $N_2$. The mixture was stirred for 8 hours. The reaction solution was cooled to room temperature, and water (30 mL) and ethyl acetate (30 mL) were added to extract an organic phase. The organic phase was concentrated under vacuum and then purified by column chromatography to obtain 1.2 g of white solid. The solid was dissolved in methanol. Pd/C (0.12 g, 30% wt.) was added into the mixture. The mixture was stirred overnight at room temperature under hydrogen. The mixture was filtered to get a filtrate. The filtrate was collected to concentrate to afford a solid. The solid was prepared by chiral Pre-HPLC to obtain A-4, 0.6 g, with a yield of 27.3%.

To a solution of A-4 (0.6 g, 1.76 mmol) in methanol/water (4 mL/2 mL), was added sodium hydroxide (0.28 g, 7.05 mmol) at room temperature. The mixture was stirred for 4 hours. The mixture was adjusted to pH 5.0 with dilute hydrochloric acid. Ethyl acetate (5 mL) was added into the mixture to extract an organic phase. The organic phase was concentrate under vacuum to afford solid A-5, 0.53 g, with a yield of 96.3%.

To a solution of A-5 (300 mg, 1.1 mmol) in dichloromethane (10 mL), was added thionyl dichloride (520 mg, 4.4 mmol) and 1 drop of DMF at room temperature. The mixture was stirred for 6 hours. The mixture was concentrated to obtain an oil. To a solution of oil in dichloromethane (5 mL), was added a solution of N-methylaniline (180 mg, 1.65 mmol) and triethylamine (222 mg, 2.2 mmol) in dichloromethane (10 mL) at ice bath. Then warm the mixture to room temperature, and the mixture was stirred for 1 hour. Water (10 mL) was added into the mixture to extract an organic phase. The organic phase was concentrated under vacuum to afford A-6, 350 mg, 87.9%.

To a solution of A-6 (100 mg, 0.25 mmol) and (4R)-4-methyl-1, 3, 2-dioxolane 2, 2-dioxide (103.6 g, 0.75 mmol) in THF (5 mL), was added dropwise lithium bis (trimethylsilylamine) (1 mL, 1M in THF) at −20° C. Then the mixture was warm to room temperature, and stirred for 24 hours. Water (5 mL) was added dropwise into the mixture to quench the reaction. Then ethyl acetate (10 mL) was added into the mixture to extract an organic phase. The organic phase was concentrated under vacuum to obtain an oil. The oil was purified by column chromatography to obtain A-7, 40 mg with a yield of 36.4%.

To a solution of A-7 (10 mg, 0.023 mmol) in DMSO (2 mL), was added hydroxylamine aqueous solution (0.6 mL, 50%) at room temperature. The mixture was stirred for 16 hours. Water (10 mL) and ethyl acetate (10 mL) were added into the mixture for extraction to get an organic phase. The organic phase was concentrated under vacuum to obtain an oil. The oil was dissolved in DMSO (3 mL), followed adding CDI (10 mg, 0.062 mmol) and DBU (10 mg, 0.066 mmol). The mixture was stirred at room temperature for 6 hours. Water (10 mL) and ethyl acetate (10 mL) were added into the mixture to extract to get an organic phase. The organic phase was concentrated under vacuum to obtain A-8, 10 mg, with a yield of 88.2%.

To a solution of A-8 (220 mg, 0.44 mmol) in ethylene glycol methyl ether (3 mL), was added potassium hydroxide (494 mg, 8.8 mmol). The mixture was heated to 130° C. and stirred for 5 hours. After cooling down the mixture to room temperature, the mixture was adjusted to pH 5.0 with hydrochloric acid (6 N). Ethyl acetate (10 mL) was added into the mixture for extraction to afford an organic phase. The organic phase was dried with anhydrous sodium sulfate, and concentrated under vacuum to obtain intermediate A, 180 mg, with a yield of 99.0%.

Preparation of Intermediate B1

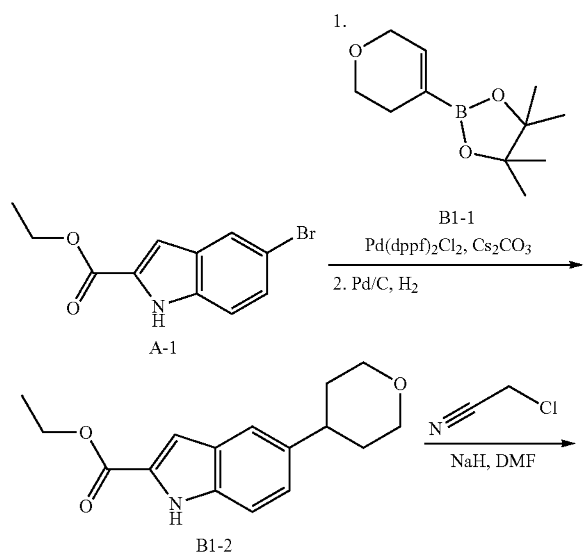

A-1

B1-2

-continued

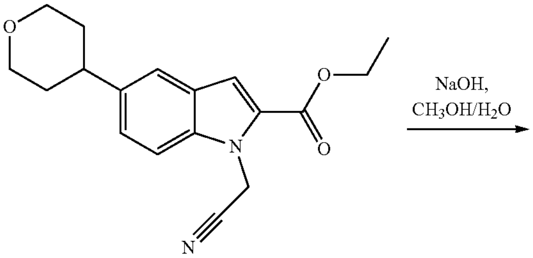

B1-3

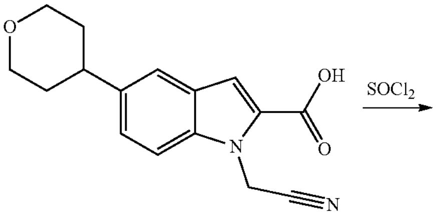

B1-4

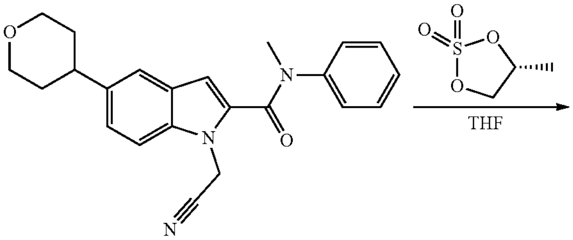

B1-5

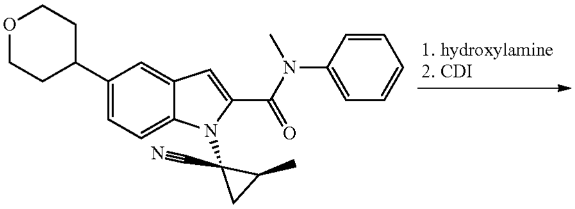

B1-6

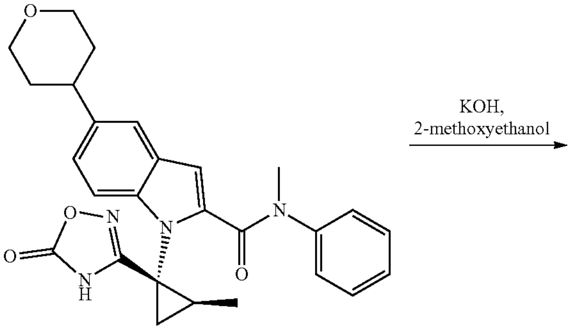

B1-7

-continued

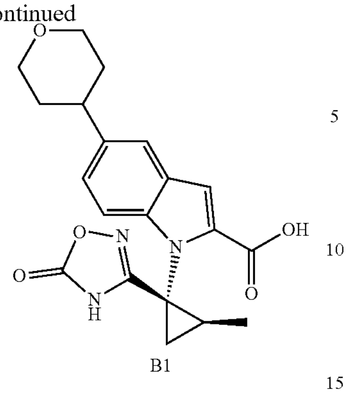

B1

To a solution of A-1 (120 g, 447.58 mmol) and B1-1 (103.43 g, 492.34 mmol) in a mixture solution of dioxane (1200 mL) and $H_2O$ (300 mL), was added $Cs_2CO_3$(123.72 g, 895.16 mmol) and $Pd(dppt)_2Cl_2$ (18.28 g, 22.38 mmol). The mixture was stirred for 12 hours at 90° C. After cooling down the mixture, saturated $NH_4Cl$ (500 mL) solution and ethyl acetate was added and extracted to obtain an organic phase. The organic phase was concentrated and purified by column chromatography to afford a white solid. The solid was dissolved in THF (1000 mL). Then Pd/C (12 g, 50% wt.) was added into the mixture. The mixture was stirred for 4 hours under $H_2$. The mixture was filtrated and concentrated to afford B1-2, 120 g.

To a solution of B1-2 (80 g, 292.69 mmol) in DMF (1000 mL), was added NaH (23.42 g, 585.38 mmol, 60%) at 0° C. The mixture was stirred for 30 mins. Then chloroacetonitrile was added dropwise into the mixture and stirred for 3 hours at room temperature. A saturated $NH_4Cl$ solution (500 mL) was added dropwise into the mixture. The solution was stirred for 10 mins, and a solid was precipitated. The mixture was filtrated to afford B1-3, 75 g.

For the subsequent reactions, the preparation of intermediate A can be referred to in order to obtain B1.

Preparation of Intermediates B, C, A1, A2, A3, A4 and A5

Following the preparation methods of intermediates A and B1, the following intermediates can be prepared:

B

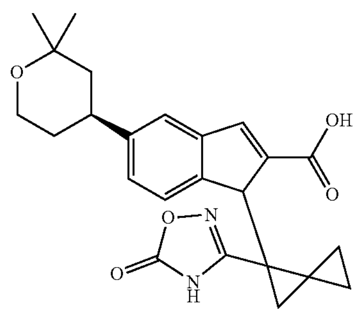

-continued

C

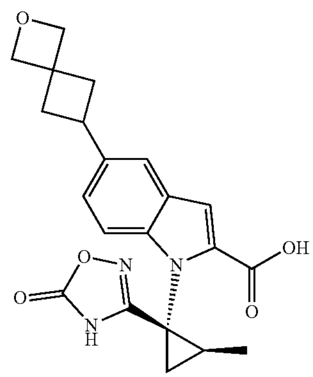

A1

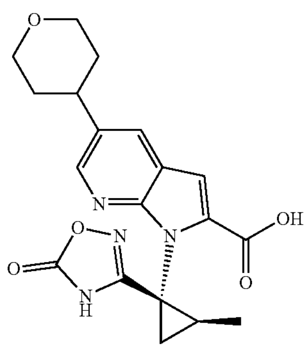

A2

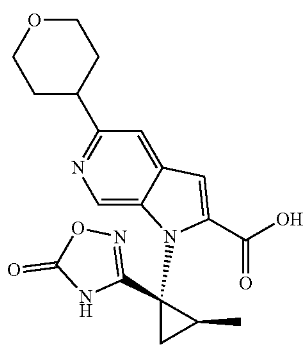

A3

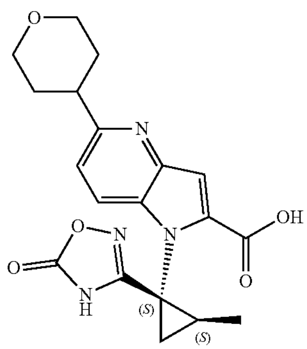

-continued

A4

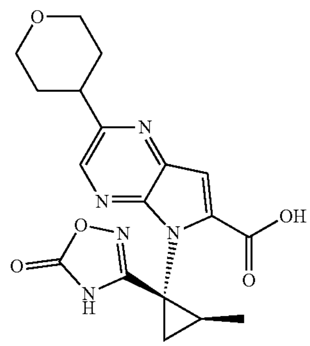

A5

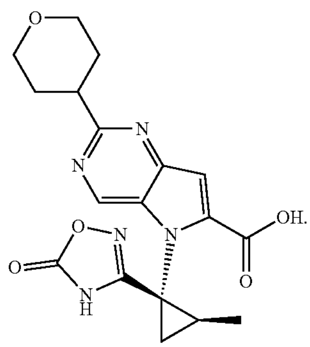

Preparation of Intermediate D

D

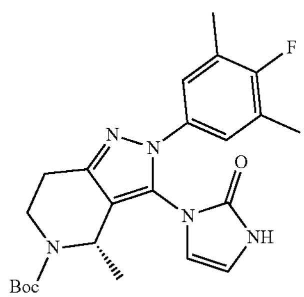

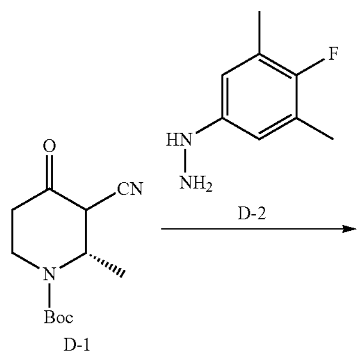

D-2

D-1

-continued

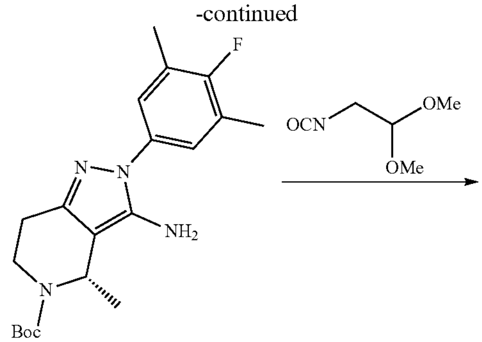

D-3

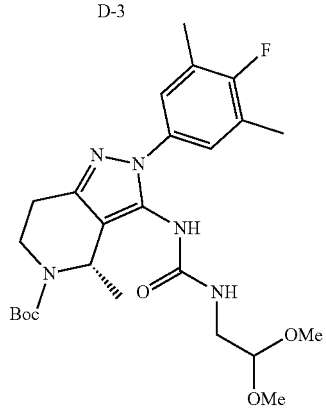

HCOOH

D-4

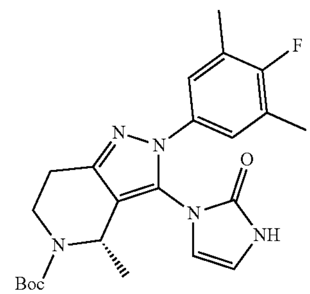

D-5

D-1 (2.0 g, 8.4 mmol), D-2 (1.29 g, 8.4 mmol) and pyridine hydrochloride (0.97 g, 8.4 mmol) were dissolved in toluene (10 mL). The mixture was heated to reflux for 1 hour. After cooling the reaction mixture, water (10 mL) and ethyl acetate (10 mL) were added into the mixture to extract to an organic phase. The organic phase was concentrated under vacuum to afford compound D-3, 2.4 g, a yield of 76.4%.

To a solution of D-3 (2.0 g, 5.34 mmol) in dichloromethane (20 mL), was added dropwise a solution of 2-isocyanate-1, 1-dimethoxyethane (0.84 g, 6.41 mmol) in dichloromethane (5 mL) at room temperature. The mixture was stirred at room temperature for 2 hours. Water (20 mL) was added into mixture to extract to get an organic phase. The organic phase was concentrated under vacuum to afford D-4, which was used without purification in the next step.

To a solution of D-4 in dichloromethane (20 mL), was added formic acid (10 mL) under an ice bath. The mixture was stirred overnight at room temperature. Water (20 mL) was added into the mixture. The mixture was extracted to separate out an organic phase. The organic phase was concentrated to obtain a crude product. The crude was slurry washed with a mixture of ethyl acetate and n-heptane to obtain D-5, 1.2 g.

Preparation of Intermediates E and F

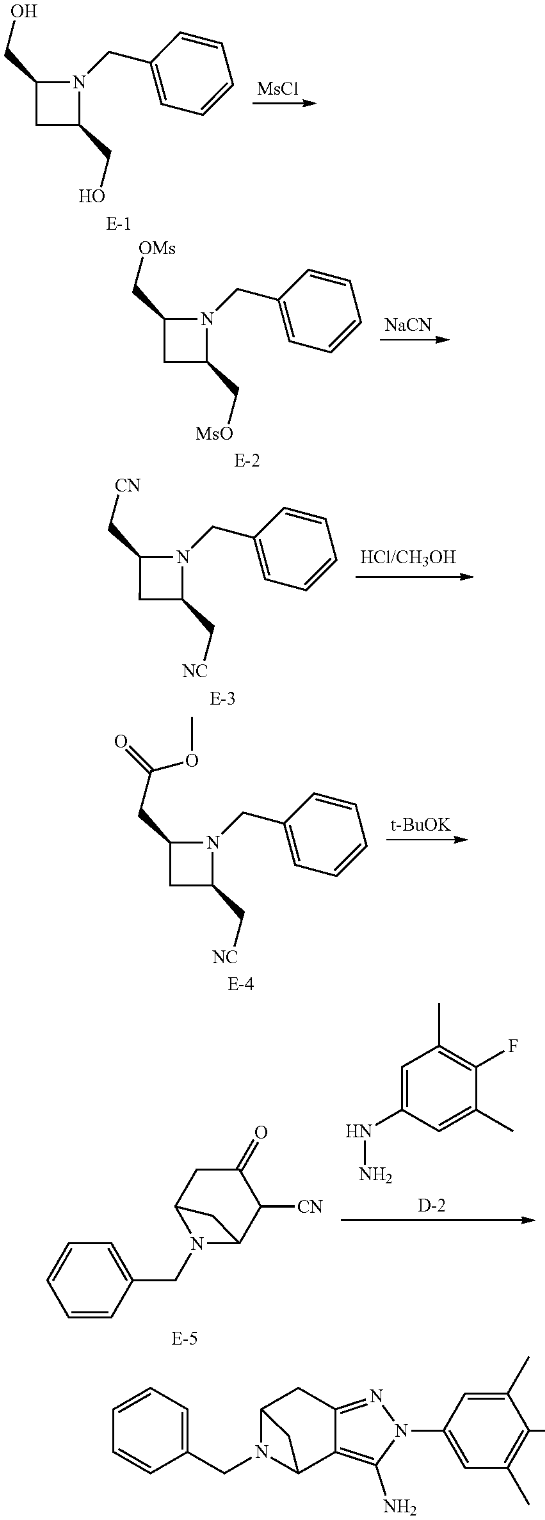

To a solution of E-1 (5.0 g, 24.12 mmol) and triethylamine (7.31 g, 72.36 mmol) in dichlorohexane (25 mL), was added dropwise MsCl (6.08 g, 53.07 mmol) under ice bath. The mixture was stirred at room temperature for 30 min. The mixture was added water (20 mL) to extract to get an organic phase. The organic phase was dried by anhydrous sodium sulfate, and concentrated under vacuum to obtain E-2, 7.5 g, with a yield of 85.6%.

To a solution of E-2 (3.0 g, 8.25 mmol) in DMF (30 mL), was slowly added NaCN (850 mg, 17.3 mmol). The mixture was stirred 1 hour at 60° C. After cooling, the mixture was added sodium hypochlorite saturated solution (30 mL) and stirred for 1 hour. Then ethyl acetate (30 mL) was added into the mixture. The mixture was extracted to get an organic phase. The organic phase was concentrated under vacuum to obtain E-3, 1.54 g, with a yield of 82.8%.

E-3 (1.2 g, 5.33 mmol) was dissolved in a methanol solution of hydrogen chloride (1M, 7 mL). The mixture was stirred overnight at room temperature. Water was added into the mixture and the mixture was stirred for 2 hours. Ethyl acetate (20 mL) was added into the mixture. An organic phase was separated by extraction from the mixture. The organic phase was concentrated under vacuum to afford an oil. The oil was purified by column chromatography to afford E-4, 0.6 g, with a yield of 43.6%.

E-4 (0.5 g, 1.9 mmol) and potassium tert-butoxide (1.09 g, 9.7 mmol) were added into THF (5 mL). The mixture was stirred overnight at room temperature. The mixture was adjusted to pH 7.0 with dilute hydrochloric acid. Ethyl acetate was added into the mixture for extraction to afford an organic phase. The organic phase was concentrated under vacuum and purified by column chromatography to afford E-5, 0.34 g with a yield of 68%.

E-5 (0.2 g, 0.88 mmol), D-2 (126 mg, 0.88 mmol) and pyridine hydrochloride (0.1 g, 0.88 mmol) were dissolved into toluene (4 mL). The mixture was heated to reflux for 1 hour. After cooling the mixture, water (10 mL) and ethyl acetate (10 mL) were added into the mixture. The mixture was extracted to get an organic phase. The organic phase was concentrated to afford compound E, 260 mg, with a yield of 81.2%.

Intermediate F was prepared by the same method:

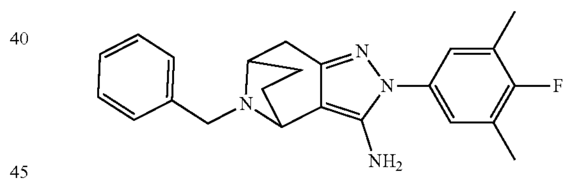

Preparation of Intermediate G

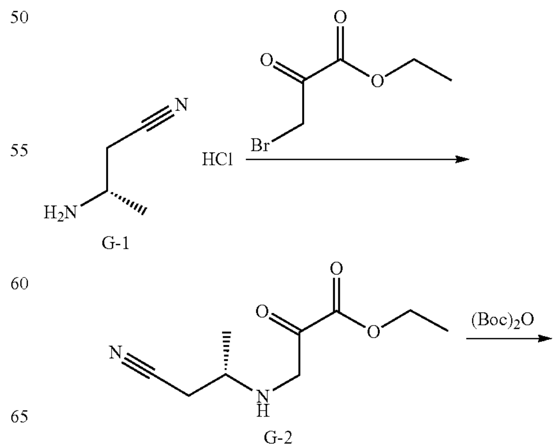

-continued

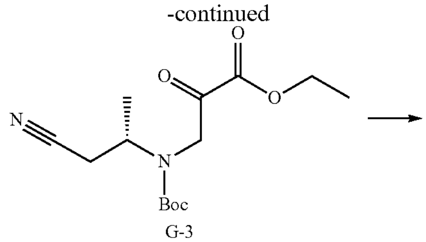

G-3

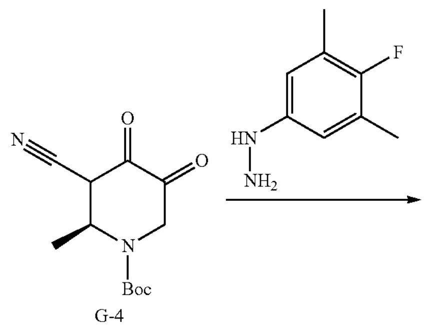

G-4

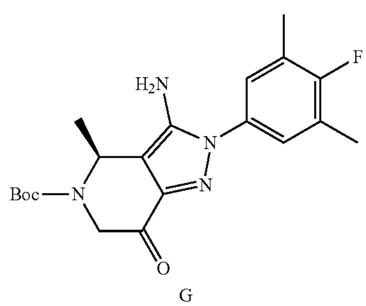

G

G-1 (5.0 g, 41.5 mmol), ethyl 3-bromopyruvate (8.90 g, 45.61 mmol) and cesium carbonate (20.3 g, 62.2 mmol) were dissolved in DMF (100 mL). The mixture was heated to 65° C. and stirred for 4 hours. The mixture was cooled to room temperature, and water (200 mL) was added into the mixture. A solid was precipitated and the mixture was filtered to obtain G-2, 4.80 g, with a yield of 58.4%.

G-2 (4.0 g, 20.2 mmol), $(Boc)_2O$ (6.6 g, 30.3 mmol) and triethylamine (6.13 g, 60.5 mmol) were dissolved in THF (40 mL). The mixture was stirred overnight at room temperature. Water (50 mL) and ethyl acetate (50 mL) were added into the mixture to extract to separate out an organic phase. The organic phase was concentrated under vacuum to obtain G-3, 5.6 g and 93.2%.

To a solution of G-3 (5.6 g, 18.8 mmol) in THF (50 mL), was added potassium tert-butoxide (10.5 g, 94 mmol) at room temperature. The mixture was stirred overnight. The mixture was adjusted to pH 7.0 with dilute hydrochloric acid. Then ethyl acetate was added into the mixture for extraction to separate an organic phase. The organic phase was concentrated under vacuum to afford a crude. The crude was purified by column chromatography to afford G-4, 3.6 g, with a yield of 76%.

G-4 (2.0 g, 7.93 mmol). D-2 (1.22 g, 7.93 mmol) and pyridine hydrochloride (0.9 g, 7.93 mmol) were dissolved in toluene (40 mL). The mixture was heated to reflux for 1 hour. After cooling the reaction solution, water (40 mL) and ethyl acetate (40 mL) were added to the mixture. The mixture was extracted to get an organic phase. The organic phase was concentrated under vacuum to afford compound G, 1.2 g, with a yield of 39%.

Preparation of Intermediate H

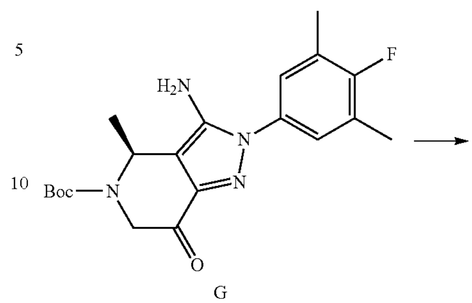

G

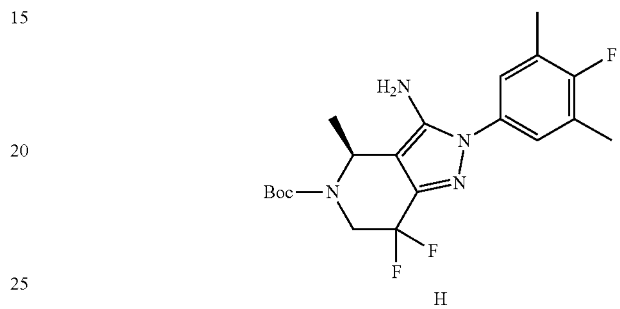

H

To a solution of compound G (200 mg, 0.52 mmol) in DCM (2 mL), was added DAST (165 mg, 1.0 mmol) under an ice bath. The mixture was stirred at 0° C. overnight. Saturated sodium bicarbonate solution (4 mL) and DCM (4 mL) were added into the mixture. The mixture was extracted to separate an organic phase. The organic phase was concentrated under vacuum and purified by column chromatography to obtain compound H, 0.12 g, with a yield of 56.8%.

Preparation of Intermediate I

I

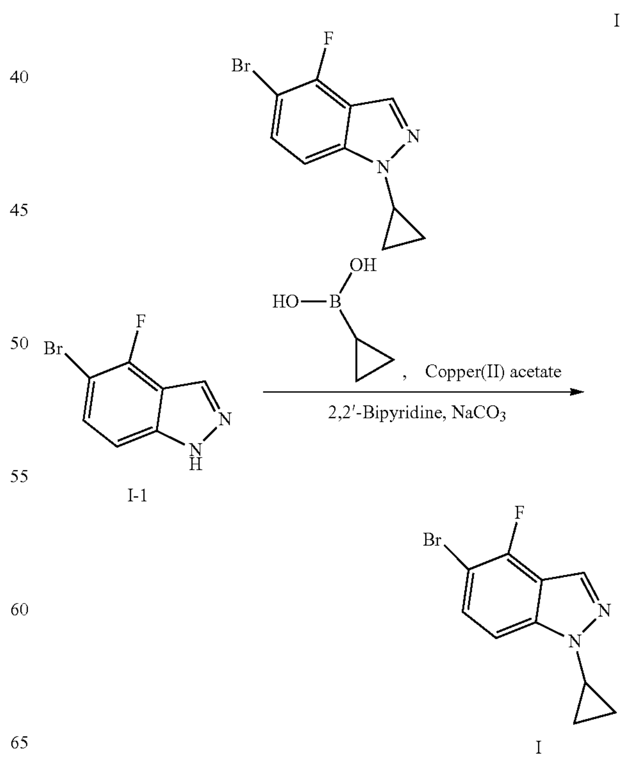

I-1

I

Compound I-1 (5.0 g, 23.3 mmol), cyclopropylboronic acid (3.99 g, 46.5 mmol), copper acetate (3.48 g, 23.2 mmol), 2, 2' bipyridine (3.9 g, 23.3 mmol) and sodium carbonate (4.9 g, 46.5 mmol) were added into dichloroethane. The mixture was stirred overnight at 70° C. After cooling down the mixture, the mixture was filtered to afford a filtrate. The filtrate was extracted with water and dichloromethane to separate an organic phase. The organic phase was concentrated under vacuum and then purified by column chromatography to obtain I, 3.6 g, with a yield of 61%.

Preparation of Intermediate J

J

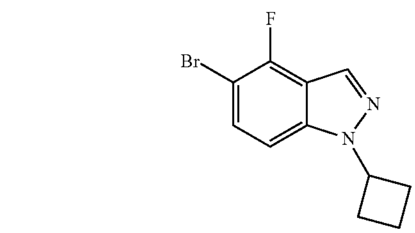

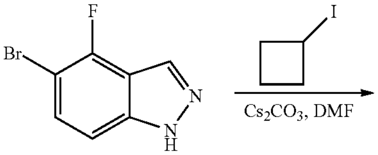

I-1

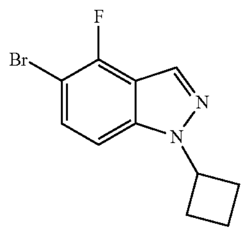

J

To a solution of I-1 (2.0 g, 9.3 mmol) in DMF (20 mL), was added iodocyclobutane (1.78 g, 9.8 mmol) and $Cs_2CO_3$ (4.55 g, 13.9 mmol). The mixture was stirred 6 hours at 50-60° C. Water (50 mL) was added into the mixture, and then a solid was precipitated. The suspension was filtrated to afford J, 1.6 g, yield: 63.9%.

Preparation of Intermediate J-1

J-1

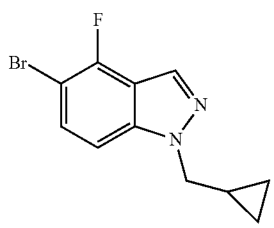

-continued

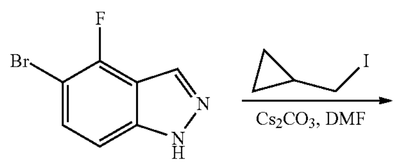

I-1

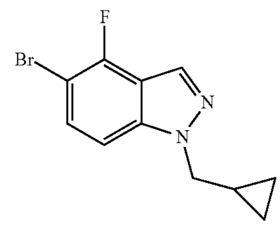

J-1

To a solution of I-1 (1.0 g, 4.65 mmol) in DMF (10 mL), was added (iodomethyl)cyclopropane (0.89 g, 4.9 mmol) and $Cs_2CO_3$ (2.27 g, 6.98 mmol). The mixture was stirred 4 hours at 50-60° C. Water (50 mL) was added into the mixture, and then a solid was precipitated. The suspension was filtrated to afford J-1, 0.87 g, yield: 69.51%.

Preparation of Intermediates K, L, M and N

K

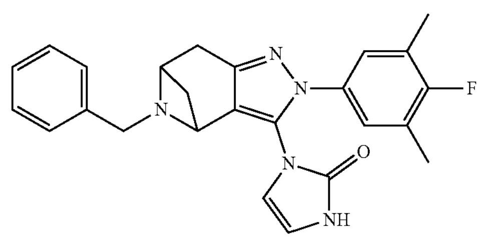

L

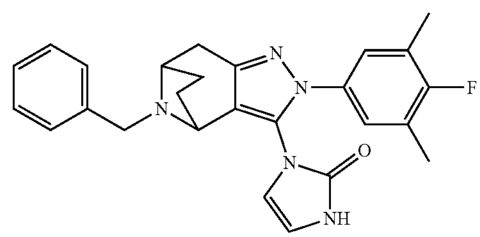

M

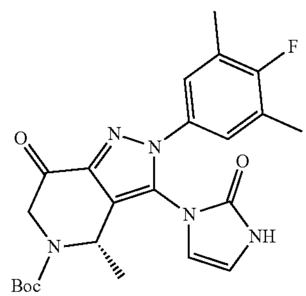

-continued

N

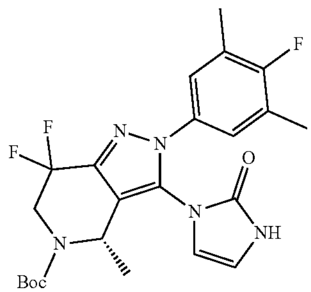

According to the preparation method of intermediates K, L, M and N would be obtained.

Preparation of Intermediate O

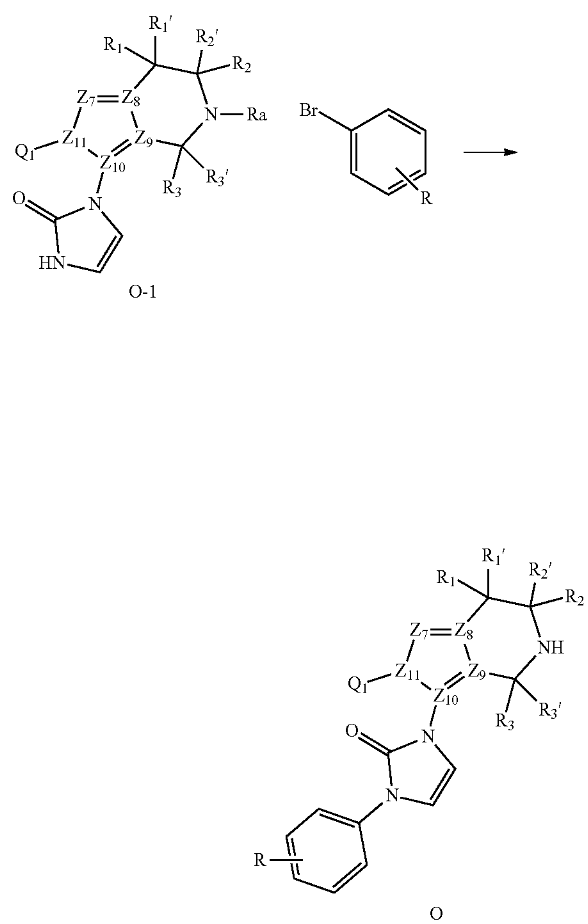

O-1

O

O-1(1 eq.) and (1R, 2R)-(−)-N, N'-dimethyl-1, 2-cyclohexanediamine (0.5 eq.), CuI (0.5 eq.), bromide (1.5 eq.) and potassium carbonate (3 eq.) were added to NMP. The mixture was stirred overnight at 100~110° C. After cooling down, the mixture was filtered to afford a filtrate, then water (10 V) and ethyl acetate (10 V) was added into the filtrate. The mixture was extracted to separate out an organic phase. The organic phase was concentrated under vacuum and then purified by column chromatography to obtain the target compound.

The following compounds can be prepared by this method:

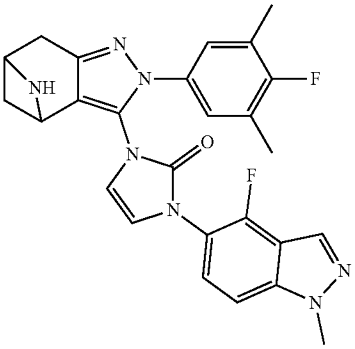

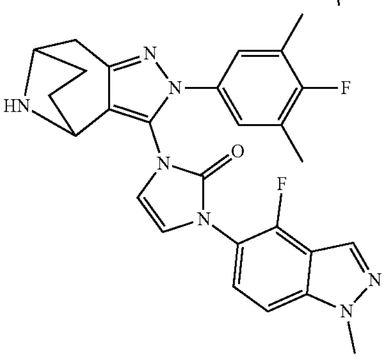

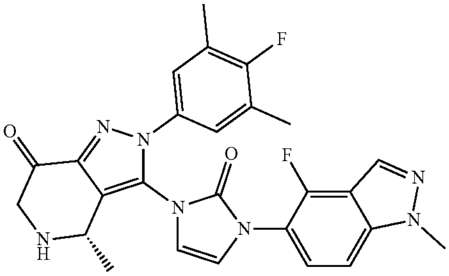

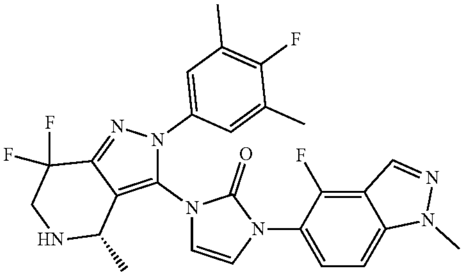

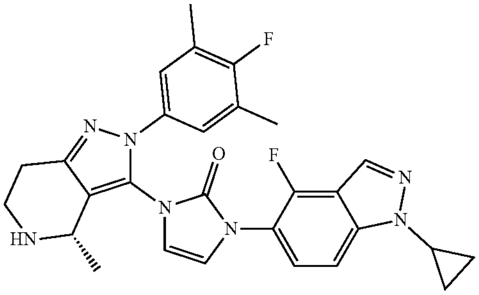

-continued
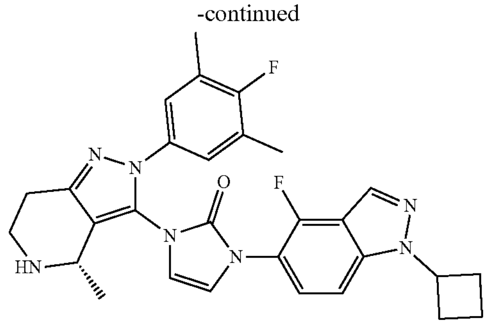
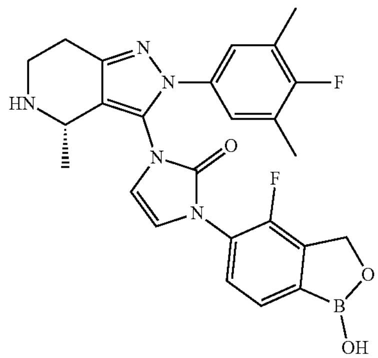
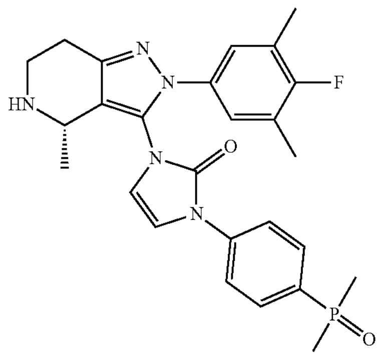
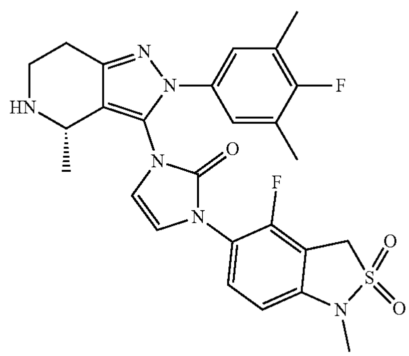
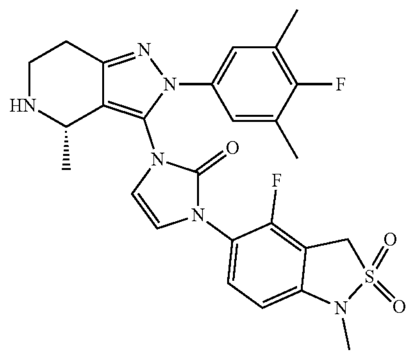
-continued
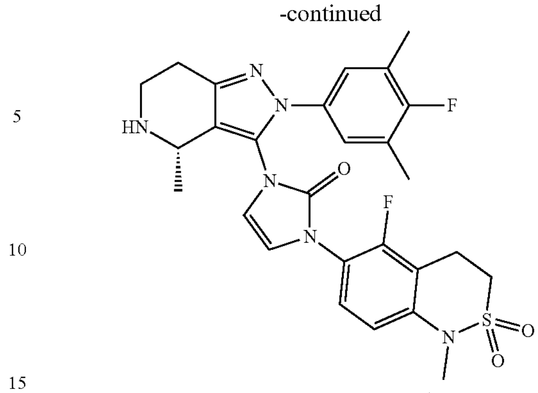
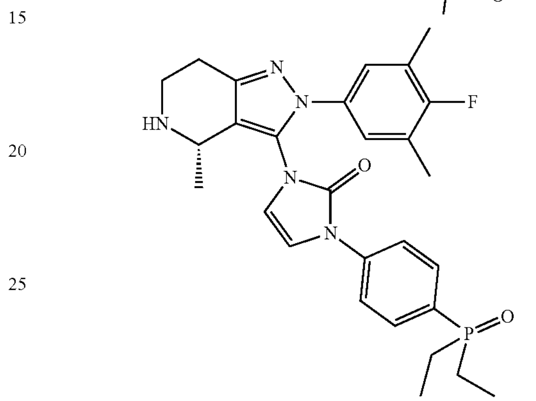
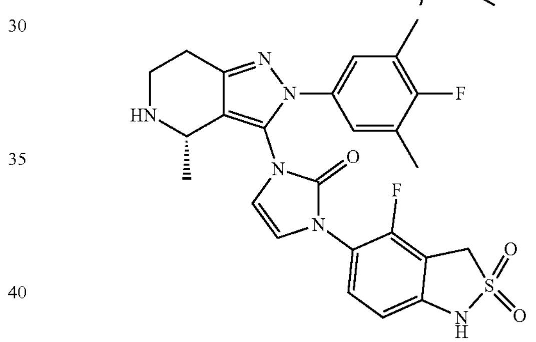
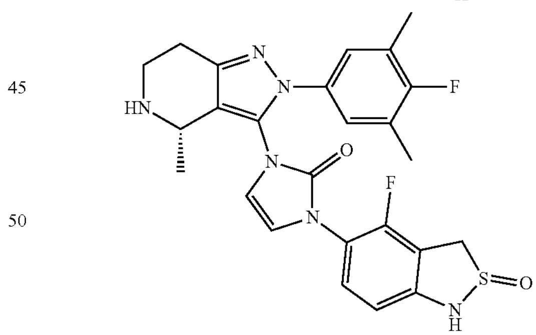
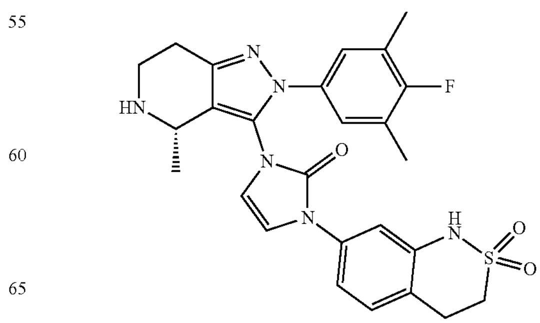
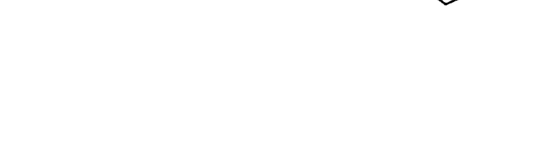

-continued

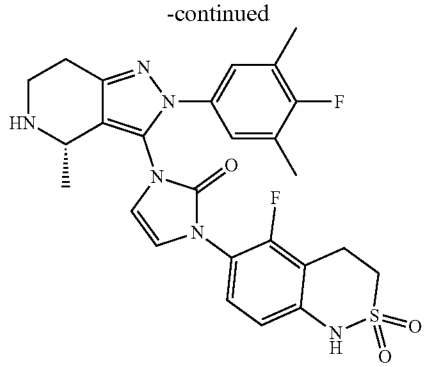

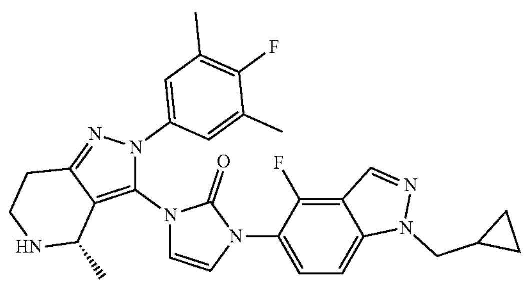

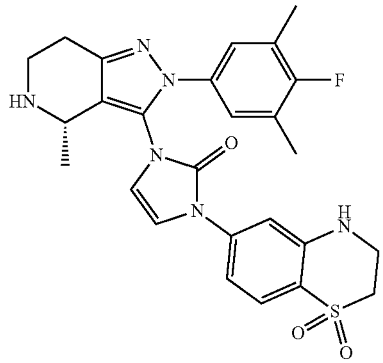

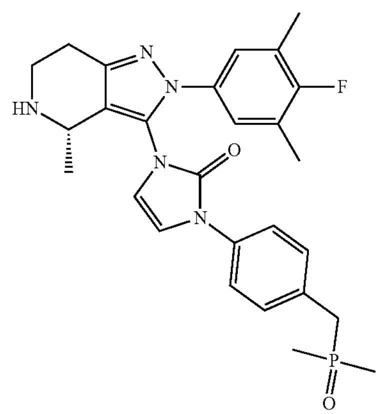

Preparation of Intermediate P

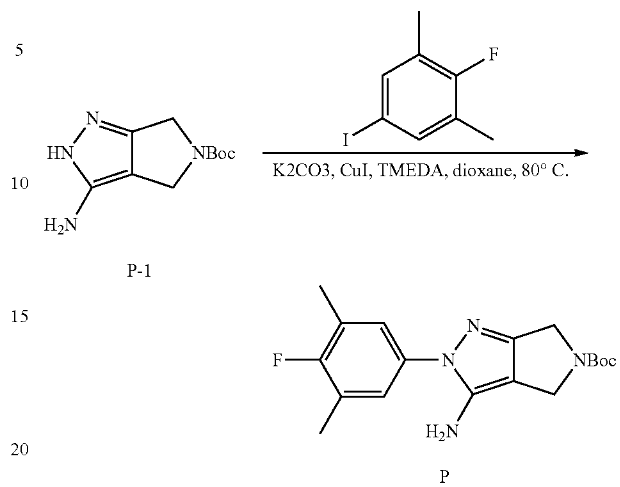

P-1

P

P-1 (1.0 g, 4.46 mmol), 2-fluoro-5-iodo-1, 3-xylene (1.12 g, 4.46 mmol), CuI (0.8 g, 4.46 mmol), TMEDA (0.52 g, 4.46 mmol) and potassium carbonate (0.92 g, 6.69 mmol) were added into dioxane (10 mL). The mixture was stirred overnight at 100~110° C. After the mixture was cooled, the mixture was filtered to get a filtrate. Ethyl acetate (20 mL) and water (20 mL) was added into the filtrate to extract to separate an organic phase. The organic phase was concentrated under vacuum, and then purified by column chromatography to obtain P, 0.6 g, with a yield of 38.8%.

Preparation of Intermediate Q

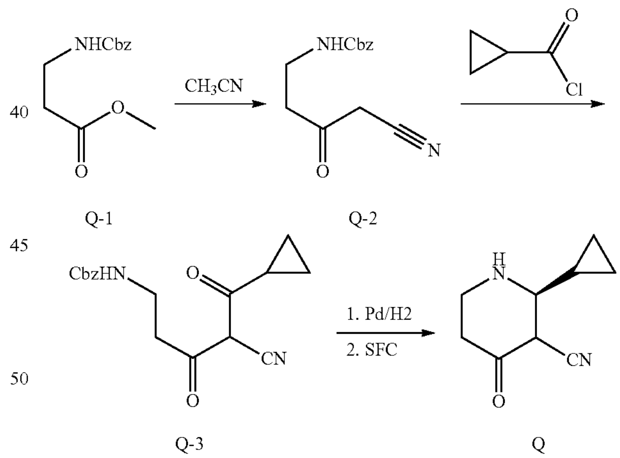

Q-1 Q-2

Q-3 Q

To a solution of acetonitrile (15.57 g, 379.34 mmol, Purity 100%) in tetrahydrofuran (300 mL) at −78° C. under $N_2$, was added dropwise Lithium bis(trimethylsilyl)amide (63.47 g, 379.34 mmol). The mixture was stirred for 1 h at −78° C. A solution of Q-1 (45.0 g, 189.67 mmol) in THF (5 mL) was added dropwise into the above solution. The resulting mixture was allowed to warm to −50° C. over 30 min. The reaction mixture was quenched with saturated $NH_4Cl$ (aq.) (100 mL) and extracted with EA (150 mL). The mixture was separated to get an organic layer which was washed with brine, and dried over $MgSO_4$. The organic layer was concentrated under vacuum and purified by silica gel column chromatography (PE/EtOAc: 0%-50%) to give a yellow oil.

To a solution of benzyl N-(4-cyano-3-oxobutyl)carbamate (246.26 mg, 1 mmol) and Triethylamine (202.38 mg, 2 mmol) in dichloromethane (10 mL), was added dropwise cyclopropanecarbonyl chloride (209.06 mg, 2 mmol). The mixture was stirred for overnight at room temperature. The reaction mixture was quenched with water (10 mL) and extracted with dichloromethane (10 mL). The mixture was separated to get an organic layer which was washed with brine, dried over $MgSO_4$. The organic layer was concentrated under vacuum and purified by silica gel column chromatography (PE/EtOAc: 0%-50%) to give an oil.

Q-3 (150 mg, 0.47 mmol) and Pd/C (15 mg, 30% wt) were added into MeOH (15 mL). The mixture was stirred 3 hours under $H_2$. The mixture was filtrated and concentrated under vacuum to get a crude. The crude was purified by SFC to get the title compound, 32 mg, yield: 40.8%. $^1$HNMR (d-DMSO, 500 MHZ): δ 4.12 (d, 1H, J=8.0 Hz), 3.35 (m, 1H), 3.12-3.07 (m, 2H), 2.63-2.55 (m, 2H), 1.47-1.32 (m, 5H).

Preparation of Intermediate R

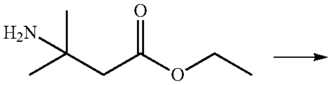

R-1

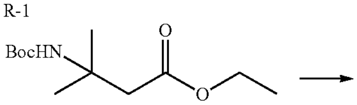

R-2

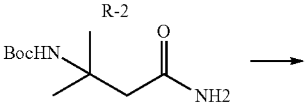

R-3

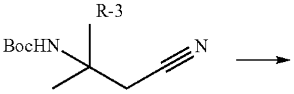

R-4

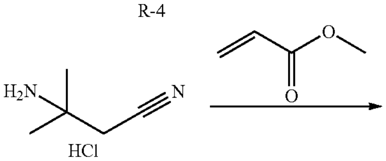

R-5

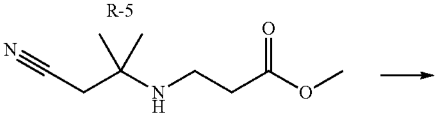

R-6

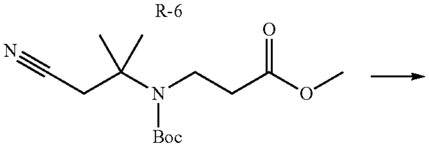

R-7

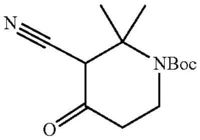

R

To a solution of R-1 (10.0 g, 68.87 mmol) and triethylamine (13.9 g, 138 mmol) in dichloromethane (100 mL), was added $(Boc)_2O$ (18.0 g, 82.64 mmol). The mixture was stirred for overnight at room temperature. The reaction mixture was quenched with water (100 mL) and extracted with dichloromethane (100 mL) to get an organic layer. The organic layer was washed with brine, dried over $MgSO_4$, and concentrated under vacuum to get R-2, 15.3 g, yield: 90.56%.

R-2 (15.0 g, 61.1 mmol) was dissolved in $NH_3/CH_3OH$ (10M, 300 mL). The mixture was stirred for 4 hours in an autoclave at 90~100° C. After cooling, the mixture was concentrated under vacuum to get a crude R-3 without purification for the next step reaction.

R-3, TFAA (6.90 mL, 49.5 mmol) and pyridine (8.0 mL, 99.0 mmol) were added into a three-neck bottle. The mixture was stirred at room temperature for 1 h. The reaction mixture was quenched with $H_2O$ (100 mL) and extracted with EtOAc to afford an organic layer. The organic layer was washed with brine (100 mL), dried over $Na_2SO_4$, and concentrated under vacuum and then purified by flash chromatography (PE/EtOAc: 20/1) to afford R-4, 5.3 g.

R-4 (5.3 g, 26.7 mmol) was dissolved in HCl/EtOAc (4M, 30 mL). The mixture was stirred for 2 hours at room temperature. A solid was precipitated. The mixture was filtrated to afford R-5, 3.2 g, 88.9%.

To a solution of R-5 (3.2 g, 23.7 mmol) in EtOH (20 mL), was added $Et_3N$ (7.22 g, 71.3 mmol) and methyl acrylate (2.15 g, 24.9 mmol) at room temperature. The mixture was stirred 3 hours at 70° C. Then the mixture was cooled to room temperature, and $(Boc)_2O$ (6.74 g, 30.9 mmol) was added into the mixture. The solution was stirred at room temperature overnight and then diluted with $H_2O$ (50 mL). The mixture was extracted with EtOAc to afford an organic layer. The organic layer were washed with brine (50 mL), dried over $Na_2SO_4$, concentrated and then purified by flash chromatography (PE/EtOAc: 10/1) to afford R-7, 4.3 g, yield: 63.6%.

To a solution of R-7 (4.0 g, 14.1 mmol) in THF (50 mL), was added t-BuOK (2.37 g, 21.1 mmol). The mixture was stirred at room temperature for 1 h and then quenched with 2N HCl solution. The mixture was diluted with H2O (50 mL) and extracted with EtOAc to afford an organic layer. The organic layer were washed with brine, dried over $Na_2SO_4$, concentrated under vacuum, and then purified by flash chromatography to afford R, 2.5 g, yield: 70.4%.

Preparation of Intermediate S

Following the synthetic route of intermediate R, the intermediate S was obtained by a SFC separation.

S

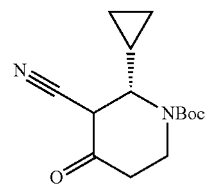

Preparation of Intermediate T

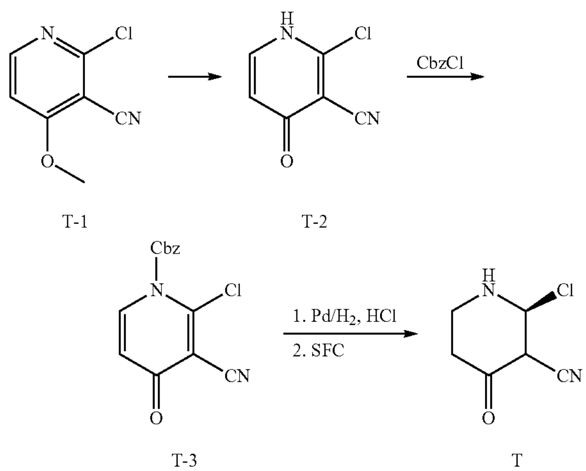

T-1 T-2 T-3 T

To a solution of T-1 (10.0 g, 59.3 mmol) in THF (100 mL), was added boron tribromide (120 mL, 1M in DCM). The mixture was stirred for 3 hours at room temperature. The mixture was quenched with $Na_2CO_3$ (aq.) and extracted with DCM. The organic layer was washed with brine, dried over $Na_2SO_4$, and concentrated under vacuum to afford T-2, 8.5 g, yield: 92.7%.

To a solution of T-2 (8.0 g, 51.8 mmol) in DCM, was added $Et_3N$ (7.8 g, 77.6 mmol). The mixture was cooled to 0° C., and Cbz-Cl (9.71 g, 56.9 mmol) was added into the mixture. After the mixture was stirred for 2 hours, the mixture was quenched with $Na_2CO_3$ (aq.) and extracted with DCM. The organic layer were washed with brine, dried over $Na_2SO_4$, and concentrated under vacuum to afford T-3, 11.2 g, yield: 74.9%.

A solution of T-3 (10.0 g, 34.6 mmol), Pd/C (1.0 g, 30% wt) and 0.5 mL HCl (1M in $H_2O$) in MeOH (150) mL was stirred under 50 psi $H_2$ at room temperature for 2 hours. The mixture was filtrated and concentrated under vacuum to get a residue. The residue was dissolved into DCM. The solution was washed by $NaHCO_3$(aq) and brine. The organic layer were dried over $Na_2SO_4$, concentrated under vacuum and purified by flash chromatography to afford a racemate. Then, the racemate was purified by SFC to afford T, 1.2 g, yield of 21.8%.

Preparation of Intermediate AA

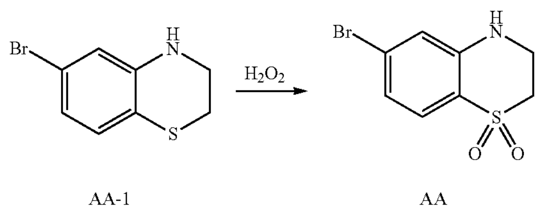

AA-1 AA

To a solution of compound AA-1 (1.0 g, 4.35 mmol) in ethanol (10 mL), was added hydrogen peroxide (30%, 10 mL) at room temperature. The mixture was stirred overnight. The reaction solution was filtered to afford AA, 1.1 g, yield: 96.6%.

Preparation of Intermediate AB

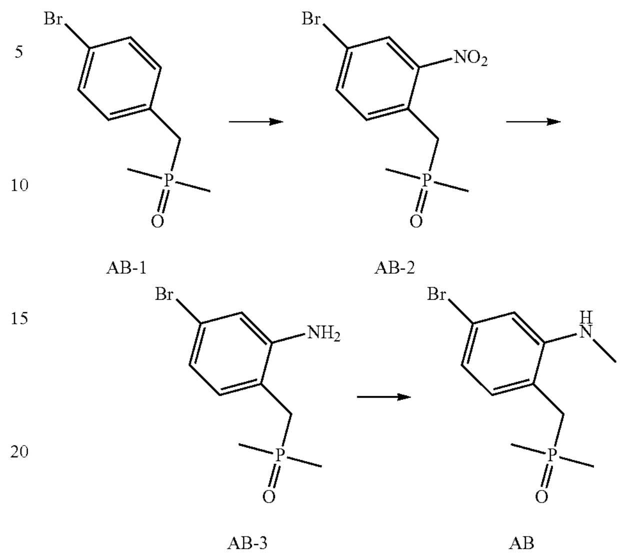

AB-1 AB-2 AB-3 AB

AB-1 (5.0 g, 20.2 mmol) was dissolved in sulfuric acid (25 mL, 98%) at −20° C. Potassium nitrate (2.1 g, 20.2 mmol) was added into the mixture in batches. The mixture was stirred for 4 hours. The reaction solution was poured into an ice water, and a solid was precipitated. The solid was dried and then purified by column chromatography to obtain AB-20.7 g, yield: 11%.

AB-2 (0.7 g, 2.4 mmol) was dissolved in methanol (5 mL). The saturated ammonium chloride (5 mL) and iron powder (0.54 g, 9.6 mmol) was added into the mixture. The mixture was heated to 80° C. for 3 hours. After the mixture was cooled to room temperature, ethyl acetate (20 mL) was added into the mixture to extract to afford an organic layer. The organic layer was concentrated under vacuum to afford AB-3, 0.54 g, yield: 86%.

To a solution of AB-3 (0.54 g, 2.0 mmol) in dichloromethane (5 mL), was added triethylamine (0.20 g, 2.0 mmol) and $(Boc)_2O$ (0.45 mmol) at room temperature. The mixture was stirred it at room temperature overnight. Iodomethane (0.29 g, 2.0 mmol) was added dropwise to the reaction solution and stirred for 1 hour. The reaction solution was concentrated under vacuum. The residue was added into ethyl hydrogen chloride acetate solution (5 mL, 2N). The mixture was stirred at room temperature for 1 hour. The mixture was precipitated and filtered to produce AB, 0.32 g. yield: 49.7%.

Preparation of Intermediate AC

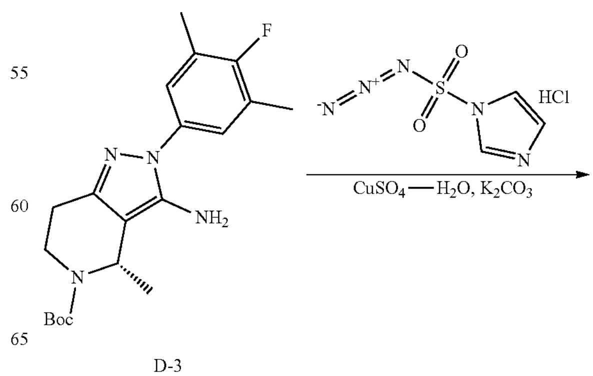

D-3

-continued

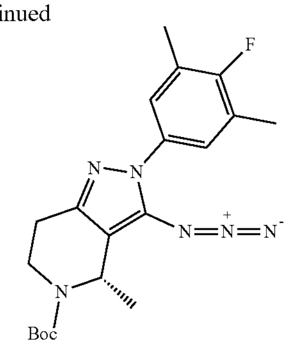

AC

D-3 (290 mg, 0.77 mmol), 1H-imidazole-1-sulfonyl azide (139.99 mg, 0.81 mmol) and potassium carbonate (212.84 mg, 1.54 mmol) were added to methanol (3 mL) at 0° C. Copper sulfate hydrate (1.9 mg, 0.0077 mmol) was added into the mixture. The mixture was stirred for 12 hours at room temperature. The mixture was extracted with ethyl acetate and water to afford an organic phase. The organic phase was washed with 1N hydrochloric acid, saturated sodium bicarbonate, and brine. Then the solution was dried over anhydrous sodium sulfate and concentrated under vacuum to obtain AC as an oil, 0.15 g, 48%.

Preparation of Intermediate AD

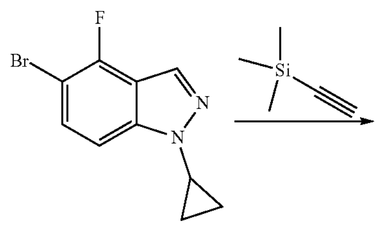

AD-1

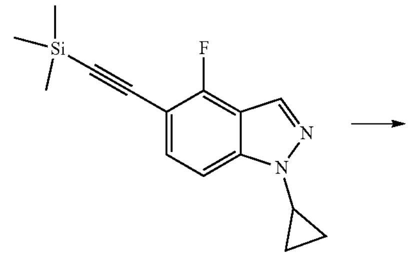

AD-2

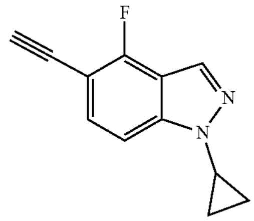

AD

AD-1 (2.0 g, 7.84 mmol), TMSCN (1.16 g, 11.8 mmol), triethylamine (1.59 g, 15.7 mmol), cuprous iodide (1.49 g, 7.8 mmol), and palladium tetrakis(triphenylphosphine) (900 mg, 0.8 mmol) were added into dioxane (20 mL). The mixture was heated under nitrogen to 70° C. The reaction was stirred overnight. The mixture was cooled to room temperature, water and ethyl acetate was added to extracted to get an organic layer. The organic layer was concentrated and then purified by column chromatography to produce AD-2, 1.1 g, yield: 51.5%.

To a solution of AD-2 (1.1 g, 4.0 mmol) in methanol (10 mL), was added potassium carbonate (1.1 g, 8.1 mmol). The mixture was stirred at room temperature for 4 hours. Water and ethyl acetate was added into the mixture to extract to get an organic phase. The organic phase was concentrated under vacuum and then purified by column chromatography to obtain AD, 0.35 g, yield: 43.3%.

Preparation of Intermediate AE

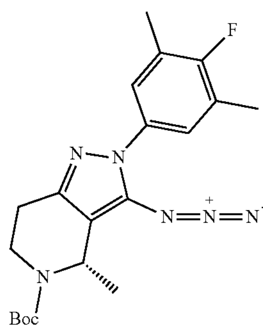

+

AC

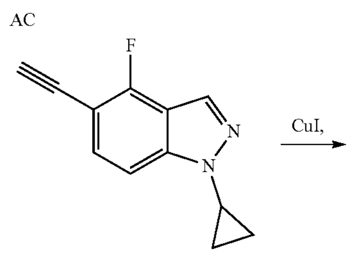

AD

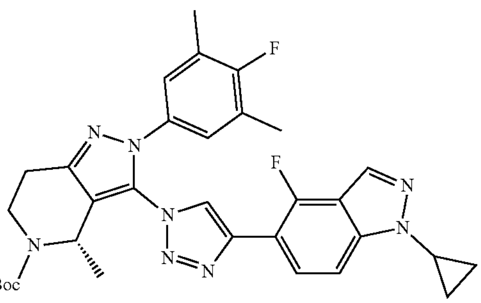

AE

To a solution of AC (100 mg, 0.25 mmol) and AD (55 mg, 0.27 mmol) in PEG200 (2 mL), was added CuI (9.5 mg, 0.05 mmol). The reaction was stirred at 50° C. for 2 h. After the mixture was cooled to room temperature, the reaction solution was filtered. The filtrate was washed by brine to get an organic phase. The organic phase was concentrated under vacuum and purified by pre-HPLC (C18) to yield AE, 123 mg, 82%.

Preparation of Intermediate AF

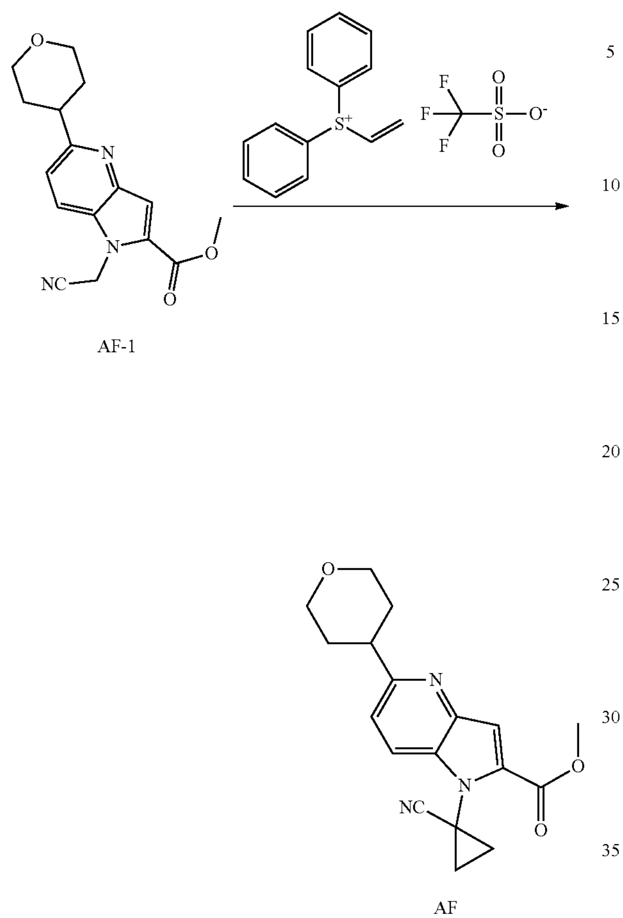

AF-1

AF

To a solution of AF-1 (300 mg, 1.00 mmol) in DMSO (10 mL), was added diphenyl(vinyl)sulfonium triflate (0.40 g, 1.1 mmol) and DBU (0.46 g, 3 mmol). The mixture was stirred 2 hours at room temperature. Ethyl acetate (50 mL) and water (20 mL) were added dropwise into the reaction mixture, and the organic phase was extracted from the mixture. The organic phase was washed with brine, dried over anhydrous sodium sulfate, and then concentrated under vacuum. The residue was purified by column chromatography to yield AF, 154 mg, with a yield of 47.22%.

Preparation of Compound 1

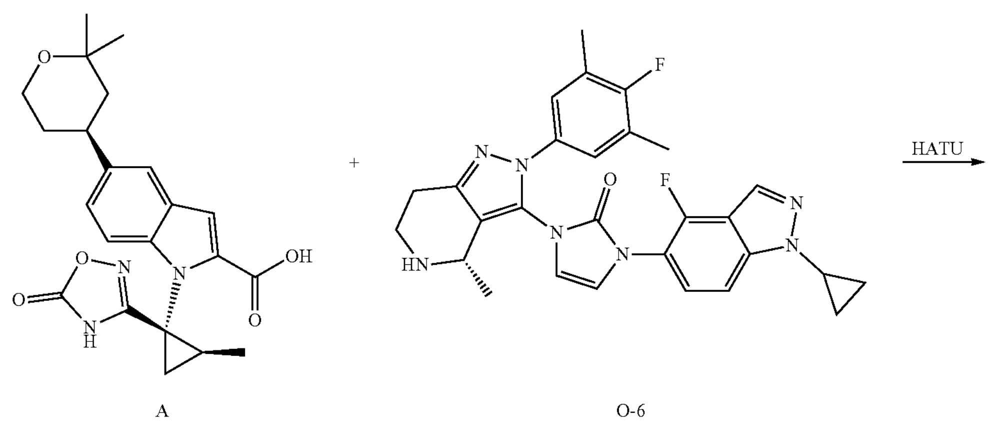

A

O-6

-continued

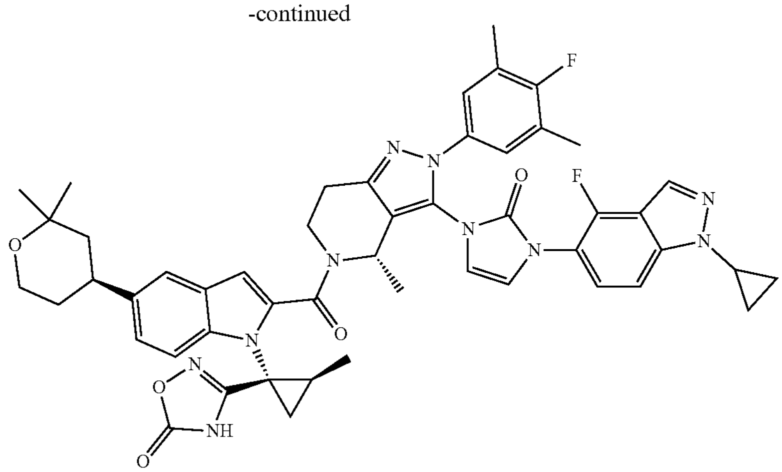

1

Intermediate A (180 mg, 0.44 mmol), O-6 (280 mg, 0.57 mmol), HATU (250.95 mg, 0.66 mmol) and DIPEA (170 mg, 1.32 mmol) were dissolved in DMF (5 mL). The mixture was stirred at room temperature for 3 hours. Water was added into the mixture to extract with dichloromethane to afford an organic phase. The organic phases was concentrated under vacuum. The residue was purified by pre-HPLC (acetonitrile: 0.1% formic acid aqueous solution) to afford compound 1, 200 mg, with a yield of 51%.

Preparation of the Sodium Salt of Compound 19

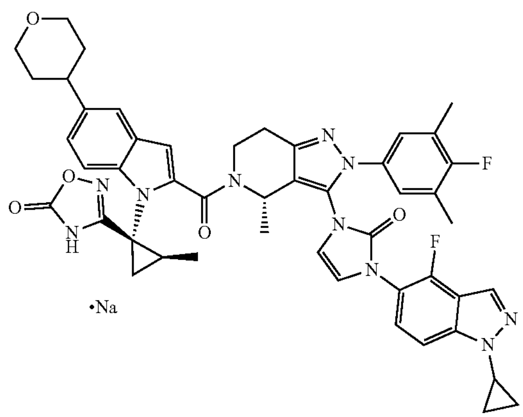

•Na

To a solution of compound 19 (1 g, 1.14 mmol) in a mixture solution of dichloromethane (5 mL) and methanol (5 mL), was added a solution of NaOH (50 mg, 1.25 mmol) in MeOH (1 mL). The mixture was stirred overnight. The reaction mixture was concentrated under vacuum. Then the residue was slurry washed with diethyl ether to afford the sodium salt of compound 19, 0.95 g with a yield of 95%. Melting point: 255-260° C.

Preparation of the Calcium Salt of Compound 19

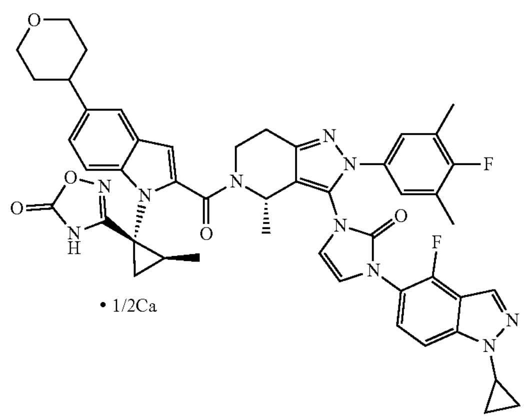 [SMILES: Cc1cc(-n2nc3c(c2-n2ccn(-c4ccc5c(cnn5C5CC5)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F]

• 1/2Ca

The sodium salt of compound 19 (0.5 g, 0.55 mmol) was added into THF (5 mL). Calcium acetate (89.34 mg, 0.56 mmol) was added into the reaction mixture. After the reaction mixture became clear, the mixture was stirred for 8 hours. The reaction mixture was concentrated under vacuum, then the residue was slurry washed with a mixture of dichloromethane (1 mL) and diethyl ether (10 mL) to afford a white solid, 0.45 g, with a yield of 88%. Melting point: 272-277° C.

According to the preparation method described in this paper, the following compounds were prepared by using appropriate starting materials and intermediates and, if necessary, appropriate protective group chemistry. The structures were confirmed by MS and $^1$HNMR.

TABLE 1
| The MS and 1HNMR of the compounds | | | |
|---|---|---|---|
| Compounds | Structures | MS | $^1$HNMR |
| 1 | 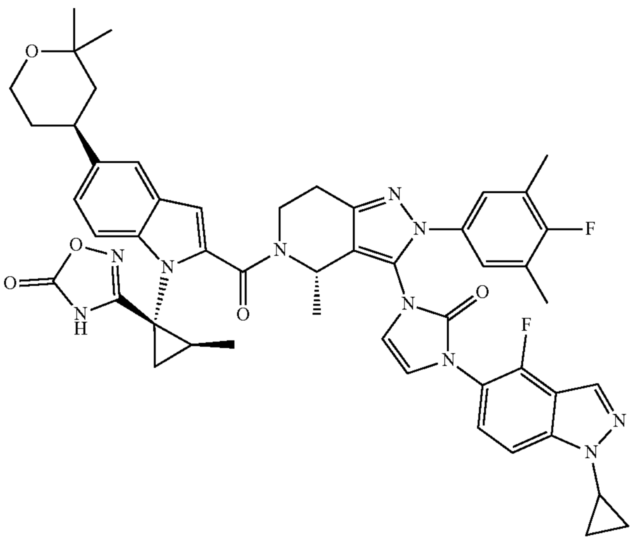 [SMILES: Cc1cc(-n2nc3c(c2-n2ccn(-c4ccc5c(cnn5C5CC5)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] | 909.39 | $^1$H NMR (500 MHZ, Chloroform-d) δ 11.15 (s, 1H), 8.37-8.29 (m, 2H), 8.21-8.14 (m, 1H), 7.89-7.82 (m, 1H), 7.62-7.56 (m, 1H), 7.51-7.41 (m, 4H), 7.25-7.20 (m, 1H), 7.11-7.04 (m, 1H), 5.24-5.14 (m, 1H), 4.57-4.49 (m, 1H), 4.14-4.05 (m, 1H), 3.86-3.61 (m, 3H), 3.08-2.90 (m, 3H), 2.49-2.32 (m, 3H), 2.26-2.23 (m, 6H), 2.08-1.91 (m, 2H), 1.86-1.69 (m, 2H), 1.61-1.57 (m, 3H), 1.39-1.31 (m, 2H), 1.29-1.22 (m, 5H), 1.19 (s, 3H), 1.01-0.98 (m, 3H). |
| 2 | 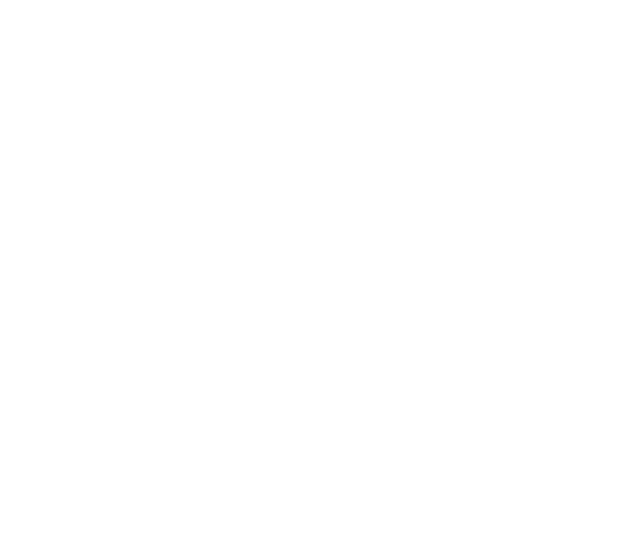 | 923.41 | $^1$H NMR (500 MHz, Chloroform-d) δ 10.92 (s, 1H), 8.38-8.28 (m, 2H), 8.18 (d, J = 6.0 Hz, 1H), 7.89-7.82 (m, 1H), 7.63-7.57 (m, 1H), 7.52-7.40 (m, 4H), 7.22 (d, J = 2.0 Hz, 1H), 7.12-7.04 (m, 1H), 5.23-5.13 (m, 1H), 4.53-4.47 (m, 1H), 4.14-4.05 (m, 1H), 3.86-3.78 (m, 1H), 3.76-3.62 (m, 2H), 3.08-2.90 (m, 3H), 2.48-2.31 (m, 3H), 2.24 (s, 6H), 2.14-1.98 (m, 7H), 1.97-1.92 (m, 1H), 1.87-1.77 (m, 3H), 1.75-1.69 (m, 1H), 1.59 (d, J = 7.8 Hz, 2H), 1.24 (s, 3H), 1.19-1.03 (s, 6H). |

TABLE 1-continued
| The MS and 1HNMR of the compounds | | | |
|---|---|---|---|
| Compounds | Structures | MS | $^1$HNMR |
| 3 | 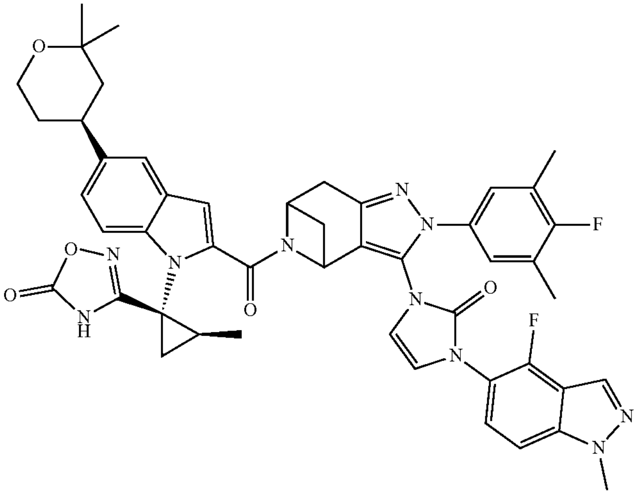 [SMILES: Cc1cc(-n2nc3c(c2-n2ccn(-c4ccc5c(cnn5C)c4F)c2=O)C2CC(C3)N2C(=O)c2cc3cc([C@H]4CCOC(C)(C)C4)ccc3n2[C@@]2(c3noc(=O)[nH]3)C[C@@H]2C)cc(C)c1F] | 881.36 | $^1$H NMR (500 MHZ, DMSO-$d_6$) δ 8.36-8.27 (m, 2H), 8.14 (d, J = 4.9 Hz, 1H), 7.83-7.75 (m, 1H), 7.67-7.63 (m, 1H), 7.54 (d, J = 8.9 Hz, 1H), 7.47-7.36 (m, 3H), 7.25 (d, J = 2.0 Hz, 1H), 7.10-7.03 (m, 1H), 5.68-5.50 (m, 1H), 4.74-4.60 (m, 1H), 3.93 (s, 3H), 3.78-3.57 (m, 2H), 3.09-2.94 (m, 3H), 2.67-2.60 (m, 1H), 2.52-2.39 (m, 3H), 2.24 (s, 6H), 2.21-2.14 (m, 1H), 2.08-2.00 (m, 1H), 1.98-1.92 (m, 1H), 1.86-1.79 (m, 1H), 1.75-1.68 (m, 1H), 1.26-1.15 (m, 6H), 0.99 (d, J = 5.9 Hz, 3H). |
| 4 | 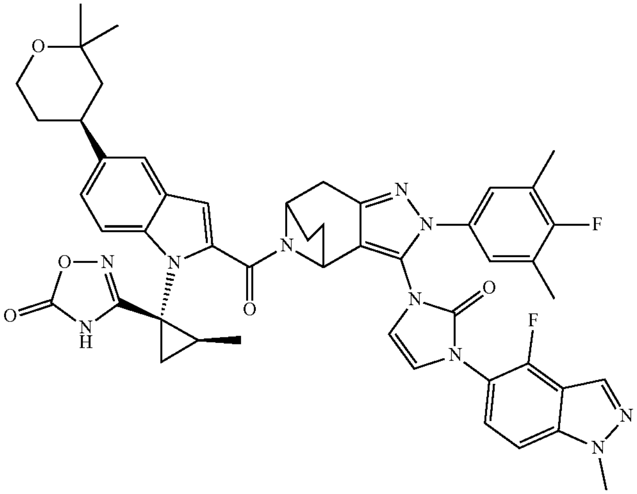 [SMILES: Cc1cc(-n2nc3c(c2-n2ccn(-c4ccc5c(cnn5C)c4F)c2=O)C2CCC(C3)N2C(=O)c2cc3cc([C@H]4CCOC(C)(C)C4)ccc3n2[C@@]2(c3noc(=O)[nH]3)C[C@@H]2C)cc(C)c1F] | 895.38 | $^1$H NMR (500 MHZ, DMSO-$d_6$) δ 10.16 (s, 1H), 8.36-8.28 (m, 2H), 8.14 (d, J = 4.9 Hz, 1H), 7.82-7.75 (m, 1H), 7.67-7.62 (m, 1H), 7.54 (d, J = 8.9 Hz, 1H), 7.46-7.37 (m, 3H), 7.25 (d, J = 2.0 Hz, 1H), 7.10-7.04 (m, 1H), 5.07-5.00 (m, 1H), 4.55-4.46 (m, 1H), 3.93 (s, 3H), 3.71-3.61 (m, 2H), 3.05-2.85 (m, 3H), 2.49-2.42 (m, 1H), 2.37-2.29 (m, 2H), 2.26-2.16 (m, 7H), 2.08-1.89 (m, 5H), 1.89-1.81 (m, 1H), 1.77-1.71 (m, 1H), 1.23 (s, 3H), 1.18 (s, 3H), 0.99 (d, J = 6.0 Hz, 3H). |

TABLE 1-continued
| The MS and 1HNMR of the compounds | | | |
|---|---|---|---|
| Compounds | Structures | MS | $^1$HNMR |
| 5 | 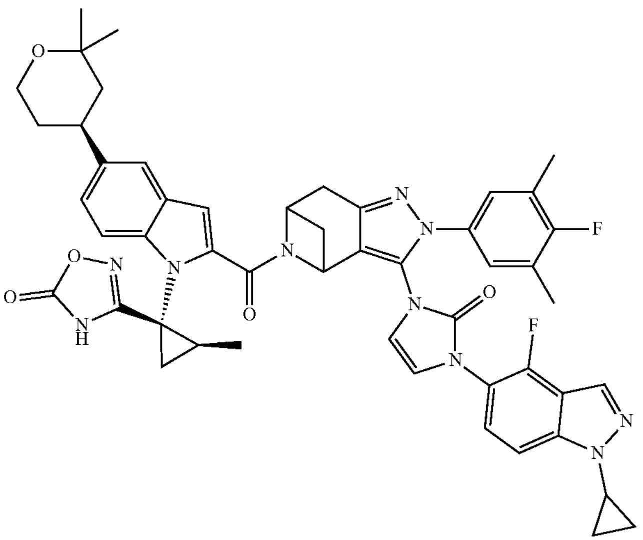 [SMILES: Cc1cc(-n2nc3c(c2-n2ccn(-c4ccc5c(cnn5C5CC5)c4F)c2=O)C2CC(C3)N2C(=O)c2cc3cc([C@H]4CCOC(C)(C)C4)ccc3n2[C@@]2(c3noc(=O)[nH]3)C[C@@H]2C)cc(C)c1F] | 907.38 | $^1$H NMR (500 MHZ, DMSO-$d_6$) δ 11.21 (s, 1H), 8.39-8.29 (m, 3H), 7.94-7.88 (m, 1H), 7.68-7.58 (m, 2H), 7.46-7.38 (m, 3H), 7.25 (d, J = 2.0 Hz, 1H), 7.09-7.05 (m, 1H), 5.63-5.57 (m, 1H), 4.70-4.63 (m, 1H), 4.56-4.50 (m, 1H), 3.74-3.59 (m, 2H), 3.10-3.03 (m, 1H), 3.02-2.94 (m, 2H), 2.67-2.60 (m, 1H), 2.49-2.39 (m, 2H), 2.36-2.30 (m, 1H), 2.27-2.17 (m, 7H), 2.08-2.01 (m, 1H), 1.97-1.92 (m, 1H), 1.86-1.78 (m, 1H), 1.75-1.68 (m, 1H), 1.39-1.29 (m, 2H), 1.29-1.20 (m, 5H), 1.18 (s, 3H), 0.99 (d, J = 6.0 Hz, 3H). |
| 6 | 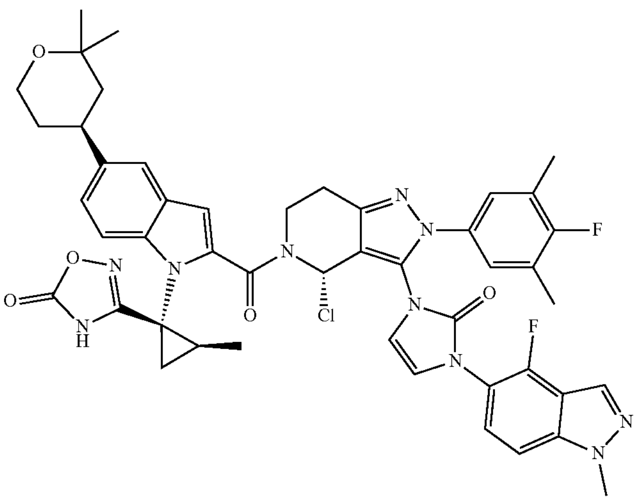 [SMILES: Cc1cc(-n2nc3c(c2-n2ccn(-c4ccc5c(cnn5C)c4F)c2=O)[C@H](Cl)N(C(=O)c2cc4cc([C@H]5CCOC(C)(C)C5)ccc4n2[C@@]2(c4noc(=O)[nH]4)C[C@@H]2C)CC3)cc(C)c1F] | 903.32 | $^1$H NMR (500 MHZ, DMSO-$d_6$) δ 11.23 (s, 1H), 8.38-8.28 (m, 2H), 8.14 (d, J = 4.9 Hz, 1H), 7.81-7.75 (m, 1H), 7.68-7.63 (m, 1H), 7.54 (d, J = 8.9 Hz, 1H), 7.46-7.37 (m, 3H), 7.21 (d, J = 2.0 Hz, 1H), 7.10-7.04 (m, 1H), 6.94 (s, 1H), 4.33-4.25 (m, 1H), 4.09-4.03 (m, 1H), 3.93 (s, 3H), 3.74-3.67 (m, 1H), 3.66-3.58 (m, 1H), 3.07-2.94 (m, 3H), 2.49-2.41 (m, 1H), 2.38-2.28 (m, 2H), 2.24 (s, 6H), 2.07-2.00 (m, 1H), 1.99-1.91 (m, 1H), 1.87-1.78 (m, 1H), 1.75-1.68 (m, 1H), 1.23 (s, 3H), 1.18 (s, 3H), 0.99 (d, J = 6.0 Hz, 3H). |

TABLE 1-continued
| The MS and 1HNMR of the compounds | | | |
|---|---|---|---|
| Compounds | Structures | MS | $^1$HNMR |
| 7 | 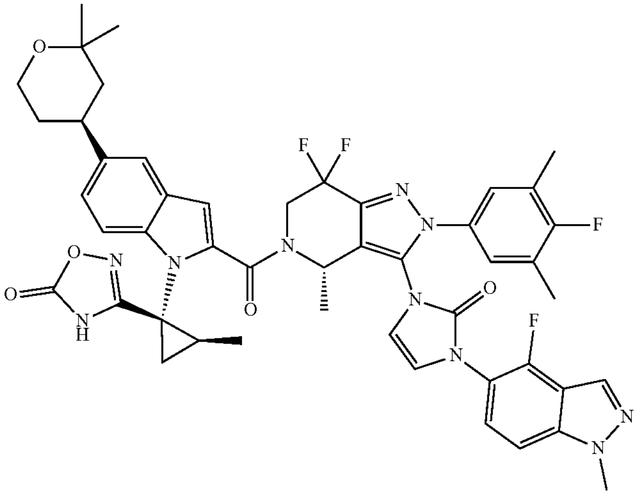 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3(F)F)cc(C)c1F] | 919.36 | $^1$H NMR (500 MHZ, DMSO-$d_6$) δ 8.39-8.28 (m, 2H), 8.14 (d, J = 4.9 Hz, 1H), 7.81-7.75 (m, 1H), 7.68-7.64 (m, 1H), 7.54 (d, J = 8.9 Hz, 1H), 7.45-7.38 (m, 3H), 7.21 (d, J = 2.0 Hz, 1H), 7.09-7.05 (m, 1H), 5.27-5.19 (m, 1H), 4.89-4.76 (m, 2H), 3.93 (s, 3H), 3.74-3.58 (m, 2H), 3.03-2.94 (m, 1H), 2.50-2.38 (m, 1H), 2.38-2.28 (m, 2H), 2.24 (s, 6H), 2.08-1.99 (m, 1H), 1.98-1.90 (m, 1H), 1.87-1.78 (m, 1H), 1.76-1.68 (m, 1H), 1.60 (d, J = 7.5 Hz, 3H), 1.25-1.15 (m, 6H), 0.99 (d, J = 6.0 Hz, 3H). |
| 8 | 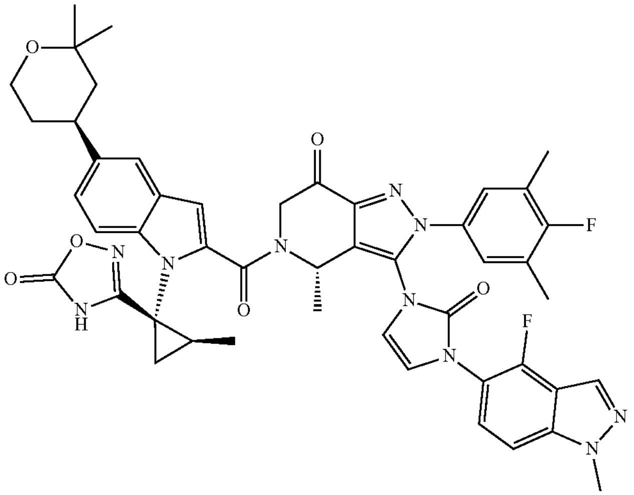 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3=O)cc(C)c1F] | 897.36 | $^1$H NMR (500 MHZ, DMSO-$d_6$) δ 11.26 (s, 1H), 8.36-8.29 (m, 2H), 8.17-8.11 (m, 1H), 7.83-7.75 (m, 1H), 7.68-7.63 (m, 1H), 7.57-7.51 (m, 1H), 7.47-7.40 (m, 3H), 7.21 (d, J = 2.0 Hz, 1H), 7.10-7.03 (m, 1H), 5.11-4.96 (m, 3H), 3.93 (s, 3H), 3.74-3.58 (m, 2H), 3.02-2.95 (m, 1H), 2.49-2.28 (m, 3H), 2.24 (s, 6H), 2.08-2.00 (m, 1H), 1.98-1.91 (m, 1H), 1.87-1.78 (m, 1H), 1.75-1.68 (m, 1H), 1.60 (d, J = 7.8 Hz, 3H), 1.27-1.15 (m, 6H), 0.99 (d, J = 6.0 Hz, 3H). |

TABLE 1-continued
| The MS and 1HNMR of the compounds | | | |
|---|---|---|---|
| Compounds | Structures | MS | $^1$HNMR |
| 9 | 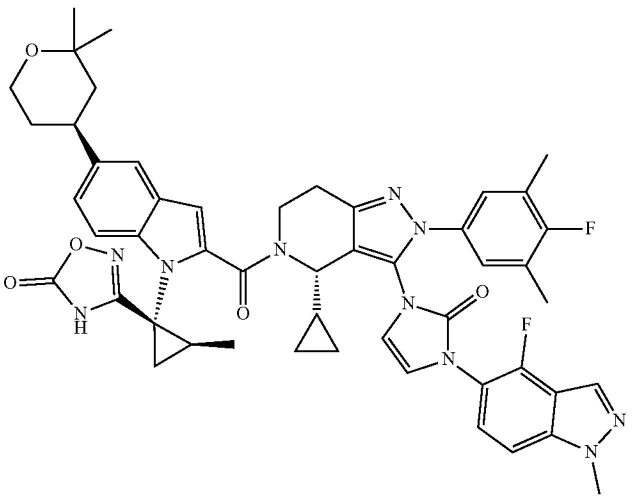 [SMILES: Cc1cc(-n2nc3c(c2-n2ccn(-c4ccc5c(cnn5C)c4F)c2=O)[C@H](C2CC2)N(C(=O)c2cc4cc([C@H]5CCOC(C)(C)C5)ccc4n2[C@@]2(c4noc(=O)[nH]4)C[C@@H]2C)CC3)cc(C)c1F] | 895.38 | $^1$H NMR (500 MHZ, DMSO-$d_6$) δ 11.19 (s, 1H), 8.36-8.29 (m, 2H), 8.14 (d, J = 4.9 Hz, 1H), 7.83-7.76 (m, 1H), 7.68-7.63 (m, 1H), 7.57-7.51 (m, 1H), 7.48-7.37 (m, 3H), 7.21 (d, J = 2.0 Hz, 1H), 7.11-7.04 (m, 1H), 4.89 (d, J = 6.7 Hz, 1H), 4.18-4.08 (m, 1H), 3.93 (s, 3H), 3.87-3.79 (m, 1H), 3.75-3.58 (m, 2H), 3.05-2.88 (m, 3H), 2.51-2.44 (m, 1H), 2.37-2.29 (m, 2H), 2.24 (s, 6H), 2.08-2.00 (m, 1H), 1.98-1.89 (m, 2H), 1.87-1.78 (m, 1H), 1.75-1.69 (m, 1H), 1.25-1.15 (m, 6H), 0.99 (d, J = 6.0 Hz, 3H), 0.68-0.57 (m, 2H), 0.49-0.39 (m, 2H). |
| 10 | 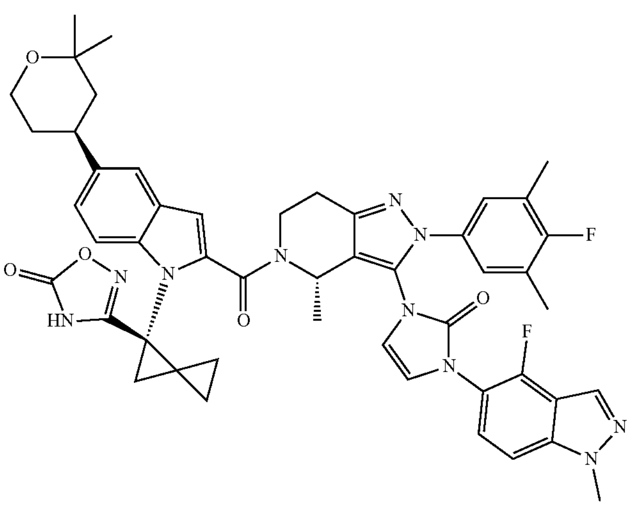 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)CC24CC4)CC3)cc(C)c1F] | 895.38 | $^1$H NMR (500 MHZ, DMSO-$d_6$) δ 10.29(s, 1H), 8.36-8.29 (m, 2H), 8.14 (d, J = 4.9 Hz, 1H), 7.81-7.76 (m, 1H), 7.67-7.64 (m, 1H), 7.54 (d, J = 8.9 Hz, 1H), 7.46-7.37 (m, 3H), 7.21 (d, J = 2.0 Hz, 1H), 7.10-7.04 (m, 1H), 5.22-5.14 (m, 1H), 4.11-4.05 (m, 1H), 3.96-3.85 (m, 4H), 3.74-3.58 (m, 2H), 3.04-2.90 (m, 3H), 2.35 (s, 2H), 2.24 (s, 6H), 2.07-1.91 (m, 2H), 1.86-1.78 (m, 1H), 1.75-1.68 (m, 1H), 1.65-1.47 (m, 7H), 1.25-1.16 (m, 6H). |

TABLE 1-continued
| The MS and 1HNMR of the compounds | | | |
|---|---|---|---|
| Compounds | Structures | MS | $^1$HNMR |
| 11 | 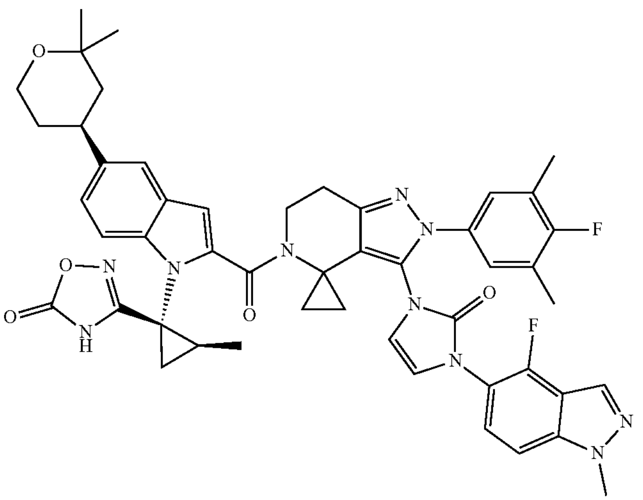 [SMILES: Cc1cc(-n2nc3c(c2-n2ccn(-c4ccc5c(cnn5C)c4F)c2=O)C2(CC2)N(C(=O)c2cc4cc([C@H]5CCOC(C)(C)C5)ccc4n2[C@@]2(c4noc(=O)[nH]4)C[C@@H]2C)CC3)cc(C)c1F] | 895.38 | $^1$H NMR (500 MHZ, DMSO-$d_6$) δ 11.21 (s, 1H), 8.34-8.23 (m, 2H), 8.14 (d, J = 4.9 Hz, 1H), 7.82-7.76 (m, 1H), 7.67-7.63 (m, 1H), 7.54 (d, J = 8.9 Hz, 1H), 7.46-7.37 (m, 3H), 7.24 (d, J = 2.0 Hz, 1H), 7.11-7.04 (m, 1H), 3.96-3.83 (m, 5H), 3.74-3.59 (m, 2H), 3.01-2.95 (m, 1H), 2.91-2.84 (m, 2H), 2.51-2.44 (m, 1H), 2.37-2.19 (m, 12H), 2.07-2.00 (m, 1H), 1.97-1.92 (m, 1H), 1.87-1.79 (m, 1H), 1.75-1.69 (m, 1H), 1.26-1.16 (m, 6H), 0.99 (d, J = 6.0 Hz, 3H). |
| 12 | 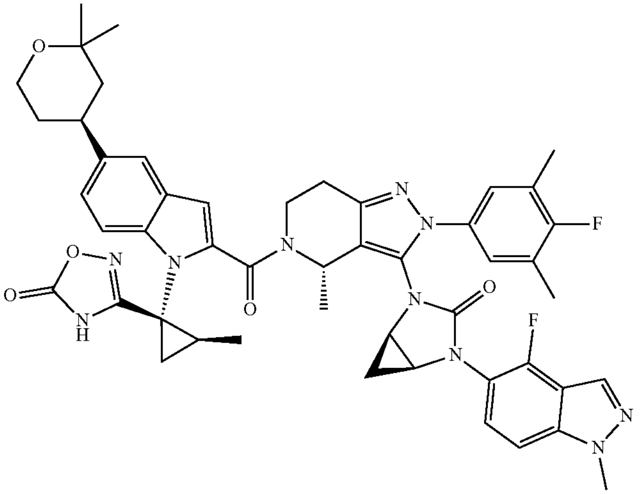 [SMILES: Cc1cc(-n2nc3c(c2N2C(=O)N(c4ccc5c(cnn5C)c4F)[C@H]4C[C@H]42)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] | 898.00 | $^1$H NMR (500 MHZ, DMSO-$d_6$) δ 8.13 (d, J = 5.2 Hz, 1H), 7.68-7.63 (m, 1H), 7.53 (d, J = 9.0 Hz, 1H), 7.51-7.41 (m, 2H), 7.37 (d, J = 4.9 Hz, 2H), 7.21 (d, J = 2.0 Hz, 1H), 7.10-7.05 (m, 1H), 5.22-5.11 (m, 1H), 4.34-4.29 (m, 2H), 4.10-4.03 (m, 1H), 3.96-3.87 (m, 4H), 3.74-3.59 (m, 2H), 3.04-2.89 (m, 3H), 2.48-2.42 (m, 1H), 2.38-2.29 (m, 2H), 2.24 (s, 6H), 2.07-1.91 (m, 3H), 1.86-1.68 (m, 3H), 1.60 (d, J = 8.0 Hz, 3H), 1.23 (s, 3H), 1.18 (s, 3H), 0.99 (d, J = 6.0 Hz, 3H). |

TABLE 1-continued
The MS and 1HNMR of the compounds
| Compounds | Structures | MS | $^1$HNMR |
|---|---|---|---|
| 13 | 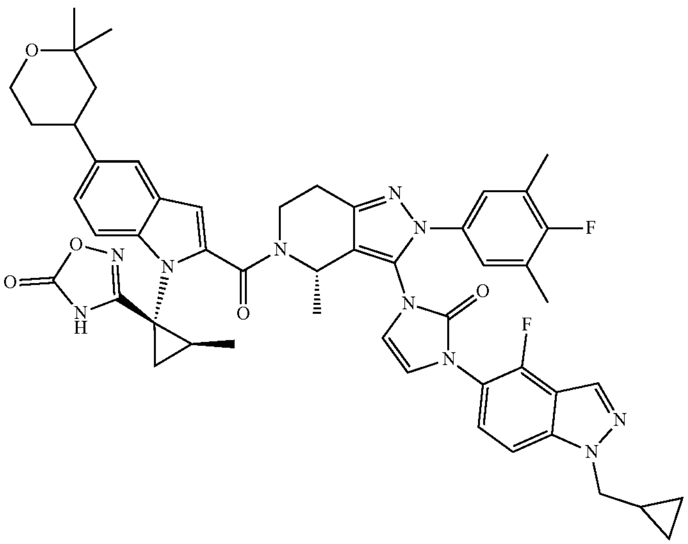 [SMILES: Cc1cc(-n2nc3c(c2-n2ccn(-c4ccc5c(cnn5CC5CC5)c4F)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 923.41 | $^1$H NMR (500 MHZ, DMSO-$d_6$) δ 11.21 (s, 1H), 8.37-8.29 (m, 2H), 8.25 (d, J = 4.9 Hz, 1H), 7.85-7.78 (m, 1H), 7.67-7.62 (m, 1H), 7.48-7.37 (m, 4H), 7.21 (d, J = 2.0 Hz, 1H), 7.09-7.04 (m, 1H), 5.22-5.13 (m, 1H), 4.13-3.84 (m, 4H), 3.73-3.59 (m, 2H), 3.03-2.89 (m, 3H), 2.49-2.20 (m, 9H), 2.08-1.91 (m, 2H), 1.87-1.68 (m, 2H), 1.63-1.45 (m, 4H), 1.23 (s, 3H), 1.18 (s, 3H), 0.99 (d, J = 6.0 Hz, 3H), 0.61-0.38 (m, 4H). |
| 14 | 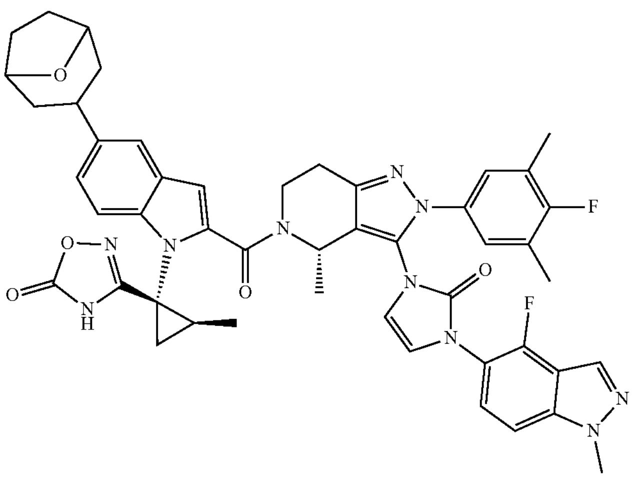 [SMILES: Cc1cc(-n2nc3c(c2-n2ccn(-c4ccc5c(cnn5C)c4F)c2=O)[C@H](C)N(C(=O)c2cc4cc(C5CC6CCC(C5)O6)ccc4n2[C@@]2(c4noc(=O)[nH]4)C[C@@H]2C)CC3)cc(C)c1F] | 881.36 | $^1$H NMR (500 MHZ, DMSO-$d_6$) δ 11.09 (S, 1H), 8.37-8.28 (m, 2H), 8.14 (d, J = 4.9 Hz, 1H), 7.82-7.75 (m, 1H), 7.66-7.61 (m, 1H), 7.54 (d, J = 8.8 Hz, 1H), 7.46-7.37 (m, 3H), 7.21 (d, J = 2.0 Hz, 1H), 7.11-7.06 (m, 1H), 5.22-5.14 (m, 1H), 4.12-4.03 (m, 3H), 3.95-3.85 (m, 4H), 3.07-2.89 (m, 3H), 2.42-2.21 (m, 9H), 1.99-1.73 (m, 8H), 1.60 (d, J = 8.0 Hz, 3H), 0.99 (d, J = 5.8 Hz, 3H). |

TABLE 1-continued
The MS and 1HNMR of the compounds
| Compounds | Structures | MS | $^1$HNMR |
|---|---|---|---|
| 15 | 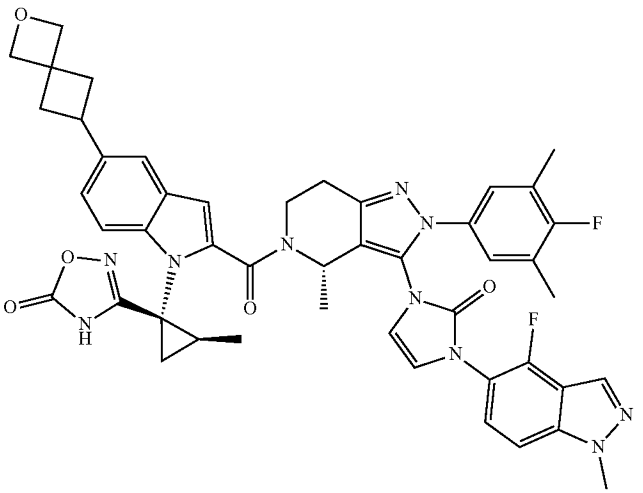 [SMILES: Cc1cc(-n2nc3c(c2-n2ccn(-c4ccc5c(cnn5C)c4F)c2=O)[C@H](C)N(C(=O)c2cc4cc(C5CC6(COC6)C5)ccc4n2[C@@]2(c4noc(=O)[nH]4)C[C@@H]2C)CC3)cc(C)c1F] | 867.35 | $^1$H NMR (500 MHZ, DMSO-$d_6$) δ 11.11(S, 1H), 8.36-8.28 (m, 2H), 8.14 (d, J = 4.9 Hz, 1H), 7.82-7.76 (m, 1H), 7.66-7.61 (m, 1H), 7.54 (d, J = 8.9 Hz, 1H), 7.46-7.38 (m, 3H), 7.21 (d, J = 2.0 Hz, 1H), 7.08-7.03 (m, 1H), 5.24-5.12 (m, 1H), 4.11-4.02 (m, 1H), 3.96-3.87 (m, 4H), 3.81 (d, J = 6.0 Hz, 2H), 3.72 (d, J = 6.2 Hz, 2H), 3.04-2.80 (m, 3H), 2.52-2.43 (m, 1H), 2.39-2.28 (m, 2H), 2.24 (s, 6H), 2.15-2.00 (m, 4H), 1.60 (d, J = 8.0 Hz, 3H), 0.99 (d, J = 6.0 Hz, 3H). |
| 16 | 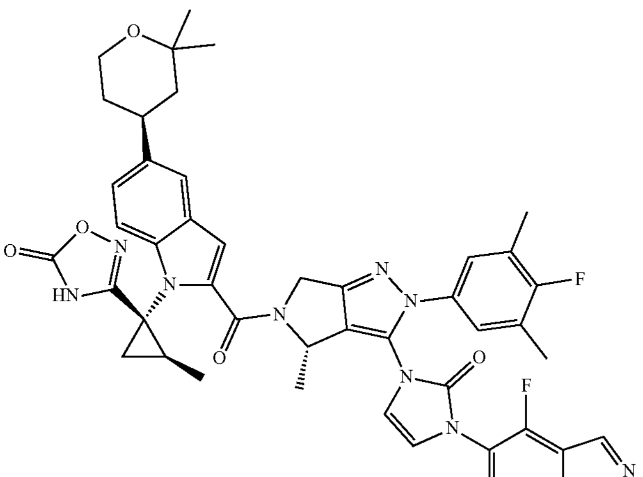 | 869.36 | $^1$H NMR (500 MHZ, DMSO-$d_6$) δ 11.16 (s, 1H), 8.37-8.28 (m, 2H), 8.14 (d, J = 4.9 Hz, 1H), 7.81-7.76 (m, 1H), 7.66-7.64 (m, 1H), 7.54 (d, J = 8.9 Hz, 1H), 7.45-7.37 (m, 3H), 7.21 (d, J = 2.0 Hz, 1H), 7.10-7.05 (m, 1H), 5.02-4.95 (m, 1H), 4.61 (d, J = 1.0 Hz, 2H), 3.93 (s, 3H), 3.71-3.62 (m, 2H), 3.03-2.94 (m, 1H), 2.49-2.40 (m, 1H), 2.38-2.21 (m, 8H), 2.06-1.81 (m, 3H), 1.77-1.70 (m, 1H), 1.57 (d, J = 7.0 Hz, 3H), 1.27-1.15 (m, 6H), 0.99 (d, J = 6.0 Hz, 3H). |

TABLE 1-continued
| The MS and 1HNMR of the compounds | | | |
|---|---|---|---|
| Compounds | Structures | MS | $^1$HNMR |
| 17 | 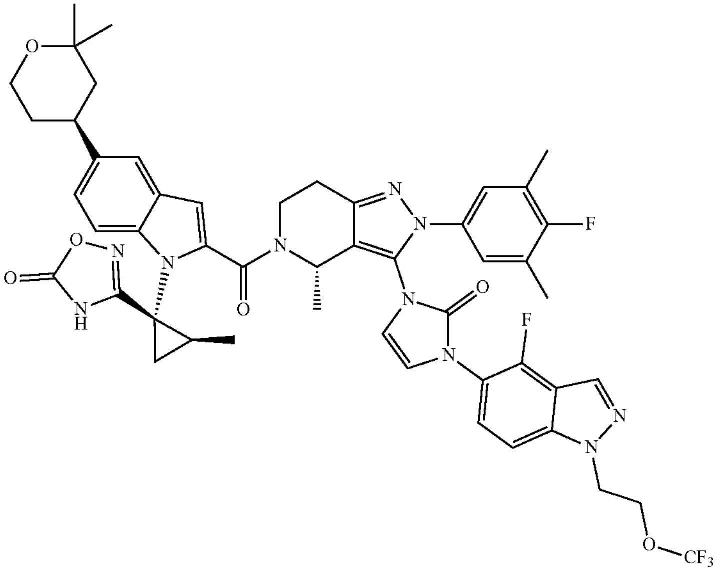 [SMILES: Cc1cc(-n2nc3c(c2-n2ccn(-c4ccc5c(cnn5CCOC(F)(F)F)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] | 981.38 | $^1$H NMR (500 MHZ, Chloroform-d) δ 10.79 (s, 1H), 8.37-8.29 (m, 2H), 8.21-8.14 (m, 1H), 7.89-7.82 (m, 1H), 7.62-7.56 (m, 1H), 7.51-7.41 (m, 4H), 7.25-7.20 (m, 1H), 7.11-7.04 (m, 1H), 5.24-5.14 (m, 1H), 4.59-4.49 (m, 3H), 4.14-4.05 (m, 1H), 3.86-3.61 (m, 5H), 3.08-2.90 (m, 3H), 2.49-2.32 (m, 3H), 2.26-2.23 (m, 6H), 2.08-1.91 (m, 2H), 1.86-1.69 (m, 2H), 1.61-1.57 (m, 3H), 1.39-1.31 (m, 2H), 1.19 (s, 3H), 1.01-0.98 (m, 3H). |

TABLE 1-continued
| The MS and 1HNMR of the compounds | | | |
|---|---|---|---|
| Compounds | Structures | MS | $^{1}$HNMR |
| 18 | 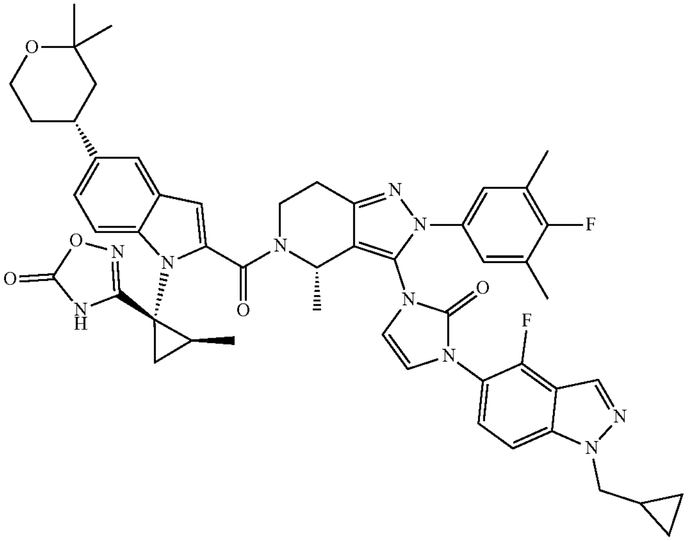 [SMILES: Cc1cc(-n2nc3c(c2-n2ccn(-c4ccc5c(cnn5CC5CC5)c4F)c2=O)[C@H](C)N(C(=O)c2cc4cc([C@@H]5CCOC(C)(C)C5)ccc4n2[C@@]2(c4noc(=O)[nH]4)C[C@@H]2C)CC3)cc(C)c1F] | 923.04 | $^{1}$H NMR (500 MHZ, DMSO-$d_6$) δ C 11.16 (s, 1H), 8.37-8.29 (m, 2H), 8.25 (d, J = 4.9 Hz, 1H), 7.85-7.78 (m, 1H), 7.67-7.62 (m, 1H), 7.48-7.37 (m, 4H), 7.21 (d, J = 2.0 Hz, 1H), 7.09-7.04 (m, 1H), 5.22-5.13 (m, 1H), 4.13-3.84 (m, 4H), 3.73-3.59 (m, 2H), 3.03-2.89 (m, 3H), 2.49-2.20 (m, 9H), 2.08-1.91 (m, 2H), 1.87-1.68 (m, 2H), 1.63-1.45 (m, 4H), 1.23 (s, 3H), 1.18 (s, 3H), 0.99 (d, J = 6.0 Hz, 3H), 0.61-0.38 (m, 4H). |

TABLE 1-continued
| The MS and 1HNMR of the compounds | | | |
|---|---|---|---|
| Compounds | Structures | MS | $^1$HNMR |
| 19 | 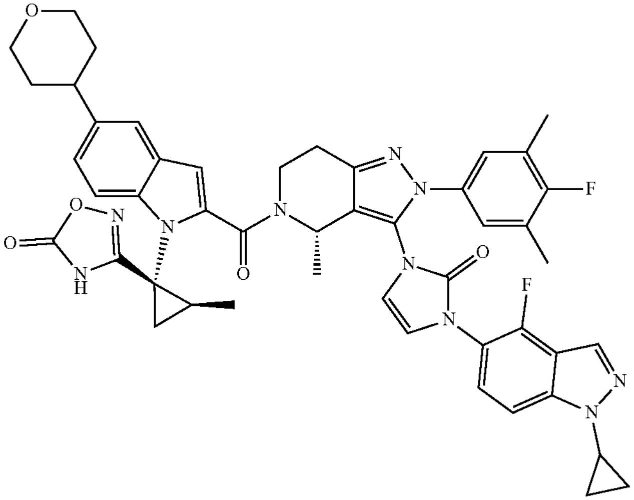 [SMILES: Cc1cc(-n2nc3c(c2-n2ccn(-c4ccc5c(cnn5C5CC5)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F] | 881.36 | $^1$H NMR (500 MHZ, DMSO-$d_6$) δ 11.76 (s, 1H), 8.28 (s, 1H), 7.69-7.63 (m, 1H), 7.56-7.50 (m, 2H), 7.42-7.40 (m, 1H), 7.28-7.26 (m, 1H), 7.19-7.18 (m, 2H), 7.09-7.08 (m, 1H), 6.96-6.93 (m, 2H), 5.59-5.58 (m, 1H), 4.41-4.36 (m, 1H), 3.97-3.96 (m, 3H), 3.85-3.83 (m, 1H), 3.63-3.62 (m, 1H), 3.46-3.44 (m, 3H), 3.19-3.17 (m, 1H), 2.87-2.85 (m, 3H), 2.26 (s, 6H), 1.79-1.75 (m, 1H), 1.70-1.63 (m, 4H), 1.44 (d, J = 12.0 Hz, 3H), 1.36-1.30 (m,2H), 1.19-1.12 (m, 7H). |
| 20 | 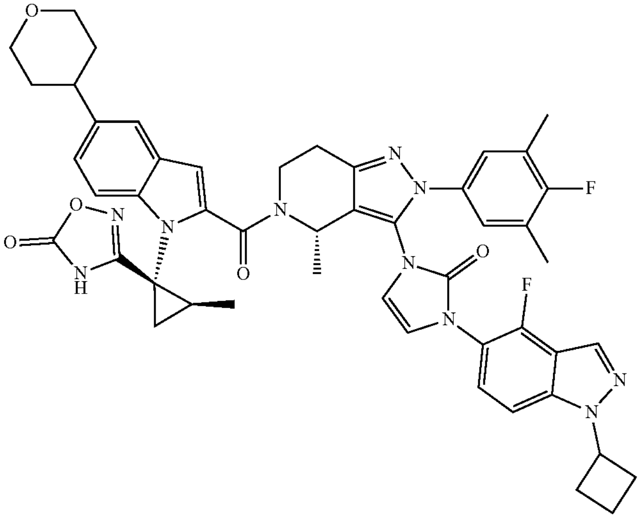 [SMILES: Cc1cc(-n2nc3c(c2-n2ccn(-c4ccc5c(cnn5C5CCC5)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F] | 895.38 | $^1$H NMR (500 MHZ, DMSO-$d_6$) δ 11.72 (s, 1H), 8.34 (s, 1H), 7.63 (d, J = 8.9 Hz, 1H), 7.55-7.29 (m, 4H), 7.28-7.00 (m, 5H), 6.90 (d, J = 16.7 Hz, 2H), 5.55 (d, J = 6.8 Hz, 1H), 5.30-5.27 (m, 1H), 4.35-4.33 (m, 1H), 3.92-3.75(m, 3H), 3.59 (t, J = 12.6 Hz, 1H), 3.43 (d, J = 13.8 Hz, 4H), 3.14 (d, J = 12.9 Hz, 1H), 2.94-2.76 (m, 3H), 2.65-2.52 (m, 3H), 2.43 (d, J = 9.6 Hz, 1H), 2.28-2.20 (m, 6H), 1.86 (dq, J = 10.5, 4.2, 3.0 Hz, 3H), 1.80-1.52 (m, 10H), 1.40 (d, J = 6.7 Hz, 3H), 1.29 (s, 2H), 1.21-1.08 (m, 3H). |

TABLE 1-continued
The MS and 1HNMR of the compounds
| Compounds | Structures | MS | $^1$HNMR |
|---|---|---|---|
| 21 | 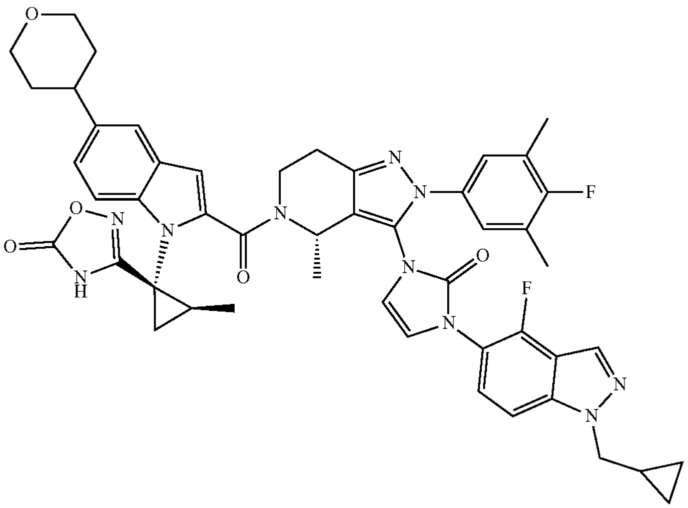 [SMILES: Cc1cc(-n2nc3c(c2-n2ccn(-c4ccc5c(cnn5CC5CC5)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F] | 895.44 | $^1$H NMR (500 MHZ, DMSO-$d_6$) δ 11.72 (s, 1H), 8.35-8.23 (m, 3H), 7.86-7.78 (m, 1H), 7.66-7.62 (m, 1H), 7.48-7.38 (m, 4H), 7.21 (d, J = 2.0 Hz, 1H), 7.09-7.03 (m, 1H), 5.21-5.13 (m, 1H), 4.10-3.87 (m, 4H), 3.60-3.46 (m, 4H), 3.02-2.88 (m, 3H), 2.53-2.28 (m, 3H), 2.24 (s, 6H), 2.17-2.07 (m, 2H), 1.89-1.79 (m, 2H), 1.60 (d, J = 8.0 Hz, 3H), 1.53-1.45 (m, 1H), 0.99 (d, J = 6.0 Hz, 3H), 0.59-0.39 (m, 4H). |
| 22 | 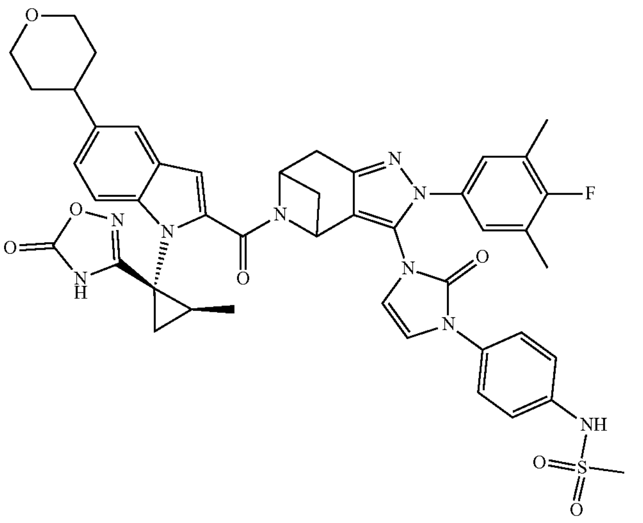 [SMILES: Cc1cc(-n2nc3c(c2-n2ccn(-c4ccc(NS(C)(=O)=O)cc4)c2=O)C2CC(C3)N2C(=O)c2cc3cc(C4CCOCC4)ccc3n2[C@@]2(c3noc(=O)[nH]3)C[C@@H]2C)cc(C)c1F] | 874.44 | $^1$H NMR (500 MHZ, DMSO-$d_6$) δ 11.68 (s, 1H), 9.16 (s, 1H), 8.36 (d, J = 6.0 Hz, 1H), 8.17 (d, J = 6.0 Hz, 1H), 7.64 (t, J = 2.0 Hz, 1H), 7.46-7.35 (m, 5H), 7.29-7.15 (m, 3H), 7.09-7.02 (m, 1H), 5.60 (t, J = 5.7 Hz, 1H), 4.70-4.62 (m, 1H), 3.58-3.47 (m, 4H), 3.09-2.96 (m, 3H), 2.95 (s, 3H), 2.67-2.61 (m, 1H), 2.45-2.26 (m, 4H), 2.24 (s, 6H), 2.17-2.06 (m, 2H), 1.89-1.76 (m, 2H), 0.99 (d, J = 5.8 Hz, 3H). |

TABLE 1-continued
| The MS and 1HNMR of the compounds | | | |
|---|---|---|---|
| Compounds | Structures | MS | $^1$HNMR |
| 23 | 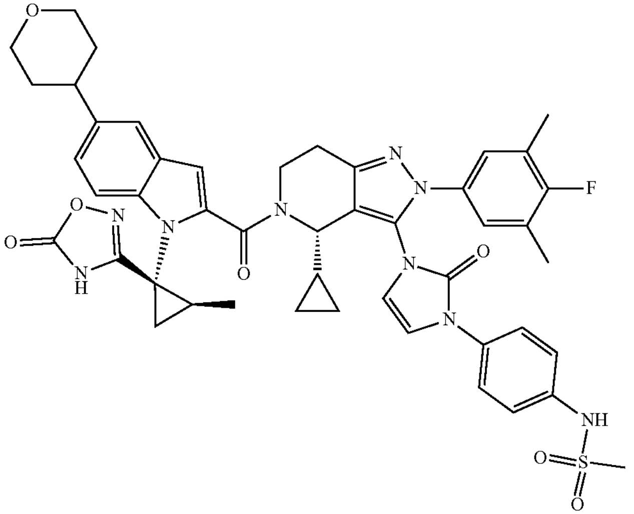 [SMILES: Cc1cc(-n2nc3c(c2-n2ccn(-c4ccc(NS(C)(=O)=O)cc4)c2=O)[C@H](C2CC2)N(C(=O)c2cc4cc(C5CCOCC5)ccc4n2[C@@]2(c4noc(=O)[nH]4)C[C@@H]2C)CC3)cc(C)c1F] | 902.33 | $^1$H NMR (500 MHZ, DMSO-$d_6$) δ 11.54 (s, 1H), 9.16 (s, 1H), 8.36 (d, J = 6.0 Hz, 1H), 8.17 (d, J = 6.0 Hz, 1H), 7.64 (t, J = 2.0 Hz, 1H), 7.47-7.36 (m, 5H), 7.25-7.15 (m, 3H), 7.09-7.03 (m, 1H), 4.89 (d, J = 6.7 Hz, 1H), 4.16-4.07 (m, 1H), 3.89-3.81 (m, 1H), 3.58-3.47 (m, 4H), 3.04-2.89 (m, 6H), 2.40-2.26 (m, 3H), 2.24 (s, 6H), 2.16-2.07 (m, 2H), 1.97-1.79 (m, 3H), 0.99 (d, J = 5.8 Hz, 3H), 0.58-0.54 (m, 4H). |
| 24 | 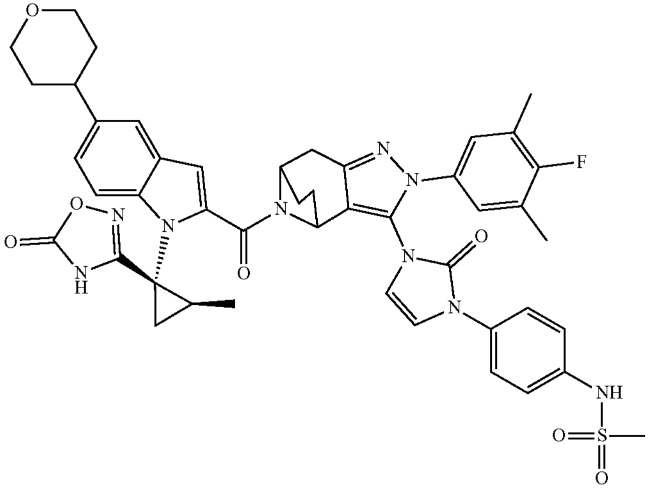 [SMILES: Cc1cc(-n2nc3c(c2-n2ccn(-c4ccc(NS(C)(=O)=O)cc4)c2=O)C2CCC(C3)N2C(=O)c2cc3cc(C4CCOCC4)ccc3n2[C@@]2(c3noc(=O)[nH]3)C[C@@H]2C)cc(C)c1F] | 888.34 | $^1$H NMR (500 MHZ, DMSO-$d_6$) δ 11.81 (s, 1H), 9.16 (s, 1H), 8.36 (d, J = 6.0 Hz, 1H), 8.17 (d, J = 6.0 Hz, 1H), 7.64 (t, J = 2.1 Hz, 1H), 7.48-7.35 (m, 5H), 7.31-7.18 (m, 3H), 7.08-7.03 (m, 1H), 5.04 (t, J = 4.8 Hz, 1H), 4.55-4.48 (m, 1H), 3.59-3.48 (m, 4H), 3.02-2.86 (m, 6H), 2.48-2.42 (m, 1H), 2.37-2.28 (m, 2H), 2.24 (s, 6H), 2.23-2.16 (m, 1H), 2.15-2.01 (m, 3H), 2.00-1.89 (m, 2H), 1.88-1.80 (m, 2H), 0.99 (d, J = 6.0 Hz, 3H). |

TABLE 1-continued
| The MS and 1HNMR of the compounds | | | |
|---|---|---|---|
| Compounds | Structures | MS | $^1$HNMR |
| 25 | 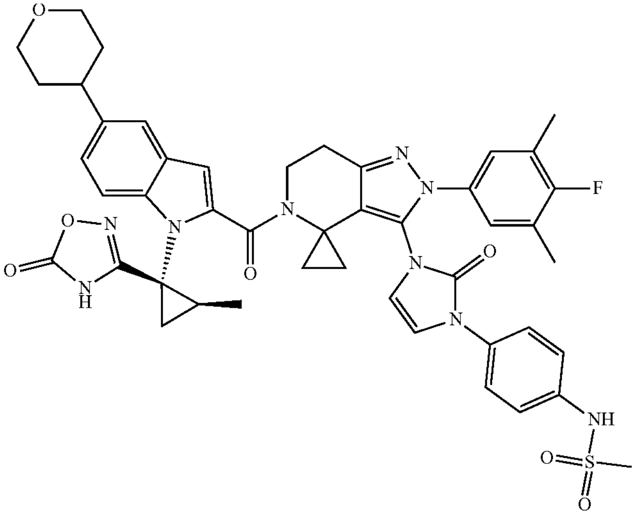 [SMILES: Cc1cc(-n2nc3c(c2-n2ccn(-c4ccc(NS(C)(=O)=O)cc4)c2=O)C2(CC2)N(C(=O)c2cc4cc(C5CCOCC5)ccc4n2[C@@]2(c4noc(=O)[nH]4)C[C@@H]2C)CC3)cc(C)c1F] | 888.32 | $^1$H NMR (500 MHZ, DMSO-$d_6$) δ 11.76 (s, 1H), 9.16 (s, 1H), 8.34 (d, J = 6.0 Hz, 1H), 8.17 (d, J = 6.0 Hz, 1H), 7.64 (t, J = 2.1 Hz, 1H), 7.47-7.36 (m, 5H), 7.27-7.16 (m, 3H), 7.10-7.02 (m, 1H), 3.92-3.83 (m, 2H), 3.57-3.48 (m, 4H), 3.01-2.96 (m, 1H), 2.95 (s, 3H), 2.91-2.85 (m, 2H), 2.40-2.18 (m, 13H), 2.15-2.07 (m, 2H), 1.88-1.80 (m, 2H), 0.99 (d, J = 5.8 Hz, 3H). |

TABLE 1-continued
| The MS and 1HNMR of the compounds | | | |
|---|---|---|---|
| Compounds | Structures | MS | $^1$HNMR |
| 26 | 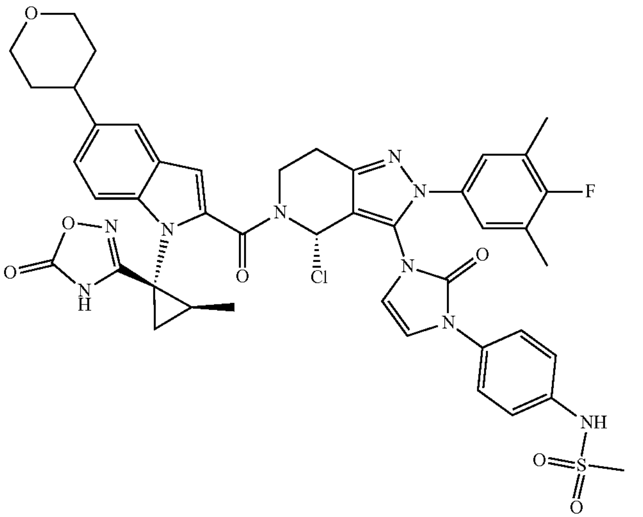 [SMILES: Cc1cc(-n2nc3c(c2-n2ccn(-c4ccc(NS(C)(=O)=O)cc4)c2=O)[C@H](Cl)N(C(=O)c2cc4cc(C5CCOCC5)ccc4n2[C@@]2(c4noc(=O)[nH]4)C[C@@H]2C)CC3)cc(C)c1F] | 895.32 | $^1$H NMR (500 MHZ, DMSO-$d_6$) δ 11.29 (s, 1H), 9.16 (s, 1H), 8.37 (d, J = 6.0 Hz, 1H), 8.18 (d, J = 6.0 Hz, 1H), 7.64 (s, 1H), 7.64 (d, J = 4.1 Hz, OH), 7.43 (d, J = 7.5 Hz, 1H), 7.42-7.37 (m, 4H), 7.23-7.17 (m, 3H), 7.08-7.03 (m, 1H), 6.94 (s, 1H), 4.31-4.23 (m, 1H), 4.11-4.03 (m, 1H), 3.59-3.47 (m, 4H), 3.06-2.96 (m, 3H), 2.95 (s, 3H), 2.40-2.33 (m, 1H), 2.36-2.26 (m, 2H), 2.24 (s, 6H), 2.16-2.07 (m, 2H), 1.88-1.79 (m, 2H), 0.99 (d, J = 5.8 Hz, 3H). |
| 27 | 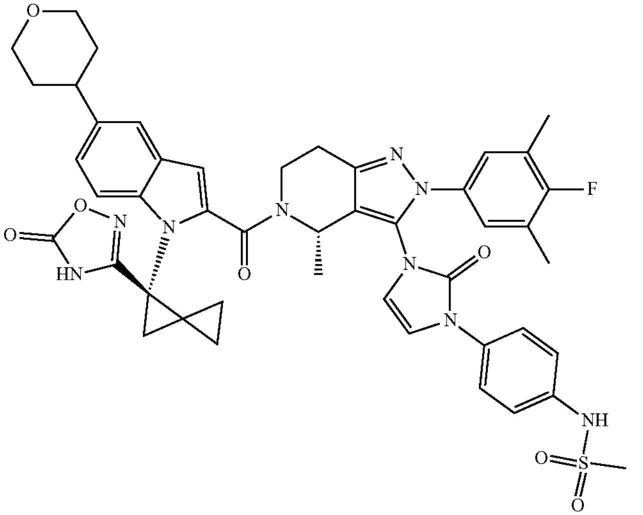 [SMILES: Cc1cc(-n2nc3c(c2-n2ccn(-c4ccc(NS(C)(=O)=O)cc4)c2=O)[C@H](C)N(C(=O)c2cc4cc(C5CCOCC5)ccc4n2[C@@]2(c4noc(=O)[nH]4)CC24CC4)CC3)cc(C)c1F] | 888.32 | $^1$H NMR (500 MHZ, DMSO-$d_6$) δ 11.28 (s, 1H), 8.76 (s, 1H), 8.36 (d, J = 6.0 Hz, 1H), 8.17 (d, J = 6.0 Hz, 1H), 7.64 (s, 1H), 7.46-7.37 (m, 5H), 7.23-7.17 (m, 3H), 7.08-7.03 (m, 1H), 5.22-5.14 (m, 1H), 4.10-4.02 (m, 1H), 3.95-3.87 (m, 1H), 3.59-3.47 (m, 4H), 3.03-2.89 (m, 6H), 2.43-2.37 (m, 1H), 2.30-2.25 (m, 1H), 2.24 (s, 6H), 2.16-2.07 (m, 2H), 1.88-1.79 (m, 2H), 1.66-1.56 (m, 5H), 1.56-1.50 (m, 1H), 1.53-1.46 (m, 1H). |

TABLE 1-continued
The MS and 1HNMR of the compounds
| Compounds | Structures | MS | $^1$HNMR |
| --- | --- | --- | --- |
| 28 | 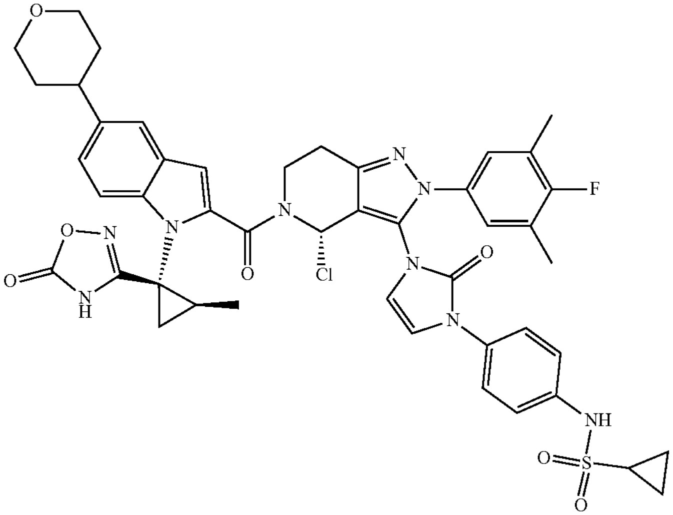 [SMILES: Cc1cc(-n2nc3c(c2-n2ccn(-c4ccc(NS(=O)(=O)C5CC5)cc4)c2=O)[C@H](Cl)N(C(=O)c2cc4cc(C5CCOCC5)ccc4n2[C@@]2(c4noc(=O)[nH]4)C[C@@H]2C)CC3)cc(C)c1F] | 922.28 | $^1$H NMR (500 MHZ, DMSO-$d_6$) δ 11.31 (s, 1H), 9.16 (s, 1H), 8.37 (d, J = 6.0 Hz, 1H), 8.18 (d, J = 6.0 Hz, 1H), 7.64 (s, 1H), 7.64 (d, J = 4.1 Hz, OH), 7.43 (d, J = 7.5 Hz, 1H), 7.42-7.37 (m, 4H), 7.23-7.17 (m, 3H), 7.08-7.03 (m, 1H), 6.94 (s, 1H), 4.31-4.23 (m, 1H), 4.11-4.03 (m, 1H), 3.59-3.47 (m, 4H), 3.47-3.40 (m, 1H), 3.06-2.99 (m, 1H), 3.03-2.94 (m, 2H), 2.40-2.33 (m, 1H), 2.36-2.26 (m, 2H), 2.24 (s, 6H), 2.16-2.07 (m, 2H), 1.88-1.79 (m, 2H), 1.79-1.58 (m, 4H), 0.99 (d, J = 5.8 Hz, 3H). |
| 29 | 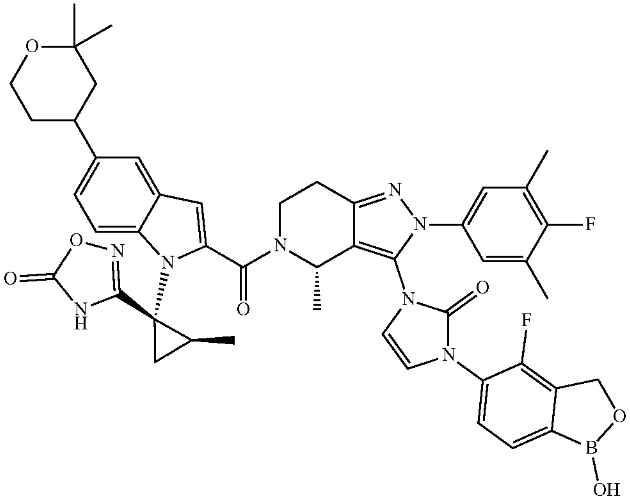 [SMILES: Cc1cc(-n2nc3c(c2-n2ccn(-c4ccc5c(c4F)COB5O)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 885.34 | $^1$H NMR (500 MHZ, DMSO-$d_6$) δ 11.29 (s, 1H), 8.36-8.29 (m, 2H), 7.65 (d, J = 3.8 Hz, 2H), 7.56-7.49 (m, 1H), 7.47-7.33 (m, 4H), 7.21 (d, J = 2.0 Hz, 1H), 7.11-7.04 (m, 1H), 5.23-5.11 (m, 3H), 4.11-4.02 (m, 1H), 3.96-3.87 (m, 1H), 3.74-3.62 (m, 2H), 3.13-2.89 (m, 3H), 2.51-2.43 (m, 1H), 2.38-2.29 (m, 2H), 2.24 (s, 6H), 2.17-2.09 (m, 1H), 2.00-1.87 (m, 2H), 1.78-1.71 (m, 1H), 1.60 (d, J = 8.0 Hz, 3H), 1.20 (d, J = 25.2 Hz, 6H), 0.99 (d, J = 6.0 Hz, 3H). |

TABLE 1-continued
| The MS and 1HNMR of the compounds | | | |
| --- | --- | --- | --- |
| Compounds | Structures | MS | $^1$HNMR |
| 30 | 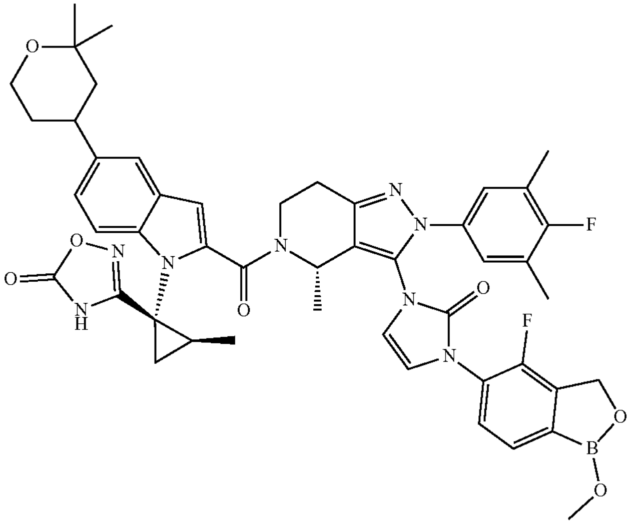 [SMILES: COB1OCc2c1ccc(-n1ccn(-c3c4c(nn3-c3cc(C)c(F)c(C)c3)CCN(C(=O)c3cc5cc(C6CCOC(C)(C)C6)ccc5n3[C@@]3(c5noc(=O)[nH]5)C[C@@H]3C)[C@H]4C)c1=O)c2F] | 899.38 | $^1$H NMR (500 MHZ, DMSO-$d_6$) δ 11.51 (s, 1H), 8.36-8.29 (m, 2H), 7.67-7.63 (m, 1H), 7.57-7.51 (m, 1H), 7.43 (d, J = 7.5 Hz, 1H), 7.41-7.36 (m, 3H), 7.21 (d, J = 2.0 Hz, 1H), 7.10-7.04 (m, 1H), 5.22-5.15 (m, 1H), 5.14 (s, 1H), 5.12 (s, 1H), 4.10-4.02 (m, 1H), 3.95-3.87 (m, 1H), 3.74-3.61 (m, 2H), 3.65 (s, 3H), 3.13-3.04 (m, 1H), 3.03-2.89 (m, 2H), 2.52-2.43 (m, 1H), 2.38-2.28 (m, 2H), 2.24 (s, 6H), 2.18-2.09 (m, 1H), 1.99-1.86 (m, 2H), 1.79-1.71 (m, 1H), 1.60 (d, J = 8.0 Hz, 3H), 1.23 (s, 3H), 1.18 (s, 3H), 0.99 (d, J = 6.0 Hz, 3H). |
| 31 | 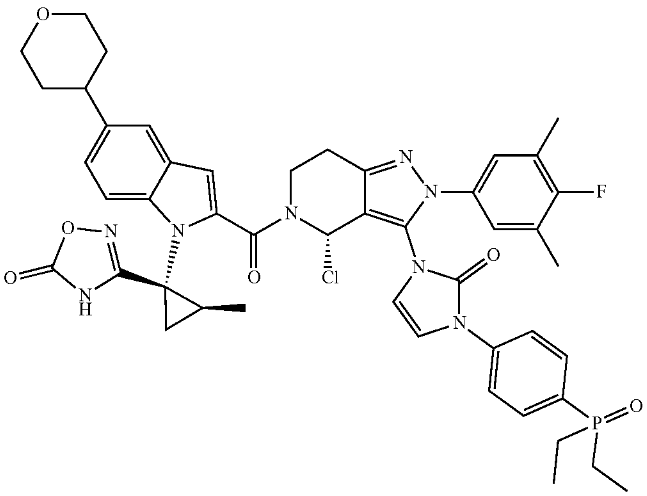 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4Cl)c2=O)cc1] | 907.34 | $^1$H NMR (500 MHZ, DMSO-$d_6$) δ 11.73 (s, 1H), 8.37 (d, J = 6.0 Hz, 1H), 8.18 (d, J = 6.0 Hz, 1H), 7.81-7.75 (m, 2H), 7.75-7.69 (m, 2H), 7.66-7.62 (m, 1H), 7.43 (d, J = 7.5 Hz, 1H), 7.40 (d, J = 5.1 Hz, 2H), 7.21 (d, J = 2.0 Hz, 1H), 7.08-7.03 (m, 1H), 6.94 (s, 1H), 4.31-4.23 (m, 1H), 4.11-4.03 (m, 1H), 3.59-3.47 (m, 4H), 3.06-2.99 (m, 1H), 3.03-2.94 (m, 2H), 2.72-2.63 (m, 4H), 2.41-2.26 (m, 3H), 2.24 (s, 6H), 2.16-2.07 (m, 2H), 1.88-1.79 (m, 2H), 1.51-1.47 (m, 6H), 0.99 (d, J = 5.8 Hz, 3H). |

TABLE 1-continued
| The MS and 1HNMR of the compounds | | | |
|---|---|---|---|
| Compounds | Structures | MS | $^1$HNMR |
| 32 | 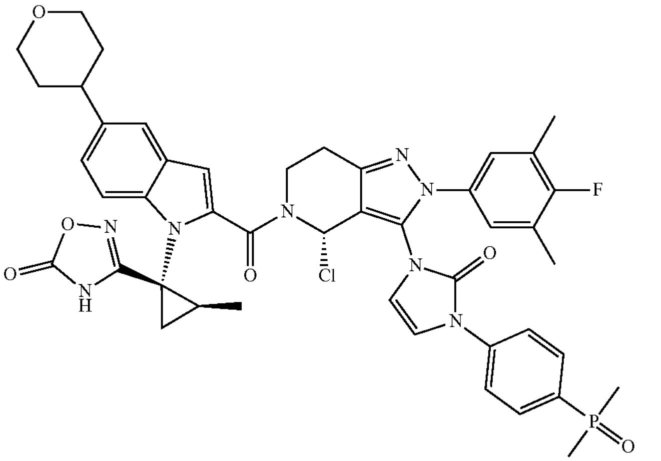 [SMILES: Cc1cc(-n2nc3c(c2-n2ccn(-c4ccc(P(C)(C)=O)cc4)c2=O)[C@H](Cl)N(C(=O)c2cc4cc(C5CCOCC5)ccc4n2[C@@]2(c4noc(=O)[nH]4)C[C@@H]2C)CC3)cc(C)c1F] | 879.29 | $^1$H NMR (500 MHZ, DMSO-$d_6$) δ 11.76 (s, 1H), 8.37 (d, J = 6.0 Hz, 1H), 8.18 (d, J = 6.0 Hz, 1H), 7.81-7.75 (m, 2H), 7.75-7.69 (m, 2H), 7.66-7.62 (m, 1H), 7.43 (d, J = 7.5 Hz, 1H), 7.40 (d, J = 5.1 Hz, 2H), 7.21 (d, J = 2.0 Hz, 1H), 7.08-7.03 (m, 1H), 6.94 (s, 1H), 4.31-4.23 (m, 1H), 4.11-4.03 (m, 1H), 3.59-3.47 (m, 4H), 3.06-2.99 (m, 1H), 3.03-2.94 (m, 2H), 2.41-2.26 (m, 3H), 2.24 (s, 6H), 2.16-2.07 (m, 2H), 1.88-1.79 (m, 2H), 1.51-1.47 (m, 6H), 0.99 (d, J = 5.8 Hz, 3H). |
| 34 | 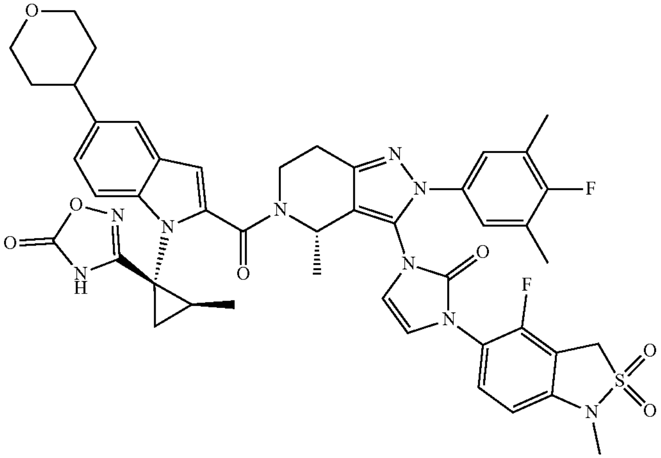 [SMILES: Cc1cc(-n2nc3c(c2-n2ccn(-c4ccc5c(c4F)CS(=O)(=O)N5C)c2=O)[C@H](C)N(C(=O)c2cc4cc(C5CCOCC5)ccc4n2[C@@]2(c4noc(=O)[nH]4)C[C@@H]2C)CC3)cc(C)c1F] | 906.32 | $^1$H NMR (500 MHZ, DMSO-$d_6$) δ 11.31 (s, 1H), 8.41-8.29 (m, 2H), 7.99-7.89 (m, 1H), 7.64-7.54 (m, 2H), 7.46-7.36 (m, 3H), 7.21 (d, J = 2.0 Hz, 1H), 7.11-7.08 (m, 1H), 5.26-5.16 (m, 1H), 4.57-4.52 (m, 3H), 4.11-3.81 (m, 2H), 3.55-3.49 (m, 4H), 3.13-2.85 (m, 6H), 2.42-2.33 (m, 3H), 2.30 (s, 6H), 2.15-2.11 (m, 2H), 1.88-1.79 (m, 2H), 1.61 (d, J = 8.0 Hz, 3H), 1.01-0.95 (m, 3H). |

TABLE 1-continued
| The MS and 1HNMR of the compounds | | | |
|---|---|---|---|
| Compounds | Structures | MS | $^1$HNMR |
| 35 | 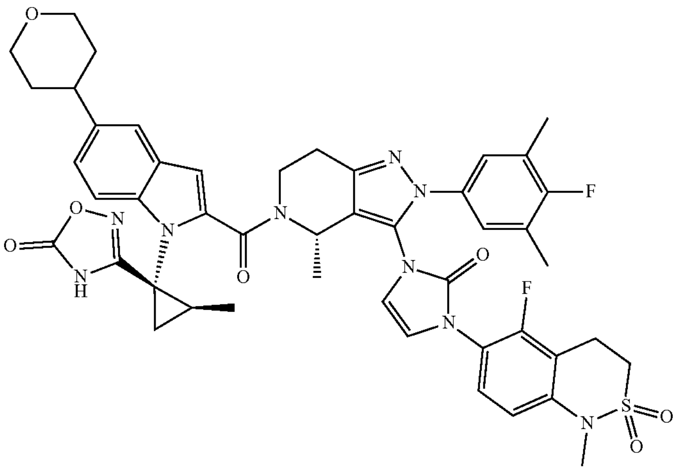 [SMILES: Cc1cc(-n2nc3c(c2-n2ccn(-c4ccc5c(c4F)CCS(=O)(=O)N5C)c2=O)[C@H](C)N(C(=O)c2cc4cc(C5CCOCC5)ccc4n2[C@@]2(c4noc(=O)[nH]4)C[C@@H]2C)CC3)cc(C)c1F] | 920.34 | $^1$H NMR (500 MHZ, DMSO-$d_6$) δ 11.27 (s, 1H), 8.40-8.29 (m, 2H), 7.97-7.87 (m, 1H), 7.65-7.55 (m, 2H), 7.48-7.39 (m, 3H), 7.22 (d, J = 2.0 Hz, 1H), 7.13-7.09 (m, 1H), 5.29-5.19 (m, 1H), 4.55-4.52 (m, 1H), 4.13-3.80 (m, 2H), 3.79-3.61 (m, 2H), 3.58-3.49 (m, 4H), 3.16-2.89 (m, 8H), 2.43-2.35 (m, 3H), 2.28 (s, 6H), 2.16-2.13 (m, 2H), 1.85-1.79 (m, 2H), 1.63 (d, J = 8.0 Hz, 3H), 1.01-0.95 (m, 3H). |
| 36 | 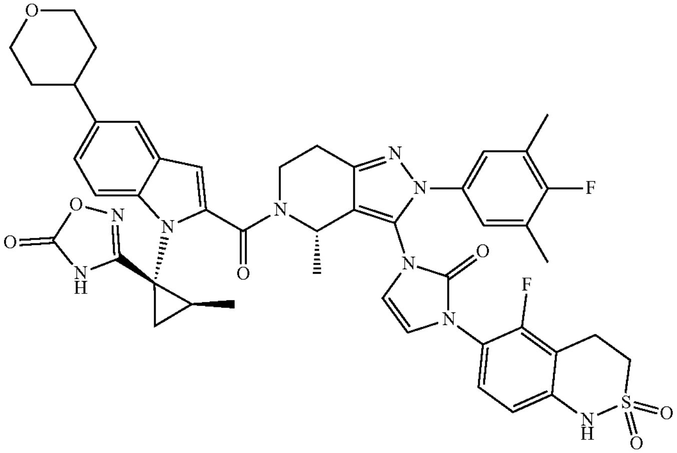 [SMILES: Cc1cc(-n2nc3c(c2-n2ccn(-c4ccc5c(c4F)CCS(=O)(=O)N5)c2=O)[C@H](C)N(C(=O)c2cc4cc(C5CCOCC5)ccc4n2[C@@]2(c4noc(=O)[nH]4)C[C@@H]2C)CC3)cc(C)c1F] | 906.32 | $^1$H NMR (500 MHZ, DMSO-$d_6$) δ 11.17 (s, 1H), 8.40-8.29 (m, 2H), 7.97-7.87 (m, 1H), 7.65-7.55 (m, 2H), 7.48-7.39 (m, 3H), 7.22 (d, J = 2.0 Hz, 1H), 7.13-7.09 (m, 1H), 5.29-5.19 (m, 1H), 4.55-4.52 (m, 1H), 4.13-3.80 (m, 2H), 3.79-3.61 (m, 2H), 3.58-3.49 (m, 4H), 3.16-2.89 (m, 5H), 2.43-2.35 (m, 3H), 2.28 (s, 6H), 2.16-2.13 (m, 2H), 1.85-1.79 (m, 2H), 1.63 (d, J = 8.0 Hz, 3H), 1.01-0.95 (m, 3H). |

TABLE 1-continued
| The MS and 1HNMR of the compounds | | | |
|---|---|---|---|
| Compounds | Structures | MS | $^1$HNMR |
| 37 | 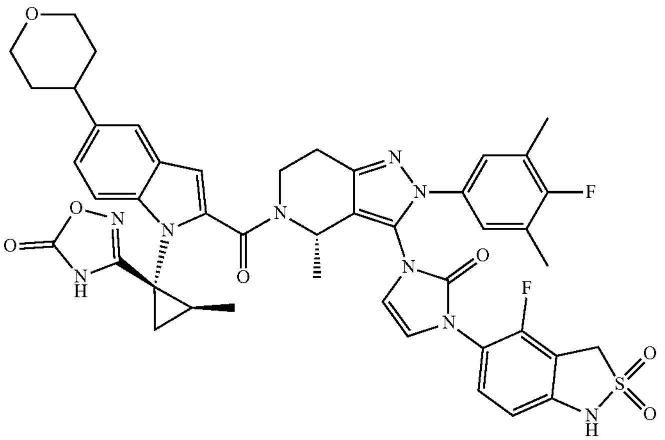 [SMILES: Cc1cc(-n2nc3c(c2-n2ccn(-c4ccc5c(c4F)CS(=O)(=O)N5)c2=O)[C@H](C)N(C(=O)c2cc4cc(C5CCOCC5)ccc4n2[C@@]2(c4noc(=O)[nH]4)C[C@@H]2C)CC3)cc(C)c1F] | 892.30 | $^1$H NMR (500 MHZ, DMSO-$d_6$) δ 11.18 (s, 1H), 8.41-8.29 (m, 2H), 7.99-7.89 (m, 1H), 7.64-7.54 (m, 2H), 7.46-7.36 (m, 3H), 7.21 (d, J = 2.0 Hz, 1H), 7.11-7.08 (m, 1H), 5.26-5.16 (m, 1H), 4.57-4.52 (m, 3H), 4.11-3.81 (m, 2H), 3.55-3.49 (m, 4H), 3.13-2.85 (m, 3H), 2.42-2.33 (m, 3H), 2.30 (s, 6H), 2.15-2.11 (m, 2H), 1.88-1.79 (m, 2H), 1.61 (d, J = 8.0 Hz, 3H), 1.01-0.95 (m, 3H). |
| 38 | 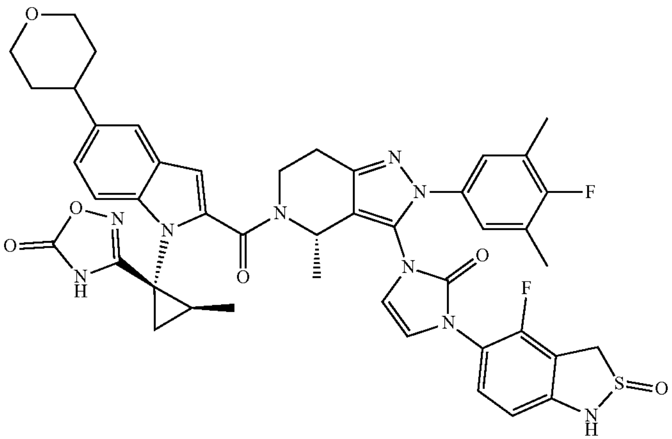 [SMILES: Cc1cc(-n2nc3c(c2-n2ccn(-c4ccc5c(c4F)CS(=O)N5)c2=O)[C@H](C)N(C(=O)c2cc4cc(C5CCOCC5)ccc4n2[C@@]2(c4noc(=O)[nH]4)C[C@@H]2C)CC3)cc(C)c1F] | 876.31 | $^1$H NMR (500 MHZ, DMSO-$d_6$) δ 11.18 (s, 1H), 8.41-8.29 (m, 2H), 7.99-7.89 (m, 1H), 7.64-7.54 (m, 2H), 7.46-7.36 (m, 3H), 7.21 (d, J = 2.0 Hz, 1H), 7.11-7.08 (m, 1H), 5.26-5.16 (m, 1H), 4.57-4.52 (m, 1H), 4.11-3.81 (m, 4H), 3.55-3.49 (m, 4H), 3.13-2.85 (m, 3H), 2.42-2.33 (m, 3H), 2.30 (s, 6H), 2.15-2.11 (m, 2H), 1.88-1.79 (m, 2H), 1.61 (d, J = 8.0 Hz, 3H), 1.01-0.95 (m, 3H). |

TABLE 1-continued
| The MS and 1HNMR of the compounds | | | |
|---|---|---|---|
| Compounds | Structures | MS | $^1$HNMR |
| 39 | 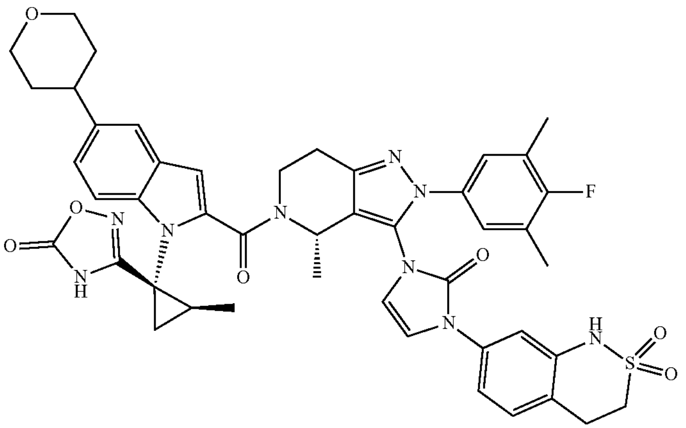 | 888.33 | $^1$H NMR (500 MHZ, DMSO-$d_6$) δ 11.20 (s, 1H), 8.43-8.33 (m, 2H), 7.95-7.87 (m, 1H), 7.69-7.59 (m, 2H), 7.48-7.39 (m, 3H), 7.22 (d, J = 2.0 Hz, 1H), 7.13-7.09 (m, 1H), 6.43-6.40 (m, 1H), 5.29-5.19 (m, 1H), 4.55-4.52 (m, 1H), 4.13-3.80 (m, 2H), 3.79-3.61 (m, 2H), 3.58-3.49 (m, 4H), 3.16-2.89 (m, 5H), 2.43-2.35 (m, 3H), 2.28 (s, 6H), 2.16-2.13 (m, 2H), 1.85-1.79 (m, 2H), 1.63 (d, J = 8.0 Hz, 3H), 1.01-0.95 (m, 3H). |
| 42 | 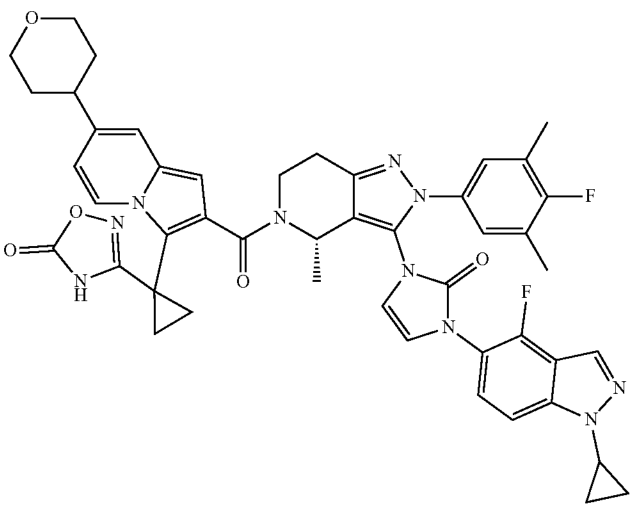 [SMILES: Cc1cc(-n2nc3c(c2-n2ccn(-c4ccc5c(cnn5C5CC5)c4F)c2=O)[C@H](C)N(C(=O)c2cc4cc(C5CCOCC5)ccn4c2C2(c4noc(=O)[nH]4)CC2)CC3)cc(C)c1F] | 867.35 | $^1$H NMR (500 MHZ, DMSO-$d_6$) δ 11.15 (s, 1H), 8.41-8.36 (m, 3H), 7.90-7.80 (m, 1H), 7.67-7.55 (m, 2H), 7.46-7.37 (m, 2H), 7.11-7.07 (m, 1H), 6.52-6.43 (m, 2H), 5.34-5.25 (m, 1H), 4.63-4.51 (m, 1H), 4.17-3.87 (m, 2H), 3.69-3.49 (m, 4H), 3.12-2.96 (m, 3H), 2.44-2.33 (m, 9H), 2.22-2.13 (m, 2H), 1.91-1.83 (m, 2H), 1.45-1.25 (m, 9H), 1.14-1.08 (m, 5H). |

TABLE 1-continued
| The MS and 1HNMR of the compounds | | | |
|---|---|---|---|
| Compounds | Structures | MS | $^1$HNMR |
| 43 | 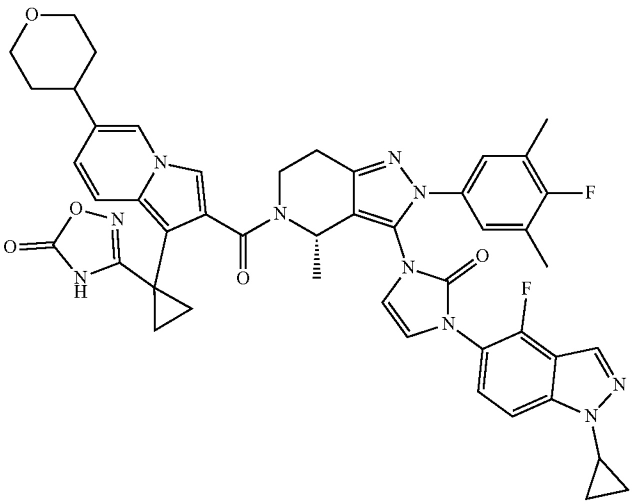 [SMILES: Cc1cc(-n2nc3c(c2-n2ccn(-c4ccc5c(cnn5C5CC5)c4F)c2=O)[C@H](C)N(C(=O)c2cn4cc(C5CCOCC5)ccc4c2C2(c4noc(=O)[nH]4)CC2)CC3)cc(C)c1F] | 867.35 | $^1$H NMR (500 MHZ, DMSO-$d_6$) δ 11.14 (s, 1H), 8.42-8.38 (m, 3H), 7.88-7.77 (m, 2H), 7.69-7.59 (m, 2H), 7.49-7.39 (m, 2H), 6.73-6.54 (m, 1H), 6.44-6.35 (m, 1H), 5.33-5.24 (m, 1H), 4.65-4.53 (m, 1H), 4.19-3.88 (m, 2H), 3.71-3.59 (m, 4H), 3.16-2.99 (m, 3H), 2.48-2.38 (m, 9H), 2.26-2.16 (m, 2H), 1.97-1.87 (m, 2H), 1.43-1.23 (m, 9H), 1.12-1.08 (m, 5H). |
| 48 | 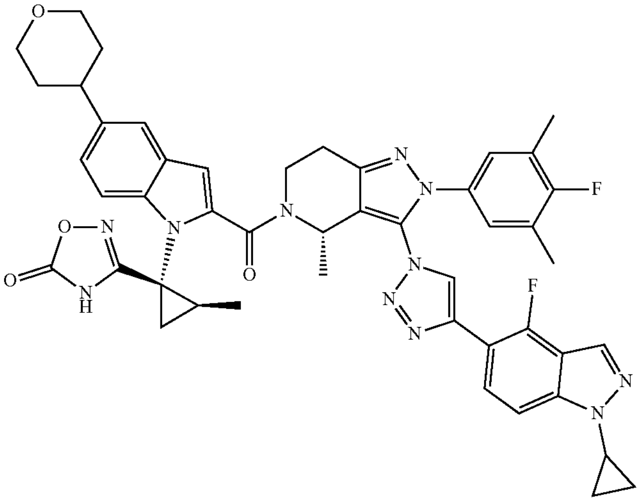 [SMILES: Cc1cc(-n2nc3c(c2-n2cc(-c4ccc5c(cnn5C5CC5)c4F)nn2)[C@H](C)N(C(=O)c2cc4cc(C5CCOCC5)ccc4n2[C@@]2(c4noc(=O)[nH]4)C[C@@H]2C)CC3)cc(C)c1F] | 866.37 | $^1$H NMR (500 MHZ, DMSO-$d_6$) δ 11.60 (s, 1H), 8.48-8.38 (m, 2H), 7.98-7.88 (m, 1H), 7.68-7.58 (m, 2H), 7.47-7.37 (m, 3H), 7.20 (d, J = 2.0 Hz, 1H), 7.16-7.12 (m, 1H), 6.47-6.44 (m, 1H), 5.36-5.26 (m, 1H), 4.72-4.62 (m, 1H), 4.37-3.95 (m, 2H), 3.77-3.68 (m, 4H), 3.13-2.95 (m, 3H), 2.47-2.38 (m, 9H), 2.27-2.17 (m, 5H), 1.94-1.87 (m, 2H), 1.44-1.24 (m, 5H), 1.12-1.08 (m, 6H). |

TABLE 1-continued
| The MS and 1HNMR of the compounds | | | |
|---|---|---|---|
| Compounds | Structures | MS | $^1$HNMR |
| 49 | 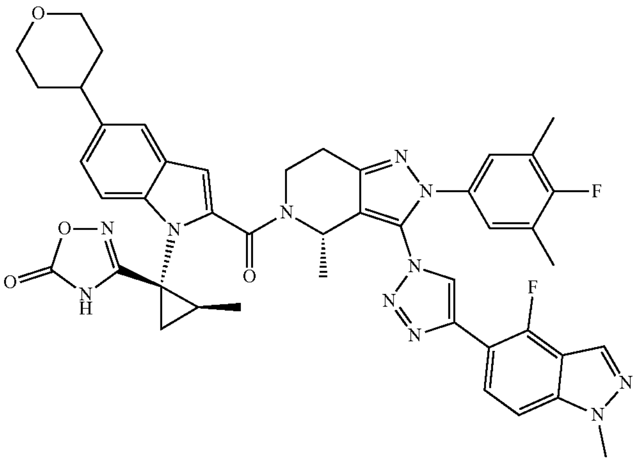 [SMILES: Cc1cc(-n2nc3c(c2-n2cc(-c4ccc5c(cnn5C)c4F)nn2)[C@H](C)N(C(=O)c2cc4cc(C5CCOCC5)ccc4n2[C@@]2(c4noc(=O)[nH]4)C[C@@H]2C)CC3)cc(C)c1F] | 840.35 | $^1$H NMR (500 MHz, DMSO-$d_6$) δ 11.51 (s, 1H), 8.47-8.37 (m, 2H), 7.97-7.87 (m, 1H), 7.69-7.59 (m, 2H), 7.49-7.39 (m, 3H), 7.21 (d, J = 2.0 Hz, 1H), 7.14-7.12 (m, 1H), 6.48-6.44 (m, 1H), 5.36-5.26 (m, 1H), 4.71-4.62 (m, 1H), 4.36-3.95 (m, 2H), 3.79-3.68 (m, 4H), 3.12-2.96 (m, 5H), 2.45-2.38 (m, 9H), 2.25-2.16 (m, 5H), 1.95-1.87 (m, 2H), 1.45-1.24 (m, 3H), 1.11-1.08 (m, 4H). |
| 50 | 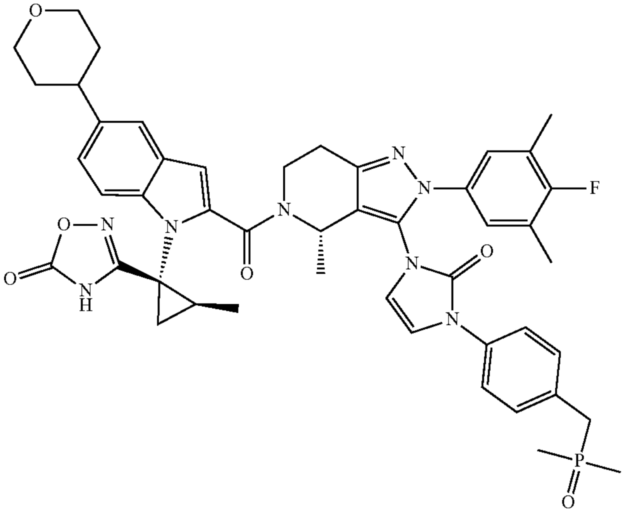 [SMILES: Cc1cc(-n2nc3c(c2-n2ccn(-c4ccc(CP(C)(C)=O)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 873.36 | $^1$H NMR (500 MHZ, DMSO-$d_6$) δ 11.50 (s, 1H), 8.48-8.38 (m, 2H), 7.98-7.88 (m, 1H), 7.68-7.58 (m, 2H), 7.47-7.37 (m, 3H), 7.20 (d, J = 2.0 Hz, 1H), 7.16-7.12 (m, 1H), 5.36-5.26 (m, 1H), 4.73-4.62 (m, 1H), 4.36-3.95 (m, 2H), 3.79-3.68 (m, 6H), 3.12-2.96 (m, 2H), 2.45-2.38 (m, 9H), 2.25-2.16 (m, 5H), 1.95-1.87 (m, 2H), 1.45-1.24 (m, 3H), 1.11-1.08 (m, 4H). |

TABLE 1-continued
| The MS and 1HNMR of the compounds | | | |
|---|---|---|---|
| Compounds | Structures | MS | $^1$HNMR |
| 53 | 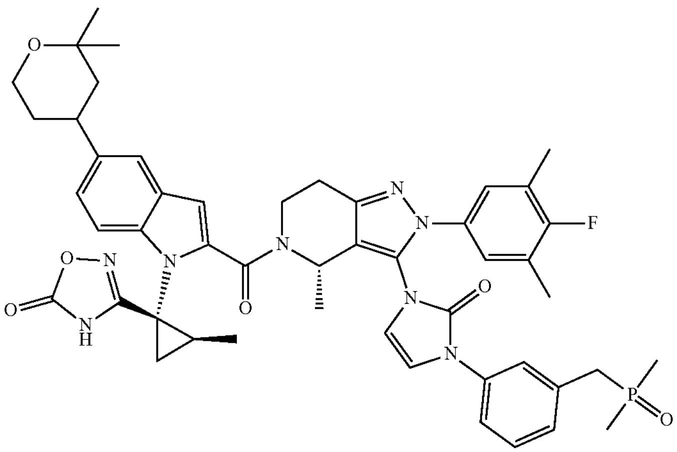 [SMILES: Cc1cc(-n2nc3c(c2-n2ccn(-c4cccc(CP(C)(C)=O)c4)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 901.39 | $^1$H NMR (500 MHz, Chloroform-d) δ 10.94 (s, 1H), 8.36-8.29 (m, 2H), 8.21-8.14 (m, 1H), 7.89-7.82 (m, 1H), 7.62-7.56 (m, 2H), 7.51-7.41 (m, 4H), 7.25-7.20 (m, 1H), 7.11-7.04 (m, 1H), 5.24-5.14 (m, 1H), 4.57-4.49 (m, 1H), 4.14-4.05 (m, 1H), 3.35(s, 2H), 3.86-3.61 (m, 3H), 3.08-2.90 (m, 3H), 2.49-2.32 (m, 3H), 2.26-2.23 (m, 6H), 2.08-1.91 (m, 2H), 1.86-1.69 (m, 2H), 1.61-1.57 (m, 7H), 1.39-1.31 (m, 5H), 1.19 (s, 6H), 1.01-0.98 (m, 3H). |
| 55 | 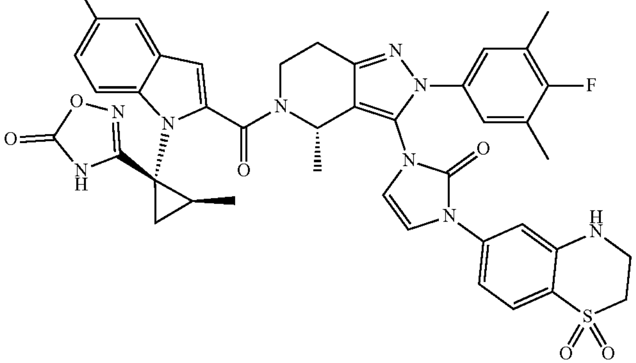 | 888.32 | $^1$H NMR (500 MHZ, DMSO-$d_6$) δ 11.15 (s, 1H), 8.42-8.38 (m, 3H), 7.90-7.82 (m, 1H), 7.65-7.56 (m, 1H), 7.44-7.41 (m, 2H), 7.13-7.09 (m, 1H), 6.54-6.53(m, 1H), 6.51-6.46 (m, 2H), 5.33-5.23 (m, 1H), 4.61-4.49 (m, 1H), 4.15-3.85 (m, 2H), 3.67-3.47 (m, 8H), 3.09-2.91 (m, 3H), 2.42-2.29 (m, 4H), 2.24-2.11 (m, 8H), 1.92-1.82 (m, 2H), 1.42-1.25 (m, 4H), 1.11-1.07 (m, 3H). |

TABLE 1-continued
| The MS and 1HNMR of the compounds | | | |
|---|---|---|---|
| Compounds | Structures | MS | $^1$HNMR |
| 58 | 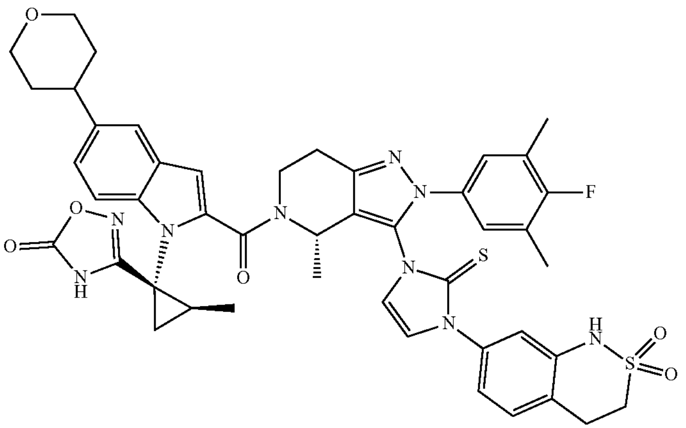 [SMILES: Cc1cc(-n2nc3c(c2-n2ccn(-c4ccc5c(c4)NS(=O)(=O)CC5)c2=S)[C@H](C)N(C(=O)c2cc4cc(C5CCOCC5)ccc4n2[C@@]2(c4noc(=O)[nH]4)C[C@@H]2C)CC3)cc(C)c1F] | 904.30 | $^1$H NMR (500 MHZ, DMSO-$d_6$) δ 11.77 (s, 1H), 8.40-8.29 (m, 2H), 7.97-7.87 (m, 1H), 7.65-7.55 (m, 2H), 7.48-7.39 (m, 3H), 7.22 (d, J = 2.0 Hz, 1H), 7.13-7.09 (m, 1H), 6.43-6.40 (m, 1H), 5.29-5.19 (m, 1H), 4.55-4.52 (m, 1H), 4.13-3.80 (m, 2H), 3.79-3.61 (m, 2H), 3.58-3.49 (m, 4H), 3.16-2.89 (m, 5H), 2.43-2.35 (m, 3H), 2.28 (s, 6H), 2.16-2.13 (m, 2H), 1.85-1.79 (m, 2H), 1.63 (d, J = 8.0 Hz, 3H), 1.02-0.96 (m, 3H). |
| 65 | 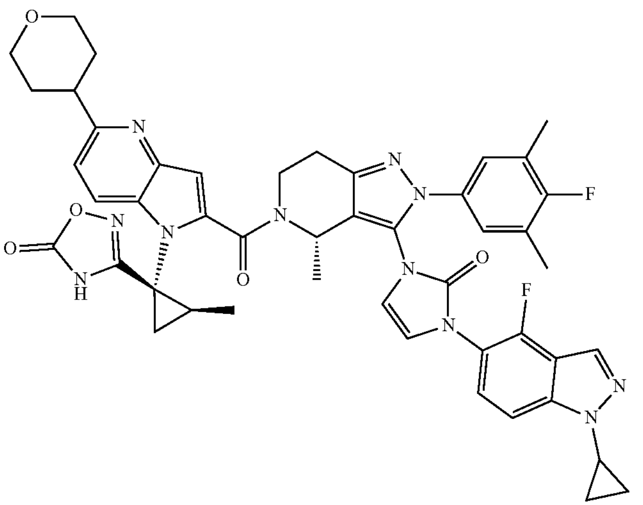 | 882.36 | $^1$H NMR (500 MHZ, DMSO-$d_6$) δ 11.62 (s, 1H), 8.40-8.28 (m, 3H), 7.96-7.86 (m, 1H), 7.60-7.58 (m, 1H), 7.47-7.36 (m, 3H), 7.21 (d, J = 2.0 Hz, 1H), 7.09-7.03 (m, 1H), 5.23-5.13 (m, 1H), 4.56-4.49 (m, 1H), 4.12-3.85 (m, 2H), 3.59-3.47 (m, 4H), 3.04-2.88 (m, 3H), 2.39-2.27 (m, 3H), 2.24 (s, 6H), 2.14-2.08 (m, 2H), 1.88-1.79 (m, 2H), 1.60 (d, J = 8.0 Hz, 3H), 1.39-1.20 (m, 4H), 1.01-0.95 (m, 3H). |

TABLE 1-continued
| The MS and 1HNMR of the compounds | | | |
|---|---|---|---|
| Compounds | Structures | MS | $^1$HNMR |
| 66 | 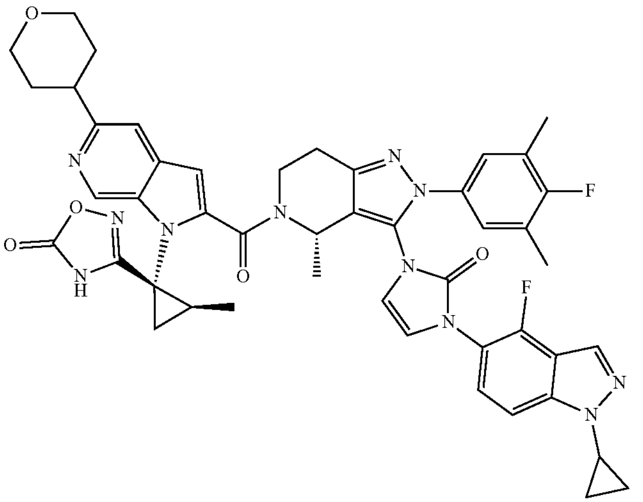 | 882.36 | $^1$H NMR (500 MHZ, DMSO-$d_6$) δ 11.52 (s, 1H), 8.40-8.28 (m, 3H), 7.96-7.86 (m, 1H), 7.62-7.58 (m, 2H), 7.47-7.33 (m, 2H), 7.21 (d, J = 2.0 Hz, 1H), 7.09-7.03 (m, 1H), 5.23-5.13 (m, 1H), 4.56-4.49 (m, 1H), 4.12-3.85 (m, 2H), 3.59-3.47 (m, 4H), 3.04-2.88 (m, 3H), 2.39-2.27 (m, 3H), 2.24 (s, 6H), 2.14-2.08 (m, 2H), 1.88-1.79 (m, 2H), 1.60 (d, J = 8.0 Hz, 3H), 1.39-1.20 (m, 4H), 1.01-0.95 (m, 3H). |
| 67 | 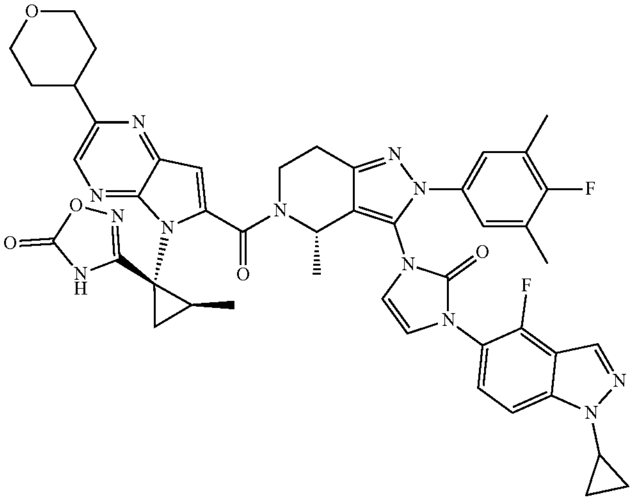 [SMILES: Cc1cc(-n2nc3c(c2-n2ccn(-c4ccc5c(cnn5C5CC5)c4F)c2=O)[C@H](C)N(C(=O)c2cc4nc(C5CCOCC5)ccc4n2[C@@]2(c4noc(=O)[nH]4)C[C@@H]2C)CC3)cc(C)c1F] | 883.35 | $^1$H NMR (500 MHZ, DMSO-$d_6$) δ 11.70 (s, 1H), 8.40-8.28 (m, 3H), 7.96-7.86 (m, 1H), 7.60-7.58 (m, 1H), 7.47-7.34 (m, 2H), 7.21 (d, J = 2.0 Hz, 1H), 7.09-7.03 (m, 1H), 5.23-5.13 (m, 1H), 4.56-4.49 (m, 1H), 4.12-3.85 (m, 2H), 3.59-3.47 (m, 4H), 3.04-2.88 (m, 3H), 2.39-2.27 (m, 3H), 2.24 (s, 6H), 2.14-2.08 (m, 2H), 1.88 1.79 (m, 2H), 1.60 (d, J = 8.0 Hz, 3H), 1.39-1.20 (m, 4H), 1.01-0.95 (m, 3H). |

TABLE 1-continued
The MS and 1HNMR of the compounds
| Compounds | Structures | MS | $^1$HNMR |
|---|---|---|---|
| 68 | 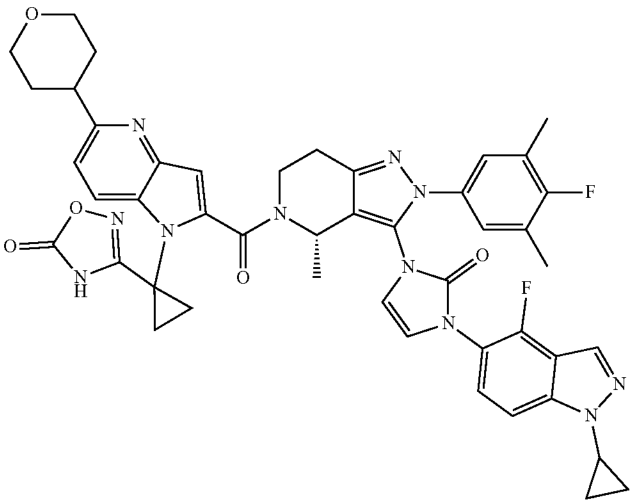 [SMILES: Cc1cc(-n2nc3c(c2-n2ccn(-c4ccc5c(cnn5C5CC5)c4F)c2=O)[C@H](C)N(C(=O)c2cc4nc(C5CCOCC5)ccc4n2C2(c4noc(=O)[nH]4)CC2)CC3)cc(C)c1F] | 868.34 | $^1$H NMR (500 MHZ, DMSO-$d_6$) δ 11.64 (s, 1H), 8.40-8.28 (m, 3H), 7.96-7.86 (m, 1H), 7.60-7.58 (m, 1H), 7.47-7.36 (m, 3H), 7.21 (d, J = 2.0 Hz, 1H), 7.09-7.03 (m, 1H), 5.23-5.13 (m, 1H), 4.56-4.49 (m, 1H), 4.12-3.85 (m, 2H), 3.59-3.47 (m, 4H), 3.04-2.88 (m, 3H), 2.39-2.27 (m, 3H), 2.24 (s, 6H), 2.14-2.08 (m, 2H), 1.88-1.79 (m, 2H), 1.39-1.20 (m, 4H), 1.01-0.95 (m, 4H). |
| 69 | 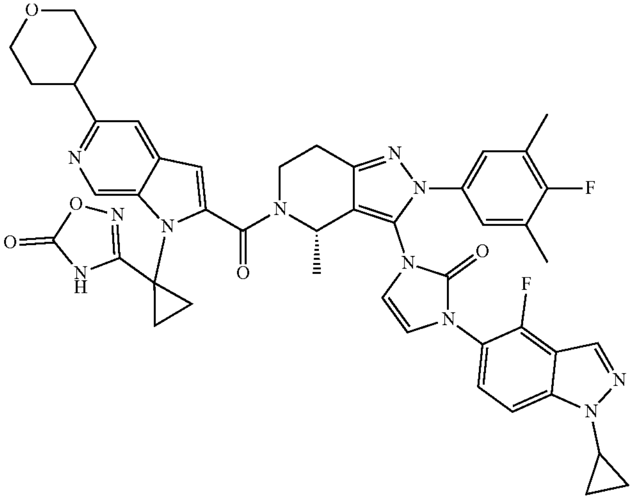 [SMILES: Cc1cc(-n2nc3c(c2-n2ccn(-c4ccc5c(cnn5C5CC5)c4F)c2=O)[C@H](C)N(C(=O)c2cc4cc(C5CCOCC5)ncc4n2C2(c4noc(=O)[nH]4)CC2)CC3)cc(C)c1F] | 868.34 | $^1$H NMR (500 MHZ, DMSO-$d_6$) δ 11.74 (s, 1H), 8.40-8.28 (m, 3H), 7.96-7.86 (m, 1H), 7.63-7.58 (m, 2H), 7.47-7.33 (m, 2H), 7.21 (d, J = 2.0 Hz, 1H), 7.09-7.03 (m, 1H), 5.23-5.13 (m, 1H), 4.56-4.49 (m, 1H), 4.12-3.85 (m, 2H), 3.59-3.47 (m, 4H), 3.04-2.88 (m, 3H), 2.39-2.27 (m, 3H), 2.24 (s, 6H), 2.14-2.08 (m, 2H), 1.88-1.79 (m, 2H), 1.39-1.20 (m, 4H), 1.01-0.95 (m, 4H). |

TABLE 1-continued
The MS and 1HNMR of the compounds
| Compounds | Structures | MS | $^1$HNMR |
|---|---|---|---|
| 70 | 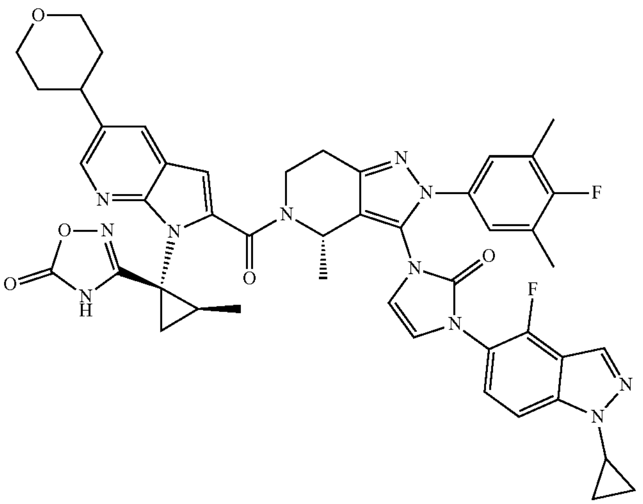 [SMILES: Cc1cc(-n2nc3c(c2-n2ccn(-c4ccc5c(cnn5C5CC5)c4F)c2=O)[C@H](C)N(C(=O)c2cc4cc(C5CCOCC5)cnc4n2[C@@]2(c4noc(=O)[nH]4)C[C@@H]2C)CC3)cc(C)c1F] | 882.36 | $^1$H NMR (500 MHZ, DMSO-$d_6$) δ 11.76 (s, 1H), 8.40-8.28 (m, 3H), 7.96-7.86 (m, 1H), 7.67-7.58 (m, 2H), 7.47-7.36 (m, 2H), 7.21 (d, J = 2.0 Hz, 1H), 7.09-7.03 (m, 1H), 5.23-5.13 (m, 1H), 4.56-4.49 (m, 1H), 4.12-3.85 (m, 2H), 3.59-3.47 (m, 4H), 3.04-2.88 (m, 3H), 2.39-2.27 (m, 3H), 2.24 (s, 6H), 2.14-2.08 (m, 2H), 1.88-1.79 (m, 2H), 1.60 (d, J = 8.0 Hz, 3H), 1.39-1.20 (m, 4H), 1.01-0.95 (m, 3H). |
| 74 | 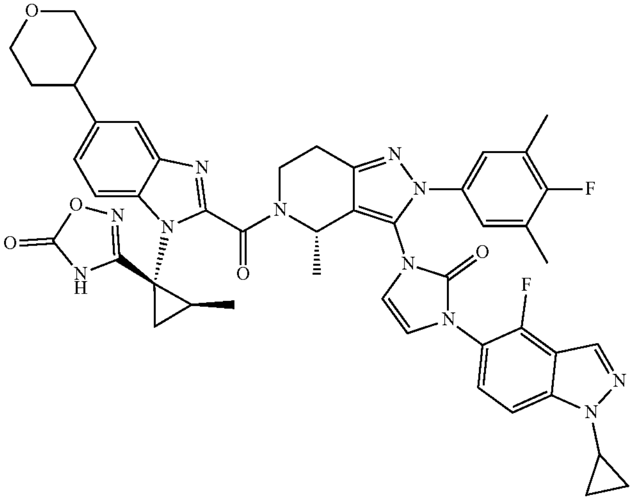 [SMILES: Cc1cc(-n2nc3c(c2-n2ccn(-c4ccc5c(cnn5C5CC5)c4F)c2=O)[C@H](C)N(C(=O)c2nc4cc(C5CCOCC5)ccc4n2[C@@]2(c4noc(=O)[nH]4)C[C@@H]2C)CC3)cc(C)c1F] | 882.36 | $^1$H NMR (500 MHZ, DMSO-$d_6$) δ 11.61 (s, 1H), 8.40-8.29 (m, 3H), 7.96-7.86 (m, 1H), 7.67-7.58 (m, 3H), 7.47-7.36 (m, 3H), 7.21 (d, J = 2.0 Hz, 1H), 5.23-5.13 (m, 1H), 4.56-4.49 (m, 1H), 4.12-3.85 (m, 2H), 3.59-3.47 (m, 4H), 3.04-2.88 (m, 3H), 2.39-2.27 (m, 3H), 2.24 (s, 6H), 2.14-2.08 (m, 2H), 1.88-1.79 (m, 2H), 1.60 (d, J = 8.0 Hz, 3H), 1.39-1.20 (m, 4H), 1.01-0.95 (m, 3H). |

TABLE 1-continued
| The MS and 1HNMR of the compounds | | | |
|---|---|---|---|
| Compounds | Structures | MS | $^1$HNMR |
| 75 | 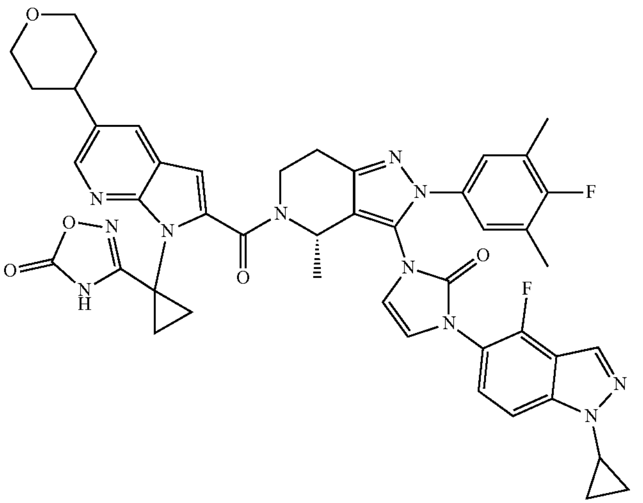 [SMILES: Cc1cc(-n2nc3c(c2-n2ccn(-c4ccc5c(cnn5C5CC5)c4F)c2=O)[C@H](C)N(C(=O)c2cc4cc(C5CCOCC5)cnc4n2C2(c4noc(=O)[nH]4)CC2)CC3)cc(C)c1F] | 868.34 | $^1$H NMR (500 MHZ, DMSO-$d_6$) δ 11.65 (s, 1H), 8.41-8.36 (m, 3H), 7.90-7.80 (m, 1H), 7.65-7.55 (m, 1H), 7.46-7.37 (m, 2H), 7.11-7.07 (m, 1H), 6.52-6.43 (m, 2H), 5.34-5.25 (m, 1H), 4.63-4.51 (m, 1H), 4.17-3.87 (m, 2H), 3.69-3.49 (m, 4H), 3.12-2.96 (m, 3H), 2.44-2.33 (m, 9H), 2.22-2.13 (m, 2H), 1.91-1.83 (m, 2H), 1.45-1.25 (m, 9H), 1.14-0.95 (m, 5H). |
| 76 | 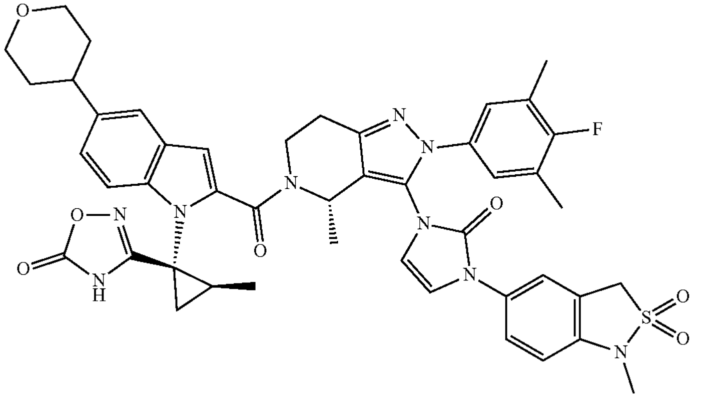 [SMILES: Cc1cc(-n2nc3c(c2-n2ccn(-c4ccc5c(c4)CS(=O)(=O)N5C)c2=O)[C@H](C)N(C(=O)c2cc4cc(C5CCOCC5)ccc4n2[C@@]2(c4noc(=O)[nH]4)C[C@@H]2C)CC3)cc(C)c1F] | 888.32 | $^1$H NMR (500 MHZ, DMSO-$d_6$) δ 11.78 (s, 1H), 8.41-8.29 (m, 2H), 7.99-7.89 (m, 1H), 7.64-7.54 (m, 2H),7.50-7.49(m, 1H), 7.46-7.36 (m, 3H), 7.21 (d, J = 2.0 Hz, 1H), 7.11-7.08 (m, 1H), 5.26-5.16 (m, 1H), 4.57-4.52 (m, 3H), 4.11-3.81 (m, 2H), 3.55-3.49 (m, 4H), 3.45(s, 3H), 3.13-2.85 (m, 3H), 2.42-2.33 (m, 3H), 2.30 (s, 6H), 2.15-2.11 (m, 2H), 1.88-1.79 (m, 2H), 1.61 (d, J = 8.0 Hz, 3H), 1.01-0.95 (m, 3H). |

TABLE 1-continued
| The MS and 1HNMR of the compounds | | | |
|---|---|---|---|
| Compounds | Structures | MS | $^1$HNMR |
| 77 | 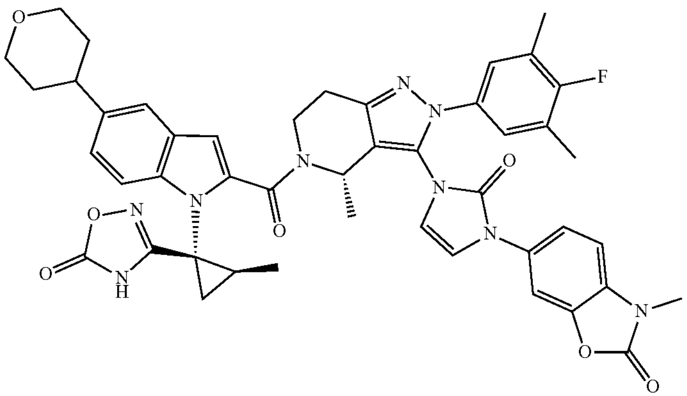 [SMILES: Cc1cc(-n2nc3c(c2-n2ccn(-c4ccc5c(c4)oc(=O)n5C)c2=O)[C@H](C)N(C(=O)c2cc4cc(C5CCOCC5)ccc4n2[C@@]2(c4noc(=O)[nH]4)C[C@@H]2C)CC3)cc(C)c1F] | 854.33 | $^1$H NMR (500 MHZ, DMSO-$d_6$) δ 11.78 (s, 1H), 8.41-8.29 (m, 2H), 7.99-7.89 (m, 1H), 7.64-7.54 (m, 2H), 7.50-7.49(m, 1H), 7.46-7.36 (m, 3H), 7.21 (d, J = 2.0 Hz, 1H), 7.11-7.08 (m, 1H), 5.26-5.16 (m, 1H), 4.53-4.50 (m, 1H), 4.11-3.81 (m, 2H), 3.55-3.49 (m, 4H), 3.28(s, 3H), 3.13-2.85 (m, 3H), 2.42-2.33 (m, 3H), 2.30 (s, 6H), 2.15-2.11 (m, 2H), 1.88-1.79 (m, 2H), 1.61 (d, J = 8.0 Hz, 3H), 1.01-0.95 (m, 3H). |
| 78 | 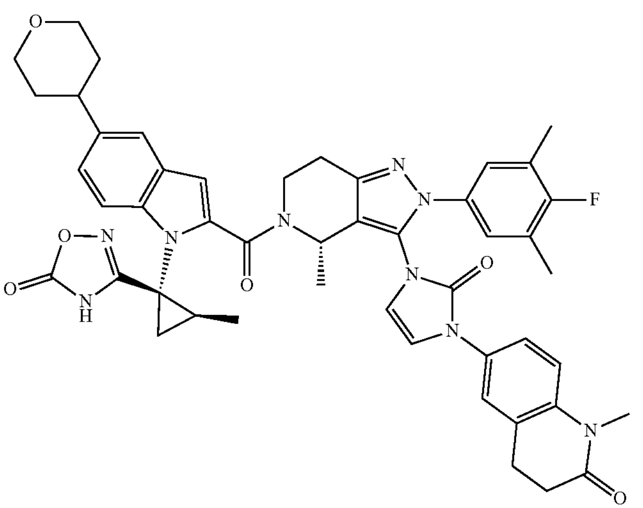 [SMILES: Cc1cc(-n2nc3c(c2-n2ccn(-c4ccc5c(c4)CCC(=O)N5C)c2=O)[C@H](C)N(C(=O)c2cc4cc(C5CCOCC5)ccc4n2[C@@]2(c4noc(=O)[nH]4)C[C@@H]2C)CC3)cc(C)c1F] | 866.37 | $^1$H NMR (500 MHZ, DMSO-$d_6$) δ 11.78 (s, 1H), 8.41-8.29 (m, 2H), 7.99-7.89 (m, 1H), 7.64-7.54 (m, 2H), 7.50-7.49(m, 1H), 7.46-7.36 (m, 3H), 7.21 (d, J = 2.0 Hz, 1H), 7.11-7.08 (m, 1H), 5.26-5.16 (m, 1H), 4.53-4.50 (m, 1H), 4.11-3.81 (m, 2H), 3.55-3.49 (m, 4H), 3.35(s, 3H), 3.13-2.81 (m, 5H), 2.66-2.63(m, 2H), 2.42-2.33 (m, 3H), 2.30 (s, 6H), 2.15-2.11 (m, 2H), 1.88-1.79 (m, 2H), 1.61 (d, J = 8.0 Hz, 3H), 1.01-0.95 (m, 3H). |

TABLE 1-continued
| The MS and 1HNMR of the compounds | | | |
|---|---|---|---|
| Compounds | Structures | MS | $^1$HNMR |
| 79 | 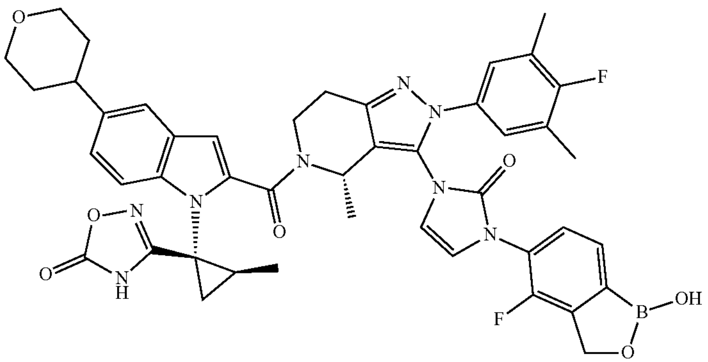 [SMILES: Cc1cc(-n2nc3c(c2-n2ccn(-c4ccc5c(c4F)COB5O)c2=O)[C@H](C)N(C(=O)c2cc4cc(C5CCOCC5)ccc4n2[C@@]2(c4noc(=O)[nH]4)C[C@@H]2C)CC3)cc(C)c1F] | 857.33 | $^1$H NMR (500 MHz, DMSO-$d_6$) δ 11.78 (s, 1H), 8.41-8.29 (m, 2H), 7.99-7.89 (m, 1H), 7.64-7.54 (m, 2H), 7.50-7.49(m, 1H), 7.46-7.36 (m,2H), 7.21 (d, J = 2.0 Hz, 1H), 7.11-7.08 (m, 1H), 5.26-5.16 (m, 1H), 5.10-5.08(s, 2H), 4.53-4.50 (m, 1H), 4.11-3.81 (m, 2H), 3.55-3.49 (m, 4H), 3.13-2.85 (m, 3H), 2.42-2.33 (m, 3H), 2.30 (s, 6H), 2.15-2.11 (m, 2H), 1.88-1.79 (m, 2H), 1.61 (d, J = 8.0 Hz, 3H), 1.01-0.95 (m, 3H). |
| 80 | 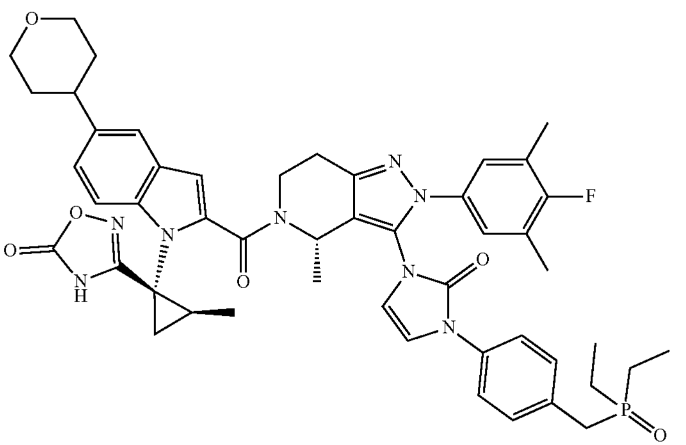 [SMILES: CCP(=O)(CC)Cc1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1] | 901.39 | $^1$H NMR (500 MHZ, DMSO-$d_6$) δ 11.76 (s, 1H), 8.37 (d, J = 6.0 Hz, 1H), 8.18 (d, J = 6.0 Hz, 1H), 7.81-7.75 (m, 2H), 7.75-7.69 (m, 2H), 7.66-7.62 (m, 1H), 7.43 (d, J = 7.5 Hz, 1H), 7.40 (d, J = 5.1 Hz, 2H), 7.21 (d, J = 2.0 Hz, 1H), 7.08-7.03 (m, 1H), 6.94 (s, 1H), 4.31-4.23 (m, 1H), 4.11-4.03 (m, 1H), 3.89(s, 2H), 3.59-3.47 (m, 4H), 3.06-2.99 (m, 1H), 3.03-2.94 (m, 2H), 2.72-2.63 (m, 4H), 2.41-2.26 (m, 3H), 2.24 (s, 6H), 2.16-2.07 (m, 2H), 1.88-1.79 (m, 2H), 1.75(d, J=6.4Hz, 3H), 1.51-1.47 (m, 6H), 0.99 (d, J = 5.8 Hz, 3H). |

TABLE 1-continued
| The MS and 1HNMR of the compounds | | | |
|---|---|---|---|
| Compounds | Structures | MS | $^1$HNMR |
| 81 | 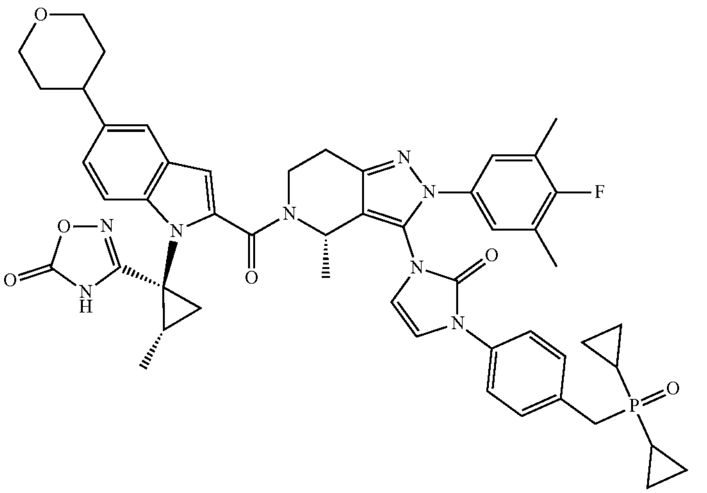 [SMILES: Cc1cc(-n2nc3c(c2-n2ccn(-c4ccc(CP(=O)(C5CC5)C5CC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 925.39 | $^1$H NMR (500 MHZ, DMSO-$d_6$) δ 11.76 (s, 1H), 8.37 (d, J = 6.0 Hz, 1H), 8.18 (d, J = 6.0 Hz, 1H), 7.81-7.75 (m, 2H), 7.75-7.69 (m, 2H), 7.66-7.62 (m, 1H), 7.43 (d, J = 7.5 Hz, 1H), 7.40 (d, J = 5.1 Hz, 2H), 7.21 (d, J = 2.0 Hz, 1H), 7.08-7.03 (m, 1H), 6.94 (s, 1H), 4.31-4.23 (m, 1H), 4.11-4.03 (m, 1H), 3.89(s, 2H), 3.59-3.47 (m, 4H), 3.06-2.99 (m, 1H), 3.03-2.94 (m, 2H), 2.72-2.63 (m, 4H), 2.41-2.26 (m, 3H), 2.24 (s, 6H), 2.16-2.07 (m, 4H), 1.88-1.79 (m, 2H), 1.75(d, J=6.4Hz, 3H), 1.14-0.89 (m, 7H). |
| 82 | 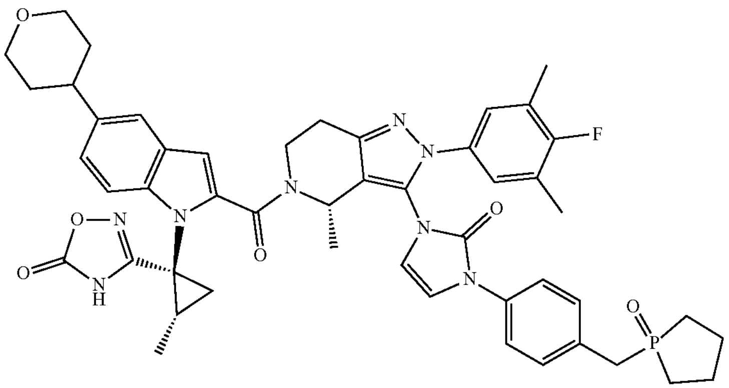 [SMILES: Cc1cc(-n2nc3c(c2-n2ccn(-c4ccc(CP5(=O)CCCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 899.37 | $^1$H NMR (500 MHZ, DMSO-$d_6$) δ 11.76 (s, 1H), 8.37 (d, J = 6.0 Hz, 1H), 8.18 (d, J = 6.0 Hz, 1H), 7.81-7.75 (m, 2H), 7.75-7.69 (m, 2H), 7.66-7.62 (m, 1H), 7.43 (d, J = 7.5 Hz, 1H), 7.40 (d, J = 5.1 Hz, 2H), 7.21 (d, J = 2.0 Hz, 1H), 7.08-7.03 (m, 1H), 6.94 (s, 1H), 4.31-4.23 (m, 1H), 4.11-4.03 (m, 1H), 3.89(s, 2H), 3.59-3.47 (m, 4H), 3.06-2.99 (m, 1H), 3.03-2.94 (m, 2H), 2.72-2.63 (m, 4H), 2.41-2.26 (m, 3H), 2.24 (s, 6H), 2.19-2.01 (m, 6H), 1.88-1.79 (m, 2H), 1.75 (d, J = 6.4 Hz, 3H), 1.51-1.47 (m, 4H), 0.99 (d, J = 5.8 Hz, 3H). |

TABLE 1-continued
| The MS and 1HNMR of the compounds | | | |
|---|---|---|---|
| Compounds | Structures | MS | $^1$HNMR |
| 84 | 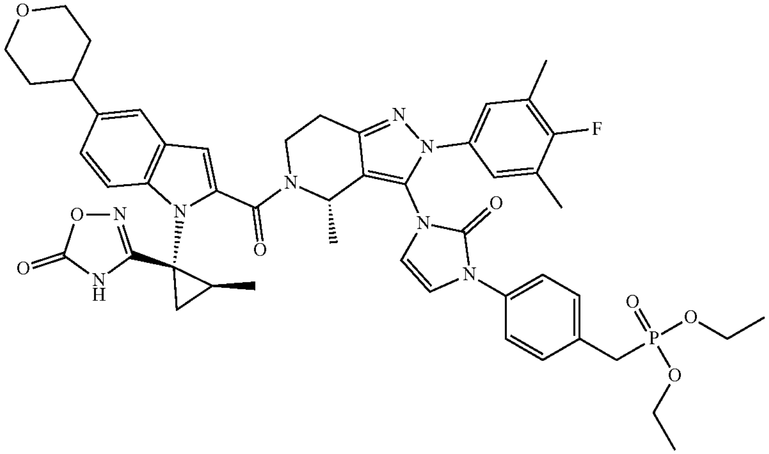 [SMILES: CCOP(=O)(Cc1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1)OCC] | 933.38 | $^1$H NMR (500 MHZ, DMSO-$d_6$) δ 11.72 (s, 1H), 8.37 (d, J = 6.0 Hz, 1H), 8.18 (d, J = 6.0 Hz, 1H), 7.81-7.75 (m, 2H), 7.75-7.69 (m, 2H), 7.66-7.62 (m, 1H), 7.43 (d, J = 7.5 Hz, 1H), 7.40 (d, J = 5.1 Hz, 2H), 7.21 (d, J = 2.0 Hz, 1H), 7.08-7.03 (m, 1H), 6.94 (s, 1H), 4.31-4.21 (m, 5H), 4.11-4.03 (m, 1H), 3.89(s, 2H), 3.59-3.47 (m, 4H), 3.06-2.99 (m, 1H), 3.03-2.94 (m, 2H), 2.72-2.63 (m, 4H), 2.41-2.26 (m, 1H), 2.24 (s, 6H), 2.16-2.07 (m, 2H), 1.88-1.79 (m, 2H), 1.75(d, J = 6.4 Hz, 3H), 1.36-1.35 (m, 6H), 0.99 (d, J = 5.8 Hz, 3H). |

Example 2 In Vitro Activity Evaluation hGLP-1R cAMP Assay

1. Cell Line and Reagent Preparation
   1) Cell line: Flp-In-293-GLP1R
   2) Medium: DMEM+10% FBS+1× Penicillin-Streptomycin+200 μg/mL HB
   3) Test buffer: 1×HBSS+20 mM HEPES+0.1% BSA+500 μM IBMX
2. Agonist Test
   a) Flpin-293-GLP1R cells were incubated in a 384-well assay plate (6007680-50, PE) using a complete medium with 2,000 cells per well.
   b) Prepared a 4× complex working solution with assay buffer.
   c) Added 5 μL of 4× Compound Working Solution to the cell plate and incubated at 37° C. for 30 minutes.
   d) Diluted the Eu-cAMP tracer (1/50) with lysis buffer and added 10 μl/well to the assay plate.
   e) Diluted Ulight-anti-cAMP (1/150) with lysis buffer and added 10 μl/well to the assay plate.
   f) The assay plate was incubated at constant temperature for 1 hour.
   g) Read the plate on Envision 2105 plate reader at 665 nM and 615 nM.
3. Data Analysis
   3.1 The formula for calculating % Activity was as follows $$\%\ \text{Activity} = 100 - (\text{Signal}_{cmpd} - \text{Signal}_{Ave\_PC})/(\text{Signal}_{Ave-}\text{VC} - \text{Signal}_{Ave\_PC}) \times 100.$$

3.2 Calculate $EC_{50}$ and plot the effect-dose curve for cmpds:

$$Y = \text{Bottom} + (\text{Top} - \text{Bottom})/(1 + 10\text{^}((\text{Log}EC50 - X) * HillSlope))$$

X: logarithm of agonist concentration;

Y: percentage activity.

Table 2 shows the biological activity of the compounds in the hGLP-1R agonist cAMP stimulation assay.

TABLE 2

Bioactivity of different compounds in hGLP-1R agonist cAMP stimulation assay

| Compounds | hGLP-1R CAMP: $EC_{50}$ (nM) |
|---|---|
| 1 | 0.094 |
| 13 | 0.228 |
| 18 | 0.265 |
| 19 | 0.012 |
| 20 | 0.018 |
| 21 | 0.044 |
| 24 | 0.868 |
| 29 | 0.063 |
| 35 | 0.025 |
| 36 | 0.05 |
| 37 | 0.06 |
| 55 | 0.15 |
| 65 | 0.092 |
| 66 | 0.014 |
| 70 | 0.064 |
| 76 | 0.019 |
| 77 | 0.022 |

TABLE 2-continued

Bioactivity of different compounds in hGLP-1R agonist cAMP stimulation assay

| Compounds | hGLP-1R CAMP: $EC_{50}$ (nM) |
|---|---|
| 78 | 0.012 |
| 79 | 0.171 |
| 80 | 0.038 |
| 81 | 0.042 |
| 82 | 0.011 |
| 84 | 0.08 |
| 50 | 0.028 |

Example 3 Pharmacokinetic Studies

Pharmacokinetic Studies in Sprague-Dawley (SD) Rats

1. Single-Dose Subcutaneous Injection Pharmacokinetic Studies Sprague-Dawley (SD) Rats Pharmacokinetic (PK) studies after a single-dose subcutaneous injection for compounds: 1, 13, 18, 19, 20, 21 and orforglipron. Protocol: Animals: Male Sprague-Dawley (SD) rats; Vehicle: 80% MCT (Medium-Chain Triglycerides)+20% benzyl alcohol; Dose: 30 mg/kg in the vehicle; Dosing concentration: 30 mg/mL; Dosing volume: 1 mL/kg; Administration site: Subcutaneous injection at the back of the animal. Blood sampling time points: pre-dose, 1 h, 2 h, 8 h, 24 h, 48 h, 72 h, 96 h, 120 h, 144 h, 216 h, 312 h, 480 h, 696 h. Blood samples were collected, and the blood samples were analyzed by LC-MS/MS. Pharmacokinetic parameters were calculated by Phoenix WinNonlin 8.0 and summarized in Table 3.

TABLE 3

Drug exposure of different compounds after a single-dose subcutaneous injection

| Compounds | Dosing route | Dose, mg/kg | $AUC_{0-696\ h}$, ng · h/mL |
|---|---|---|---|
| 1 | Subcutaneous | 30 | 60,272 |
| 13 | Subcutaneous | 30 | 23,399 |
| 18 | Subcutaneous | 30 | 51,234 |
| 19 | Subcutaneous | 30 | 234,473 |
| 20 | Subcutaneous | 30 | 77,688 |
| 21 | Subcutaneous | 30 | 61,479 |
| Orforglipron | Subcutaneous | 30 | 5,390 |

Note:

$AUC_{0-696\ h}$ is an important pharmacokinetic parameter, representing the area under the curve from 0 hour to the study endpoint time 696 hours, which indicates the drug exposure in the body during that time period.

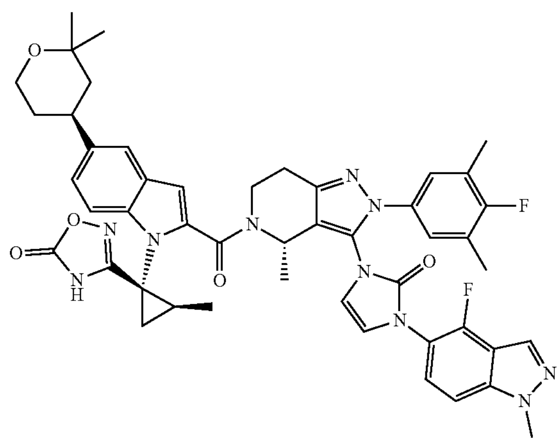 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

The structure of orforglipron is shown above.

2. Single-Dose Oral Administration Pharmacokinetic (PK) Studies in Sprague-Dawley (SD) Rats Pharmacokinetic (PK) studies after a single-dose oral administration for compounds. Protocol: Animals: Sprague-Dawley (SD) rats; Solvent: Solutol: PEG400: Tween80: Saline=10:40:2:48 (v/v/v/v); Dose: 5 mg/kg; Dosing concentration: 0.5 mg/mL in the solvent; Dosing volume: 10 mL/kg: Blood sampling time points: pre-dose, 0.25 h, 0.5 h, 1 h, 2 h, 3 h, 4 h, 8 h, 12 h, 18, 24 h, 32 h, 40 h, 48 h. Sample Collection: At each time point, approximately 0.15 mL of blood was drawn from the jugular vein sinus, and the collected whole blood was placed in an anticoagulant tube containing EDTA-K2. After collecting blood samples, they were processed with protein precipitation and then analyzed by LC-MS/MS. Pharmacokinetic parameters were calculated by Phoenix WinNonlin 8.0 and summarized in Table 4.

TABLE 4

Pharmacokinetic parameters of different compounds after a single-dose oral administration

| Compounds | Dosing route | Dose, mg/kg | $C_{max}$, ng/ml | $AUC_{0-48\ h}$, ng · h/mL |
|---|---|---|---|---|
| 19 | Oral | 5 | 4,460 | 60,043 |
| 20 | Oral | 5 | 1,900 | 16,982 |
| 65 | Oral | 5 | 10,993 | 71,836 |
| Orforglipron | Oral | 5 | 799 | 7,222 |

Note:
$C_{max}$ refers to the maximum plasma concentration of a drug after administration Example 4 Pharmacodynamics Study In Vivo Animal screening: Within one week prior to the administration of the test compounds, 28 male cynomolgus monkeys were anesthetized with Zoletil (5.0 mg/kg, intramuscular injection, i.m.), and then 50% glucose was administered intravenously at a dose of 0.5 g/kg (1 mL/kg), completed within 30 seconds. Blood samples were collected at 10 time points: 45 minutes before glucose injection (non-anesthetized), 6 minutes before glucose injection (under anesthesia), and 1, 5, 10, 15, 20, 30, 40, and 60 minutes after glucose injection. At each time point, 10 μL of whole blood was collected from the saphenous vein for blood glucose testing using a glucometer. Approximately 1.5 mL of whole blood was collected at each time point from the saphenous vein into a vacuum blood collection tube containing a coagulant. The tube was immediately inverted gently several times to mix well, placed at room temperature, and then centrifuged at 4° C. (2000 g, 10 minutes) to obtain serum. The collected serum samples were stored in an ultra-low temperature freezer until all samples were tested for blood glucose, insulin, and C-peptide. For the selection of cynomolgus monkeys, 15 cynomolgus monkeys were chosen for the formal experiment based on the trends of changes in blood glucose, insulin, and C-peptide.

Formal Experiment

Grouping: The 15 selected cynomolgus monkeys were randomly divided into 3 groups, with 5 animals in each group.

Sample preparation: An appropriate amount of the compound of the present invention was weighed and dissolved in the solvent: 5% DMSO/10% Cremophor EL/20% PEG400/65% 100 mM Glycine-NaOH pH 10 to prepare a suitable concentration for intravenous bolus injection.

Dosing method: 5 minutes before the glucose injection, the test substance was administered via intravenous bolus (iv bolus). The syringe was filled with the corresponding volume of the test substance for each animal, and the injection was completed within 30 seconds.

Intravenous glucose tolerance test: 5 minutes after the intravenous bolus administration of the test substance, the intravenous glucose tolerance test was initiated, with the animals remaining anesthetized throughout the procedure (anesthetized with Zoletil at 5.0 mg/kg, i.m.). 5 minutes after the intravenous bolus administration of the test substance, 50% glucose at a dose of 0.5 g/kg (1.0 mL/kg) was administered intravenously, completed within 30 seconds.

Sample collection: Blood was collected 45 minutes before the glucose injection (non-anesthetized) and 6 minutes before the glucose injection (under anesthesia). After the glucose injection (under anesthesia), blood was collected at the following time points: 1, 5, 10, 15, 20, 30, 40, and 60 minutes. At each time point, 10 μL of whole blood was collected from the saphenous vein for blood glucose testing using a glucometer. Approximately 1.5 mL of whole blood was collected from the saphenous vein at each time point into a vacuum blood collection tube containing a coagulant. The tube was immediately inverted gently several times to mix well, placed at room temperature, and then centrifuged at 4° C. (2000 g, 10 minutes) to obtain serum. The collected serum samples were stored in an ultra-low temperature freezer until all samples were analyzed for blood glucose, insulin, and C-peptide.

Sample Analysis: The serum samples were analyzed for insulin, C-peptide, and blood glucose levels.

Results: The compound of the present disclosure significantly increased the secretion of insulin and C-peptide in cynomolgus monkeys, while blood glucose levels were reduced as well.

What is claimed is:
1. A compound, selected from the group consisting of
O-6′
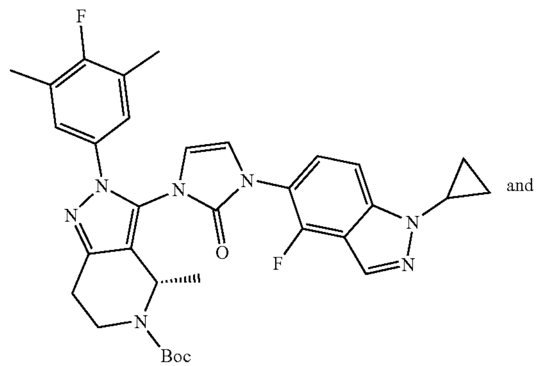
and
O-6
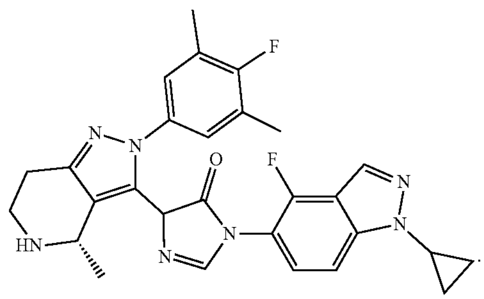
.
* * * * *